(12) United States Patent
Warf et al.

(10) Patent No.: US 11,584,967 B2
(45) Date of Patent: *Feb. 21, 2023

(54) GENES AND GENE SIGNATURES FOR DIAGNOSIS AND TREATMENT OF MELANOMA

(71) Applicant: MYRIAD MYPATH, LLC, Salt Lake City, UT (US)

(72) Inventors: Michael Bryan Warf, Salt Lake City, UT (US); Benjamin Roa, Salt Lake City, UT (US); Alexander Gutin, Salt Lake City, UT (US); Darl Flake, Salt Lake City, UT (US)

(73) Assignee: MYRIAD MYPATH, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/786,780

(22) Filed: Feb. 10, 2020

(65) Prior Publication Data

US 2020/0255908 A1    Aug. 13, 2020

Related U.S. Application Data

(63) Continuation of application No. 15/388,979, filed on Dec. 22, 2016, now Pat. No. 10,612,099, which is a
(Continued)

(51) Int. Cl.
*C12Q 1/6886* (2018.01)
*C12Q 1/6851* (2018.01)
(Continued)

(52) U.S. Cl.
CPC ......... *C12Q 1/6886* (2013.01); *C12Q 1/6851* (2013.01); *G16B 20/00* (2019.02);
(Continued)

(58) Field of Classification Search
CPC ................ C12Q 1/6886; C12Q 1/6851; C12Q 2600/106; C12Q 2600/112; C12Q 2600/158
See application file for complete search history.

(56) References Cited

U.S. PATENT DOCUMENTS

| 6,586,181 B1 | 7/2003 | Fox et al. |
| 2009/0203011 A1 | 8/2009 | Liebenberg |

(Continued)

FOREIGN PATENT DOCUMENTS

| EP | 2080140 | 7/2009 |
| EP | 2481813 | 8/2012 |

(Continued)

OTHER PUBLICATIONS

Mauerer et al, Experimental Dermatology, 2011, vol. 20, pp. 502-507.*

(Continued)

*Primary Examiner* — Sarae L Bausch
(74) *Attorney, Agent, or Firm* — McDonnell Boehnen Hulbert & Berghoff LLP

(57) ABSTRACT

Panels of biomarkers, methods and systems are disclosed for determining gene expression, and diagnosing and treating melanoma.

18 Claims, 16 Drawing Sheets

Related U.S. Application Data continuation of application No. PCT/US2015/038038, filed on Jun. 26, 2015.

(60) Provisional application No. 62/020,302, filed on Jul. 2, 2014.

(51) Int. Cl.

| | |
|---|---|
| *G16B 25/00* | (2019.01) |
| *G16B 20/00* | (2019.01) |
| *G16B 20/20* | (2019.01) |
| *G16B 25/10* | (2019.01) |
| *G16B 25/20* | (2019.01) |

(52) U.S. Cl.
CPC ............ *G16B 20/20* (2019.02); *G16B 25/00* (2019.02); *G16B 25/10* (2019.02); *G16B 25/20* (2019.02); *C12Q 2600/106* (2013.01); *C12Q 2600/112* (2013.01); *C12Q 2600/158* (2013.01)

(56) References Cited

U.S. PATENT DOCUMENTS

| | | | |
|---|---|---|---|
| 2011/0070268 | A1 | 3/2011 | Brichard et al. |
| 2011/0171632 | A1 | 7/2011 | Fujimoto |
| 2012/0008838 | A1 | 1/2012 | Guyon et al. |
| 2012/0071343 | A1 | 3/2012 | Xiao-Jun et al. |
| 2012/0323594 | A1 | 12/2012 | Tsao et al. |
| 2013/0344481 | A1 | 12/2013 | Kashani-Sabet et al. |

FOREIGN PATENT DOCUMENTS

| | | |
|---|---|---|
| WO | WO 2006/092610 | 9/2006 |
| WO | WO 2009/140550 | 11/2009 |
| WO | WO 2010/019120 | 2/2010 |
| WO | WO 2010/105815 | 9/2010 |
| WO | WO 2011/039734 | 4/2011 |
| WO | WO 2012/104388 | 8/2012 |
| WO | WO 2013/030310 | 3/2013 |
| WO | WO 2013/192616 | 12/2013 |
| WO | WO2013/192616 A1 * | 12/2013 ............... C12Q 1/68 |

OTHER PUBLICATIONS

Affymetrix GeneChip Human Genome U133 Array Set HG-U133A, Geo, Mar. (2002), XP002355386.

Antonicelli et al., "CXCL10 reduces melanoma proliferation and invasiveness in vitro and in vivo", British Journal of Dermatology, 164(4):720-28 (2011).

Baker, "The Central Role of Receiver Operating Characteristic (ROC) Curves in Evaluating Tests for the Early Detection of Cancer", Journal of the National Cancer Institute, 95(7):511-15 (2003).

Bastian et al., "Classifying Melanocytic Tumors Based on DNA Copy Number Changes" American Journal of Pathology, 163(5):1765-70 (2003).

Bauer et al., "Distinguishing melanocytic nevi from melanoma by DNA copy number changes: comparative genomic hybridization as a research and diagnostic tool", Dermatologic Therapy, vol. 19, pp. 40-49 (2006).

Buck, et al., "Design Strategies and Performance of Custom DNA Sequencing Primers", Biotechniques, 27(3):528-36 (1999).

Burroni, et al., "Melanoma computer-aided diagnosis: reliability and feasibility study." Clinical Cancer Research, 10(6):1881-86 (2004).

Chan et al, Integrating Trascriptomic and Proteomics , pp. 1-4 (2006).

Cheung et al, Cold Spring Harbor Symposia Quant. Biol., vol. LXVIII, pp. 403-407 (2003).

Clarke et al., "Clinical validation of a gene expression signature that differentiates benign nevi from malignant melanoma", Journal of Cutaneous Pathology, 42(4):244-52 (2015).

Cockerelle et al., Medicine, (2016), 95(40):1-7.

Database Biosis [Online] Biosciences Information Service, Henrike et al., "Expression of MCSP and PRAME in conjunctival melanoma", Database Accession No. PREV201000608036 & British Journal of Opthalmology, 94(10):1322-27 (2010).

DeJonge (PLoS One, vol. 2, e898, pp. 1-5 (2007).

Della Ragione et al., "Differential DNA methylation as a tool for noninvasive prenatal diagnosis (NIPD) of X chromosome aneuploidies" J Mol Diag, 12(6):797-807 (2010).

Enard et al, "Intra-and interspecific variation in primate gene expression patterns", Science, 296(5566):340-43 (2002).

Enerback et al., "Expression of S100 proteins in the progression of melanocytic lesions", European Journal of Cancer. Supplement, 6(9):133 (2008).

Gast et al., "Somatic alterations in the melanoma genome: A high-resolution array-based comparative genomic hybridization study", Genes, Chromosomes, Cancer, vol. 49(8), pp. 733-745 (2010).

Hernandez, "Optimizing methodologies for PCR-based DNA methylation analysis", Biotechniques,55(4) pp. 181-197 (2013).

Hoshikawa et al, "Hypoxia induces different genes in the lungs of rats compared with mice", Physiol Genomics, vol. 12, pp. 209-219 (2003).

Jack et al., "The treatment of melanoma with an emphasis on immunotherapeutic strategies", Surgical Oncology, 15(1):13-24 (2006).

Kashani-Sabet et al., "A multi-marker assay to distinguish malignant melanomas from benign nevi." PNAS, 106 (15):6268-72 (2009).

Kwak et al., "Updates in adjuvant systemic therapy for melanoma" J. Surg. Oncol, 119:222-31 (2009).

Mauerer et al., "Identification of new genes associated with melanoma", Experimental Dermatology, 20(6):502-07 (2011).

Mothy et al., "Induction of IP-10/CXCL10 secretion as an immunomodulatory effect of low-dose adjuvant interferon-alpha during treatment of melanoma", Immunobiology, Urban Und Fischer Verlag, DE, 215(2):113-23 (2010).

Riker, et al., "The gene expression profiles of primary and metastatic melanoma yields a transition point of tumor progression and metastasis", BMC Medial Genomics, vol. 1(1), pp. 1-16 (2008).

Rother, et al., "Molecular markers of tumor progression in melanoma", Current Genomics, vol. 10(4), pp. 231-239 (2009).

Schmidt, et al., "SHOX2 DNA Methylation is a Biomarker for the diagnosis of lung cancer based on bronchial aspirates", BMC Cancer, 10(600), pp. 1-9 (2010).

Slonim, "From Patterns to Pathways: Gene Expression Data Analysis. Comes of Age", Nature Genetics Supplement, vol. 32, pp. 502-508 (2002).

Talantov, et al., "Novel Genes Associated with Malignant Melanoma but not Benign Melanocytic Lesions" Clinical Cancer Research, 11(20), pp. 7234-7242 (2005).

Tanese, et al., "The role of melanoma tumor-derived nitric oxide in the tumor inflammatory microenvironment: Its impact on chemokine expression profile, including suppression of CXCL10", International Journal of Cancer, vol. 131 (4), pp. 891-901 (2012).

Trolet et al., "Genomic Profiling and Identification of High-Risk Uveal Melanoma by Array CGH Analysis of Primary Tumors and Liver Metastases" IOVS, 50(6):2572-80 (Jun. 2009).

Wang et al., "A Genome-Wide High-Resolution Array-CGH Analysis of Cutaneous Melanoma and Comparison of Array-GGH to Fish in Diagnostic Evaluation", The Journal of Molecular Diagnostics, vol. 15(5) pp. 581-591 (2013).

Wang et al., "Cell Cycle Gene Networks Are Associated with Melanoma Prognosis" PLoS One, 7(4):e34247 (2012).

Weinstein, et al., "Diagnostic and prognostic biomarkers in melanoma", The Journal of Clinical and Aesthetic Dermatology, vol. 7(6), pp. 13-24 (2014).

PCT/US2014/024790 International Search Report and Written Opinion, completed on Aug. 20, 2014.

PCT/US2015/038038 International Search Report and Written Opinion, dated Aug. 24, 2015.

(56) References Cited

OTHER PUBLICATIONS

The International Search Report for PCT/US2017/012513, dated Apr. 17, 2017, pp. 1-5.

Fujimoto et al., "Allelic imbalance of 12Q22-23 associated with APAF-1 locus correlates with poor disease outcome in cutaneous melanoma". Cancer Research, vol. 64, pp. 2245-2250 (Mar. 2004).

Noll et al., "Loss of heterozygosity on chromosome 11q22-23 in melanoma is associated with retention of the insertion polymorphism in the matrix metalloproteinase-1 promoter", American Journal of Pathology, vol. 158, No. 2, pp. 691-697 (Feb. 2001).

Stefanaki et al., "Replication and predictive value of SNPs associated with melanoma and pigmentation traits in a southern european case-control study", Plos One, vol. 8, Issue 2, Article No. e55712, pp. 1-10 (Feb. 2013).

Takata, "Genetic/Epigenetic biomarkers: distinction of melanoma from other melanocytic neoplasms", Diagnostic and Prognostic Biomarkers and Therapeutic Targets in Melanoma, Chapter 6, p. 69-77 (Nov. 2011).

Van Dijk et al., "Allelic imbalance in the diagnosis of benign, atypical and malignant Spitz tumours", Journal of Pathology, vol. 197, pp. 170-178 (2002).

Garbe et al., "Systematic Review of Medical Treatment in Melanoma: Current Status and Future Prospects", The Oncologist, 16(1):5-24 (Jan. 2011).

\* cited by examiner

GENES AND GENE SIGNATURES FOR DIAGNOSIS AND TREATMENT OF MELANOMA

RELATED APPLICATIONS

This application claims priority to International Application Serial No. PCT/US15/038038, filed Jun. 26, 2015. This application and International Serial No. PCT/US15/038038 are related to and claim the priority benefit of U.S. provisional application No. 62/020,302, filed Jul. 2, 2014, the entire contents of which are hereby incorporated by reference.

FIELD OF THE INVENTION

The invention generally relates to a molecular classification of disease and particularly to genes and gene signatures for diagnosis of melanoma and methods of use thereof.

BACKGROUND OF THE INVENTION

In the United States, over 76,000 new cases of melanoma will be diagnosed in 2013. American Cancer Society, FACTS AND FIGURES 2013. Treatment of melanoma at an earlier stage is associated with higher survival rates in patients. There is therefore a great need for advances in methods of early diagnosis and treatment of melanoma.

BRIEF SUMMARY OF THE INVENTION

Panels of biomarkers, methods and systems are disclosed for determining gene expression, and diagnosing and treating melanoma.

In a first aspect the disclosure is related to methods of diagnosing melanoma in a patient. In general, said methods comprise measuring in a sample obtained from the patient the expression of one or more genes, or a panel of genes. The genes may be cell cycle genes, immune genes or additional genes as defined herein. The genes may be selected from Table 1, Table 3, or one of the many specifically defined panels (Panels A-I, or panels in Tables WW-ZZ). The method may also comprise comparing the measured expression levels of the one or more genes to the expression levels of the same one or more genes measured in a reference sample. Detecting a difference in the expression levels of the one or more genes indicates that the patient has melanoma.

In a second aspect, the disclosure is related to methods of detecting abnormal levels of gene expression in a skin lesion. In general, the methods comprise measuring in a skin lesion obtained from a patient the expression of one or more genes, or a panel of genes. The genes may be cell cycle genes, immune genes or additional genes as defined herein. The genes may be selected from Table 1, Table 3, or one of the many specifically defined panels (Panels A-I, or panels in Tables WW-ZZ). The method may also comprise comparing the measured expression levels of the one or more genes to the expression levels of the same one or more genes measured in a reference sample. The method may also comprise detecting an abnormal level of gene expression of at least one of the one or more genes.

In a third aspect, the disclosure is related to treating a patient with melanoma. In general, the methods comprise measuring in a skin lesion obtained from a patient the expression of one or more genes, or a panel of genes. The genes may be cell cycle genes, immune genes or additional genes as defined herein. The genes may be selected from Table 1, Table 3, or one of the many specifically defined panels (Panels A-I, or panels in Tables WW-ZZ). The method may also comprise comparing the measured expression levels of the one or more genes to the expression levels of the same one or more genes measured in a reference sample. The method may also comprise detecting an abnormal level of gene expression of at least one of the one or more genes, and altering the patient's treatment based at least in part on the difference.

Also disclosed are systems, compositions and kits to aid in detecting abnormal levels of gene expression, diagnosing melanoma or treating melanoma.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Genes and Panels

Figure 1:
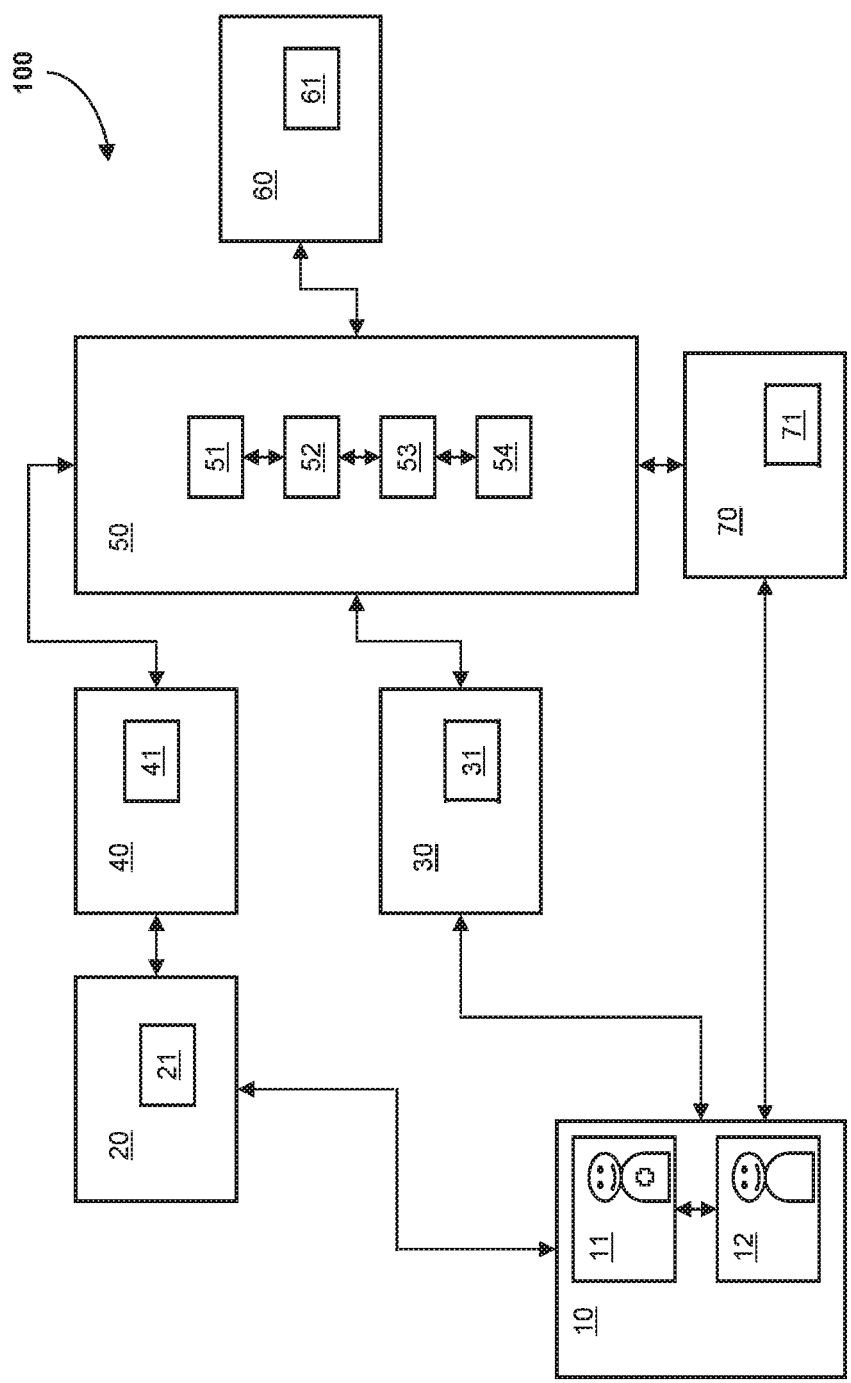
FIG. 1 shows a system for performing computer-assisted methods of diagnosing, detecting, screening and/or treating melanoma in a patient.

Disclosed herein are gene biomarkers and panels of biomarkers, methods and systems for determining gene expression, and methods for diagnosing and treating melanoma. It should be understood that the methods and systems disclosed are all intended to be utilized in conjunction with biomarkers as described herein. In particular, any panel disclosed may be used with any method or system of this disclosure. Furthermore, subpanels of any panel disclosed may furthermore be used, as described below.

The gene biomarkers and panels of biomarkers are useful, at least in part, for their predictive power in determining whether an individual has melanoma. It has been discovered that the predictive power of a panel or group of genes often ceases to increase significantly beyond a certain number. More specifically, the optimal number of genes in a panel, or used to generate a test value can be found wherever the following is true $$(P_{n+1} - P_n) < CO,$$

wherein P is the predictive power (i.e., Pn is the predictive power of a signature with n genes and Pn+1 is the predictive power of a signature with n genes plus one) and CO is some optimization constant. Predictive power can be defined in many ways known to those skilled in the art including, but not limited to, the signature's p-value. CO can be chosen by the artisan based on his or her specific constraints. For example, if cost is not a critical factor and extremely high levels of sensitivity and specificity are desired, CO can be set very low such that only trivial increases in predictive power are disregarded. On the other hand, if cost is decisive and moderate levels of sensitivity and specificity are acceptable, CO can be set higher such that only significant increases in predictive power warrant increasing the number of genes in the signature.

Additionally, a skilled person would recognize that individual panels may be combined to generate additional panels according to this disclosure, and that combining two panels with acceptable predictive power will result in a combined panel with acceptable predictive power. Additionally, a skilled person would recognize that while individual genes are described herein as belonging to certain groups (i.e. Cell Cycle Genes, immune genes, etc.), all panels and genes disclosed herein are unified by their common ability to aid in determining gene expression, and treating and diagnosing melanoma.

CCP Genes

The present invention is based in part on the discovery that the expression levels of CCP genes in a sample from a patient suspected of having melanoma predict whether the patient will be diagnosed with melanoma, and further that other genes, add significant prediction power when combined with CCP genes ("CCGs").

"Cell-cycle gene" and "CCG" herein refer to a gene whose expression level closely tracks the progression of the cell through the cell-cycle. See, e.g., Whitfield et al., Mol. Biol. Cell (2002) 13:1977-2000. The term "cell-cycle progression" or "CCP" will also be used in this application and will generally be interchangeable with CCG (i.e., a CCP gene is a CCG; a CCP score is a CCG score). More specifically, CCGs show periodic increases and decreases in expression that coincide with certain phases of the cell cycle—e.g., STK15 and PLK show peak expression at G2/M. Id. Often CCGs have clear, recognized cell-cycle related function—e.g., in DNA synthesis or repair, in chromosome condensation, in cell-division, etc. However, some CCGs have expression levels that track the cell-cycle without having an obvious, direct role in the cell-cycle—e.g., UBE2S encodes a ubiquitin-conjugating enzyme, yet its expression closely tracks the cell-cycle. Thus a CCG according to the present invention need not have a recognized role in the cell-cycle. Exemplary CCGs are listed in Tables 1, 2, 3, 5, 6, 7, 8 & 9. A fuller discussion of CCGs, including an extensive (though not exhaustive) list of CCGs, can be found in International Application No. PCT/US2010/020397 (pub. no. WO/2010/080933) (see, e.g., Table 1 in WO/2010/080933). International Application No. PCT/US2010/020397 (pub. no. WO/2010/080933 (see also corresponding U.S. application Ser. No. 13/177,887)) and International Application No. PCT/US2011/043228 (pub no. WO/2012/006447 (see also related U.S. application Ser. No. 13/178,380)) and their contents are hereby incorporated by reference in their entirety.

Whether a particular gene is a CCG may be determined by any technique known in the art, including those taught in Whitfield et al., Mol. Biol. Cell (2002) 13:1977-2000; Whitfield et al., Mol. Cell. Biol. (2000) 20:4188-4198; WO/2010/080933 (¶[0039]). All of the CCGs in Table 1 below form a panel of CCGs ("Panel A"). As will be shown in detail throughout this document, individual CCGs (e.g., CCGs in Table 1) and subsets of these genes can also be used.

TABLE 1

| Gene Symbol | Entrez GeneID | ABI Assay ID | RefSeq Accession Nos. |
|---|---|---|---|
| APOBEC3B* | 9582 | Hs00358981_m1 | NM_004900.3 |
| ASF1B* | 55723 | Hs00216780_m1 | NM_018154.2 |
| ASPM* | 259266 | Hs00411505_m1 | NM_018136.4 |
| ATAD2* | 29028 | Hs00204205_m1 | NM_014109.3 |
| BIRC5* | 332 | Hs00153353_m1; Hs03043576_m1 | NM_001012271.1; NM_001012270.1; NM_001168.2 |
| BLM* | 641 | Hs00172060_m1 | NM_000057.2 |
| BUB1 | 699 | Hs00177821_m1 | NM_004336.3 |
| BUB1B* | 701 | Hs01084828_m1 | NM_001211.5 |
| C12orf48* | 55010 | Hs00215575_m1 | NM_017915.2 |
| C18orf24/SKA1*# | 220134 | Hs00536843_m1 | NM_145060.3; NM_001039535.2 |
| C10orf135* | 79000 | Hs00225211_m1 | NM_024037.1 |
| C21orf45* | 54069 | Hs00219050_m1 | NM_018944.2 |
| CCDC99* | 54908 | Hs00215019_m1 | NM_017785.4 |
| CCNA2* | 890 | Hs00153138_m1 | NM_001237.3 |
| CCNB1* | 891 | Hs00259126_m1 | NM_031966.2 |
| CCNB2* | 9133 | Hs00270424_m1 | NM_004701.2 |
| CCNE1* | 898 | Hs01026536_m1 | NM_001238.1; NM_057182.1 |
| CDC2* | 983 | Hs00364293_m1 | NM_033379.3; NM_001130829.1; NM_001786.3 |
| CDC20* | 991 | Hs03004916_g1 | NM_001255.2 |
| CDC45L* | 8318 | Hs00185895_m1 | NM_003504.3 |
| CDC6* | 990 | Hs00154374_m1 | NM_001254.3 |
| CDCA3* | 83461 | Hs00229905_m1 | NM_031299.4 |
| CDCA8* | 55143 | Hs00983655_m1 | NM_018101.2 |
| CDKN3* | 1033 | Hs00193192_m1 | NM_001130851.1; NM_005192.3 |
| CDT1* | 81620 | Hs00368864_m1 | NM_030928.3 |
| CENPA | 1058 | Hs00156455_m1 | NM_001042426.1; NM_001809.3 |
| CENPE* | 1062 | Hs00156507_m1 | NM_001813.2 |
| CENPF*# | 1063 | Hs00193201_m1 | NM_016343.3 |
| CENPI* | 2491 | Hs00198791_m1 | NM_006733.2 |
| CENPM* | 79019 | Hs00608780_m1 | NM_024053.3 |
| CENPN* | 55839 | Hs00218401_m1 | NM_018455.4; NM_001100624.1; NM_001100625.1 |
| CEP55*# | 55165 | Hs00216688_m1 | NM_018131.4; NM_001127182.1 |
| CHEK1* | 1111 | Hs00967506_m1 | NM_001114121.1; NM_001114122.1; NM_001274.4 |
| CKAP2* | 26586 | Hs00217068_m1 | NM_018204.3; NM_001098525.1 |
| CKS1B* | 1163 | Hs01029137_g1 | NM_001826.2 |
| CKS2* | 1164 | Hs01048812_g1 | NM_001827.1 |
| CTPS* | 1503 | Hs01041851_m1 | NM_001905.1 |
| CTSL2* | 1515 | Hs00952036_m1 | NM_001333.2 |
| DBF4* | 10926 | Hs00272696_m1 | NM_006716.3 |
| DDX39* | 10212 | Hs00271794_m1 | NM_005804.2 |
| DLGAP5/DLG7*# | 9787 | Hs00207323_m1 | NM_014750.3 |
| DONSON* | 29980 | Hs00375083_m1 | NM_017613.2 |
| DSN1* | 79980 | Hs00227760_m1 | NM_024918.2 |
| DTL*# | 51514 | Hs00978565_m1 | NM_016448.2 |
| E2F8* | 79733 | Hs00226635_m1 | NM_024680.2 |
| ECT2* | 1894 | Hs00216455_m1 | NM_018098.4 |
| ESPL1* | 9700 | Hs00202246_m1 | NM_012291.4 |
| EXO1* | 9156 | Hs00243513_m1 | NM_130398.2; NM_003686.3; NM_006027.3 |
| EZH2* | 2146 | Hs00544830_m1 | NM_152998.1; NM_004456.3 |
| FANCI* | 55215 | Hs00289551_m1 | NM_018193.2; NM_001113378.1 |
| FBXO5* | 26271 | Hs03070834_m1 | NM_001142522.1; NM_012177.3 |
| FOXM1*# | 2305 | Hs01073586_m1 | NM_202003.1; NM_202002.1; NM_021953.2 |
| GINS1* | 9837 | Hs00221421_m1 | NM_021067.3 |
| GMPS* | 8833 | Hs00269500_m1 | NM_003875.2 |
| GPSM2* | 29899 | Hs00203271_m1 | NM_013296.4 |
| GTSE1* | 51512 | Hs00212681_m1 | NM_016426.5 |
| H2AFX* | 3014 | Hs00266783_s1 | NM_002105.2 |
| HMMR* | 3161 | Hs00234864_m1 | NM_001142556.1; NM_001142557.1; NM_012484.2; NM_012485.2 |
| HN1* | 51155 | Hs00602957_m1 | NM_001002033.1; NM_001002032.1; NM_016185.2 |
| KIAA0101* | 9768 | Hs00207134_m1 | NM_014736.4 |
| KIF11* | 3832 | Hs00189698_m1 | NM_004523.3 |
| KIF15* | 56992 | Hs00173349_m1 | NM_020242.2 |
| KIF18A* | 81930 | Hs01015428_m1 | NM_031217.3 |
| KIF20A* | 10112 | Hs00993573_m1 | NM_005733.2 |
| KIF20B/MPHOSPH1* | 9585 | Hs01027505_m1 | NM_016195.2 |
| KIF23* | 9493 | Hs00370852_m1 | NM_138555.1; NM_004856.4 |
| KIF2C* | 11004 | Hs00199232_m1 | NM_006845.3 |
| KIF4A* | 24137 | Hs01020169_m1 | NM_012310.3 |
| KIFC1* | 3833 | Hs00954801_m1 | NM_002263.3 |
| KPNA2 | 3838 | Hs00818252_g1 | NM_002266.2 |
| LMNB2* | 84823 | Hs00383326_m1 | NM_032737.2 |
| MAD2L1 | 4085 | Hs01554513_g1 | NM_002358.3 |
| MCAM* | 4162 | Hs00174838_m1 | NM_006500.2 |
| MCM10*# | 55388 | Hs00960349_m1 | NM_018518.3; NM_182751.1 |
| MCM2* | 4171 | Hs00170472_m1 | NM_004526.2 |
| MCM4* | 4173 | Hs00381539_m1 | NM_005914.2; NM_182746.1 |
| MCM6* | 4175 | Hs00195504_m1 | NM_005915.4 |
| MCM7* | 4176 | Hs01097212_m1 | NM_005916.3; NM_182776.1 |
| MELK | 9833 | Hs00207681_m1 | NM_014791.2 |
| MK167* | 4288 | Hs00606991_m1 | NM_002417.3 |
| MYBL2* | 4605 | Hs00231158_m1 | NM_002466.2 |
| NCAPD2* | 9918 | Hs00274505_m1 | NM_014865.3 |
| NCAPG* | 64151 | Hs00254617_m1 | NM_022346.3 |
| NCAPG2* | 54892 | Hs00375141_m1 | NM_017760.5 |
| NCAPH* | 23397 | Hs01010752_m1 | NM_015341.3 |
| NDC80* | 10403 | Hs00196101_m1 | NM_006101.2 |
| NEK2* | 4751 | Hs00601227_mH | NM_002497.2 |
| NUSAP1* | 51203 | Hs01006195_m1 | NM_018454.6; NM_001129897.1; NM_016359.3 |
| OIP5* | 11339 | Hs00299079_m1 | NM_007280.1 |
| ORC6L* | 23594 | Hs00204876_m1 | NM_014321.2 |
| PAICS* | 10606 | Hs00272390_m1 | NM_001079524.1; NM_001079525.1; NM_006452.3 |
| PBK*# | 55872 | Hs00218544_m1 | NM_018492.2 |
| PCNA* | 5111 | Hs00427214_g1 | NM_182649.1; NM_002592.2 |
| PDSS1* | 23590 | Hs00372008_m1 | NM_014317.3 |
| PLK1*# | 5347 | Hs00153444_m1 | NM_005030.3 |
| PLK4* | 10733 | Hs00179514_m1 | NM_014264.3 |
| POLE2* | 5427 | Hs00160277_m1 | NM_002692.2 |
| PRC1* | 9055 | Hs00187740_m1 | NM_199413.1; NM_199414.1; NM_003981.2 |
| PSMA7* | 5688 | Hs00895424_m1 | NM_002792.2 |
| PSRC1* | 84722 | Hs00364137_m1 | NM_032636.6; NM_001005290.2; NM_001032290.1; NM_001032291.1 |
| PTTG1* | 9232 | Hs00851754_u1 | NM_004219.2 |
| RACGAP1* | 29127 | Hs00374747_m1 | NM_013277.3 |
| RAD51* | 5888 | Hs00153418_m1 | NM_133487.2; NM_002875.3 |
| RAD51AP1* | 10635 | Hs01548891_m1 | NM_001130862.1; NM_006479.4 |
| RAD54B* | 25788 | Hs00610716_m1 | NM_012415.2 |
| RAD54L* | 8438 | Hs00269177_m1 | NM_001142548.1; NM_003579.3 |
| RFC2* | 5982 | Hs00945948_m1 | NM_181471.1; NM_002914.3 |

TABLE 1-continued

| Gene Symbol | Entrez GeneID | ABI Assay ID | RefSeq Accession Nos. |
|---|---|---|---|
| RFC4* | 5984 | Hs00427469_m1 | NM_181573.2; NM_002916.3 |
| RFC5* | 5985 | Hs00738859_m1 | NM_181578.2; NM_001130112.1; NM_001130113.1; NM_007370.4 |
| RNASEH2A* | 10535 | Hs00197370_m1 | NM_006397.2 |
| RRM2*# | 6241 | Hs00357247_g1 | NM_001034.2 |
| SHCBP1* | 79801 | Hs00226915_m1 | NM_024745.4 |
| SMC2* | 10592 | Hs00197593_m1 | NM_001042550.1; NM_001042551.1; NM_006444.2 |
| SPAG5* | 10615 | Hs00197708_m1 | NM_006461.3 |
| SPC25* | 57405 | Hs00221100_m1 | NM_020675.3 |
| STIL* | 6491 | Hs00161700_m1 | NM_001048166.1; NM_003035.2 |
| STMN1* | 3925 | Hs00606370_m1; Hs01033129_m1 | NM_005563.3; NM_203399.1 |
| TACC3* | 10460 | Hs00170751_m1 | NM_006342.1 |
| TIMELESS* | 8914 | Hs01086966_m1 | NM_003920.2 |
| TK1* | 7083 | Hs01062125_m1 | NM_003258.4 |
| TOP2A* | 7153 | Hs00172214_m1 | NM_001067.2 |
| TPX2* | 22974 | Hs00201616_m1 | NM_012112.4 |
| TRIP13* | 9319 | Hs01020073_m1 | NM_004237.2 |
| TTK* | 7272 | Hs00177412_m1 | NM_003318.3 |
| TUBA1C * | 84790 | Hs00733770_m1 | NM_032704.3 |
| TYMS* | 7298 | Hs00426591_m1 | NM_001071.2 |
| UBE2C | 11065 | Hs00964100_g1 | NM_181799.1; NM_181800.1; NM_181801.1; NM_181802.1; NM_181803.1; NM_007019.2 |
| UBE2S | 27338 | Hs00819350_m1 | NM_014501.2 |
| VRK1 * | 7443 | Hs00177470_m1 | NM_003384.2 |
| ZWILCH* | 55055 | Hs01555249_m1 | NM_017975.3; NR_003105.1 |
| ZWINT* | 11130 | Hs00199952_m1 | NM_032997.2; NM_001005413.1; NM_007057.3 |

*124-gene subset of CCGs ("Panel B").
10-gene subset of CCGs (Panel C). ABI Assay ID means the catalogue ID number for the gene expression assay commercially available from Applied Biosystems Inc. (Foster City, CA) for the particular gene.

Accordingly, in a first aspect of the present disclosure, panels of genes comprising CCGs for use in determining gene expression, and for diagnosing and treating melanoma are disclosed. In some embodiments, use of panels comprising CCGs comprises determining expression of the CCGs in a sample from an individual or patient.

Gene expression can be determined either at the RNA level (i.e., mRNA or noncoding RNA (ncRNA)) (e.g., miRNA, tRNA, rRNA, snoRNA, siRNA and piRNA) or at the protein level. Measuring gene expression at the mRNA level includes measuring levels of cDNA corresponding to mRNA. Levels of proteins in a sample can be determined by any known techniques in the art, e.g., HPLC, mass spectrometry, or using antibodies specific to selected proteins (e.g., IHC, ELISA, etc.).

In one embodiment, the amount of RNA transcribed from the panel of genes including test genes is measured in the sample. In addition, the amount of RNA of one or more housekeeping genes in the sample is also measured, and used to normalize or calibrate the expression of the test genes. The terms "normalizing genes" and "housekeeping genes" are defined herein below.

In any embodiment of the invention involving a "plurality of test genes," the plurality of test genes may include at least 2, 3 or 4 cell-cycle genes, which constitute at least 50%, 75% or 80% of the plurality of test genes, and in some embodiments 100% of the plurality of test genes. In some embodiments, the plurality of test genes includes at least 5, 6, 7, or at least 8 cell-cycle genes, which constitute at least 20%, 25%, 30%, 40%, 50%, 60%, 70%, 75%, 80% or 90% of the plurality of test genes, and in some embodiments 100% of the plurality of test genes. As will be clear from the context of this document, a panel of genes is a plurality of genes. Typically these genes are assayed together in one or more samples from a patient.

In some other embodiments, the plurality of test genes includes at least 8, 10, 12, 15, 20, 25 or 30 cell-cycle genes, which constitute at least 20%, 25%, 30%, 40%, 50%, 60%, 70%, 75%, 80% or 90% of the plurality of test genes, and preferably 100% of the plurality of test genes.

As will be apparent to a skilled artisan apprised of the present invention and the disclosure herein, "sample" means any biological sample containing one or more suspected melanoma cells, or one or more RNA or protein derived from suspected melanoma cells, and obtained from a patient. For example, a tissue sample obtained from a mole or nevus is a useful sample in the present invention. The tissue sample can be an FFPE sample, or fresh frozen sample, and preferably contain largely the suspect cells. A single cell from a patient's suspected melanoma is also a useful sample. Such a cell can be obtained directly from the patient's skin, or purified from the patient's bodily fluid (e.g., blood, urine). Thus, a bodily fluid such as blood, urine, sputum and saliva containing one or more suspected to be cancerous cells, or mole or nevus-derived RNA or proteins, can also be useful as a sample for purposes of practicing the present invention.

Those skilled in the art are familiar with various techniques for determining the status of a gene or protein in a tissue or cell sample including, but not limited to, microarray analysis (e.g., for assaying mRNA or microRNA expression, copy number, etc.), quantitative real-time PCR™ ("qRT-PCR™", e.g, TaqMan™), immunoanalysis (e.g., ELISA, immunohistochemistry), etc. The activity level of a polypeptide encoded by a gene may be used in much the same way as the expression level of the gene or polypeptide. Often higher activity levels indicate higher expression levels and while lower activity levels indicate lower expression levels. Thus, in some embodiments, the invention provides any of the methods discussed above, wherein the activity level of a polypeptide encoded by the CCG is determined rather than or in addition to the expression level of the CCG. Those skilled in the art are familiar with techniques for measuring the activity of various such proteins, including those encoded by the genes listed in Table 1. The methods of the invention may be practiced independent of the particular technique used.

In some embodiments, the expression of one or more normalizing (often called "housekeeping" or "housekeeper") genes is also obtained for use in normalizing the expression of test genes. As used herein, "normalizing genes" referred to the genes whose expression is used to calibrate or normalize the measured expression of the gene of interest (e.g., test genes). Importantly, the expression of normalizing genes should be independent of cancer diagnosis, and the expression of the normalizing genes is very similar among all the samples. The normalization ensures accurate comparison of expression of a test gene between different samples. For this purpose, housekeeping genes known in the art can be used. Housekeeping genes are well known in the art, with examples including, but are not limited to, GUSB (glucuronidase, beta), HMBS (hydroxymethylbilane synthase), SDHA (succinate dehydrogenase complex, subunit A, flavoprotein), UBC (ubiquitin C), YWHAZ (tyrosine 3-monooxygenase/tryptophan 5-monooxygenase activation protein, zeta polypeptide), MRFAP1, PSMA1, RPL13A, TXNL1, SLC25A3, RPS29, RPL8, PSMC1 and RPL4. One or more housekeeping genes can be used. Preferably, at least 2, 5, 10 or 15 housekeeping genes are used to provide a combined normalizing gene set. The amount of gene expression of such normalizing genes can be averaged, combined together by straight additions or by a defined algorithm. Some examples of particularly useful housekeeper genes for use in the methods and compositions of the invention include those listed in Table 2 below.

TABLE 2

| Gene Symbol | Entrez GeneID | Applied Biosystems Assay ID | RefSeq Accession Nos. |
|---|---|---|---|
| CLTC | 1213 | Hs00191535_m1 | NM_004859.3 |
| GUSB | 2990 | Hs99999908_m1 | NM_000181.2 |
| HMBS | 3145 | Hs00609297_m1 | NM_000190.3 |
| WADHC | 27249 | Hs00739517_g1 | NM_015702.2 |
| MRFAP1* | 93621 | Hs00738144_g1 | NM_033296.1 |
| PPP2CA | 5515 | Hs00427259_m1 | NM_002715.2 |
| PSMA1* | 5682 | Hs00267631_m1 | |
| PSMC1* | 5700 | Hs02386942_g1 | NM_002802.2 |
| RPL13A* | 23521 | Hs03043885_g1 | NM_012423.2 |
| RPL37 | 6167 | Hs02340038_g1 | NM_000997.4 |
| RPL38 | 6169 | Hs00605263_g1 | NM_000999.3 |
| RPL4* | 6124 | Hs03044647_g1 | NM_000968.2 |
| RPL8* | 6132 | Hs00361285_g1 | NM_033301.1; NM_000973.3 |
| RPS29* | 6235 | Hs03004310_g1 | NM_001030001.1; NM_001032.3 |
| SDHA | 6389 | Hs00188166_m1 | NM_004168.2 |
| SLC25A3* | 6515 | Hs00358082_m1 | NM_213611.1; NM_002635.2; NM_005888.2 |
| TXNL1* | 9352 | Hs00355488_m1 | NR_024546.1; NM_004786.2 |
| UBA52 | 7311 | Hs03004332_g1 | NM_001033930.1; NM_003333.3 |
| UBC | 7316 | Hs00824723_m1 | NM_021009.4 |
| YWHAZ | 7534 | Hs00237047_m1 | NM_003406.3 |

*Subset of housekeeping genes used in, e.g., Example 3.

In the case of measuring RNA levels for the genes, one convenient and sensitive approach is real-time quantitative PCR™ (qPCR) assay, following a reverse transcription reaction. Typically, a cycle threshold ($C_t$) is determined for each test gene and each normalizing gene, i.e., the number of cycles at which the fluorescence from a qPCR reaction above background is detectable.

The overall expression of the one or more normalizing genes can be represented by a "normalizing value" which can be generated by combining the expression of all normalizing genes, either weighted equally (straight addition or averaging) or by different predefined coefficients. For example, in a simplest manner, the normalizing value $C_{tH}$ can be the cycle threshold ($C_t$) of one single normalizing gene, or an average of the $C_t$ values of 2 or more, preferably 10 or more, or 15 or more normalizing genes, in which case, the predefined coefficient is 1/N, where N is the total number of normalizing genes used. Thus, $C_{tH}=(C_{tH1}+C_{tH2}+ \ldots C_{tHn})/N$. As will be apparent to skilled artisans, depending on the normalizing genes used, and the weight desired to be given to each normalizing gene, any coefficients (from 0/N to N/N) can be given to the normalizing genes in weighting the expression of such normalizing genes. That is, $C_{tH}=xC_{tH1}+yC_{tH2}+ \ldots zC_{tHn}$, wherein $x+y+ \ldots +z=1$.

As discussed above, the methods of the invention generally involve determining the level of expression of a panel of CCGs. With modern high-throughput techniques, it is often possible to determine the expression level of tens, hundreds or thousands of genes. Indeed, it is possible to determine the level of expression of the entire transcriptome (i.e., each transcribed sequence in the genome). Once such a global assay has been performed, one may then informatically analyze one or more subsets of transcripts (i.e., panels or, as often used herein, pluralities of test genes). After measuring the expression of hundreds or thousands of transcripts in a sample, for example, one may analyze (e.g., informatically) the expression of a panel or plurality of test genes comprising primarily CCGs according to the present invention by combining the expression level values of the individual test genes to obtain a test value.

As will be apparent to a skilled artisan, the test value provided in the present invention represents the overall expression level of the plurality of test genes composed substantially of cell-cycle genes. In one embodiment, to provide a test value in the methods of the invention, the normalized expression for a test gene can be obtained by normalizing the measured $C_t$ for the test gene against the $C_{tH}$, i.e., $\Delta C_{t1}=(C_{t1}-C_{tH})$. Thus, the test value representing the overall expression of the plurality of test genes can be provided by combining the normalized expression of all test genes, either by straight addition or averaging (i.e., weighted equally) or by a different predefined coefficient. For example, the simplest approach is averaging the normalized expression of all test genes: test value=$(\Delta C_{t1}+\Delta C_{t2}+ \ldots +\Delta C_{tm})/n$. As will be apparent to skilled artisans, depending on the test genes used, different weight can also be given to different test genes in the present invention. In each case where this document discloses using the expression of a plurality of genes (e.g., "determining [in a sample from the patient] the expression of a plurality of test genes" or "correlating increased expression of said plurality of test genes to an increased likelihood of having melanoma"), this includes in some embodiments using a test value representing, corresponding to or derived or calculated from the overall expression of this plurality of genes (e.g., "determining [in a sample from the patient] a test value representing the expression of a plurality of test genes" or "correlating an increased test value [or a test value above some reference value] (optionally representing the expression of said plurality of test genes) to an increased likelihood of response").

It has been determined that, once the CCP phenomenon reported herein is appreciated, the choice of individual CCGs for a test panel can often be somewhat arbitrary. In other words, many CCGs have been found to be very good surrogates for each other. Thus any CCG (or panel of CCGs) can be used in the various embodiments of the invention. In other embodiments of the invention, optimized CCGs are used. One way of assessing whether particular CCGs will serve well in the methods and compositions of the invention is by assessing their correlation with the mean expression of CCGs (e.g., all known CCGs, a specific set of CCGs, etc.). Those CCGs that correlate particularly well with the mean are expected to perform well in assays of the invention, e.g., because these will reduce noise in the assay.

Thus, in some embodiments of each of the various aspects of the invention the plurality of test genes comprises the top 2, 3, 4, 5, 6, 7, 8, 9, 10, 11, 12, 13, 14, 15, 20, 25, 30, 35, 40 or more CCGs from Panel A. In some embodiments of each of the various aspects of the invention the plurality of test genes comprises the top 2, 3, 4, 5, 6, 7, 8, 9 or 10 CCGs from Panel B. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises at least 1, 2, 3, 4, 5, 6, 7, 8, 9 or 10 of the genes in Panel B. In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any two, three, four, five, six, seven, eight, nine, or ten of gene numbers 1 & 2, 1 to 3, 1 to 4, 1 to 5, 1 to 6, 1 to 7, 1 to 8, 1 to 9, or 1 to 10 of any of the genes in Panel B (based on order of appearance in Table 1). In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, eight, or nine or all of gene numbers 2 & 3, 2 to 4, 2 to 5, 2 to 6, 2 to 7, 2 to 8, 2 to 9, or 2 to 10 of any of the genes in Panel B (based on order of appearance in Table 1). In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, seven, or eight or all of gene numbers 3 & 4, 3 to 5, 3 to 6, 3 to 7, 3 to 8, 3 to 9, or 3 to 10 of any of the genes in Panel B (based on order of appearance in Table 1). In some embodiments the plurality of test genes comprises at least some number of CCGs (e.g., at least 3, 4, 5, 6, 7, 8, 9, 10, 15, 20, 25, 30, 35, 40, 45, 50 or more CCGs) and this plurality of CCGs comprises any one, two, three, four, five, six, or seven or all of gene numbers 4 & 5, 4 to 6, 4 to 7, 4 to 8, 4 to 9, or 4 to 10 of any of the genes in Panel B (based on order of appearance in Table 1).

In another embodiment, the plurality of CCGs or panel of CCGs comprises any set of genes from Table WW.

Immune and Additional Genes

It has additionally surprisingly been discovered that panels of immune genes are diagnostic for melanoma. Accordingly, in another aspect of the present disclosure, panels of genes comprising immune genes for use in determining gene expression, and for diagnosing and treating melanoma are disclosed. In some embodiments, use of panels comprising immune genes comprises determining expression of the immune genes in a sample from an individual or patient.

"Immune gene" herein refers to a gene associated with or expressed by one or more leukocytes. In particular embodiments, immune genes comprise genes associated with or expressed by lymphocytes. In some embodiments, the immune genes comprise genes expressed by activated lymphocytes. In some embodiments, immune genes comprise genes expressed by T cells. In some embodiments, immune genes comprise genes expressed by activated T cells. In some embodiments, immune genes comprise the immune genes identified in Table 3, below.

TABLE 3

| Gene Name | Entrez Gene ID | Ensembl Gene ID | RefSeq Accession Nos. |
|---|---|---|---|
| ARPC2 | 10109 | ENSG00000163466 | NM_005731; NM_152862 |
| BCL2A1* | 597 | ENSG00000140379 | NM_004049 |
| CCL19# | 6363 | ENSG00000172724 | NM_006274 |
| CCL3*# | 6348 | ENSG00000006075\| ENSG00000136826 | NM_002983; NM_004235 |
| CCL5*#^ | 6352 | ENSG00000161570 | NM_002985 |
| CD38*#^ | 952 | ENSG00000004468 | NM_001775 |
| CFH*# | 3075 | ENSG00000000971 | NM_000186; NM_001014975.1 |

TABLE 3-continued

| Gene Name | Entrez Gene ID | Ensembl Gene ID | RefSeq Accession Nos. |
|---|---|---|---|
| CXCL10*#^ | 3627 | ENSG00000169245 | NM_001565.2 |
| CXCL12# | 6387 | ENSG00000107562\| ENSG00000126214 | NM_000609.4; NM_001033886; NM_199168; NM_005552; NM_182923.3 |
| CXCL13*# | 10563 | ENSG00000156234 | NM_006419 |
| CXCL9*#^ | 4283 | ENSG00000138755 | NM_002416 |
| FABP7* | 2173 | ENSG00000113805 | NM_020872 |
| FN1* | 2335 | ENSG00000115414\| ENSG00000197721 | NM_002026; NM_054034.2; NM_212474; NM_212476.1; NM_212482.1; NM_175710.1 |
| GDF15 | 9518 | | |
| HCLS1*# | 3059 | ENSG00000113070\| ENSG00000180353 | NM_001945; NM_005335 |
| HEY1* | 23462 | ENSG00000164683 | NM_001040708.1; NM_012258 |
| HLA-DMA*# | 3108 | ENSG00000204257\| ENSG00000206229\| ENSG00000206293 | NM_006120 |
| HLA-DPA1# | 3113 | | |
| HLA-DPB1# | 3115 | ENSG00000112242\| ENSG00000168383 | NM_001949; NM_002121 |
| HLA-DRA*# | 3122 | ENSG00000143768\| ENSG00000204287\| ENSG00000206243 | NM_003240; NM_019111 |
| HLA-E# | 3133 | ENSG00000204592 | NM_005516 |
| IFI6*# | 2537 | ENSG00000126709\| ENSG00000135047 | NM_002038; NM_022872; NM_022873; NM_001912; NM_145918 |
| IGHM# | 3507 | | |
| IGJ*# | 3512 | ENSG00000132465\| ENSG00000182197 | NM_144646; NM_000127 |
| IGLL5/CKAP2# | 100423062 | | |
| IRF1*#^ | 3659 | | |
| IRF4# | 3662 | ENSG00000137265 | NM_002460 |
| ITGB2*# | 3689 | ENSG00000160255 | NM_000211 |
| KRT15* | 3866 | ENSG00000171346 | NM_002275 |
| LCP2*#^ | 3937 | ENSG00000043462 | NM_005565.3 |
| NCOA3 | 8202 | ENSG00000124151 | NM_006534; NM_181659 |
| NR4A1 | 3164 | ENSG00000107223\| ENSG00000123358 | NM_003792; NM_153200; NM_002135; NM_173157; NM_173158 |
| PECAM1*# | 5175 | ENSG00000173744\| ENSG00000198802 | NM_004504; NM_000442.3 |
| PHACTR1* | 221692 | ENSG00000112137 | NM_030948.1 |
| PHIP | 55023 | ENSG00000146247 | NM_017934 |
| POU5F1 | 5460 | ENSG00000204531\| ENSG00000206349\| ENSG00000206454 | NM_002701; NM_203289.3 |
| PRAME* | 23532 | ENSG00000185686 | NM_006115; NM_206953; NM_206954; NM_206955; NM_206956 |
| PTN* | 5764 | | |
| PTPN22*#^ | 26191 | ENSG00000134242 | NM_012411; NM_015967 |
| PTPRC*#^ | 5788 | ENSG00000081237 | NM_002838; NM_080921; NM_080922; NM_080923.2 |
| RGS1* | 5996 | ENSG00000090104 | NM_002922 |
| S100A9* | 6280 | ENSG00000163220 | NM_002965 |
| SELL* | 6402 | ENSG00000188404 | NM_000655.3 |
| SERPINB4# | 6318 | ENSG00000057149\| ENSG00000068796 | NM_002974; NM_004520 |

TABLE 3-continued

| Gene Name | Entrez Gene ID | Ensembl Gene ID | RefSeq Accession Nos. |
|---|---|---|---|
| SOCS3# | 9021 | ENSG00000184557 | NM_003955 |
| SPP1* | 6696 | | |
| WIF1 | 11197 | ENSG00000125285 | NM_007084 |
| WNT2 | 7472 | ENSG00000105989 | NM_003391 |

*Panel of 30 mixed genes (Panel D);
panel of 28 immune genes (Panel E);
^panel of 8 immune genes (Panel F)

Gene expression of immune genes can be determined as described above with respect to CCGs. In one embodiment, the amount of RNA transcribed from the panel of genes including immune genes is measured in the sample. In addition, the amount of RNA of one or more housekeeping genes in the sample is also measured, and used to normalize or calibrate the expression of the test genes. The terms "normalizing genes" and "housekeeping genes" are defined above.

In any embodiment of the invention involving a "plurality of test genes," the plurality of test genes may include at least 2, 3 or 4 immune genes, which constitute at least 50%, 75% or 80% of the plurality of immune genes, and in some embodiments 100% of the plurality of immune genes. In some embodiments, the plurality of immune genes includes at least 5, 6, 7, or at least 8 cell-cycle genes, which constitute at least 20%, 25%, 30%, 40%, 50%, 60%, 70%, 75%, 80% or 90% of the plurality of immune genes, and in some embodiments 100% of the plurality of immune genes. As will be clear from the context of this document, a panel of genes is a plurality of genes. Typically these genes are assayed together in one or more samples from a patient.

In some other embodiments, the plurality of immune genes includes at least 8, 10, 12, 15, 20, 25 or 30 immune, which constitute at least 20%, 25%, 30%, 40%, 50%, 60%, 70%, 75%, 80% or 90% of the plurality of immune genes, and preferably 100% of the plurality of immune genes.

The sample used to determine the expression of immune genes may be any sample as described above for CCGs.

In the case of measuring RNA levels for the immune genes, real-time quantitative PCR™ (qPCR) assay with normalized values, as described above, may be used.

As discussed above, some embodiments of the methods disclosed generally involve determining the level of expression of a panel comprising immune genes. In some embodiments of the methods disclosed, genes may be assayed at one or more location along the gene sequence. With modern high-throughput techniques, it is often possible to determine the expression level of tens, hundreds or thousands of genes. Indeed, it is possible to determine the level of expression of the entire transcriptome (i.e., each transcribed sequence in the genome). Once such a global assay has been performed, one may then informatically analyze one or more subsets of transcripts (i.e., panels or, as often used herein, pluralities of test genes). After measuring the expression of hundreds or thousands of transcripts in a sample, for example, one may analyze (e.g., informatically) the expression of a panel or plurality of test genes comprising primarily immune genes according to the present invention by combining the expression level values of the individual test genes to obtain a test value.

Thus, in some embodiments of each of the various aspects of the invention the plurality of test genes comprises any 2, 3, 4, 5, 6, 7, 8, 9, 10, 11, 12, 13, 14, 15, 20, 25, or 28 Immune genes from Panel E. In some embodiments of each of the various aspects of the invention the plurality of test genes comprises 2, 3, 4, 5, 6, 7, 8 immune genes from Panel F. In some embodiments the plurality of test genes comprises at least some number of immune genes (e.g., at least 2, 3, 4, 5, 6, 7, 8, 9, 10, 15, 20, 25, 30, 35, 40, 45, 50 or more immune genes) and this plurality of immune genes comprises at least 1, 2, 3, 4, 5, 6, 7, 8, 9, 10, 15, 20, 25, or 28 of the genes in Panel E, or 2, 3, 4, 5, 6, 7, 8, 9 or 10 immune genes from Panel F.

It has also been found that additional genes may be diagnostic for melanoma. Without being bound by theory, these additional genes are believed to be non-CCG and non-immune genes, and comprise ARPC2, BCL2A1, FABP7, FN1, GDF15, HEY1, KRT15, NCOA3, NR4A1, PHACTR1, PHIP, POU5F1, PRAME, PTN, RGS1, S100A9, SELL, SPP1, WIF1, and WNT2 (Panel G). Accordingly, in another aspect of the present disclosure, panels of genes comprising these additional genes are disclosed for use in determining gene expression, and for diagnosing and treating melanoma.

In one embodiment, the panel comprising these additional genes: BCL2A1, FABP7, FN1, HEY1, KRT15, PHACTR1, PRAME, PTN, RGS1, S100A9, SELL, and SPP1 (Panel H). In another embodiment, the panel comprising additional genes comprises PRAME and S100A9.

In additional embodiments, this disclosure provides for mixed panels of genes which are useful in determining gene expression, and for diagnosing and treating melanoma. These mixed panels may comprise immune genes and CCGs, or immune genes and genes from Panel G or H, or CCGs and genes from panel G or H. In one embodiment, the mixed panel comprises one or more CCGs, one or more immune genes, and one or more additional genes from panel G. In one embodiment, the mixed panel comprises Panel D. In another embodiment, the mixed panel comprises PRAME, S100A9 and the genes of panel F.

In another embodiment, the mixed panel comprises one or more CCGs, one or more immune genes, and one or more additional genes from panel H. In one embodiment of a mixed panel, the mixed panel (Panel I) comprises the genes from Panel C and the genes from Panel D.

In one embodiment of a mixed panel, the mixed panel) comprises S100A9 and/or S100A9-related genes. The S100A9 related genes can include genes that have highly correlated expression compared to S100A9. These S100A9-related genes may include genes that are closely clustered with S100A9 on chromosome 1. These S100A9-related genes may also include genes that have similar transcription control as S100A9. The S100A9-related proteins may also be part of the same biological pathway. The S100A9-related genes may also code for proteins that interact with the protein coded by S100A9. As a non-limiting example, the mixed panel may comprise S100A9, S100A7, S100A8, S100A12, PI3, S100A10, and S100A14 (Panel J). As a non-limiting example, the mixed panel may comprise S100A9, S100A7, S100A8, S100A12, and PI3 (Panel L).

In an alternate embodiment, the mixed panel comprises PRAME. In another embodiment, the mixed panel comprises S100A9. In yet another embodiment, the mixed panel comprises CCL5, CD38, CXCL10, CXCL9, IRF1, LCP2, PTPN22, or PTPRC. In other embodiments the mixed panel comprises S100A7, S100A8, S100A12, PI3, S100A10, and S100A14. In some embodiments, the mixed panel comprises S100A9, S100A7, S100A8, S100A12, and PI3. Thus, in some embodiments of each of the various aspects of the invention the panel of mixed genes comprises any 2, 3, 4, 5, 6, or 7 S100A9-related genes from Panel J. In other embodiments of each of the various aspects of the invention the panel of mixed genes comprises any 2, 3, 4, 5, 6, or 7 S100A9-related genes from Panel L.

Thus, in some embodiments of each of the various aspects of the invention the panel of mixed genes comprises PRAME, at least one of the genes of Panel J, and at least one of the genes of panel F. In some embodiments, the mixed panel comprises PRAME, S100A9, S100A7, S100A8, S100A12, S100A10, S100A14, PI3, CCL5, CD38, CXCL10, CXCL9, IRF1, LCP2, PTPN22, and PTPRC.

Thus, in some embodiments of each of the various aspects of the invention the panel of mixed genes comprises PRAME, at least one of the genes of Panel L, and at least one of the genes of panel F. In some embodiments, the mixed panel comprises PRAME, S100A9, S100A7, S100A8, S100A12, PI3, CCL5, CD38, CXCL10, CXCL9, IRF1, LCP2, PTPN22, and PTPRC.

Thus, in some embodiments of each of the various aspects of the invention the panel of mixed genes comprises PRAME, S100A9, and at least 1, 2, 3, 4, 5, 6, 7, or 8 genes of panel F. In some embodiments, the panel of mixed genes comprises PRAME and at least 1, 2, 3, 4, 5, 6, or 7 genes of Panel J, and at least 1, 2, 3, 4, 5, 6, 7, or 8 genes of panel F. In some embodiments, the panel of mixed genes comprises PRAME, S100A9, and at least 1, 2, 3, 4, 5, 6, 7, 8, 9, 10, 11, 12, 13, 14, 15, 16, 17, 18, 19, or 20 genes of panel E. In some embodiments, the panel of mixed genes comprises PRAME, and at least 1, 2, 3, 4, 5, 6, or 7 genes of Panel J, and at least 1, 2, 3, 4, 5, 6, 7, 8, 9, 10, 11, 12, 13, 14, 15, 16, 17, 18, 19, or 20 genes of Panel E.

Thus, in some embodiments of each of the various aspects of the invention the panel of mixed genes comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 genes of Panel D, and S100A9, and at least 1, 2, 3, 4, 5, 6, 7, or 8 genes of panel F. In some embodiments, the panel of mixed genes comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 genes of Panel D and at least 1, 2, 3, 4, 5, 6, or 7 genes of Panel J, and at least 1, 2, 3, 4, 5, 6, 7, or 8 genes of panel F. In some embodiments, the panel of mixed genes comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 genes of Panel D, S100A9, and at least 1, 2, 3, 4, 5, 6, 7, 8, 9, 10, 11, 12, 13, 14, 15, 16, 17, 18, 19, or 20 genes of panel E. In some embodiments, the panel of mixed genes comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 genes of Panel D, and at least 1, 2, 3, 4, 5, 6, or 7 genes of Panel J, and at least 1, 2, 3, 4, 5, 6, 7, 8, 9, 10, 11, 12, 13, 14, 15, 16, 17, 18, 19, or 20 genes of Panel E.

Thus, in some embodiments of each of the various aspects of the invention the panel of mixed genes comprises at least at least 1, 2, 3, 4, 5, 6, 7, 8, 9, 10, 11, 12, 13, 14, 15, 16, 17, 18, 19, or 20 genes of Panel G, and S100A9, and at least 1, 2, 3, 4, 5, 6, 7, or 8 genes of panel F. In some embodiments, the panel of mixed genes comprises at least at least 1, 2, 3, 4, 5, 6, 7, 8, 9, 10, 11, 12, 13, 14, 15, 16, 17, 18, 19, or 20 genes of Panel G, and at least 1, 2, 3, 4, 5, 6, or 7 genes of Panel J, and at least 1, 2, 3, 4, 5, 6, 7, or 8 genes of panel F. In some embodiments, the panel of mixed genes comprises at least 1 at least 1, 2, 3, 4, 5, 6, 7, 8, 9, 10, 11, 12, 13, 14, 15, 16, 17, 18, 19, or 20 genes of Panel G, S100A9, and at least 1, 2, 3, 4, 5, 6, 7, 8, 9, 10, 11, 12, 13, 14, 15, 16, 17, 18, 19, or 20 genes of panel E. In some embodiments, the panel of mixed genes comprises at least at least 1, 2, 3, 4, 5, 6, 7, 8, 9, 10, 11, 12, 13, 14, 15, 16, 17, 18, 19, or 20 genes of Panel G, and at least 1, 2, 3, 4, 5, 6, or 7 genes of Panel J, and at least 1, 2, 3, 4, 5, 6, 7, 8, 9, 10, 11, 12, 13, 14, 15, 16, 17, 18, 19, or 20 genes of Panel E.

Thus, in some embodiments of each of the various aspects of the invention the panel of mixed genes comprises at least at least 1, 2, 3, 4, 5, 6, 7, 8, 9, 10, 11, or 12 genes of Panel H, and S100A9, and at least 1, 2, 3, 4, 5, 6, 7, or 8 genes of panel F. In some embodiments, the panel of mixed genes comprises at least at least at least 1, 2, 3, 4, 5, 6, 7, 8, 9, 10, 11, or 12 genes of Panel H, and at least 1, 2, 3, 4, 5, 6, or 7 genes of Panel J, and at least 1, 2, 3, 4, 5, 6, 7, or 8 genes of panel F. In some embodiments, the panel of mixed genes comprises at least 1 at least 1 at least 1, 2, 3, 4, 5, 6, 7, 8, 9, 10, 11, or 12 genes of Panel H, S100A9, and at least 1, 2, 3, 4, 5, 6, 7, 8, 9, 10, 11, 12, 13, 14, 15, 16, 17, 18, 19, or 20 genes of panel E. In some embodiments, the panel of mixed genes comprises at least at least at least 1, 2, 3, 4, 5, 6, 7, 8, 9, 10, 11, or 12 genes of Panel H, and at least 1, 2, 3, 4, 5, 6, or 7 genes of Panel J, and at least 1, 2, 3, 4, 5, 6, 7, 8, 9, 10, 11, 12, 13, 14, 15, 16, 17, 18, 19, or 20 genes of Panel E.

In one embodiment, the panel comprises any set of two genes from Table XX. In one embodiment, the panel comprises any set of two genes from Table XX. In another embodiment, the panel comprises any set of three genes from Table YY. In another embodiment, the panel comprises any set of four genes from Table ZZ.

In one embodiment of a panel of housekeeper genes, the housekeeper panel (Panel K) comprises one or more genes for use in normalizing the expression of test genes. Panel K can be made up of any gene whose expression is used to calibrate or normalize measured expression of the gene or genes of interest. Panel K can be made up of any housekeeping or housekeeper genes known in the art. Examples of housekeeper genes that can be used in Panel K include CLTC, GUSB, HMBS, MMADHC, MRFAP1, PPP2CA, PSMA1, PSMC1, RPL13A, RPL37, RPL38, RPL4, RPL8, RPS29, SDHA, SLC25A3, TXNL1, UBA52, UBC, and YWHAZ. In some embodiments, the housekeeper genes used to normalize the expression of test genes can include at least 1, 2, 3, 4, 5, 6, 7, 8, 9, 10, 11, 12, 13, 14, 15, 16, 17, 18, 19, or 20 genes of Panel K.

Methods of Determining Gene Expression

Accordingly, in a first aspect of the present invention, a method is provided for determining gene expression in a sample from a patient (e.g., one suspected of containing melanoma). Generally, the method includes at least the following steps: (1) obtaining a sample from a patient (e.g., one suspected of containing melanoma); (2) determining the expression of a panel of genes in the sample; and (3) providing a test value by (a) weighting the determined expression of each gene from the panel of genes with a predefined coefficient, and (b) combining the weighted expression of each gene from the panel of genes to provide said test value.

Weighting the expression of each gene from the panel of genes may be performed individually for each gene, or genes may first be grouped and their normalized expression averaged or otherwise combined before weighting is performed. In some embodiments, genes are grouped based on whether they provide independent information in separating nevi from melanoma. In some examples, CCGs are grouped before weighting. In other embodiments, immune genes are grouped before weighting. The skilled artisan will understand that in some embodiments, grouping may be conceptualized as a way of individually weighting each gene in the pre-defined group to arrive at an intermediate value, which intermediate value is weighted along with other individual gene expression values to obtain a final value. In some embodiments, multiple rounds of grouping may be performed, resulting in multiple intermediate values, which may be in turn grouped to obtain a final value.

In some embodiments, weighting coefficients are determined which optimize the contribution of each expression profile to the predictive value of any resulting test value. In some embodiments, genes whose expression is more highly correlated or anti-correlated with melanoma receive a larger weighting coefficient in order to maximize the overall predictive power of any resulting test value. In some embodiments, genes whose expression is correlated or anti-correlated with melanoma, but less correlated with the expression of other genes in the panel receive a larger weighting coefficient in order to maximize the overall predictive power of any resulting test value. In some embodiments, genes whose expression is significantly, moderately, or highly correlated may be grouped.

In some embodiments, regression analyses are utilized to obtain appropriate weighting coefficients to maximize the predictive power of a test value. In some embodiments, linear regression is used to fit expression levels to a model for providing test values which are diagnostic of melanoma. In other embodiments, logistic regression is used to determine weighting coefficients for expression levels of individual genes or groups of genes in a model for diagnosis of melanoma.

In some embodiments, weighting the expression of each gene comprises grouping immune genes, and then weighting the expression of immune genes, PRAME and S100A9 to arrive at a test value which is diagnostic for melanoma. In related embodiments, there are 8 immune genes. In related embodiments, the immune genes comprise Panel F. In some embodiments, the weighting to arrive at a test value is as follows: test value=(A×PRAME)+(B×grouped immune)+(C×S100A9). In a related embodiment, A is 0.525, B is 0.677 and C is 0.357.

In some embodiments, weighting the expression of each gene comprises grouping immune genes, grouping S100A9-related genes and then weighting the expression of immune genes, PRAME and the S100A9-related genes to arrive at a test value which is diagnostic for melanoma. In related embodiments, there are 8 immune genes. In related embodiments, the immune genes comprise Panel F. In related embodiments, there are 7 S100A9-related genes. In related embodiments, the S100A9-related genes comprise Panel J. In related embodiments, the S100A9-related genes comprise Panel L. In some embodiments, the weighting to arrive at a test value is as follows: test value=(A×PRAME)+(B×grouped immune)+(C×grouped S100A9-related). In a related embodiment, A is 1.149, B is 0.698 and C is 0.922.

In some embodiments, weighting the expression of each gene comprises grouping immune genes, grouping S100A9-related genes and then weighting the expression of immune genes, PRAME and the S100A9-related genes and then adjusting by a linear scale factor to arrive at a test value which is diagnostic for melanoma. In some embodiments, the linear scale factor adjusts the cutoff value so that the cutoff value is centered about zero. In related embodiments, there are 8 immune genes. In related embodiments, the immune genes comprise Panel F. In related embodiments, there are 7 S100A9-related genes. In related embodiments, the S100A9-related genes comprise Panel J. In separate related embodiments, the S100A9-related genes comprise Panel L. In some embodiments, the weighting to arrive at a test value is as follows: test value=(A×PRAME)+(B×grouped immune)+(C×grouped S100A9-related)+D. In a related embodiment, A is 1.149, B is 0.698, C is 0.922, and D is −0.334.

In some embodiments, weighting the expression of each gene comprises grouping immune genes, grouping S100A9-related genes and then weighting the expression of immune genes, PRAME and the S100A9-related genes and then adjusting by a linear scale factor to arrive at a test value which is diagnostic for melanoma. in some embodiment, the linear scale factor adjusts the cutoff value so that the cutoff value is centered about zero. In related embodiments, there are 8 immune genes. In related embodiments, the immune genes comprise Panel F. In related embodiments, there are 5 S100A9-related genes. In related embodiments, the S100A9-related genes comprise Panel J. In separate related embodiments, the S100A9-related genes comprise Panel L. In some embodiments two areas of the PRAME gene are assayed. In some embodiments, the weighting to arrive at a test value is as follows: test value=(A×PRAME)+(B×grouped immune)+(C×grouped S100A9-related)+D. In some embodiments A=1.223, B=0.704, C=1.023, and D=0.267.

In some embodiments a test value derived from expression levels may be combined with non-expression parameters to arrive at a modified test value or score which is diagnostic for melanoma. In some embodiments, clinical factors may be combined with a test value derived from expression levels in order to provide a score which is diagnostic for melanoma. In related embodiments, clinical staging data may be weighted and combined with a test value based on expression to obtain a score which is diagnostic for melanoma.

In some embodiments a reference score may be established. In some embodiments samples may be classified by correlating their test score to the reference score. In some embodiments test scores may be classified as either above or below the reference score. In some embodiments two reference scores, a first and a second reference may be established. In some embodiments samples may be classified by correlating their test score to the reference score. In some embodiments test scores may be classified as above one, above both, below one, below both, or in between the reference scores.

Methods of Diagnosing Melanoma

Provided herein are also methods of diagnosing melanoma. Generally, a method is provided for diagnosing melanoma, which comprises a) determining in a sample from an individual the expression of a panel of genes; b) comparing the expression of the panel of genes in the sample to the expression of the panel of genes in one or more control samples; and c) diagnosing the individual with melanoma, or concluding that the individual is likely to have melanoma, based at least in part on a difference between the expression of one or more genes of the panel of genes in the sample versus the one or more control samples.

The step of comparing the expression of the panel of genes may be performed directly (i.e. obtaining an expression value for each gene in the panel of genes in the sample and in the one or more control sample, and determining on a gene by gene basis if there is a significant difference between the expression in the sample versus the one or more controls). Alternately, comparing the expression of the panel of genes in the sample to the expression in one or more control samples may be performed implicitly. In some embodiments, implicit comparison is achieved by building a model based on the one or more control samples and determining where the expression of the panel of genes in the individual sample fits within the model. In one embodiment, implicit comparison of the expression of the panel of genes in the sample to one or more control samples comprises utilizing a pre-determined set of weighting coefficients based on analysis of the one or more control samples to weight the expression of the panel of genes in the sample and arrive at a test value. In a related embodiment, the test value is compared to a pre-determined cutoff value based on analysis of the one or more control samples to achieve implicit comparison.

In some embodiments, the methods of diagnosis further comprise communicating that the individual is likely to have melanoma.

As used herein, "communicating" a particular piece of information means to make such information known to another person or transfer such information to a thing (e.g., a computer). In some methods of the invention, a patient's diagnosis or likelihood of having melanoma is communicated. In some embodiments, the information used to arrive at such a diagnosis or likelihood prediction is communicated. This communication may be auditory (e.g., verbal), visual (e.g., written), electronic (e.g., data transferred from one computer system to another), etc. In some embodiments, communicating a diagnosis or likelihood of melanoma comprises generating a report that communicates the diagnosis or likelihood of melanoma. In some embodiments the report is a paper report, an auditory report, or an electronic record. In some embodiments the report is displayed and/or stored on a computing device (e.g., handheld device, desktop computer, smart device, website, etc.). In some embodiments the diagnosis or likelihood of melanoma is communicated to a physician (e.g., a report communicating the classification is provided to the physician). In some embodiments the diagnosis or likelihood of melanoma is communicated to a patient (e.g., a report communicating the classification is provided to the patient). Communicating a diagnosis or likelihood of melanoma can also be accomplished by transferring information (e.g., data) embodying the classification to a server computer and allowing an intermediary or end-user to access such information (e.g., by viewing the information as displayed from the server, by downloading the information in the form of one or more files transferred from the server to the intermediary or end-user's device, etc.).

Wherever an embodiment of the invention comprises concluding some fact (e.g., a patient's likelihood of having melanoma), this may include a computer program concluding such fact, typically after performing an algorithm that applies information on the expression of the panel of genes in the sample, as described above.

In some embodiments, the method of diagnosis includes (1) obtaining a sample from a patient suspected of having melanoma; (2) determining the expression of a panel of genes in the sample including at least 2, 4, 6, 8 or 10 cell-cycle genes, or at least 2, 4, 6 or 8 immune genes; and (3) providing a test value by (a) weighting the determined expression of each of a plurality of test genes selected from the panel of genes with a predefined coefficient, and (b) combining the weighted expression to provide said test value, wherein at least 20%, 50%, at least 75% or at least 90% of said plurality of test genes are cell-cycle genes, and wherein high expression (or increased expression or overexpression) of the plurality of test genes indicates a increase likelihood of having melanoma. In some embodiments, the method comprises at least one of the following steps: (a) correlating high expression (or increased expression or overexpression) of the plurality of test genes to an increased likelihood of having melanoma; (b) concluding that the patient has an increased likelihood of having melanoma based at least in part on high expression (or increased expression or overexpression) of the plurality of test genes; or (c) communicating that the patient has an increased likelihood of having melanoma based at least in part on high expression (or increased expression or overexpression) of the plurality of test genes. In some embodiments, the method comprises at least one of the following steps: (a) correlating mixed expression levels of the plurality of test genes to an indeterminate likelihood of having melanoma measured in a sample are (b) concluding that the patient has may or may not have an increased likelihood of having melanoma based at least in part on mixed expression f the plurality of test genes; or (c) communicating that the patient has an indeterminate likelihood of having melanoma based at least in part on the mixed expression (or increased expression or overexpression) of the plurality of test genes.

In some embodiments, the expression levels measured in a sample are used to derive or calculate a value or score, as described above. This value may be derived solely from expression levels or optionally derived from a combination of the expression value scores with other components (e.g., clinical staging, etc.) to give a potentially more comprehensive value/score. Thus, in every case where an embodiment of the invention described herein involves determining the status of a biomarker (e.g., CCGS, immune genes or additional genes, as defines), related embodiments involve deriving or calculating a value or score from the measured status (e.g., expression score, or combined score).

In some such embodiments, multiple scores (e.g., expression test value and clinical parameters, such as clinical staging) can be combined into a more comprehensive score. Single component (e.g., CCG) or combined test scores for a particular patient can be compared to single component or combined scores for reference populations, with differences between test and reference scores being correlated to or indicative of some clinical feature. Thus, in some embodiments the invention provides a method of determining a melanoma diagnosis comprising (1) obtaining the measured expression levels of a panel of genes in a sample from the patient, (2) calculating a test value from these measured expression levels, (3) comparing said test value to a reference value calculated from measured expression levels of the panel of genes in a reference population of patients, and (4)(a) correlating a test value greater than the reference value to a diagnosis of melanoma or (4)(b) correlating a test value equal to or less than the reference value to a benign diagnosis.

In some such embodiments, multiple scores (e.g., expression test value and clinical parameters, such as clinical staging) can be combined into a more comprehensive score. Single component (e.g., CCG) or combined test scores for a particular patient can be compared to single component or combined scores for reference populations, with differences between test and reference scores being correlated to or indicative of some clinical feature. Thus, in some embodiments the invention provides a method of determining a melanoma diagnosis comprising (1) obtaining the measured expression levels of a panel of genes in a sample from the patient, (2) calculating a test value from these measured expression levels, (3) comparing said test value to a reference value calculated from measured expression levels of the panel of genes in a reference population of patients, and (4) correlating a test value to one of two reference values where (a) a test value equal or greater than the first reference value is correlated to a diagnosis of melanoma, (b) a test value equal to or less than the first reference value but greater than the second reference value is correlated to an indeterminate diagnosis, or (c) a test value equal to or less than the second reference value is correlated to a benign diagnosis.

In some such embodiments the test value is calculated by averaging the measured expression of the panel genes (as discussed below). In some embodiments the test value is calculated by weighting each of the panel of genes in a particular way, as described above.

In some embodiments the combined score includes CCP score as previously defined. In some embodiments, the combined score includes an immune score as demonstrated in the Examples. In some embodiments the immune score is an average of the expression of the genes in an immune gene panel. In some embodiments, the immune score is an average of the expression of the genes in Table 30. The immune score may be any value used to represent the expression of one or more immune genes as described herein. In some embodiments the immune score is an average of the expression of the genes in an immune gene panel. In some embodiments, the immune score is an average of the expression of the genes in Panel D. In some embodiments the immune score is an average of the expression of the genes in an immune gene panel. In some embodiments, the immune score is an average of the expression of the genes in Panel E. In some embodiments the immune score is an average of the expression of the genes in an immune gene panel. In some embodiments, the immune score is an average of the expression of the genes in Panel F. A combined score may also include individual genes with independent predictive value, and other non-expression based clinical factors. CCP and immune scores can be a continuous numeric variable.

In some embodiments the combined score is calculated according to the following formula:

$$\text{Combined score} = A*(\text{CCP score}) + B*(\text{immune score}) + \{C*\text{additional gene } X \text{ expression}) + D*\text{additional gene } Y \text{ expression} \ldots\} \quad (1)$$

Where X and Y represent any diagnostic additional gene as described herein, and the ellipsis indicates that extra additional genes, each with their own coefficient may be added.

Additionally, in some embodiments, the combined score is calculated according to the following formula:

$$\text{Combined score} = B*(\text{immune score}) + \{C*\text{additional gene } X \text{ expression}) + D*\text{additional gene } Y \text{ expression} \ldots\} \quad (2)$$

Where X and Y represent any diagnostic additional gene as described herein, and the ellipsis indicates that extra additional genes, each with their own coefficient may be added. In a related embodiment, additional gene X is PRAME and additional gene Y is S100A9.

Furthermore, in yet other embodiments, the combined score is calculated according the following formula:

$$\text{Combined score} = B*(\text{immune score}) + \{C*(\text{additional gene } X \text{ expression}) + D*\text{additional gene } Y \text{ expression} \ldots\} + \text{adjustment factor} \quad (3)$$

Where X and Y represent any diagnostic additional gene as described herein, and the ellipsis indicates that extra additional genes, each with their own coefficient may be added. The adjustment factor represents a scalar factor that can be used to adjust the linear score. For example in some embodiments, the adjustment factor can adjust the score of a particular cutoff value such that the cutoff value is centered at zero. In a related embodiment, additional gene X is PRAME and additional gene Y is S100A9.

Furthermore, in yet other embodiments, the combined score is calculated according the following formula:

$$\text{Combined score} = B*(\text{immune score}) + \{C*(S100 \text{ Score}) + D*\text{additional gene } Y \text{ expression} \ldots\} + \text{adjustment factor} \quad (4)$$

Where Y represents any diagnostic additional gene as described herein, and the ellipsis indicates that extra additional genes, each with their own coefficient may be added. The adjustment factor represents a scalar factor that can be used to adjust the linear score. For example in some embodiments, the adjustment factor can adjust the score of a particular cutoff value such that the cutoff value is centered at zero. The S100 score may be any value used to represent the expression of one or more S100A9 and/or S100A9 related genes as described herein. In some embodiments the S100 score is an average of the expression of the genes in an S100A9 and/or S100A9 related gene panel. In a related embodiment, the S100 score is an average of the expression of the genes in Panel J. In a related embodiment, the S100 score is an average of the expression of the genes in Panel L. In a related embodiment, the S100 score is an average of the expression of S100A9, S100A7, S100A8, S100A12, PI3, S100A10, and S100A14. In a related embodiment, the S100 score is an average of the expression of S100A9, S100A7, S100A8, S100A12, and PI3. In a related embodiment, additional gene Y is PRAME.

In some embodiments, formula (1) is used in the methods, systems, etc. of the invention to diagnose a patient with melanoma. In some embodiments, formula (2) is used in the methods, systems, etc. of the invention to diagnose a patient with melanoma. In some embodiments, formula (3) is used in the methods, systems, etc. of the invention to diagnose a patient with melanoma. In some embodiments, formula (4) is used in the methods, systems, etc. of the invention to diagnose a patient with melanoma. In some embodiments CCP score is the unweighted mean of CT values for expression of the CCP genes being analyzed, optionally normalized by the unweighted mean of the HK genes so that higher values indicate higher expression (in some embodiments one unit is equivalent to a two-fold change in expression). In some embodiments the CCP score ranges from $-8$ to $8$ or from $-1.6$ to $3.7$.

In some embodiments $A=0.95$, $B=0.61$, $C=0.90$ (where applicable), and $D=1.00$ (where applicable); $A=0.57$ and $B=0.39$; or $A=0.58$ and $B=0.41$. In some embodiments, A, B, C, D, and/or the adjustment factor is within rounding of these values (e.g., A is between 0.945 and 0.954, etc.). In some cases a formula may not have all of the specified coefficients (and thus not incorporate the corresponding variable(s)). For example, the embodiment mentioned immediately previously may be applied to formula (2) so that B in formula (2) is 0.61, C=0.90 (where applicable), and D=1.00 (where applicable). A would not be applicable as this coefficient and its corresponding variable is not found in formula (2). In some embodiments A is between 0.9 and 1, 0.9 and 0.99, 0.9 and 0.95, 0.85 and 0.95, 0.86 and 0.94, 0.87 and 0.93, 0.88 and 0.92, 0.89 and 0.91, 0.85 and 0.9, 0.8 and 0.95, 0.8 and 0.9, 0.8 and 0.85, 0.75 and 0.99, 0.75 and 0.95, 0.75 and 0.9, 0.75 and 0.85, or between 0.75 and 0.8. In some embodiments B is between 0.40 and 1, 0.45 and 0.99, 0.45 and 0.95, 0.55 and 0.8, 0.55 and 0.7, 0.55 and 0.65, 0.59 and 0.63, or between 0.6 and 0.62. In some embodiments C is, where applicable, between 0.9 and 1.5, between 0.9 and 1.4, between 0.9 and 1.3, between 0.9 and 1.25, between 0.9 and 1.20, between 0.9 and 1.15, between 0.9 and 1.10, between 0.9 and 1.05, between 0.9 and 1, 0.9 and 0.99, 0.9 and 0.95, 0.85 and 0.95, 0.86 and 0.94, 0.87 and 0.93, 0.88 and 0.92, 0.89 and 0.91, 0.85 and 0.9, 0.8 and 0.95, 0.8 and 0.9, 0.8 and 0.85, 0.75 and 0.99, 0.75 and 0.95, 0.75 and 0.9, 0.75 and 0.85, or between 0.75 and 0.8. In some embodiments D is, where applicable, between 0.9 and 1.5, between 0.9 and 1.4, between 0.9 and 1.3, between 0.9 and 1.25, between 0.9 and 1.20, between 0.9 and 1.15, between 0.9 and 1.10, between 0.9 and 1.05, 0.9 and 1, 0.9 and 0.99, 0.9 and 0.95, 0.85 and 0.95, 0.86 and 0.94, 0.87 and 0.93, 0.88 and 0.92, 0.89 and 0.91, 0.85 and 0.9, 0.8 and 0.95, 0.8 and 0.9, 0.8 and 0.85, 0.75 and 0.99, 0.75 and 0.95, 0.75 and 0.9, 0.75 and 0.85, or between 0.75 and 0.8.

In some embodiments A is between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1, 0.5, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; B is between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; C is, where applicable, between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; and D is, where applicable, between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, between 0.3 and 0.4, 0.5, 0.6, 0.7, 0.8, 0.9, 1, 1.5, 2, 2.5, 3, 3.5, 4, 4.5, 5, 6, 7, 8, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 1412, 5, or 14, 15, or between 0.5, or between and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; and the adjustment factor is, where applicable, positive or negative and may be infinitely large or infinitely small. In some embodiments, A, B, C, and/or D, is within rounding of any of these values (e.g., A is between 0.45 and 0.54, etc.).

As used herein, a patient has an "increased likelihood" of some clinical feature or outcome (e.g., having melanoma) if the probability of the patient having the feature or outcome exceeds some reference probability or value. The reference probability may be the probability of the feature or outcome across the general relevant patient population. For example, if the probability of having melanoma in the general population is X % and a particular patient has been determined by the methods of the present invention to have a probability of Y % of having melanoma, and if Y>X, then the patient has an "increased likelihood" of having melanoma. Alternatively, as discussed above, a threshold or reference value may be determined and a particular patient's probability of having melanoma may be compared to that threshold or reference.

In some embodiments the method correlates the patient's specific score (e.g., CCP score, combined score of CCP with clinical variables) to a specific probability (e.g., 10%, 15%, 20%, 25%, 30%, 35%, 40%, 45%, 50%, 55%, 60%, 65%, 70%, 75%, 80%, 85%, 90%, 95%, 99%, 100%) or likelihood of having melanoma.

In some embodiments the method includes classifying the sample as benign, malignant, or indeterminate based a least in part on comparing the test score to one or more reference scores. In some embodiments a test score below both a first and a second reference score indicates the sample is benign. In some embodiments a sample is classified as indeterminate where the test score is between a first and a second reference. In some embodiments a test score above both a first and a second reference score indicates the sample is benign. In some embodiments the test score and reference scores may be transformed such that a a test score above both a first and a second reference score indicates the sample is malignant, and a test score below both a first and a second reference score indicates the sample is benign. In some embodiments, the method of diagnosis includes (1) obtaining a sample from a patient suspected of having melanoma; (2) determining the expression of a panel of genes in the sample; (3) calculating test values or scores; and (4) providing a report communicating the test value or scores. In some embodiments the report is a paper report, an auditory report, or an electronic record. In some embodiments the report is displayed and/or stored on a computing device (e.g., handheld device, desktop computer, smart device, website, etc.). In some embodiments the report is communicated to a physician (e.g., a report communicating the test values or scores is provided to the physician). In some embodiments the report is communicated to a patient (e.g., a report communicating the test values or scores is provided to the patient). Providing a report can also be accomplished by transferring information (e.g., data) embodying the test values or scores to a server computer and allowing an intermediary or end-user to access such information (e.g., by viewing the information as displayed from the server, by downloading the information in the form of one or more files transferred from the server to the intermediary or end-user's device, etc.).

In other embodiments, the report may communicate scores derived from different sources and other relevant patient information. For example, the report may communicate scores derived solely from expression levels. The report may also report the scores as calculated by formula (1) formula (2), formula (3), and/or formula (4). Alternately, the report may communicate scores derived from a combination of expression value scores with other components (e.g. clinical staging, personal/family history, dermatopathology results, etc.) to give a potentially more comprehensive score. In other cases, the report can communicate multiple scores (e.g. expression test value and clinical parameters, such as clinical staging) and/or a more comprehensive score. The report can also communicate scores for individual genes. In some instances, the report can communicate scores along with control or reference values. Some reports may communicate a specific probability (e.g., 10%, 15%, 20%, 25%, 30%, 35%, 40%, 45%, 50%, 55%, 60%, 65%, 70%, 75%, 80%, 85%, 90%, 95%, 99%, 100%) or likelihood of having melanoma. Other reports may communicate classification of the sample as benign or malignant, predictions of melanoma risk, comparisons of melanoma risk, clinically actionable items, recommendations for cancer risk management and/or recommendations for treatment. Yet other reports may include personal and family medical history.

Methods of Treating Melanoma

In one aspect, the present invention provides methods of treating a patient comprising obtaining gene expression status information for a panel of genes (e.g., obtained by the method described herein), and recommending a treatment, prescribing a treatment, administering a treatment, creating a treatment plan, or modifying a treatment plan for the patient based on the gene expression status. In some embodiments, the method comprises obtaining CCG expression status. In some embodiments, the method comprises obtaining immune gene expression status. In some embodiments, the method comprises obtaining expression status for additional genes as described herein. For example, the invention provides a method of treating a patient comprising:

(1) determining the status of at least one CCG;
  (2) determining the status of at least one immune gene;
  (3) determining the status of at least one additional gene; and
  (4) recommending, prescribing or administering either
    (a) an active (including aggressive) treatment if the patient has at least one of increased expression of the CCG, increased expression of immune gene, or expression of an additional gene that differs significantly from expression in a control sample, or
    (b) a passive (or less aggressive) treatment if the patient has none of increased expression of the CCG, increased expression of immune gene, or expression of an additional gene that differs significantly from expression in a control sample.

In a related embodiment, the invention provides a method of treating a patient comprising:

(1) determining the status of at least one immune gene;

(2) determining the status of at least one additional gene; and (3) recommending, prescribing or administering either (a) an active (including aggressive) treatment if the patient has at least one of increased expression of immune gene, or expression of an additional gene that differs significantly from expression in a control sample, or (b) a passive (or less aggressive) treatment if the patient has none of increased expression of immune gene, or expression of an additional gene that differs significantly from expression in a control sample. In a related embodiment, the invention provides a method of treating a patient comprising:

(1) determining the status of at least one immune gene;

(2) determining the status of at least one additional gene; and (3) creating a treatment plan comprising either (a) more aggressive therapy components if the patient has at least one of increased expression of immune gene, or expression of an additional gene that differs significantly from expression in a control sample, or (b) less aggressive therapy components if the patient has none of increased expression of immune gene, or expression of an additional gene that differs significantly from expression in a control sample; and (4) implementing the treatment plan. In one aspect, the present invention provides methods of treating a patient comprising obtaining gene expression status information for a panel of genes (e.g., obtained by the method described herein), and recommending a treatment, prescribing a treatment, administering a treatment, creating a treatment plan, or modifying a treatment plan for the patient based on the gene expression status. In some embodiments, the method comprises obtaining CCG expression status. In some embodiments, the method comprises obtaining immune gene expression status. In some embodiments, the method comprises obtaining expression status for additional genes as described herein. For example, the invention provides a method of treating a patient comprising:

(1) determining the status of at least one CCG;

(2) determining the status of at least one immune gene;

(3) determining the status of at least one additional gene; and (4) recommending, prescribing or administering any of (a) an active (including aggressive) treatment if the patient has at least one of increased expression of the CCG, increased expression of immune gene, or expression of an additional gene that differs significantly from expression in a control sample, (b) a passive (or less aggressive) treatment if the patient has none of increased expression of the CCG, increased expression of immune gene, or expression of an additional gene that differs significantly from expression in a control sample, (c) an intermediary treatment plan if the patient has some mixed increased, decreased or neutral expression of the CCG, immune or additional genes compared to the expression in a control sample.

In a related embodiment, the invention provides a method of treating a patient comprising:

(1) determining the status of at least one immune gene;

(2) determining the status of at least one additional gene; and (3) recommending, prescribing or administering any of (a) an active (including aggressive) treatment if the patient has at least one of increased expression of immune gene, or expression of an additional gene that differs significantly from expression in a control sample, or (b) a passive (or less aggressive) treatment if the patient has none of increased expression of immune gene, or expression of an additional gene that differs significantly from expression in a control sample, or (c) an intermediate treatment if the patients has some mixed increased, decreased or neutral expression of the CCG, immune or additional genes compared to the expression in a control sample.

In a related embodiment, the invention provides a method of treating a patient comprising:

(1) determining the status of at least one immune gene;

(2) determining the status of at least one additional gene; and (3) creating a treatment plan comprising any of (a) more aggressive therapy components if the patient has at least one of increased expression of immune gene, or expression of an additional gene that differs significantly from expression in a control sample, or (b) less aggressive therapy components if the patient has none of increased expression of immune gene, or expression of an additional gene that differs significantly from expression in a control sample, or (c) an intermediate treatment if the patients has some mixed increased, decreased or neutral expression of the CCG, immune or additional genes compared to the expression in a control sample; and (4) implementing the treatment plan.

In some embodiments, the recommending, prescribing, or administering steps comprise receiving a report communicating the relevant expression status (e.g., CCG status). In some embodiments, the creating a treatment plan step comprises receiving a report communicating the relevant expression status (e.g., CCG status). In some embodiments this report communicates such status in a qualitative manner (e.g., "high" or "increased" expression). In some embodiments this report communicates such status indirectly by communicating a test value or score (e.g., score reflecting likelihood of having melanoma, etc.) that incorporates such status.

Whether a treatment is aggressive or not will generally depend on the diagnosis or likelihood of having melanoma. For individuals diagnosed with melanoma, or having a high likelihood of having melanoma, aggressive treatment is preferred. Those skilled in the art are familiar with various other aggressive and less aggressive treatments for each type of cancer. On the other hand, if an individual has a low likelihood of having melanoma, a less aggressive therapy could be prescribed. Therefore, for an individual having a low risk of having melanoma, a medical provider could recommend a regime of "watchful-waiting." If an individual has an indeterminate likelihood of having melanoma, further testing could be prescribed. Therefore, for an individual having an indeterminate score, a medical provider could recommend further testing of the lesion.

A range of melanoma treatments and/or therapies are known by those skilled in the art. This range of melanoma therapies can vary in their aggressiveness. In general, as the melanoma therapy increases in aggressiveness, the effectiveness of the treatment increases, but the adverse effects to the patient also increases. Skilled artisans can understand that the aggressiveness of the melanoma therapy that is used to treat the patient must be balanced to take into account both the effectiveness of the treatment and the adverse effects that will likely be experienced by the patient. Therefore, the skilled artisan will seek to maximize the effectiveness of the treatment while minimizing the adverse effects of the treatment by selecting an appropriate level of aggressiveness tailored to the individual patient. The appropriate level of treatment can be selected based at least in part on the report communicating the relevant expression status.

In some embodiments, a skilled artisan can incorporate the report communicating the relevant expression status into the selection of aggressiveness of treatment. A report communicating a score indicating a high likelihood of melanoma would indicate a more aggressive treatment while a report communicating a score indicating a lower likelihood of melanoma would indicate a less aggressive treatment. In some embodiments, a less aggressive treatment may comprise the removal of the suspected melanoma during a biopsy. In some embodiments, a more aggressive treatment may include removal of the suspected melanoma as well as removal of a small border of normal skin and a layer of tissue beneath both the suspected melanoma and the small border of skin. In other embodiments, a more aggressive treatment may comprise a reexcision of the biopsy site to remove additional tissue that borders the removed biopsy sample. In yet other embodiments, a more aggressive treatment may comprise reexcision of additional tissue surrounding the biopsy site.

In other embodiments an even more aggressive treatment may include surgery to remove any affected lymph nodes or a lymph node dissection (lymphadenoectomy). In other embodiments an even more aggressive treatment may include surgery to remove any affected lymph nodes or a lymph node dissection (lymphadenoectomy) followed by adjuvant therapy with interferon. In other embodiments, an even more aggressive treatment may include surgery to remove any affected lymph nodes as well as additional treatments such as chemotherapy and/or radiation therapy. In other embodiments, an even more aggressive treatment can include surgery to remove any affected tissue or organs. In alternate embodiments, even more aggressive treatments can include chemotherapy. Some methods of administering chemotherapy include oral and intravenous treatments. Some methods of administering chemotherapy include isolated limb perfusion of chemotherapy drugs. In other embodiments, even more aggressive treatments can include radiation therapy. In yet other embodiments, even more aggressive treatments can include biological therapy. Some biological therapies can include interferon and/or interleukin-2. Some biological therapies can include antibody-based therapies such as ipilimumab (Yervoy). In other embodiments, even more aggressive therapy can include immunotherapy. Some immunotherapies can include Interferon-alpha, Anti-CTLA-4, vaccines, Bacille Calmette-Guerin vaccine, Interleukin 2, and/or T-cell therapy. Some immunotherapies can also be combined with chemotherapy and/or radiation therapy. In alternate embodiments, even more aggressive therapies can include targeted therapy. Some targeted therapies can include drugs such as vemurafenib (Zelboraf) used to treat advanced melanoma. Other targeted therapies include B-RAF inhibitors and/or KIT inhibitors.

In some embodiments, the selection of the specific treatment can be based in part on the relative expression status of the tested genes. For example in some embodiments, the expression profile of the individual genes within the panel would be indicative of the selection of the type and/or the class of therapy. A certain expression profile of the individual genes within the panel may be indicative of melanoma that can be effectively treated with surgery alone. On the other hand, another expression profile may be indicative of melanoma that can be effectively treated with surgery combined with radiation therapy. In other cases, another expression profile may be indicative of melanoma that can be effectively treated with surgery combined with chemotherapy. In yet other cases, the expression profile may be indicative of melanoma that can be effectively treated with only careful monitoring and regular follow-up. In alternate embodiments, the expression profile might be indicative of melanoma that can be effectively treated with higher dosages of therapy administered at shorter intervals whereas other expression profiles might be indicative of lower dosages of therapy administered at longer intervals. In some embodiments, the expression profile may indicate certain combinations, dosages, and/or frequencies of therapies.

In other embodiments, a skilled artisan can utilize at least in part the report communicating the relevant expression status to guide the selection of appropriate melanoma drugs. For example in some embodiments, the expression profile of the individual genes within the panel may be indicative of the selection of particular melanoma drugs. In some embodiments melanoma drugs may be selected from Aldesleukin, Dabrafenib, Dacarbazine, DTIC-Dome (Dacarbazine), Intron A (Recombinant Interferon Alfa-2b), Ipilimumab, Mekinist (Trametinib), Peginterferon Alfa-2b, PEG-Intron (Peginterferon Alfa-2b), Proleukin (Aldesleukin), Recombinant Interferon Alfa-2b, Sylatron (Peginterferon Alfa-2b), Tafinlar (Dabrafenib), Trametinib, Vemurafenib, Yervoy (Ipilimumab), and/or Zelboraf (Vemurafenib). In other embodiments, melanoma drugs may be selected from Bacille Calmette-Guerin (BCG) vaccine, interleukin-2, imiquimod, cytokines, dacarbazine (DTIC), temozolomide (Temodar), mitogen-activated protein kinase kinase (MEK) inhibitor (trametinib), and/or beta-adrenergic-blocking drugs.

In some embodiments, patients with melanoma can be treated by selecting the relative aggressiveness of the melanoma therapy based at least in part on the report communicating the relevant expression status (or test values or scores) and then administering this selected therapy. In other embodiments, patients with melanoma can be treated by selecting the relative aggressiveness of the melanoma therapy based at least in part on the report communicating the relevant expression status, administering this selected therapy, measuring the relevant expression status again, comparing the latter expression status with the previous expression status, and continuing or modifying treatment based on the comparison of the previous and latter expression status. In alternate embodiments, the comparison of the relevant expression status can be used to monitor the efficacy of treatment. In some cases a change in the relevant expression status from a score indicative of a higher likelihood of melanoma to a score indicative of a lower likelihood of melanoma may indicate that the treatment is effective. In other cases a change in the relevant expression status from a score indicative of a lower likelihood of melanoma to a score indicative of a higher likelihood of melanoma may indicate that the treatment is less effective. Where a change in the expression status indicates an effective treatment the treatment may be continued or modified to comprise a less aggressive treatment. Where a change in the expression status indicates a less effective treatment the treatment may be continued or modified to comprise a more aggressive treatment.

In yet other embodiments, the skilled artisan can create or modify a treatment plan for the individual patient based at least in part on the report communicating the relevant expression status. In some embodiments, the selection of different therapy components that comprise the treatment plan can be based at least in part on the report communicating the relevant expression status (or test values or scores). For example, in some instances, the report will indicate a low likelihood of melanoma and the treatment plan may comprise less aggressive therapy components. The less aggressive therapy components can include removal of the suspected melanoma and follow up monitoring of the patient. In other cases, the report may indicate a high likelihood of melanoma and the treatment plan may comprise more aggressive therapy components. Components of a more aggressive treatment plan can include removal of the suspected melanoma and surrounding tissue, reexcision of the biopsy site to remove additional surrounding tissue, chemotherapy, radiation therapy and/or biological therapy. In alternate embodiments, the report communicating the relevant expression status can be used in part to select the different elements within each component of the treatment plan. As a non-limiting example, the report can be used to select individual melanoma drugs that comprise the chemotherapy component of the treatment plan. In other non-limiting examples, the report can be used to select the types of radiation, the amounts of radiation, and/or the dosing regime of the radiation component of the treatment plan. In some embodiments, the treatment plan can further comprise continued measurement of the relevant expression status to determine the efficacy of the treatment plan. In other embodiments, this continued measurement of the efficacy of treatment can be used to modify the treatment plan.

Systems for Diagnosing and Treating Melanoma

The results of any analyses according to the invention will often be communicated to physicians, genetic counselors and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. For example, graphs showing expression or activity level or sequence variation information for various genes can be used in explaining the results. Diagrams showing such information for additional target gene(s) are also useful in indicating some testing results. The statements and visual forms can be recorded on a tangible medium such as papers, computer readable media such as floppy disks, compact disks, etc., or on an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an expression level, activity level, or sequencing (or genotyping) assay is conducted outside the United States, the information and data on a test result may be generated, cast in a transmittable form as described above, and then imported into the United States. Accordingly, the present invention also encompasses a method for producing a transmittable form of information on at least one of (a) expression level or (b) activity level for at least one patient sample. The method comprises the steps of (1) determining at least one of (a) or (b) above according to methods of the present invention; and (2) embodying the result of the determining step in a transmittable form. The transmittable form is the product of such a method.

Techniques for analyzing such expression, activity, and/or sequence data (indeed any data obtained according to the invention) will often be implemented using hardware, software or a combination thereof in one or more computer systems or other processing systems capable of effectuating such analysis.

Thus, the present invention further provides a system for determining gene expression in a tumor sample, comprising: (1) a sample analyzer for determining the expression levels of a panel of genes in a patient sample, wherein the sample analyzer contains the patient sample, or cDNA molecules from mRNA expressed of the panel of genes derived from the sample; (2) a first computer program for (a) receiving gene expression data from the panel of genes, (b) weighting the determined expression of each of the test genes, and (c) combining the weighted expression to provide a test value; and optionally (3) a second computer program for comparing the test value to one or more reference values each associated with a predetermined degree of risk of melanoma.

In another embodiment, the amount of RNA transcribed from the panel of genes including test genes is measured in the sample. In addition, the amount of RNA of one or more housekeeping genes in the sample is also measured, and used to normalize or calibrate the expression of the test genes, as described above.

The sample analyzer can be any instruments useful in determining gene expression, including, e.g., a sequencing machine, a real-time PCR machine, and a microarray instrument.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™ JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out gene status analysis. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instructions which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

Thus one aspect of the present invention provides a system for determining whether a patient has increased likelihood of having melanoma. Generally speaking, the system comprises (1) computer program for receiving, storing, and/or retrieving a patient's gene status data (e.g., expression level, activity level, variants) and optionally clinical parameter data (e.g., clinical staging); (2) computer program for querying this patient data; (3) computer program for concluding whether there is an increased likelihood of having melanoma based on this patient data; and optionally (4) computer program for outputting/displaying this conclusion. In some embodiments this computer program for outputting the conclusion may comprise a computer program for informing a health care professional of the conclusion The practice of the present invention may also employ conventional biology methods, software and systems. Computer software products of the invention typically include computer readable media having computer-executable Instructions for performing the logic steps of the method of the invention. Suitable computer readable medium include floppy disk, CD-ROM/DVD/DVD-ROM, hard-disk drive, flash memory, ROM/RAM, magnetic tapes and etc. Basic computational biology methods are described in, for example, Setubal et al., Introduction to Computational Biology Methods (PWS Publishing Company, Boston, 1997); Salzberg et al. (Ed.), Computational Methods in Molecular Biology, (Elsevier, Amsterdam, 1998); Rashidi & Buehler, Bioinformatics Basics: Application in Biological Science and Medicine (CRC Press, London, 2000); and Ouelette & Bzevanis, Bioinformatics: A Practical Guide for Analysis of Gene and Proteins (Wiley & Sons, Inc., 2nd ed., 2001); see also, U.S. Pat. No. 6,420,108.

The present invention may also make use of various computer program products and software for a variety of purposes, such as probe design, management of data, analysis, and instrument operation. See U.S. Pat. Nos. 5,593,839; 5,795,716; 5,733,729; 5,974,164; 6,066,454; 6,090,555; 6,185,561; 6,188,783; 6,223,127; 6,229,911 and 6,308,170. Additionally, the present invention may have embodiments that include methods for providing genetic information over networks such as the Internet as shown in U.S. Ser. No. 10/197,621 (U.S. Pub. No. 20030097222); Ser. No. 10/063,559 (U.S. Pub. No. 20020183936), Ser. No. 10/065,856 (U.S. Pub. No. 20030100995); Ser. No. 10/065,868 (U.S. Pub. No. 20030120432); Ser. No. 10/423,403 (U.S. Pub. No. 20040049354).

Techniques for analyzing such expression, activity, and/or sequence data (indeed any data obtained according to the invention) will often be implemented using hardware, software or a combination thereof in one or more computer systems or other processing systems capable of effectuating such analysis.

Thus one aspect of the present invention provides systems related to the above methods of the invention. In one embodiment the invention provides a system for determining gene expression in a sample, comprising:
(1) a sample analyzer for determining the expression levels in a sample of a panel of genes, wherein the sample analyzer contains the sample, RNA from the sample and expressed from the panel of genes, or DNA synthesized from said RNA;
(2) a first computer program for
    (a) receiving gene expression data on one or more test genes selected from the panel of genes,
    (b) weighting the determined expression of each of the one or more test genes with a predefined coefficient, and
    (c) combining the weighted expression to provide a test value; and optionally
(3) a second computer program for comparing the test value to one or more reference values each associated with a predetermined degree of risk of having melanoma.

In another embodiment the invention provides a system for determining gene expression in a sample, comprising: (1) a sample analyzer for determining the expression levels of a panel of genes in a sample, wherein the sample analyzer contains the sample which is a nevus or mole suspected of having melanoma, RNA from the sample and expressed from the panel of genes, or DNA synthesized from said RNA; (2) a first computer program for (a) receiving gene expression data on one or more test genes selected from the panel of genes, (b) weighting the determined expression of each of the test genes with a predefined coefficient, and (c) combining the weighted expression to provide a test value, wherein the test genes comprise immune genes and additional genes; and optionally (3) a second computer program for comparing the test value to one or more reference values each associated with a predetermined degree of risk of having melanoma. In some embodiments, the system further comprises a display module displaying the comparison between the test value and the one or more reference values, or displaying a result of the comparing step, or displaying the patient's diagnosis and/or degree of risk of having melanoma.

In a preferred embodiment, the amount of RNA transcribed from the panel of genes including test genes (and/or DNA reverse transcribed therefrom) is measured in the sample. In addition, the amount of RNA of one or more housekeeping genes in the sample (and/or DNA reverse transcribed therefrom) is also measured, and used to normalize or calibrate the expression of the test genes, as described above.

The sample analyzer can be any instrument useful in determining gene expression, including, e.g., a sequencing machine (e.g., Illumina HiSeq™, Ion Torrent PGM, ABI SOLiD™ sequencer, PacBio RS, Helicos Heliscope™, etc.), a real-time PCR machine (e.g., ABI 7900, Fluidigm BioMark™, etc.), a microarray instrument, etc.

FIG. 1 illustrates a system 100 for performing computer-assisted methods of diagnosing, detecting, screening and/or treating melanoma in a patient. System 100 comprises a patient/medical provider interface module 10 comprising a medical provider 11 and a patient 12. The medical provider 11 comprises a doctor and/or other medical staff that care for patient 12. The medical provider collects a complete medical history from patient 12 including but not limited to symptoms, past medical history, and/or family history. The medical provider 11 also conducts a physical examination of the patient 12 and obtains a sample of the patient 12.

System 100 further comprises a data processing device 20 comprising a sample analyzer module 21. The sample of the patient is conveyed from patient/medical provider interface module 10 to the sample analyzer device 20. The sample analyzer module 21 determines the gene expression levels of a panel of biomarkers in the patient sample. The panel of biomarkers may comprise biomarkers useful for determining the presence of melanoma in the patient 12. The panel of biomarkers may further comprise housekeeper genes useful for normalizing the levels of biomarker panel. The sample analyzer module 21 can comprise any instrument useful in determining gene expression levels including, e.g. a sequencing machine (e.g., Illumina HiSeq™, Ion Torrent PGM, ABI SOLiD™ sequencer, PacBio RS, Helicos Helicope™, etc.), a real-time PCR machine (e.g., ABI 7900, Fluidigm BioMark™, etc.), a microarray instrument, etc.

System 100 further comprises a data processing device 30 comprising a medical history database module 31. The medical history database module 31 may comprise a complete medical history from patient 12 including family history information comprising the number of family members of a patient diagnosed with cancer, including melanoma. The family history information may also comprise the degree of relationship to a patient of each family member diagnosed with cancer, including melanoma. The medical history database module 31 may be in communication with patient/medical provider interface module 10. The medical history database module 31 may be configured to receive the patient's medical history from patient/medical provider interface module 10 either as a physical record or as an electronic transmission.

The system 100 further comprises a data processing device 40 comprising a patient information database module 41. The patient information database module 41 comprises patient information comprising gene expression levels of a panel of biomarkers of the patient 12. The patient information database module 41 may be in communication with sample analyzer module 41. The patient information database module 41 may be configured to receive the patient's gene expression levels from the sample analyzer module 21 either as a physical record or as an electronic transmission.

System 100 further comprises a data processing device 50 and a data processing device 60. Data processing device 50 comprises a scoring module 51. Data processing device 60 comprises a biomarker information database module 61. The biomarker information database module 61 comprises biomarker information comprising threshold level information for each biomarker of a panel of biomarkers, wherein the panel of biomarkers comprises positive biomarkers, negative biomarkers, or both, wherein a level statistically significantly above a threshold level for each particular positive biomarker is indicative of melanoma in a patient and a level statistically significantly below a threshold level for each particular negative biomarker is indicative of the presence of melanoma in a patient.

The scoring module 51 may be in communication with the biomarker information database module 61 and the patient information database module 41. The scoring module 51 may be configured to compare biomarker information and patient information to generate a score representing the comparison between the biomarker information and the patient information. The scoring module 51 may be further configured to normalize, average, and apply weighting of sub-groups of biomarkers during the generation of the score. The scoring module 51 may be further configured to algebraically add and/or subtract subgroups of biomarkers during the generation of the score.

The data processing device 50 may further comprise an evaluation module 52 in communication with the scoring module 51. The evaluation module 22 may further be in communication with the biomarker information database module 61. The evaluation module 52 may further be in communication the medical history database module 31. The evaluation module 52 may be configured to determine a probability of the presence of melanoma in the patient based on the patient score as compared to scores of groups of patients diagnosed with melanoma and scores of groups of patients that were not diagnosed with melanoma. The evaluation module 52 may be further configured to determine a probability of the presence of melanoma in the patient based on the patient score and the patient information. The data processing device 50 may further comprise a diagnostic module 53 in communication with the evaluation module 52. The diagnostic module 53 may be configured to determine additional suggested diagnostic procedures based on a patient's probability of melanoma. The data processing device 50 may further comprise a report generation module 54. The report generation module 54 can comprise any device that aggregates the data and process of data processing device 50 into a report. The report produced by report generation module 54 can comprise the score. The report can further comprise the probability of the presence of melanoma. The report can further comprise additional suggested diagnostic procedures. The report can further comprise suggested treatments.

System 100 further comprises a data processing device 70. Data processing device 70 comprises communication means 71. Communication means 71 is in communication with report generation module 54 and patient/medical provider interface module 10. Communication means 71 is configured to transmit the report generated by report generation module 54 to the patient/medical provider interface module 10. The report can further be transmitted by electronic means to the patient/medical provider interface module 10. Communication means 71 can also transmit the report by printing on a tangible medium such as paper and conveying the report to patient/medical provider interface module 10. Upon receiving the transmitted report, the medical provider 11 can treat the patient 12 according to the information in the report. The medical provider 11 can further diagnose the patient 12 based on the report. The medical provider 11 can further create or modify a treatment plan for the patient 12 based on the report. The medical provider 11 can further follow the suggested additional diagnostic test from the report and/or follow the suggested treatments in the report.

Accordingly, the various components, modules, systems, and/or features disclosed herein may be embodied as modules within a system. Such a system may be implemented in software, firmware, hardware, and/or physical infrastructure. Although not always explicitly named herein, a module may be identified (named) based on a function it performs.

For example, a module that is configured to calculate something may comprise specific hardware, software, or firmware and be properly referred to as a "calculation module."

Embodiments may also be provided as a computer program product including a non-transitory machine-readable medium having stored thereon instructions that may be used to program, or be executed on, a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions. Moreover, a computer program product may be run, executed, downloaded, and/or otherwise used locally or remotely via a network.

It should be understood that references to "a data processing device" may refer to the same device or one or more different devices. For example, certain steps of the computer-assisted methods may be performed on a device controlled by a diagnostic service provider and other steps may be performed on a device controlled by a medical practitioner. Likewise, the data processing devices 10, 20, 30, 40, 50, 60, and 70 may be a single device or, for example, the data processing device 50 may be multiple data processing devices.

In certain embodiments, the computer-implemented method may be configured to identify a patient as having or not having pancreatic cancer. For example, the computer-implemented method may be configured to inform a physician that a particular patient has pancreatic cancer. Alternatively or additionally, the computer-implemented method may be configured to actually suggest a particular course of treatment based on the answers to/results for various queries.

Probes and Kits

In some embodiments the invention provides a probe comprising an isolated oligonucleotide capable of selectively hybridizing to at least one of the genes in Table 1, 3 or Panels A through I. The terms "probe" and "oligonucleotide" (also "oligo"), when used in the context of nucleic acids, interchangeably refer to a relatively short nucleic acid fragment or sequence. The invention also provides primers useful in the methods of the invention. "Primers" are probes capable, under the right conditions and with the right companion reagents, of selectively amplifying a target nucleic acid (e.g., a target gene). In the context of nucleic acids, "probe" is used herein to encompass "primer" since primers can generally also serve as probes.

The probe can generally be of any suitable size/length. In some embodiments the probe has a length from about 8 to 200, 15 to 150, 15 to 100, 15 to 75, 15 to 60, or 20 to 55 bases in length. They can be labeled with detectable markers with any suitable detection marker including but not limited to, radioactive isotopes, fluorophores, biotin, enzymes (e.g., alkaline phosphatase), enzyme substrates, ligands and antibodies, etc. See Jablonski et al., Nucleic Acids Res. (1986) 14:6115-6128; Nguyen et al., Biotechniques (1992) 13:116-123; Rigby et al., J. Mol. Biol. (1977) 113:237-251. Indeed, probes may be modified in any conventional manner for various molecular biological applications. Techniques for producing and using such oligonucleotide probes are conventional in the art.

Probes according to the invention can be used in the hybridization/amplification/detection techniques discussed above. Thus, some embodiments of the invention comprise probe sets suitable for use in a microarray. In some embodiments the probe sets have a certain proportion of their probes directed to CCGs—e.g., a probe set consisting of 10%, 20%, 30%, 40%, 50%, 55%, 60%, 65%, 70%, 75%, 80%, 85%, 90%, 95%, 96%, 97%, 98%, 99%, or 100% probes specific for CCGs. In some embodiments the probe set comprises probes directed to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 60, 70, 80, 90, 100, 125, 150, or more, or all, of the genes in Table 1, 3 or Panels A through I, or any of the panels disclosed in Tables WW-ZZ. Such probe sets can be incorporated into high-density arrays comprising 5,000, 10,000, 20,000, 50,000, 100,000, 200,000, 300,000, 400,000, 500,000, 600,000, 700,000, 800,000, 900,000, or 1,000,000 or more different probes.

In another aspect of the present invention, a kit is provided for practicing the diagnosis of the present invention. The kit may include a carrier for the various components of the kit. The carrier can be a container or support, in the form of, e.g., bag, box, tube, rack, and is optionally compartmentalized. The carrier may define an enclosed confinement for safety purposes during shipment and storage. The kit includes various components useful in determining the status of one or more panels of genes as described herein, and one or more housekeeping gene markers, using the above-discussed detection techniques. For example, the kit many include oligonucleotides specifically hybridizing under high stringency to mRNA or cDNA of the genes in Table 1, 3 or Panels A through I, or any of the panels disclosed in Tables WW-ZZ. Such oligonucleotides can be used as PCR primers in RT-PCR reactions, or hybridization probes. In some embodiments the kit comprises reagents (e.g., probes, primers, and or antibodies) for determining the expression level of a panel of genes, where said panel comprises at least 25%, 30%, 40%, 50%, 60%, 75%, 80%, 90%, 95%, 99%, or 100% CCGs. In some embodiments the kit consists of reagents (e.g., probes, primers, and or antibodies) for determining the expression level of no more than 2500 genes, wherein at least 5, 10, 15, 20, 30, 40, 50, 60, 70, 80, 90, 100, 120, 150, 200, 250, or more of these genes are CCGs.

The oligonucleotides in the detection kit can be labeled with any suitable detection marker including but not limited to, radioactive isotopes, fluorophores, biotin, enzymes (e.g., alkaline phosphatase), enzyme substrates, ligands and antibodies, etc. See Jablonski et al., Nucleic Acids Res., 14:6115-6128 (1986); Nguyen et al., Biotechniques, 13:116-123 (1992); Rigby et al., J. Mol. Biol., 113:237-251 (1977). Alternatively, the oligonucleotides included in the kit are not labeled, and instead, one or more markers are provided in the kit so that users may label the oligonucleotides at the time of use.

In another embodiment of the invention, the detection kit contains one or more antibodies selectively immunoreactive with one or more proteins encoded by any of the genes in Table 1, 3 or Panels A through I, or any of the panels disclosed in Tables WW-ZZ.

Various other components useful in the detection techniques may also be included in the detection kit of this invention. Examples of such components include, but are not limited to, Taq polymerase, deoxyribonucleotides, dideoxyribonucleotides, other primers suitable for the amplification of a target DNA sequence, RNase A, and the like. In addition, the detection kit preferably includes instructions on using the kit for practice the diagnosis method of the present invention using human samples.

EXAMPLES

Example 1

In this example we determined whether cell cycle progression genes can differentiate between malignant melanoma and non-malignant nevi. Specifically, this example assesses whether melanoma can be differentiated from benign nevi, as well as dysplastic nevi.

Materials and Methods

Samples: 31 FFPE skin samples, with 3×10 mm slides for each sample, and a 4 mm slide for H&E review between the ages of 10-11 years old were obtained from an academic institution. The samples consisted of 11 benign nevi, 10 dysplastic nevi and 10 melanoma samples. Table 4 lists samples and corresponding clinical details.

TABLE 4

Skin samples with diagnosis, clinical data, and CCP score.

| BLD | Slide ID | Diagnosis | CCP | HK Mean | CCP STdv | Quality | Biopsy date | Sex | Age | Location |
|---|---|---|---|---|---|---|---|---|---|---|
| 01095572-BLD | MG12-23 | Compound nevus | 0.61 | 19.81 | 0.04 | Very Good | Jan. 3, 2001 | F | 21 | Chest |
| 01095574-BLD | MG12-29 | Compound nevus | 0.79 | 19370 | 0.02 | Very Good | Jan. 5, 2001 | F | 31 | Neck |
| 01095579-BLD | MG12-27 | Compound nevus | 1.60 | 23.02 | 0.08 | Very Good | Jan. 16, 2001 | M | 17 | Jaw |
| 01095624-BLD | MG12-30 | Compound nevus | 0.74 | 20.22 | 0.13 | Very Good | Jan. 8, 2001 | F | 57 | Ear |
| 01095553-BLD | MG12-24 | Intradermal nevus | 0.67 | 17.41 | 0.02 | Very Good | Jan. 5, 2001 | M | 56 | Neck |
| 01095559-BLD | MG12-33 | Intradermal nevus | 0.39 | 19.48 | 0.04 | Very Good | Feb. 2, 2001 | M | 43 | Back |
| 01095560-BLD | MG12-25 | Intradermal nevus | −0.18 | 18.04 | 0.04 | Very Good | Jan. 16, 2001 | F | 31 | Jaw |
| 01095569-BLD | MG12-32 | Intradermal nevus | 0.27 | 19.75 | 0.08 | Very Good | Jan. 5, 2001 | M | 30 | Shoulder |
| 01095571-BLD | MG12-28 | Intradermal nevus | 1.05 | 19.66 | 0.02 | Very Good | Jan. 2, 2001 | M | 36 | Cheek |
| 01095576-BLD | MG12-26 | Intradermal nevus | 0.42 | 18.34 | 0.12 | Very Good | Jan. 16, 2001 | M | 17 | Chin |
| 01095580-BLD | MG12-31 | Intradermal nevus | 0.74 | 20.36 | 0.05 | Very Good | Jan. 18, 2001 | F | 53 | Neck |
| 01095556-BLD | MG12-35 | Compound dysplastic nevus | 1.03 | 20.23 | 0.04 | Very Good | Jan. 29, 2001 | F | 26 | Chest |
| 01095570-BLD | MG12-42 | Compound dysplastic nevus | 0.23 | 19.56 | 0.10 | Very Good | Feb. 1, 2001 | M | 52 | Thigh |
| 01095577-BLD | MG12-40 | Compound dysplastic nevus | 0.93 | 19.21 | 0.02 | Very Good | Mar. 19, 2001 | M | 41 | Back |
| 01095620-BLD | MG12-39 | Compound dysplastic nevus | 1.33 | 20.48 | 0.02 | Very Good | Feb. 22, 2001 | F | 30 | Back |
| 01095622-BLD | MG12-34 | Compound dysplastic nevus | 0.54 | 17.07 | 0.02 | Very Good | Jan. 25, 2001 | M | 35 | Back |
| 01095626-BLD | MG12-36 | Compound dysplastic nevus | 0.67 | 24.95 | 0.26 | Good | Feb. 7, 2001 | F | 32 | Abdomen |
| 01095552-BLD | MG12-41 | Junctional dysplastic nevus | 0.91 | 20.74 | 0.16 | Very Good | Mar. 5, 2001 | M | 27 | Neck |
| 01095554-BLD | MG12-38 | Junctional dysplastic nevus | 0.70 | 21.11 | 0.02 | Very Good | Feb. 21, 2001 | M | 45 | Chest |
| 01095562-BLD | MG12-37 | Junctional dysplastic nevus | 1.45 | 21.86 | 0.04 | Very Good | Feb. 14, 2001 | F | 40 | Back |
| 01095578-BLD | MG12-43 | Junctional dysplastic nevus | 1.28 | 20.47 | 0.05 | Very Good | Jan. 17, 2001 | F | 69 | Thigh |
| 01095621-BLD | MG12-46 | Nodular melanoma | NA | 30.34 | NA | Rejected | Nov. 13, 2001 | F | 9 | Back |
| 01095551-BLD | MG12-50 | SSM | 1.50 | 21.13 | 0.01 | Very Good | Sep. 26, 2001 | M | 51 | Arm |
| 01095555-BLD | MG12-53 | SSM | 1.28 | 19.73 | 0.07 | Very Good | Jul. 1, 2002 | M | 61 | Back |
| 01095557-BLD | MG12-52 | SSM | 2.20 | 21.07 | 0.06 | Very Good | Jun. 24, 2001 | F | 36 | Chest |
| 01095558-BLD | MG12-44 | SSM | 1.67 | 19.19 | 0.03 | Very Good | Jan. 4, 2001 | F | 68 | Arm |

TABLE 4-continued

Skin samples with diagnosis, clinical data, and CCP score.

| BLD | Slide ID | Diagnosis | CCP | HK Mean | CCP STdv | Quality | Biopsy date | Sex | Age | Location |
|---|---|---|---|---|---|---|---|---|---|---|
| 01095561-BLD | MG12-51 | SSM | 1.76 | 20.20 | 0.03 | Very Good | Mar. 1, 2001 | M | 36 | Back |
| 01095573-BLD | MG12-45 | SSM | 1.67 | 20.02 | 0.05 | Very Good | Mar. 14, 2001 | F | 36 | Knee |
| 01095575-BLD | MG12-49 | SSM | 2.39 | 19.54 | 0.04 | Very Good | Aug. 16, 2001 | F | 38 | Back |
| 01095623-BLD | MG12-48 | SSM | 2.12 | 19.82 | 0.02 | Very Good | Jul. 21, 2001 | M | 38 | Shoulder |
| 01095625-BLD | MG12-47 | SSM | 2.01 | 20.46 | 0.05 | Very Good | Aug. 7, 2001 | M | 43 | shoulder |

SSM = superficial spreading melanoma

Sample Processing, CCP score generation, and analysis: 4 mm slides were stained to make H&E slides and reviewed by a pathologist who circled the lesion (either the nevus or the melanoma). Using the H&E slide, the lesions were dissected and removed from each of the three 10 μM slides. All three dissected lesions from a single patient were pooled.

RNA was extracted from samples and RNA expression levels were determined using standard qPCR techniques. Of the 31 samples, 30 were successfully run and generated a CCP score (see Table 4 for data).

CCP scores of the melanoma samples were compared to the other two groups, benign nevi and dysplastic nevi, as well as to dysplastic nevi alone, using the Student's t-test, to determine if the CCP scores of the groups were different in a statistically significant manner.

Results

Figure 2:
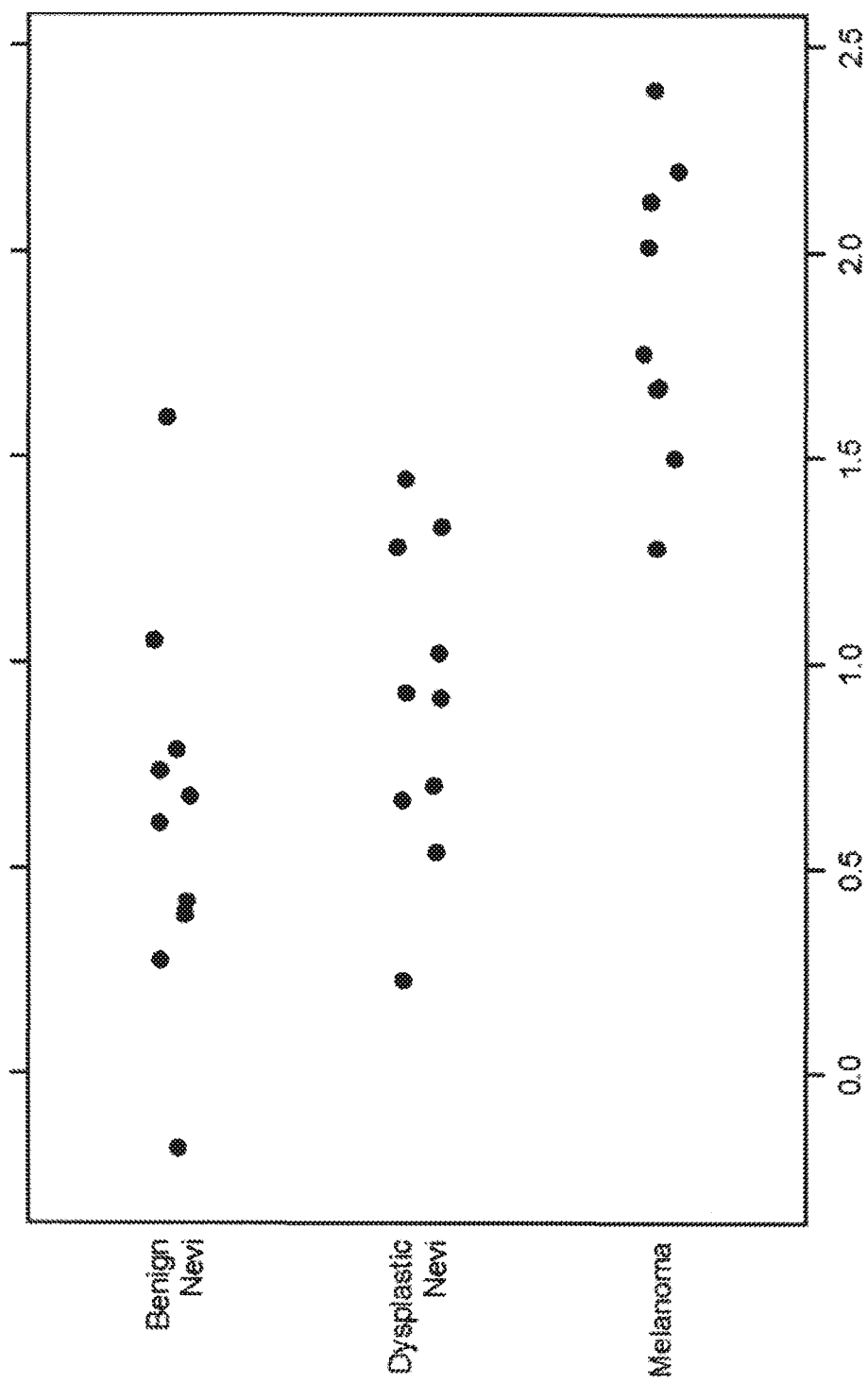
FIG. 2 shows the distribution of the CCP scores from all 30 samples with a score and separated by clinical diagnosis. The melanoma samples have statistically different distributions when compared to the nevi samples.

We observed the melanoma samples had different CCP scores than both nevi subgroups combined, in a very statistically significant manner (p-value, 1.4×10-6, see FIG. 2). When using this data in a diagnostic model, the melanoma samples could be identified with an AUC of 0.97. On average, melanoma CCP scores were 1.08 higher than nevi CCP scores. See Table 4 for a list of all data. FIG. 2 shows the distribution of the CCP scores from all 30 samples with a score, separated by the clinical diagnosis.

We also observed the melanoma samples had different CCP scores compared to just dysplastic nevi, in a statistically significant manner (p-value, 3.9×10-5, see FIG. 2). When using this data in a diagnostic model, the melanoma samples could be identified, compared to just the dysplastic nevi, with an AUC of 0.97. On average, melanoma CCP scores were 0.94 higher than nevi CCP scores.

Finally, we observed the benign nevi were not statistically different than the dysplastic nevi (p-value, 0.17), indicating that when nevi become dysplastic they are not replicating at a faster rate, and only upon transitioning to a melanoma do the cells begin to replicate faster. The data indicates that the melanoma samples are replicating at a 2-fold higher rate than nevi.

Discussion

These data show the measurement of CCP scores can differentiate between malignant melanoma and nonmalignant nevi. More specifically these data show that a CCP score can differentiate between melanoma and dysplastic nevi. While the average difference between the two groups is moderate (~1 CCP unit), precision of the measurements allows for good separation of the two datasets.

Example 2

In this example we determined whether certain CCP genes differentiated nevi and melanoma more effectively (Table 6).

We indeed observed that there were certain CCP genes that had much better AUC values than others, even though all but one gene had an AUC >0.8, which was still quite impressive. We decided to move forward and selected ten CCP genes whose AUC scores were >0.95 (see Table 6). Ten CCP genes were sufficient to produce a robust and reliable CCP score.

TABLE 6

| CCPGene | Assay | AUC | Correlation with overall CCP Score | Continue to next stage |
|---|---|---|---|---|
| SKA1 | Hs00536843_m1 | 1.00 | 0.88 | Yes |
| DTL | Hs00978565_m1 | 1.00 | 0.87 | Yes |
| CEP55 | Hs00216688_m1 | 0.99 | 0.81 | Yes |
| FOXM1 | Hs01073586_m1 | 0.98 | 0.94 | Yes |
| PLK1 | Hs00153444_m1 | 0.98 | 0.87 | Yes |
| PBK | Hs00218544_m1 | 0.97 | 0.96 | Yes |
| CENPF | Hs00193201_m1 | 0.97 | 0.85 | Yes |
| DLGAP5 | Hs00207323_m1 | 0.96 | 0.95 | Yes |
| MCM10 | Hs00960349_m1 | 0.96 | 0.84 | Yes |
| RRM2 | Hs00357247_g1 | 0.96 | 0.96 | Yes |
| ORC6L | Hs00204876_m1 | 0.95 | 0.88 | |
| BIRC5 | Hs00153353_m1 | 0.95 | 0.82 | |
| NUSAP1 | Hs01006195_m1 | 0.95 | 0.95 | |
| ASF1B | Hs00216780_m1 | 0.93 | 0.89 | |
| RAD54L | Hs00269177_m1 | 0.93 | 0.84 | |
| CDKN3 | Hs00193192_m1 | 0.93 | 0.92 | |
| ASPM | Hs00411505_m1 | 0.93 | 0.95 | |
| BUB1B | Hs01084828_m1 | 0.92 | 0.94 | |
| TK1 | Hs01062125_m1 | 0.92 | 0.93 | |
| KIF20A | Hs00993573_m1 | 0.91 | 0.81 | |
| CDK1 | Hs00364293_m1 | 0.91 | 0.91 | |
| CDC20 | Hs03004916_g1 | 0.91 | 0.92 | |
| RAD51 | Hs001534L8_m1 | 0.91 | 0.91 | |
| CDCA8 | Hs0098365S_m1 | 0.91 | 0.89 | |
| KIF11 | Hs00189698_m1 | 0.90 | 0.65 | |
| PTTG1 | Hs00851754_u1 | 0.90 | 0.90 | |
| PRC1 | Hs00187740_m1 | 0.89 | 0.92 | |
| TOP2A | Hs00172214_m1 | 0.86 | 0.77 | |
| KIAA0101 | Hs00207134_m1 | 0.86 | 0.89 | |
| CENPM | Hs00608780_m1 | 0.81 | 0.63 | |
| CDCA3 | Hs00229905_m1 | 0.71 | 0.65 | |

AUC indicates differentiation between melanoma and all nevi.

Example 3

This example assesses a variety of potential biomarkers to determine if their altered expression can differentiate between malignant melanoma and non-malignant nevi.

Materials and Methods

Samples: Biomarker discovery was performed using two independent datasets. The first dataset consisted of 31 samples (Group 1). See Table 7 for a list of these samples and their clinical details. The second dataset consisted of 53 samples (Group 2). See Table 8 for a list of these samples and their clinical details.

TABLE 7

Group 1 samples.

| Sample ID | Diagnosis | Subtype | Biopsy date | Age | Sex | Location |
|---|---|---|---|---|---|---|
| MG12-50 | Melanoma | Superficial Spreading | Sep. 26, 2001 | 51 | M | Arm |
| MG12-41 | Nevus | Dysplastic low/Junctional | Mar. 5, 2001 | 27 | M | Neck |
| MG12-24 | Nevus | Intradermal | Jan. 5, 2001 | 56 | M | Neck |
| MG12-38 | Nevus | Dysplastic low/Junctional | Feb. 21, 2001 | 45 | M | Chest |
| MG12-53 | Melanoma | Superficial Spreading | Jul. 1, 2002 | 61 | M | Chest |
| MG12-35 | Nevus | Dysplastic low/Compound | Jan. 29, 2001 | 26 | F | Chest |
| MG12-52 | Melanoma | Superficial Spreading | Jun. 24, 2002 | 36 | F | Chest |
| MG12-44 | Melanoma | Superficial Spreading | Jan. 4, 2001 | 68 | F | arm |
| MG12-33 | Nevus | Intradermal | Feb. 2, 2001 | 43 | M | back |
| MG12-25 | Nevus | Intradermal | Jan. 16, 2001 | 31 | F | jaw |
| MG12-51 | Melanoma | Superficial Spreading | Mar. 1, 2002 | 36 | M | Back |
| MG12-37 | Nevus | Dysplastic low/Junctional | Feb. 14, 2001 | 40 | F | Back |
| MG12-32 | Nevus | Intradermal | Jan. 5, 2001 | 30 | M | shoulder |
| MG12-42 | Nevus | Dysplastic low/Compound | Feb. 1, 2001 | 52 | M | Thigh |
| MG12-28 | Nevus | Intradermal | Jan. 2, 2001 | 36 | M | Cheek |
| MG12-23 | Nevus | Compound | Jan. 3, 2001 | 21 | F | Chest |
| MG12-45 | Melanoma | Superficial Spreading | Mar. 14, 2001 | 36 | F | Knee |
| MG12-29 | Nevus | Compound | Jan. 5, 2001 | 31 | F | Neck |
| MG12-49 | Melanoma | Superficial Spreading | Aug. 16, 2001 | 38 | F | Back |
| MG12-26 | Nevus | Intradermal | Jan. 16, 2001 | 17 | M | Chin |
| MG12-40 | Nevus | Dysplastic low/Compound | Mar. 19, 2001 | 41 | M | Back |
| MG12-43 | Nevus | Dysplastic low/Junctional | Jan. 17, 2001 | 69 | F | Thigh |
| MG12-27 | Nevus | Compound | Jan. 16, 2001 | 17 | M | Jaw |
| MG12-31 | Nevus | Intradermal | Jan. 18, 2001 | 53 | F | Neck |
| MG12-39 | Nevus | Dysplastic low/Compound | Feb. 22, 2001 | 30 | F | Back |
| MG12-46 | Melanoma | Nodular | Nov. 13, 2001 | 9 | F | Back |
| MG12-34 | Nevus | Dysplastic low/Compound | Jan. 25, 2001 | 35 | M | back |
| MG12-48 | Melanoma | Superficial Spreading | Jul. 21, 2001 | 38 | M | Shoulder |
| MG12-30 | | Lost sample | | | | |
| MG12-47 | Melanoma | Superficial Spreading | Aug. 7, 2001 | 43 | M | Shoulder |
| MG12-36 | Nevus | Dysplastic low/Compound | Feb. 7, 2001 | 32 | F | abdomen |

TABLE 8

Group 2 Samples

| qPCR ID | Sample ID | Diagnosis | Subtype | Biopsy Date | Age | Sex | Location |
|---|---|---|---|---|---|---|---|
| 1 | P09-3235 | Nevus | Intradermal | Nov. 25, 2009 | 44 | F | Torso |
| 2 | P08-1961 | Nevus | Compound | Feb. 8, 2008 | 65 | M | Torso |
| 3 | P05-363 | Melanoma | Nodular | Jan. 11, 2005 | 38 | M | Leg |
| 4 | P10-2736 F1 | Nevus | Intradermal | Jan. 27, 2010 | 34 | M | Head |
| 5 | CPP-11-33494 | Melanoma | Nodular | Nov. 1, 2011 | 69 | M | Head |
| 6 | CPP-09-27303 | Melanoma | Superficial Spreading | Oct. 1, 2009 | 47 | F | Torso |
| 7 | CPP-10-2397 | Nevus | Blue | Jan. 26, 2010 | 51 | M | Head |
| 8 | P09-35648 | Nevus | Dysplastic low | Dec. 18, 2009 | 44 | M | Leg |
| 9 | CPP-11-07506 | Nevus | Dysplastic low | Mar. 1, 2011 | 40 | F | Torso |
| 10 | P10-1574 A1 | Nevus | Intradermal | Jan. 17, 2010 | 335 | F | Torso |
| 11 | C07-896 E4 | Melanoma | Nodular | Jan. 18, 2007 | 59 | M | Head |
| 12 | P10-494 A1 | Nevus | Intradermal | Jan. 6, 2010 | 53 | M | Head |
| 13 | CPP-09-36545 A9 | Melanoma | Nodular | | 60 | M | Torso |
| 14 | P10-3676 A11 | Melanoma | Superficial Spreading | Feb. 6, 2010 | 79 | M | Leg |
| 15 | C06-10614 | Melanoma | Superficial Spreading | Jan. 11, 2006 | 34 | M | Head |
| 16 | CPP-10-10782 B1 | Nevus | Dysplastic low | Apr. 1, 2010 | 30 | M | Torso |
| 17 | CPP-10-3651 | Nevus | Blue | Feb. 5, 2010 | 39 | F | Head |
| 18 | CPP-10-10782 A1 | Nevus | Dysplastic low | Apr. 1, 2010 | 30 | M | Torso |
| 19 | CPP-10-04915 | Melanoma | Acral | Feb. 1, 2010 | 71 | M | Leg |
| 20 | CPP-09-8204 | Melanoma | Nodular | Apr. 3, 2009 | 60 | M | Head |
| 21 | P01-6845 | Nevus | Compound | Oct. 12, 2001 | 25 | F | Arm |
| 22 | C07-3665 A2 | Melanoma | Lentigo Maligna | Jul. 31, 2006 | 34 | M | Head |
| 23 | CPC-03-00227 | Nevus | Spitz | Jan. 1, 2003 | 74 | F | Torso |
| 24 | CPC-07-03023 | Nevus | Compound | Feb. 1, 2007 | 45 | F | arm |
| 25 | CPP-10-12821 | Melanoma | Acral | May 1, 2010 | 63 | F | Leg |
| 26 | CPP-10-03836 | Nevus | Dysplastic low | Feb. 1, 2010 | 37 | M | Torso |
| 27 | CPP-01-7511 | Nevus | Blue | Nov. 9, 2001 | 25 | F | Arm |
| 28 | CPC-06-430 | Nevus | Intradermal | Jan. 11, 2006 | 40 | F | Head |
| 29 | CPP-10-1094 | Melanoma | Nodular | Jan. 4, 2010 | 54 | M | Arm |
| 30 | CPP-11-33384 | Melanoma | Lentigo Maligna | Nov. 3, 2011 | 67 | F | Head |

TABLE 8-continued

Group 2 Samples

| qPCR ID | Sample ID | Diagnosis | Subtype | Biopsy Date | Age | Sex | Location |
|---|---|---|---|---|---|---|---|
| 31 | CPP-12-23457 | Melanoma | Desmoplastic | Aug. 21, 2012 | 48 | M | Head |
| 32 | CPP-11-13421 | Nevus | Dysplastic low | Apr. 29, 2011 | 32 | F | Torso |
| 33 | CPP-11-15636 | Nevus | Compound | May 19, 2011 | 22 | M | Torso |
| 34 | CPP-10-9267 | Nevus | Dysplastic high/ Junctional | Mar. 31, 2010 | 36 | M | Torso |
| 35 | CPP-10-22878 | Melanoma | Superficial Spreading | Aug. 6, 2010 | 67 | F | Head |
| 36 | CPP-10-9477 A | Nevus | Dysplastic low/ Junctional | Apr. 4, 2010 | 40 | M | Torso |
| 37 | CPP-10-7786 | Nevus | Dysplastic low/ Junctional | Mar. 18, 2010 | 52 | M | Torso |
| 38 | CPP-10-18433 | Nevus | Compound | Jun. 24, 2010 | 48 | M | Leg |
| 39 | CPP-08-7203 | Nevus | Dysplastic low | May 19, 2008 | 38 | F | Leg |
| 40 | CPP-10-19572 | Nevus | Spitz | Jul. 7, 2010 | 29 | F | Torso |
| 41 | CPP-11-13681 | Nevus | Dysplastic low | May 3, 2011 | 48 | M | Torso |
| 42 | CPP-12-14855 | Melanoma | Acral | May 25, 2012 | 71 | M | Leg |
| 43 | CPP-11-19854 | Nevus | Dysplastic low/ Compound | Jun. 27, 2011 | 31 | M | Torso |
| 44 | CPP-11-24358 | Melanoma | Lentigo Maligna | Aug. 9, 2011 | 89 | F | Head |
| 45 | CPP-10-9477 B | Nevus | Dysplastic low/ Junctional | Apr. 1, 2010 | 40 | M | Torso |
| 46 | CPP-10-16714 | Melanoma | Lentigo Maligna | Jun. 10, 2010 | 58 | M | Head |
| 47 | CPP-12-17349 | Melanoma | Desmoplastic | Jun. 20, 2012 | 62 | M | Leg |
| 48 | CPP-10-8105 | Nevus | Dysplastic low/ Junctional | Mar. 22, 2010 | 48 | F | Torso |
| 49 | CPP-12-17027 | Nevus | Spitz | Jun. 18, 2012 | 25 | M | Arm |
| 50 | CPP-11-17106 | Melanoma | Superficial Spreading | Jun. 2, 2011 | 52 | M | Head |
| 51 | CPP-12-14808 | Melanoma | Desmoplastic | May 24, 2012 | 66 | F | Head |
| 52 | CPP-11-32490 | Melanoma | Superficial Spreading | Oct. 27, 2011 | 58 | F | Arm |
| 53 | CPP-11-17723 | Nevus | Dysplastic low | Jun. 8, 2011 | 36 | F | Torso |

RNA extraction: The 31 group 1 samples were anonymized with a qPCRID and a 4 mm H&E slide was reviewed by a pathologist who circled the lesion of interest (either the nevus or the melanoma). The lesions were then macro-dissected and removed from three 10 μM slides. All three dissected lesions from a single patient were pooled into a single tube. RNA was extracted from samples, RNA expression levels were determined using standard qPCR techniques, and a standard CCP score was generated.

RNA from 30 of the samples was then used in the first two rounds of biomarker discovery. RNA was DNased and quantified. RNA with concentrations >40 ng/uL were normalized to 40 ng/uL.

The 53 group 2 samples were anonymized with a qPCR ID, and a H&E slide was reviewed by a pathologist who circled the lesion of interest. The lesions were then macro-dissected from five 4 mm slides. All five dissected lesions from a single patient were pooled into a single tube. The RNA from each tube was extracted using standard RNA extraction techniques. RNA was DNased and quantified. All RNA samples with concentrations >40 ng/uL were normalized to 40 ng/uL.

Measurement of gene expression: RNA expression was measured using standard qPCR techniques. Ct values were determined, and the expression of each gene was normalized to the expression of housekeeper genes.

Biomarkers were assessed in three rounds of testing. Only samples from group 1 were analyzed in rounds 1 and 2 of testing. Samples from groups 1 and 2 were analyzed in round 3 of testing. Data from each round of testing was analyzed separately and aggregated. The housekeeping genes tested for normalization in all three rounds included MRFAP1, PSMA1, RPL13A, and TXNL1. In addition, housekeeping genes SLC25A3, RPS29, RPL8, PSMC1 and RPL4 were included in the first round of testing.

Results

Table 9 lists all amplicons used in biomarker discovery and lists p-values for separate rounds of analysis, and aggregated analysis as indicated in the round tested column. P-values are Wilcoxon Rank Sum P-values, and p-values and AUC indicate differentiation all melanomas subtypes from all nevi subtypes.

TABLE 9

All amplicons used during biomarker discovery

| Gene | Assay ID | P-Value | AUC | Round Tested |
|---|---|---|---|---|
| ARPC2 | Hs00194852_m1 | 4.1E−02 | 0.76 | 2 |
|  | Hs01031743_m1 | 1.5E−01 | 0.60 | 1, 3 |
|  | Hs01031746_g1 | 8.3E−03 | 0.81 | 1 |
|  | Hs01031748_m1 | 8.8E−02 | 0.62 | 2, 3 |
| BCL2A1 | Hs00187845_m1 | 8.7E−06 | 0.80 | 1, 3 |
| CCL3 (MIP-1α) | Hs00234142_m1 | 5.3E−08 | 0.87 | 2, 3 |
|  | Hs04194942_s1 | 2.5E−04 | 0.75 | 1, 3 |
| FN1 | Hs01565276_m1 | 1.3E−06 | 0.82 | 1, 3 |
| IFI6 | Hs01564161_g1 | 3.8E−06 | 0.81 | 1, 3 |
| NCOA3 | Hs01105241_m1 | 4.3E−01 | 0.55 | 1, 3 |
|  | Hs01105267_m1 | 5.2E−01 | 0.54 | 1, 3 |
| PHIP | Hs06611782_m1 | 1.8E−01 | 0.66 | 1 |
|  | Hs01059904_m1 | 1.5E−01 | 0.60 | 1, 3 |
| POU5F1 | Hs04195369_s1 | 5.0E−01 | 0.58 | 1, 3 |
|  | Hs04260367_gH | 1.1E−01 | 0.61 | 1, 3 |
| RGS1 | Hs00175260_m1 | 5.2E−04 | 0.94 | 2 |
|  | Hs01023770_g1 | 4.0E−11 | 0.94 | 1, 3 |
|  | Hs01023772_m1 | 1.0E−11 | 0.95 | 1, 3 |
| SPP1 | Hs00167093_m1 | 8.3E−09 | 0.87 | 2, 3 |
|  | Hs00959006_g1 | 3.3E−02 | 0.81 | 2 |

TABLE 9-continued

All amplicons used during biomarker discovery

| Gene | Assay ID | P-Value | AUC | Round Tested |
|---|---|---|---|---|
|  | Hs00959008_g1 | 3.3E−09 | 0.88 | 2, 3 |
|  | Hs00959010_m1 | 5.3E−09 | 0.89 | 1 |
|  | Hs00960641_m1 | 4.0E−01 | 1.00 | 1, 3 |
| WNT2 | Hs00608222_m1 | 3.2E−01 | 0.92 | 1 |
|  | Hs00608224_m1 | 4.5E−01 | 0.61 | 3 |
|  | Hs01128652_m1 | 8.3E−01 | 0.55 | 1 |
| WIF1 | Hs00183662_m1 | 5.3E−02 | 0.63 | 1, 3 |
|  | Hs01548029_m1 | 7.6E−01 | 0.54 | 1 |
| NR4A1 | Hs00374226_m1 | 2.9E−01 | 0.57 | 1, 3 |
|  | Hs00926542_g1 | 1.0E−01 | 0.72 | 1 |
| SOCS3 | Hs00269575_s1 | 9.3E−09 | 0.87 | 1, 3 |
|  | Hs01000485_g1 | 9.4E−08 | 0.85 | 2, 3 |
|  | Hs02330328_s1 | 5.4E−03 | 0.84 | 1 |
| PRAME | Hs00196132_m1 | 2.0E−02 | 0.88 | 2 |
|  | Hs01022299_m1 | 1.0E+0 | 0.50 | 2 |
|  | Hs01022301_m1 | 1.3E−09 | 0.89 | 2, 3 |
|  | Hs04186846_m1 | 3.8E−06 | 0.84 | 2, 3 |
| KRT15 | Hs00267035_m1 | 1.0E−01 | 0.71 | 2 |
|  | Hs00951967_g1 | 1.3E−08 | 0.89 | 2, 3 |
|  | Hs00951968_gH | 1.0E−08 | 0.89 | 2, 3 |
|  | Hs02558897_s1 | 8.3E−02 | 0.74 | 2 |
| FABP7 | Hs00361424_g1 | 1.2E−05 | 0.80 | 2, 3 |
|  | Hs00361426_m1 | 3.5E−02 | 0.77 | 2 |
|  | Hs00953719_g1 | 1.7E−03 | 0.72 | 2, 3 |
| CFH | Hs00962362_g1 | 1.4E−03 | 0.72 | 2, 3 |
|  | Hs00962365_g1 | 5.0E−01 | 0.59 | 2 |
|  | Hs00962373_m1 | 6.3E−03 | 0.69 | 2, 3 |
| PTN | Hs00383235_m1 | 1.5E−02 | 0.67 | 2, 3 |
|  | Hs01085690_m1 | 5.5E−02 | 0.75 | 2 |
|  | Hs01085691_m1 | 1.4E−03 | 0.72 | 2, 3 |
| HEY1 | Hs01114111_g1 | 1.0E−04 | 0.76 | 2, 3 |
|  | Hs01114112_g1 | 4.5E−04 | 0.74 | 2, 3 |
|  | Hs01114113_m1 | 6.9E−01 | 0.56 | 2 |
| GDF15 | Hs00171132_m1 | 5.0E−02 | 0.64 | 2,3 |
| PHACTR1 | Hs01116208_m1 | 9.4E−02 | 0.72 | 2 |
|  | Hs01116210_m1 | 2.1E−01 | 0.59 | 2, 3 |
|  | Hs01116212_m1 | 4.8E−02 | 0.76 | 2 |
|  | Hs01116214_m1 | 2.1E−07 | 0.86 | 2, 3 |
| LCP2 | Hs00175501_m1 | 2.2E−07 | 0.89 | 3 |
|  | Hs01092638_m1 | 2.4E−06 | 0.86 | 3 |
| CXCL9 | Hs00171065_m1 | 4.7E−11 | 0.97 | 3 |
|  | Hs00970537_m1 | 3.6E−11 | 0.97 | 3 |
| CXCL10 | Hs01124251_g1 | 8.9E−07 | 0.92 | 3 |
|  | Hs01124252_g1 | 8.1E−12 | 0.98 | 3 |
| CXCL13 | Hs00757930_m1 | 4.0E−10 | 0.96 | 3 |
|  | Hs99999094_m1 | 4.5E−09 | 0.95 | 3 |
| S100A9 | Hs00610058_m1 | 6.1E−05 | 0.82 | 3 |
| SERPINB4 | Hs00741313_g1 | 1.6E−01 | 0.65 | 3 |
| CCL19 | Hs00171149_m1 | 8.3E−02 | 0.64 | 3 |
| CCL5 | Hs00174575_m1 | 1.5E−10 | 0.96 | 3 |
| CD38 | Hs01120071_m1 | 2.2E−09 | 0.95 | 3 |
| CXCL12 | Hs00171022_m1 | 3.5E−01 | 0.58 | 3 |
| HCLS1 | Hs00945386_m1 | 1.1E−03 | 0.76 | 3 |
| HLA-DMA | Hs00185435_m1 | 3.7E−04 | 0.78 | 3 |
| HLA-DPA1 | Hs01072899_m1 | 3.8E−02 | 0.67 | 3 |
| HLA-DPB1 | Hs00157955_m1 | 2.9E−01 | 0.59 | 3 |
| HLA-DRA | Hs00219575_m1 | 6.4E−04 | 0.77 | 3 |
| HLA-E | Hs03045171_m1 | 1.1E−01 | 0.63 | 3 |
| IGHM | Hs00378435_m1 | 1.8E−02 | 0.76 | 3 |
| IGJ | Ha00950678_g1 | 5.2E−03 | 0.73 | 3 |
| IGLL5; CKAP2 | Hs00382306_m1 | 1.8E−01 | 0.64 | 3 |
| IRF1 | Hs00971966_g1 | 2.0E−08 | 0.92 | 3 |
| IRF4 | Hs00180031_m1 | 2.4E−02 | 0.69 | 3 |
| ITGB2 | Hs01051739_m1 | 1.7E−05 | 0.84 | 3 |
| PECAM1 | Hs00169777_m1 | 1.8E−03 | 0.75 | 3 |
| PTPN22 | Hs00249262_m1 | 1.4E−05 | 0.84 | 3 |
| PTPRC | Hs00894732_m1 | 1.5E−04 | 0.80 | 3 |
| SELL | Hs01046459_m1 | 9.0E−09 | 0.93 | 3 |

Figure 3A:
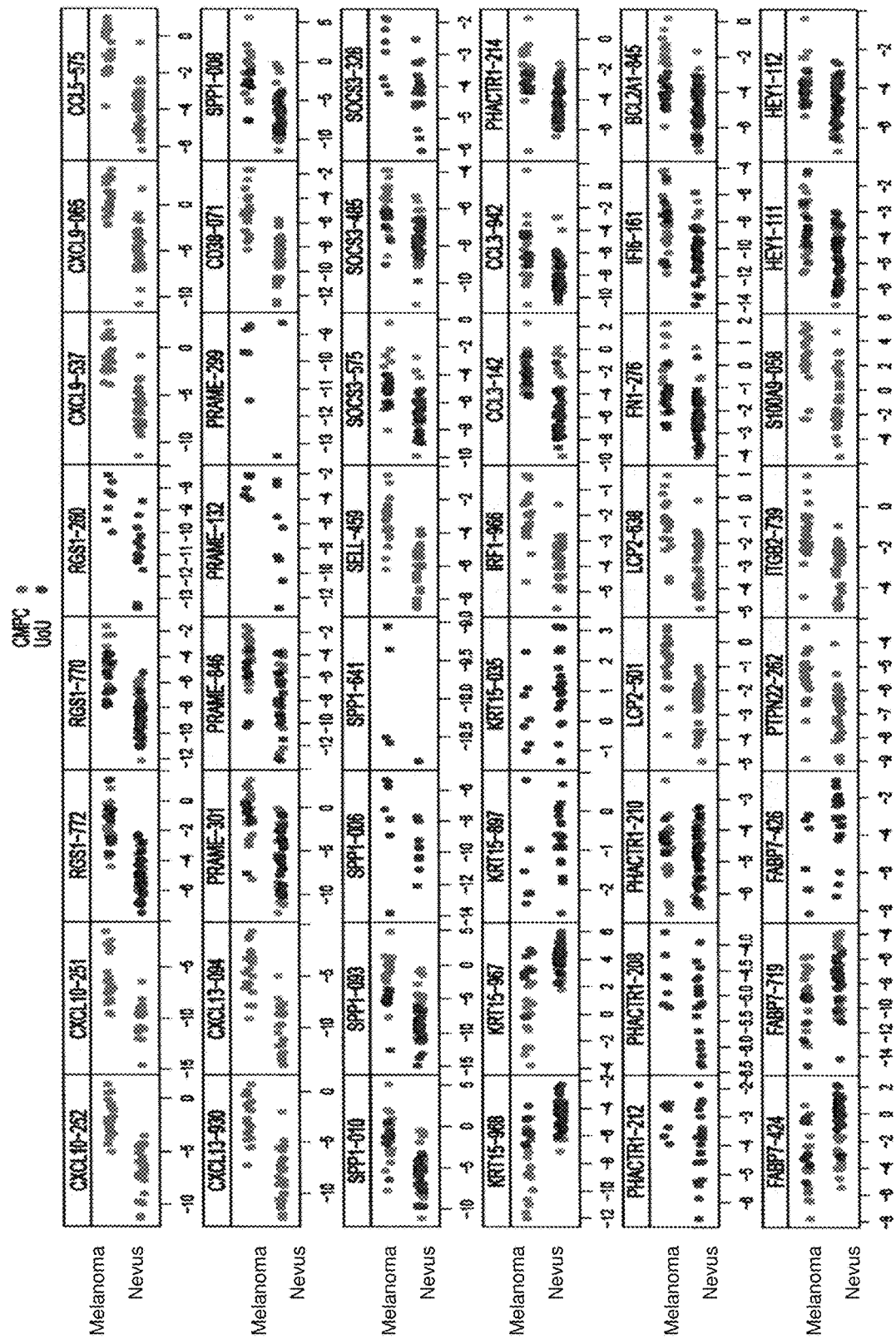
FIG. 3A shows the distributions of all 88 individual amplicon assays tested in Rounds 1, 2, and 3 of biomarker discovery. The analysis was performed on 30 Group 1 samples (black circles) and 53 Group 2 samples (grey circles).
Figure 3B:
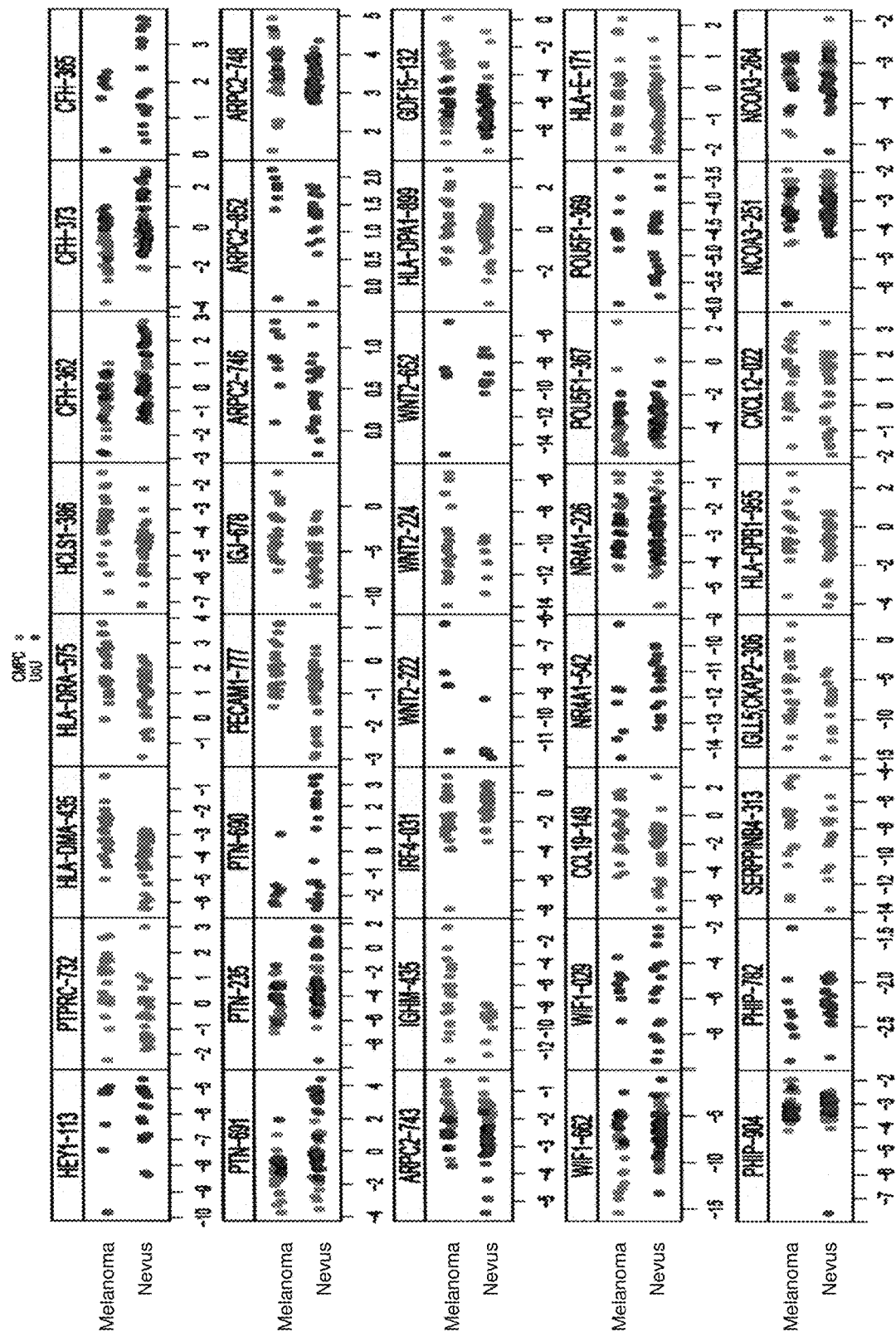
FIG. 3B shows the distributions of all 88 individual amplicon assays tested in Rounds 1, 2, and 3 of biomarker discovery. The analysis was performed on 30 Group 1 samples (black circles) and 53 Group 2 samples (grey circles).
Figure 4A:
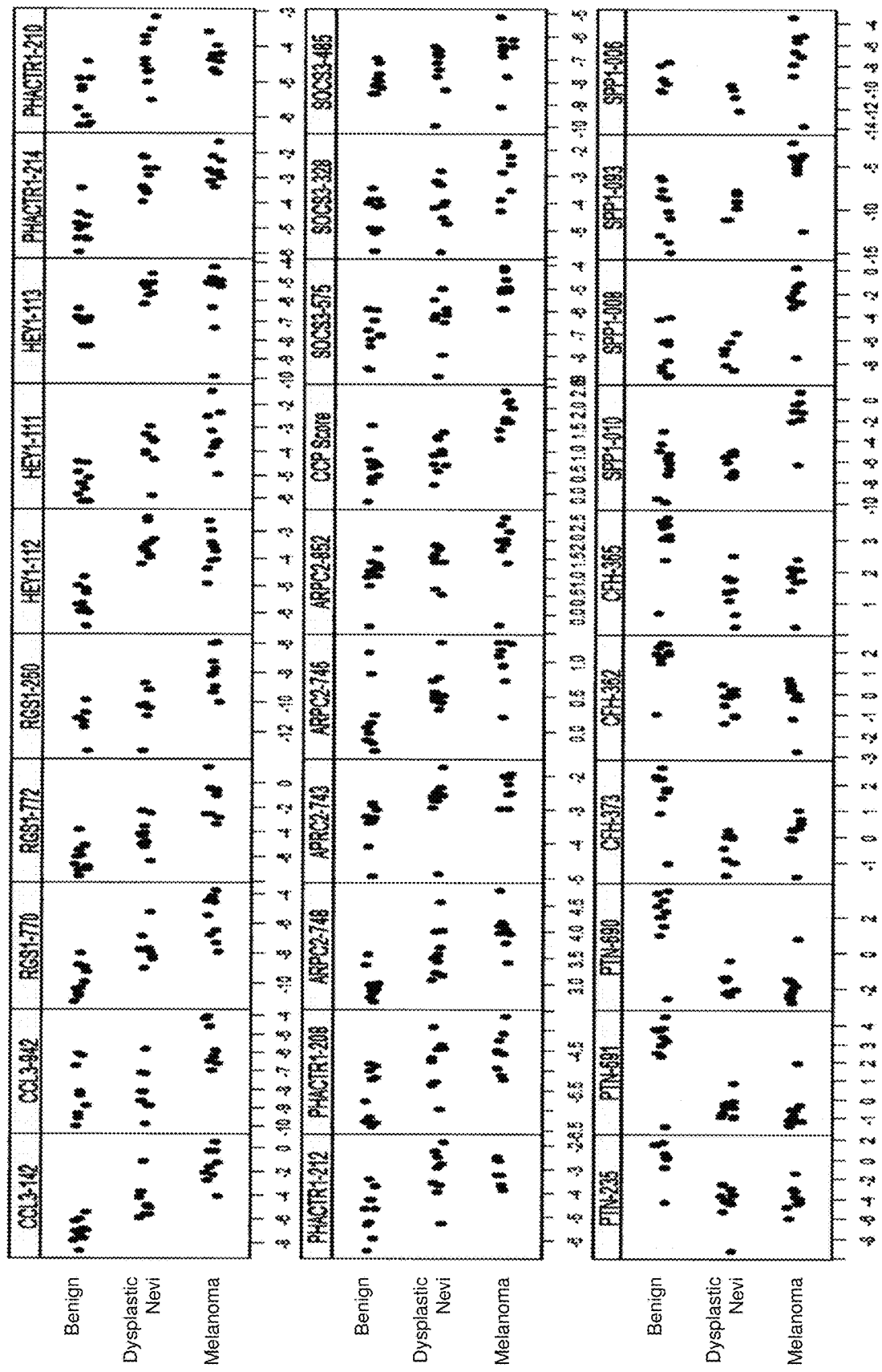
FIG. 4A shows distributions of each individual amplicon tested in Round 1 and 2 of biomarker discovery. Samples are differentiated based on their pathological subtype on the Y-axis. The relative expression (Ct) of each gene (compared to the expression of the housekeeper genes) is graphed on the X-axis. Each amplicon is identified by the gene name and the last three digits of the assay ID.
Figure 4B:
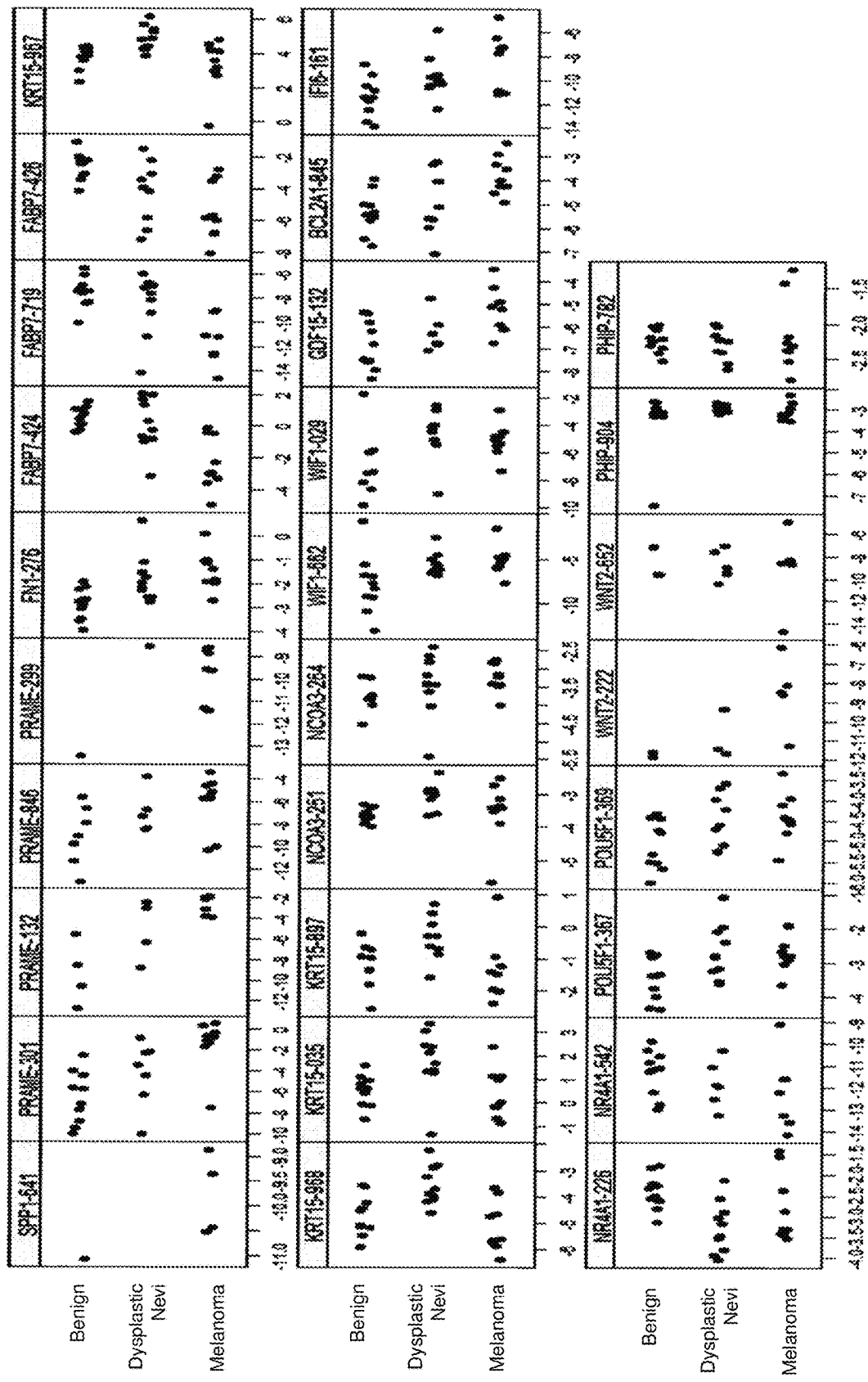
FIG. 4B shows distributions of each individual amplicon tested in Round 1 and 2 of biomarker discovery. Samples are differentiated based on their pathological subtype on the Y-axis. The relative expression (Ct) of each gene (compared to the expression of the housekeeper genes) is graphed on the X-axis. Each amplicon is identified by the gene name and the last three digits of the assay ID.

FIG. 3 shows the distribution of all amplicons tested in all three rounds of biomarker discovery. Samples are differentiated based on diagnosis on the Y-axis. The relative expression (Ct) of each gene (compared to the expression of the housekeeper genes) is graphed on the X axis FIG. 4 shows the distributions of each individual amplicon tested in rounds one and two of biomarker discovery. Samples are differentiated based on their pathological subtype on the Y axis. The relative expression (Ct) of each gene (compared to the expression of the housekeeper genes) is graphed on the X axis. Each amplicon is identified by the gene and the last three digits of the assay ID Discussion These data strongly indicate that expression of specific biomarker genes can be used to differentiate malignant melanoma from non-malignant nevi. Nonetheless, a larger dataset is needed to determine with higher confidence how effective each individual biomarker is in differentiating melanoma, as well as to determine how heavily each biomarker would need to be weighted in a diagnostic model.

Table 10 lists the best performing assay/amplicon of each biomarkers determined by its AUC, P-value, and lack of missing data. P-values are Wilcoxon Rank Sum P-values. P-values and AUC indicate differentiation of all melanomas subtypes from all nevi subtypes.

TABLE 10

| Gene | Assay_ID | P-Value | AUC |
|---|---|---|---|
| CXCL10 | Hs01124252_g1 | 8.1E−12 | 0.98 |
| CXCL9 | Hs0171065_m1 | 4.7E−11 | 0.97 |
| CXCL13 | Hs00757930_m1 | 4.0E−10 | 0.96 |
| CCL5 | Hs00174575_m1 | 1.5E−10 | 0.96 |
| RGS1 | Hs01023772_m1 | 1.0E−11 | 0.95 |
| CD38 | Hs01120071_m1 | 2.2E−09 | 0.95 |
| SELL | Hs01046459_m1 | 9.0E−09 | 0.93 |
| IRF1 | Hs00971966_g1 | 2.0E−08 | 0.92 |
| SPP1 | Hs00959010_m1 | 5.3E−09 | 0.89 |
| PRAME | Hs01022301_m1 | 1.3E−09 | 0.89 |
| KRT15 | Hs00951967_g1 | 1.3E−08 | 0.89 |
| LCP2 | Hs00175501_m1 | 2.2E−07 | 0.89 |
| CCL3 (MIP-1α) | Hs00234142_m1 | 5.3E−08 | 0.87 |
| PHACTR1 | Hs01116217_m1 | 2.1E−07 | 0.86 |
| ITGB2 | Hs01051739_m1 | 1.7E−05 | 0.84 |
| PTPN22 | Hs00249262_m1 | 1.4E−05 | 0.84 |
| FN1 | Hs01565276_m1 | 1.3E−06 | 0.82 |
| S100A9 | Hs00610058_m1 | 6.1E−05 | 0.82 |
| IFI6 | Hs01564161_m1 | 3.8E−06 | 0.81 |
| BCL2A1 | Hs00187845_m1 | 8.7E−06 | 0.80 |
| FABP7 | Hs00361424_g1 | 1.2E−05 | 0.80 |
| PTPRC | Hs00894732_m1 | 1.5E−04 | 0.80 |
| HLA-DMA | Hs00185435_m1 | 3.7E−04 | 0.78 |
| HLA-DRA | Hs00219575_m1 | 6.4E−04 | 0.77 |
| HCLS1 | Hs00945386_m1 | 1.1E−03 | 0.76 |
| PECAM1 | Hs00169777_m1 | 1.8E−03 | 0.75 |
| HEY1 | Hs01114112_g1 | 4.5E−04 | 0.74 |
| IGJ | Ha00950678_g1 | 5.2E−03 | 0.73 |
| CFH | Hs00962362_g1 | 1.4E−03 | 0.72 |
| PTN | Hs01085691_m1 | 1.4E−03 | 0.72 |

Example 4

P-values were calculated for distinguishing melanoma from nevi for all combinations of two, three, and four genes from Panel I with data from the same samples used above. Firth's logistic regression was used to assign the best weights to each of the genes in each combination. The p-values were calculated using a likelihood ratio test comparing a model containing all genes in each combination with a reduced model containing no predictor variables. The number of samples with data for all genes in each combination and whether the combination contains CCP genes, other genes, or a mix of CCP and other genes are included in the results.

Additionally, p-values were calculated for average CCP expression of all combinations of one to ten of the CCP genes in panel C as continuing to the next stage for use in a potential training set. The average of each combination of CCP genes was calculated and a t-test was performed to test for a difference in average expression between melanomas and nevi.

Table WW contains the results for the combinations of between one and 4 CCP gene averages. Table XX contains the results for all combinations of two genes. Table YY contains the results for the top 500 combinations of three genes. Table ZZ contains the results for the top 500 combinations of four genes.

TABLE WW

| n.genes | genes | pval |
|---|---|---|
| 1 | C18orf24 | 3.23E−08 |
| 1 | PBK | 2.72E−06 |
| 1 | PLK1 | 2.16E−07 |
| 1 | DLGAP5 | 1.32E−06 |
| 1 | FOXM1 | 2.80E−07 |
| 1 | MCM10 | 1.57E−06 |
| 1 | CEP55 | 2.25E−06 |
| 1 | RRM2 | 2.71E−05 |
| 1 | DTL | 2.13E−07 |
| 1 | CENPF | 1.70E−05 |
| 2 | C18orf24 PBK | 1.19E−07 |
| 2 | C18orf24 PLK1 | 2.00E−08 |
| 2 | C18orf24 DLGAP5 | 4.51E−09 |
| 2 | C18orf24 FOXM1 | 4.70E−08 |
| 2 | C18orf24 MCM10 | 6.76E−09 |
| 2 | C18orf24 CEP55 | 4.70E−09 |
| 2 | C18orf24 RRM2 | 3.08E−07 |
| 2 | C18orf24 DTL | 3.42E−09 |
| 2 | C18orf24 CENPF | 2.64E−07 |
| 2 | PBK PLK1 | 3.48E−07 |
| 2 | PBK DLGAP5 | 3.93E−07 |
| 2 | PBK FOXM1 | 3.73E−07 |
| 2 | PBK MCM10 | 3.39E−07 |
| 2 | PBK CEP55 | 1.09E−07 |
| 2 | PBK RRM2 | 1.67E−06 |
| 2 | PBK DTL | 2.68E−07 |
| 2 | PBK CENPF | 5.39E−06 |
| 2 | PLK1 DLGAP5 | 1.17E−07 |
| 2 | PLK1 FOXM1 | 2.12E−07 |
| 2 | PLK1 MCM10 | 1.10E−07 |
| 2 | PLK1 CEP55 | 1.02E−07 |
| 2 | PLK1 RRM2 | 8.79E−07 |
| 2 | PLK1 DTL | 9.73E−08 |
| 2 | PLK1 CENPF | 1.17E−06 |
| 2 | DLGAP5 FOXM1 | 9.55E−08 |
| 2 | DLGAP5 MCM10 | 7.54E−08 |
| 2 | DLGAP5 CEP55 | 4.09E−07 |
| 2 | DLGAP5 RRM2 | 1.61E−06 |
| 2 | DLGAP5 DTL | 1.12E−07 |
| 2 | DLGAP5 CENPF | 1.86E−06 |
| 2 | FOXM1 MCM10 | 1.24E−07 |
| 2 | FOXM1 CEP55 | 6.29E−08 |
| 2 | FOXM1 RRM2 | 3.72E−07 |
| 2 | FOXM1 DTL | 3.19E−08 |
| 2 | FOXM1 CENPF | 1.22E−06 |
| 2 | MCM10 CEP55 | 4.51E−08 |
| 2 | MCM10 RRM2 | 7.02E−07 |
| 2 | MCM10 DTL | 1.11E−07 |
| 2 | MCM10 CENPF | 1.06E−06 |
| 2 | CEP55 RRM2 | 1.29E−06 |
| 2 | CEP55 DTL | 8.42E−08 |
| 2 | CEP55 CENPF | 1.23E−06 |
| 2 | RRM2 DTL | 1.10E−06 |
| 2 | RRM2 CENPF | 1.24E−05 |
| 2 | DTL CENPF | 1.44E−06 |
| 3 | C18orf24 PBK PLK1 | 6.42E−08 |
| 3 | C18orf24 PBK DLGAP5 | 3.31E−08 |
| 3 | C18orf24 PBK FOXM1 | 8.71E−08 |
| 3 | C18orf24 PBK MCM10 | 3.72E−08 |
| 3 | C18orf24 PBK CEP55 | 2.45E−08 |
| 3 | C18orf24 PBK RRM2 | 2.18E−07 |
| 3 | C18orf24 PBK DTL | 3.29E−08 |
| 3 | C18orf24 PBK CENPF | 5.36E−07 |

TABLE WW-continued

| n.genes | genes | pval |
|---|---|---|
| 3 | C18orf24 PLK1 DLGAP5 | 1.15E−08 |
| 3 | C18orf24 PLK1 FOXM1 | 4.55E−08 |
| 3 | C18orf24 PLK1 MCM10 | 1.24E−08 |
| 3 | C18orf24 PLK1 CEP55 | 1.12E−08 |
| 3 | C18orf24 PLK1 RRM2 | 1.10E−07 |
| 3 | C18orf24 PLK1 DTL | 1.18E−08 |
| 3 | C18orf24 PLK1 CENPF | 1.28E−07 |
| 3 | C18orf24 DLGAP5 FOXM1 | 1.38E−08 |
| 3 | C18orf24 DLGAP5 MCM10 | 3.59E−09 |
| 3 | C18orf24 DLGAP5 CEP55 | 6.49E−09 |
| 3 | C18orf24 DLGAP5 RRM2 | 6.24E−08 |
| 3 | C18orf24 DLGAP5 DTL | 3.98E−09 |
| 3 | C18orf24 DLGAP5 CENPF | 1.01E−07 |
| 3 | C18orf24 FOXM1 MCM10 | 2.06E−08 |
| 3 | C18orf24 FOXM1 CEP55 | 1.68E−08 |
| 3 | C18orf24 FOXM1 RRM2 | 9.04E−08 |
| 3 | C18orf24 FOXM1 DTL | 9.34E−09 |
| 3 | C18orf24 FOXM1 CENPF | 2.06E−07 |
| 3 | C18orf24 MCM10 CEP55 | 4.69E−09 |
| 3 | C18orf24 MCM10 RRM2 | 5.26E−08 |
| 3 | C18orf24 MCM10 DTL | 4.24E−09 |
| 3 | C18orf24 MCM10 CENPF | 7.72E−08 |
| 3 | C18orf24 CEP55 RRM2 | 6.49E−08 |
| 3 | C18orf24 CEP55 DTL | 3.18E−09 |
| 3 | C18orf24 CEP55 CENPF | 5.69E−08 |
| 3 | C18orf24 RRM2 DTL | 6.20E−08 |
| 3 | C18orf24 RRM2 CENPF | 7.48E−07 |
| 3 | C18orf24 DTL CENPF | 7.84E−08 |
| 3 | PBK PLK1 DLGAP5 | 1.43E−07 |
| 3 | PBK PLK1 FOXM1 | 2.22E−07 |
| 3 | PBK PLK1 MCM10 | 1.37E−07 |
| 3 | PBK PLK1 CEP55 | 9.21E−08 |
| 3 | PBK PLK1 RRM2 | 4.62E−07 |
| 3 | PBK PLK1 DTL | 1.54E−07 |
| 3 | PBK PLK1 CENPF | 1.19E−06 |
| 3 | PBK DLGAP5 FOXM1 | 1.61E−07 |
| 3 | PBK DLGAP5 MCM10 | 1.29E−07 |
| 3 | PBK DLGAP5 CEP55 | 9.22E−08 |
| 3 | PBK DLGAP5 RRM2 | 4.94E−07 |
| 3 | PBK DLGAP5 DTL | 1.22E−07 |
| 3 | PBK DLGAP5 CENPF | 1.02E−06 |
| 3 | PBK FOXM1 MCM10 | 1.67E−07 |
| 3 | PBK FOXM1 CEP55 | 1.00E−07 |
| 3 | PBK FOXM1 RRM2 | 3.36E−07 |
| 3 | PBK FOXM1 DTL | 1.06E−07 |
| 3 | PBK FOXM1 CENPF | 1.15E−06 |
| 3 | PBK MCM10 CEP55 | 5.92E−08 |
| 3 | PBK MCM10 RRM2 | 3.66E−07 |
| 3 | PBK MCM10 DTL | 1.10E−07 |
| 3 | PBK MCM10 CENPF | 1.06E−06 |
| 3 | PBK CEP55 RRM2 | 2.83E−07 |
| 3 | PBK CEP55 DTL | 5.70E−08 |
| 3 | PBK CEP55 CENPF | 6.18E−07 |
| 3 | PBK RRM2 DTL | 4.40E−07 |
| 3 | PBK RRM2 CENPF | 3.26E−06 |
| 3 | PBK DTL CENPF | 1.13E−06 |
| 3 | PLK1 DLGAP5 FOXM1 | 8.52E−08 |
| 3 | PLK1 DLGAP5 MCM10 | 4.43E−08 |
| 3 | PLK1 DLGAP5 CEP55 | 9.78E−08 |
| 3 | PLK1 DLGAP5 RRM2 | 3.26E−07 |
| 3 | PLK1 DLGAP5 DTL | 7.28E−08 |
| 3 | PLK1 DLGAP5 CENPF | 6.07E−07 |
| 3 | PLK1 FOXM1 MCM10 | 1.02E−07 |
| 3 | PLK1 FOXM1 CEP55 | 8.13E−08 |
| 3 | PLK1 FOXM1 RRM2 | 2.37E−07 |
| 3 | PLK1 FOXM1 DTL | 6.80E−08 |
| 3 | PLK1 FOXM1 CENPF | 5.69E−07 |
| 3 | PLK1 MCM10 CEP55 | 4.23E−08 |
| 3 | PLK1 MCM10 RRM2 | 2.06E−07 |
| 3 | PLK1 MCM10 DTL | 6.45E−08 |
| 3 | PLK1 MCM10 CENPF | 3.81E−07 |
| 3 | PLK1 CEP55 RRM2 | 3.20E−07 |
| 3 | PLK1 CEP55 DTL | 5.89E−08 |
| 3 | PLK1 CEP55 CENPF | 3.85E−07 |
| 3 | PLK1 RRM2 DTL | 3.02E−07 |
| 3 | PLK1 RRM2 CENPF | 1.92E−06 |
| 3 | PLK1 DTL CENPF | 4.81E−07 |
| 3 | DLGAP5 FOXM1 MCM10 | 5.28E−08 |

TABLE WW-continued

| n.genes | genes | pval |
|---|---|---|
| 3 | DLGAP5 FOXM1 CEP55 | 5.47E-08 |
| 3 | DLGAP5 FOXM1 RRM2 | 1.71E-07 |
| 3 | DLGAP5 FOXM1 DTL | 3.33E-08 |
| 3 | DLGAP5 FOXM1 CENPF | 3.81E-07 |
| 3 | DLGAP5 MCM10 CEP55 | 3.16E-08 |
| 3 | DLGAP5 MCM10 RRM2 | 1.85E-07 |
| 3 | DLGAP5 MCM10 DTL | 3.39E-08 |
| 3 | DLGAP5 MCM10 CENPF | 2.95E-07 |
| 3 | DLGAP5 CEP55 RRM2 | 5.67E-07 |
| 3 | DLGAP5 CEP55 DTL | 9.06E-08 |
| 3 | DLGAP5 CEP55 CENPF | 6.16E-07 |
| 3 | DLGAP5 RRM2 DTL | 3.77E-07 |
| 3 | DLGAP5 RRM2 CENPF | 2.36E-06 |
| 3 | DLGAP5 DTL CENPF | 5.59E-07 |
| 3 | FOXM1 MCM10 CEP55 | 4.29E-08 |
| 3 | FOXM1 MCM10 RRM2 | 1.31E-07 |
| 3 | FOXM1 MCM10 DTL | 3.20E-08 |
| 3 | FOXM1 MCM10 CENPF | 3.91E-07 |
| 3 | FOXM1 CEP55 RRM2 | 1.49E-07 |
| 3 | FOXM1 CEP55 DTL | 2.40E-08 |
| 3 | FOXM1 CEP55 CENPF | 2.83E-07 |
| 3 | FOXM1 RRM2 DTL | 1.14E-07 |
| 3 | FOXM1 RRM2 CENPF | 1.17E-06 |
| 3 | FOXM1 DTL CENPF | 3.00E-07 |
| 3 | MCM10 CEP55 RRM2 | 1.25E-07 |
| 3 | MCM10 CEP55 DTL | 2.08E-08 |
| 3 | MCM10 CEP55 CENPF | 1.94E-07 |
| 3 | MCM10 RRM2 DTL | 2.08E-07 |
| 3 | MCM10 RRM2 CENPF | 1.29E-06 |
| 3 | MCM10 DTL CENPF | 3.12E-07 |
| 3 | CEP55 RRM2 DTL | 3.03E-07 |
| 3 | CEP55 RRM2 CENPF | 1.91E-06 |
| 3 | CEP55 DTL CENPF | 3.68E-07 |
| 3 | RRM2 DTL CENPF | 2.18E-06 |
| 4 | C18orf24 PBK PLK1 DLGAP5 | 3.34E-08 |
| 4 | C18orf24 PBK PLK1 FOXM1 | 7.43E-08 |
| 4 | C18orf24 PBK PLK1 MCM10 | 3.44E-08 |
| 4 | C18orf24 PBK PLK1 CEP55 | 2.85E-08 |
| 4 | C18orf24 PBK PLK1 RRM2 | 1.24E-07 |
| 4 | C18orf24 PBK PLK1 DTL | 3.58E-08 |
| 4 | C18orf24 PBK PLK1 CENPF | 2.47E-07 |
| 4 | C18orf24 PBK DLGAP5 FOXM1 | 3.79E-08 |
| 4 | C18orf24 PBK DLGAP5 MCM10 | 1.94E-08 |
| 4 | C18orf24 PBK DLGAP5 CEP55 | 2.06E-08 |
| 4 | C18orf24 PBK DLGAP5 RRM2 | 8.84E-08 |
| 4 | C18orf24 PBK DLGAP5 DTL | 2.07E-08 |
| 4 | C18orf24 PBK DLGAP5 CENPF | 1.83E-07 |
| 4 | C18orf24 PBK FOXM1 MCM10 | 4.65E-08 |
| 4 | C18orf24 PBK FOXM1 CEP55 | 3.71E-08 |
| 4 | C18orf24 PBK FOXM1 RRM2 | 1.12E-07 |
| 4 | C18orf24 PBK FOXM1 DTL | 3.40E-08 |
| 4 | C18orf24 PBK FOXM1 CENPF | 2.99E-07 |
| 4 | C18orf24 PBK MCM10 CEP55 | 1.61E-08 |
| 4 | C18orf24 PBK MCM10 RRM2 | 7.76E-08 |
| 4 | C18orf24 PBK MCM10 DTL | 1.92E-08 |
| 4 | C18orf24 PBK MCM10 CENPF | 1.85E-07 |
| 4 | C18orf24 PBK CEP55 RRM2 | 7.78E-08 |
| 4 | C18orf24 PBK CEP55 DTL | 1.55E-08 |
| 4 | C18orf24 PBK CEP55 CENPF | 1.35E-07 |
| 4 | C18orf24 PBK RRM2 DTL | 8.96E-08 |
| 4 | C18orf24 PBK RRM2 CENPF | 6.27E-08 |
| 4 | C18orf24 PBK DTL CENPF | 1.93E-07 |
| 4 | C18orf24 PLK1 DLGAP5 FOXM1 | 2.31E-08 |
| 4 | C18orf24 PLK1 DLGAP5 MCM10 | 8.15E-09 |
| 4 | C18orf24 PLK1 DLGAP5 CEP55 | 1.21E-08 |
| 4 | C18orf24 PLK1 DLGAP5 RRM2 | 5.15E-08 |
| 4 | C18orf24 PLK1 DLGAP5 DTL | 1.01E-08 |
| 4 | C18orf24 PLK1 DLGAP5 CENPF | 8.24E-08 |
| 4 | C18orf24 PLK1 FOXM1 MCM10 | 2.72E-08 |
| 4 | C18orf24 PLK1 FOXM1 CEP55 | 2.47E-08 |
| 4 | C18orf24 PLK1 FOXM1 RRM2 | 7.73E-08 |
| 4 | C18orf24 PLK1 FOXM1 DTL | 1.96E-08 |
| 4 | C18orf24 PLK1 FOXM1 CENPF | 1.43E-07 |
| 4 | C18orf24 PLK1 MCM10 CEP55 | 9.51E-09 |
| 4 | C18orf24 PLK1 MCM10 RRM2 | 4.38E-08 |
| 4 | C18orf24 PLK1 MCM10 DTL | 9.86E-09 |
| 4 | C18orf24 PLK1 MCM10 CENPF | 6.72E-08 |
| 4 | C18orf24 PLK1 CEP55 RRM2 | 5.21E-08 |
| 4 | C18orf24 PLK1 CEP55 DTL | 9.01E-09 |
| 4 | C18orf24 PLK1 CEP55 CENPF | 5.77E-08 |
| 4 | C18orf24 PLK1 RRM2 DTL | 5.41E-08 |
| 4 | C18orf24 PLK1 RRM2 CENPF | 3.11E-07 |
| 4 | C18orf24 PLK1 DTL CENPF | 7.33E-08 |
| 4 | C18orf24 DLGAP5 FOXM1 MCM10 | 1.04E-08 |
| 4 | C18orf24 DLGAP5 FOXM1 CEP55 | 1.41E-08 |
| 4 | C18orf24 DLGAP5 FOXM1 RRM2 | 4.18E-08 |
| 4 | C18orf24 DLGAP5 FOXM1 DTL | 8.19E-09 |
| 4 | C18orf24 DLGAP5 FOXM1 CENPF | 8.90E-08 |
| 4 | C18orf24 DLGAP5 MCM10 CEP55 | 5.09E-08 |
| 4 | C18orf24 DLGAP5 MCM10 RRM2 | 2.53E-08 |
| 4 | C18orf24 DLGAP5 MCM10 DTL | 3.79E-09 |
| 4 | C18orf24 DLGAP5 MCM10 CENPF | 4.23E-08 |
| 4 | C18orf24 DLGAP5 CEP55 RRM2 | 4.01E-08 |
| 4 | C18orf24 DLGAP5 CEP55 DTL | 5.40E-09 |
| 4 | C18orf24 DLGAP5 CEP55 CENPF | 5.34E-08 |
| 4 | C18orf24 DLGAP5 RRM2 DTL | 3.30E-08 |
| 4 | C18orf24 DLGAP5 RRM2 CENPF | 2.57E-07 |
| 4 | C18orf24 DLGAP5 DTL CENPF | 5.41E-08 |
| 4 | C18orf24 FOXM1 MCM10 CEP55 | 1.24E-08 |
| 4 | C18orf24 FOXM1 MCM10 RRM2 | 3.92E-08 |
| 4 | C18orf24 FOXM1 MCM10 DTL | 8.06E-09 |
| 4 | C18orf24 FOXM1 MCM10 CENPF | 9.12E-08 |
| 4 | C18orf24 FOXM1 CEP55 RRM2 | 4.91E-08 |
| 4 | C18orf24 FOXM1 CEP55 DTL | 8.24E-09 |
| 4 | C18orf24 FOXM1 CEP55 CENPF | 7.57E-08 |
| 4 | C18orf24 FOXM1 RRM2 DTL | 3.49E-08 |
| 4 | C18orf24 FOXM1 RRM2 CENPF | 2.98E-07 |
| 4 | C18orf24 FOXM1 DTL CENPF | 7.30E-08 |
| 4 | C18orf24 MCM10 CEP55 RRM2 | 2.65E-08 |
| 4 | C18orf24 MCM10 CEP55 DTL | 3.76E-09 |
| 4 | C18orf24 MCM10 CEP55 CENPF | 3.47E-08 |
| 4 | C18orf24 MCM10 RRM2 DTL | 2.74E-08 |
| 4 | C18orf24 MCM10 RRM2 CENPF | 2.03E-07 |
| 4 | C18orf24 MCM10 DTL CENPF | 4.00E-08 |
| 4 | C18orf24 CEP55 RRM2 DTL | 3.00E-08 |
| 4 | C18orf24 CEP55 RRM2 CENPF | 2.15E-07 |
| 4 | C18orf24 CEP55 DTL CENPF | 3.57E-08 |
| 4 | C18orf24 RRM2 DTL CENPF | 2.44E-07 |
| 4 | PBK PLK1 DLGAP5 FOXM1 | 1.14E-07 |
| 4 | PBK PLK1 DLGAP5 MCM10 | 7.66E-08 |
| 4 | PBK PLK1 DLGAP5 CEP55 | 7.68E-08 |
| 4 | PBK PLK1 DLGAP5 RRM2 | 2.27E-07 |
| 4 | PBK PLK1 DLGAP5 DTL | 9.18E-08 |
| 4 | PBK PLK1 DLGAP5 CENPF | 4.87E-07 |
| 4 | PBK PLK1 FOXM1 MCM10 | 1.25E-07 |
| 4 | PBK PLK1 FOXM1 CEP55 | 1.00E-07 |
| 4 | PBK PLK1 FOXM1 RRM2 | 2.25E-07 |
| 4 | PBK PLK1 FOXM1 DTL | 1.07E-07 |
| 4 | PBK PLK1 FOXM1 CENPF | 6.01E-07 |
| 4 | PBK PLK1 MCM10 CEP55 | 5.77E-08 |
| 4 | PBK PLK1 MCM10 RRM2 | 1.86E-07 |
| 4 | PBK PLK1 MCM10 DTL | 8.38E-08 |
| 4 | PBK PLK1 MCM10 CENPF | 4.59E-07 |
| 4 | PBK PLK1 CEP55 RRM2 | 1.80E-07 |
| 4 | PBK PLK1 CEP55 DTL | 6.39E-08 |
| 4 | PBK PLK1 CEP55 CENPF | 3.40E-07 |
| 4 | PBK PLK1 RRM2 DTL | 2.40E-07 |
| 4 | PBK PLK1 RRM2 CENPF | 1.14E-06 |
| 4 | PBK PLK1 DTL CENPF | 5.16E-07 |
| 4 | PBK DLGAP5 FOXM1 MCM10 | 9.06E-08 |
| 4 | PBK DLGAP5 FOXM1 CEP55 | 7.63E-08 |
| 4 | PBK DLGAP5 FOXM1 RRM2 | 1.94E-07 |
| 4 | PBK DLGAP5 FOXM1 DTL | 7.27E-08 |
| 4 | PBK DLGAP5 FOXM1 CENPF | 4.29E-07 |
| 4 | PBK DLGAP5 MCM10 CEP55 | 5.18E-08 |
| 4 | PBK DLGAP5 MCM10 RRM2 | 1.87E-07 |
| 4 | PBK DLGAP5 MCM10 DTL | 6.58E-08 |
| 4 | PBK DLGAP5 MCM10 CENPF | 3.75E-07 |
| 4 | PBK DLGAP5 CEP55 RRM2 | 1.76E-07 |
| 4 | PBK DLGAP5 CEP55 DTL | 5.50E-08 |
| 4 | PBK DLGAP5 CEP55 CENPF | 3.43E-07 |
| 4 | PBK DLGAP5 RRM2 DTL | 2.16E-07 |
| 4 | PBK DLGAP5 RRM2 CENPF | 1.03E-06 |
| 4 | PBK DLGAP5 DTL CENPF | 4.40E-07 |
| 4 | PBK FOXM1 MCM10 CEP55 | 6.51E-08 |
| 4 | PBK FOXM1 MCM10 RRM2 | 1.60E-07 |

TABLE WW-continued

| n.genes | genes | pval |
|---|---|---|
| 4 | PBK FOXM1 MCM10 DTL | 6.86E-08 |
| 4 | PBK FOXM1 MCM10 CENPF | 4.74E-07 |
| 4 | PBK FOXM1 CEP55 RRM2 | 1.47E-07 |
| 4 | PBK FOXM1 CEP55 DTL | 5.24E-08 |
| 4 | PBK FOXM1 CEP55 CENPF | 3.57E-07 |
| 4 | PBK FOXM1 RRM2 DTL | 1.53E-07 |
| 4 | PBK FOXM1 RRM2 CENPF | 9.03E-07 |
| 4 | PBK FOXM1 DTL CENPF | 4.25E-07 |
| 4 | PBK MCM10 CEP55 RRM2 | 1.17E-07 |
| 4 | PBK MCM10 CEP55 DTL | 3.76E-08 |
| 4 | PBK MCM10 CEP55 CENPF | 2.62E-07 |
| 4 | PBK MCM10 RRM2 DTL | 1.76E-07 |
| 4 | PBK MCM10 RRM2 CENPF | 9.20E-07 |
| 4 | PBK MCM10 DTL CENPF | 3.94E-07 |
| 4 | PBK CEP55 RRM2 DTL | 1.42E-07 |
| 4 | PBK CEP55 RRM2 CENPF | 8.19E-07 |
| 4 | PBK CEP55 DTL CENPF | 2.93E-07 |
| 4 | PBK RRM2 DTL CENPF | 1.11E-06 |
| 4 | PLK1 DLGAP5 FOXM1 MCM10 | 5.28E-08 |
| 4 | PLK1 DLGAP5 FOXM1 CEP55 | 6.35E-08 |
| 4 | PLK1 DLGAP5 FOXM1 RRM2 | 1.29E-07 |
| 4 | PLK1 DLGAP5 FOXM1 DTL | 4.89E-08 |
| 4 | PLK1 DLGAP5 FOXM1 CENPF | 2.84E-07 |
| 4 | PLK1 DLGAP5 MCM10 CEP55 | 3.45E-08 |
| 4 | PLK1 DLGAP5 MCM10 RRM2 | 1.02E-07 |
| 4 | PLK1 DLGAP5 MCM10 DTL | 3.53E-08 |
| 4 | PLK1 DLGAP5 MCM10 CENPF | 1.92E-07 |
| 4 | PLK1 DLGAP5 CEP55 RRM2 | 2.17E-07 |
| 4 | PLK1 DLGAP5 CEP55 DTL | 6.29E-08 |
| 4 | PLK1 DLGAP5 CEP55 CENPF | 2.99E-07 |
| 4 | PLK1 DLGAP5 RRM2 DTL | 1.79E-07 |
| 4 | PLK1 DLGAP5 RRM2 CENPF | 8.59E-07 |
| 4 | PLK1 DLGAP5 DTL CENPF | 3.16E-07 |
| 4 | PLK1 FOXM1 MCM10 CEP55 | 5.33E-08 |
| 4 | PLK1 FOXM1 MCM10 RRM2 | 1.13E-07 |
| 4 | PLK1 FOXM1 MCM10 DTL | 4.70E-08 |
| 4 | PLK1 FOXM1 MCM10 CENPF | 2.71E-07 |
| 4 | PLK1 FOXM1 CEP55 RRM2 | 1.32E-07 |
| 4 | PLK1 FOXM1 CEP55 DTL | 4.30E-08 |
| 4 | PLK1 FOXM1 CEP55 CENPF | 2.23E-07 |
| 4 | PLK1 FOXM1 RRM2 DTL | 1.16E-07 |
| 4 | PLK1 FOXM1 RRM2 CENPF | 6.11E-07 |
| 4 | PLK1 FOXM1 DTL CENPF | 2.44E-07 |
| 4 | PLK1 MCM10 CEP55 RRM2 | 9.39E-08 |
| 4 | PLK1 MCM10 CEP55 DTL | 3.03E-08 |
| 4 | PLK1 MCM10 CEP55 CENPF | 1.47E-07 |
| 4 | PLK1 MCM10 RRM2 DTL | 1.23E-07 |
| 4 | PLK1 MCM10 RRM2 CENPF | 5.31E-07 |
| 4 | PLK1 MCM10 DTL CENPF | 2.05E-07 |
| 4 | PLK1 CEP55 RRM2 DTL | 1.66E-07 |
| 4 | PLK1 CEP55 RRM2 CENPF | 7.23E-07 |
| 4 | PLK1 CEP55 DTL CENPF | 2.26E-07 |
| 4 | PLK1 RRM2 DTL CENPF | 7.86E-07 |
| 4 | DLGAP5 FOXM1 MCM10 CEP55 | 3.54E-08 |
| 4 | DLGAP5 FOXM1 MCM10 RRM2 | 8.38E-08 |
| 4 | DLGAP5 FOXM1 MCM10 DTL | 2.63E-08 |
| 4 | DLGAP5 FOXM1 MCM10 CENPF | 1.78E-07 |
| 4 | DLGAP5 FOXM1 CEP55 RRM2 | 1.03E-07 |
| 4 | DLGAP5 FOXM1 CEP55 DTL | 2.93E-08 |
| 4 | DLGAP5 FOXM1 CEP55 CENPF | 1.99E-07 |
| 4 | DLGAP5 FOXM1 RRM2 DTL | 8.20E-08 |
| 4 | DLGAP5 FOXM1 RRM2 CENPF | 4.74E-07 |
| 4 | DLGAP5 FOXM1 DTL CENPF | 1.77E-07 |
| 4 | DLGAP5 MCM10 CEP55 RRM2 | 8.27E-08 |
| 4 | DLGAP5 MCM10 CEP55 DTL | 2.04E-06 |
| 4 | DLGAP5 MCM10 CEP55 CENPF | 1.36E-07 |
| 4 | DLGAP5 MCM10 RRM2 DTL | 9.42E-08 |
| 4 | DLGAP5 MCM10 RRM2 CENPF | 4.58E-07 |
| 4 | DLGAP5 MCM10 DTL CENPF | 1.49E-07 |
| 4 | DLGAP5 CEP55 RRM2 DTL | 2.18E-07 |
| 4 | DLGAP5 CEP55 RRM2 CENPF | 9.29E-07 |
| 4 | DLGAP5 CEP55 DTL CENPF | 2.76E-07 |
| 4 | DLGAP5 RRM2 DTL CENPF | 8.77E-07 |
| 4 | FOXM1 MCM10 CEP55 RRM2 | 7.16E-08 |
| 4 | FOXM1 MCM10 CEP55 DTL | 2.05E-08 |
| 4 | FOXM1 MCM10 CEP55 CENPF | 1.51E-07 |
| 4 | FOXM1 MCM10 RRM2 DTL | 6.53E-08 |
| 4 | FOXM1 MCM10 RRM2 CENPF | 4.06E-07 |
| 4 | FOXM1 MCM10 DTL CENPF | 1.48E-07 |
| 4 | FOXM1 CEP55 RRM2 DTL | 6.90E-08 |
| 4 | FOXM1 CEP55 RRM2 CENPF | 4.43E-07 |
| 4 | FOXM1 CEP55 DTL CENPF | 1.34E-07 |
| 4 | FOXM1 RRM2 DTL CENPF | 4.26E-07 |
| 4 | MCM10 CEP55 RRM2 DTL | 6.63E-08 |
| 4 | MCM10 CEP55 RRM2 CENPF | 3.72E-07 |
| 4 | MCM10 CEP55 DTL CENPF | 1.05E-07 |
| 4 | MCM10 RRM2 DTL CENPF | 4.85E-07 |
| 4 | CEP55 RRM2 DTL CENPF | 7.19E-07 |

TABLE XX

| type | genes | pval | n |
|---|---|---|---|
| CCP | C18orf24 PBK | 2.76E-06 | 29 |
| CCP | C18orf24 PLK1 | 3.88E-06 | 29 |
| CCP | C18orf24 DLGAP5 | 1.84E-06 | 29 |
| CCP | C18orf24 FOXM1 | 1.79E-06 | 29 |
| CCP | C18orf24 MCM10 | 4.03E-06 | 29 |
| CCP | C18orf24 CEP55 | 6.28E-06 | 29 |
| CCP | C18orf24 RRM2 | 4.31E-06 | 29 |
| CCP | C18orf24 DTL | 3.78E-06 | 29 |
| CCP | C18orf24 CENPF | 4.40E-06 | 29 |
| CCP | PBK PLK1 | 3.85E-06 | 29 |
| CCP | PBK DLGAP5 | 3.79E-05 | 29 |
| CCP | PBK FOXM1 | 2.45E-05 | 29 |
| CCP | PBK MCM10 | 9.54E-06 | 29 |
| CCP | PBK CEP55 | 2.84E-06 | 29 |
| CCP | PBK RRM2 | 3.20E-05 | 29 |
| CCP | PBK DTL | 7.93E-06 | 29 |
| CCP | PBK CENPF | 3.10E-06 | 29 |
| CCP | PLK1 DLGAP5 | 3.12E-06 | 30 |
| CCP | PLK1 FOXM1 | 3.67E-06 | 29 |
| CCP | PLK1 MCM10 | 1.94E-05 | 29 |
| CCP | PLK1 CEP55 | 5.98E-06 | 30 |
| CCP | PLK1 RRM2 | 1.16E-05 | 30 |
| CCP | PLK1 DTL | 5.99E-06 | 30 |
| CCP | PLK1 CENPF | 1.72E-05 | 29 |
| CCP | DLGAP5 FOXM1 | 2.45E-05 | 29 |
| CCP | DLGAP5 MCM10 | 1.95E-06 | 29 |
| CCP | DLGAP5 CEP55 | 0.00013 | 30 |
| CCP | DLGAP5 RRM2 | 0.000132 | 30 |
| CCP | DLGAP5 DTL | 3.80E-06 | 30 |
| CCP | DLGAP5 CENPF | 1.04E-05 | 30 |
| CCP | FOXM1 MCM10 | 1.28E-05 | 29 |
| CCP | FOXM1 CEP55 | 2.57E-06 | 29 |
| CCP | FOXM1 RRM2 | 1.88E-05 | 29 |
| CCP | FOXM1 DTL | 4.61E-06 | 29 |
| CCP | FOXM1 CENPF | 2.39E-06 | 29 |
| CCP | MCM10 CEP55 | 1.51E-05 | 29 |
| CCP | MCM10 RRM2 | 4.52E-05 | 29 |
| CCP | MCM10 DTL | 5.91E-06 | 29 |
| CCP | MCM10 CENPF | 2.54E-05 | 29 |
| CCP | CEP55 RRM2 | 7.82E-05 | 30 |
| CCP | CEP55 DTL | 3.90E-06 | 30 |
| CCP | CEP55 CENPF | 2.18E-05 | 30 |
| CCP | RRM2 DTL | 4.43E-06 | 30 |
| CCP | RRM2 CENPF | 2.10E-05 | 29 |
| CCP | DTL CENPF | 7.11E-06 | 30 |
| Immune/Additional | HEY1 CXCL10 | 1.54E-10 | 50 |
| Immune/Additional | HEY1 CCL3 | 1.22E-09 | 78 |
| Immune/Additional | HEY1 FABP7 | 2.58E-07 | 79 |
| Immune/Additional | HEY1 FN1 | 1.49E-06 | 79 |
| Immune/Additional | HEY1 PTN | 0.000108 | 79 |
| Immune/Additional | HEY1 IGJ | 2.86E-06 | 50 |
| Immune/Additional | HEY1 PRAME | 6.21E-09 | 76 |
| Immune/Additional | HEY1 BCL2A1 | 2.06E-06 | 78 |
| Immune/Additional | HEY1 IFI6 | 6.07E-06 | 73 |
| Immune/Additional | HEY1 CFH | 6.34E-05 | 79 |
| Immune/Additional | HEY1 HLA | 1.91E-06 | 52 |
| Immune/Additional | HEY1 PECAM1 | 2.94E-05 | 52 |
| Immune/Additional | HEY1 PTPN22 | 2.52E-07 | 52 |
| Immune/Additional | HEY1 RGS1 | 1.44E-14 | 79 |
| Immune/Additional | HEY1 IRF1 | 5.61E-09 | 52 |

TABLE XX-continued

| type | genes | pval | n |
|---|---|---|---|
| Immune/Additional | HEY1 CCL5 | 5.43E−11 | 52 |
| Immune/Additional | HEY1 CD38 | 9.00E−11 | 49 |
| Immune/Additional | HEY1 SELL | 1.27E−10 | 52 |
| Immune/Additional | HEY1 HLA | 6.11E−06 | 52 |
| Immune/Additional | HEY1 S100A9 | 1.05E−08 | 52 |
| Immune/Additional | HEY1 ITGB2 | 4.91E−06 | 52 |
| Immune/Additional | HEY1 PTPRC | 4.07E−07 | 52 |
| Immune/Additional | HEY1 CXCL13 | 1.61E−09 | 48 |
| Immune/Additional | HEY1 PHACTR1 | 1.05E−06 | 78 |
| Immune/Additional | HEY1 SPP1 | 5.19E−10 | 78 |
| Immune/Additional | HEY1 LCP2 | 9.82E−09 | 52 |
| Immune/Additional | HEY1 KRT15 | 1.05E−11 | 79 |
| Immune/Additional | HEY1 CXCL9 | 1.84E−10 | 52 |
| Immune/Additional | HEY1 HCLS1 | 2.40E−05 | 52 |
| Immune/Additional | CXCL10 CCL3 | 2.51E−10 | 50 |
| Immune/Additional | CXCL10 FABP7 | 6.14E−11 | 50 |
| Immune/Additional | CXCL10 FN1 | 4.37E−11 | 50 |
| Immune/Additional | CXCL10 PTN | 3.58E−10 | 50 |
| Immune/Additional | CXCL10 IGJ | 2.34E−10 | 48 |
| Immune/Additional | CXCL10 PRAME | 2.26E−10 | 50 |
| Immune/Additional | CXCL10 BCL2A1 | 2.33E−10 | 50 |
| Immune/Additional | CXCL10 IFI6 | 2.64E−10 | 47 |
| Immune/Additional | CXCL10 CFH | 2.54E−10 | 50 |
| Immune/Additional | CXCL10 HLA | 1.60E−10 | 50 |
| Immune/Additional | CXCL10 PECAM1 | 2.46E−10 | 50 |
| Immune/Additional | CXCL10 PTPN22 | 2.16E−10 | 50 |
| Immune/Additional | CXCL10 RGS1 | 2.49E−11 | 50 |
| Immune/Additional | CXCL10 IRF1 | 2.39E−10 | 50 |
| Immune/Additional | CXCL10 CCL5 | 2.29E−10 | 50 |
| Immune/Additional | CXCL10 CD38 | 4.47E−10 | 48 |
| Immune/Additional | CXCL10 SELL | 1.30E−10 | 50 |
| Immune/Additional | CXCL10 HLA | 2.71E−10 | 50 |
| Immune/Additional | CXCL10 S100A9 | 1.39E−10 | 50 |
| Immune/Additional | CXCL10 ITGB2 | 3.34E−10 | 50 |
| Immune/Additional | CXCL10 PTPRC | 1.25E−10 | 50 |
| Immune/Additional | CXCL10 CXCL13 | 8.57E−10 | 46 |
| Immune/Additional | CXCL10 PHACTR1 | 5.53E−11 | 50 |
| Immune/Additional | CXCL10 SPP1 | 1.29E−10 | 49 |
| Immune/Additional | CXCL10 LCP2 | 3.18E−10 | 50 |
| Immune/Additional | CXCL10 KRT15 | 1.94E−12 | 50 |
| Immune/Additional | CXCL10 CXCL9 | 1.32E−10 | 50 |
| Immune/Additional | CXCL10 HCLS1 | 2.82E−10 | 50 |
| Immune/Additional | CCL3 FABP7 | 7.30E−09 | 78 |
| Immune/Additional | CCL3 FN1 | 3.23E−10 | 78 |
| Immune/Additional | CCL3 PTN | 5.96E−08 | 78 |
| Immune/Additional | CCL3 IGJ | 5.68E−06 | 50 |
| Immune/Additional | CCL3 PRAME | 1.42E−10 | 76 |
| Immune/Additional | CCL3 BCL2A1 | 2.24E−09 | 78 |
| Immune/Additional | CCL3 IFI6 | 5.70E−10 | 73 |
| Immune/Additional | CCL3 CFH | 4.01E−09 | 78 |
| Immune/Additional | CCL3 HLA | 4.15E−05 | 52 |
| Immune/Additional | CCL3 PECAM1 | 3.80E−05 | 52 |
| Immune/Additional | CCL3 PTPN22 | 2.20E−05 | 52 |
| Immune/Additional | CCL3 RGS1 | 2.11E−13 | 78 |
| Immune/Additional | CCL3 IRF1 | 1.96E−07 | 52 |
| Immune/Additional | CCL3 CCL5 | 3.60E−09 | 52 |
| Immune/Additional | CCL3 CD38 | 4.84E−09 | 49 |
| Immune/Additional | CCL3 SELL | 2.17E−08 | 52 |
| Immune/Additional | CCL3 HLA | 1.73E−05 | 52 |
| Immune/Additional | CCL3 S100A9 | 3.86E−06 | 52 |
| Immune/Additional | CCL3 ITGB2 | 4.55E−06 | 52 |
| Immune/Additional | CCL3 PTPRC | 8.63E−05 | 52 |
| Immune/Additional | CCL3 CXCL13 | 8.90E−09 | 48 |
| Immune/Additional | CCL3 PHACTR1 | 1.33E−09 | 78 |
| Immune/Additional | CCL3 SPP1 | 2.68E−10 | 77 |
| Immune/Additional | CCL3 LCP2 | 1.00E−06 | 52 |
| Immune/Additional | CCL3 KRT15 | 8.96E−14 | 78 |
| Immune/Additional | CCL3 CXCL9 | 1.07E−09 | 52 |
| Immune/Additional | CCL3 HCLS1 | 6.08E−05 | 52 |
| Immune/Additional | FABP7 FN1 | 1.78E−07 | 79 |
| Immune/Additional | FABP7 PTN | 2.27E−05 | 79 |
| Immune/Additional | FABP7 IGJ | 5.08E−05 | 50 |
| Immune/Additional | FABP7 PRAME | 1.28E−09 | 76 |
| Immune/Additional | FABP7 BCL2A1 | 8.49E−08 | 78 |
| Immune/Additional | FABP7 IFI6 | 1.86E−06 | 73 |
| Immune/Additional | FABP7 CFH | 3.20E−06 | 79 |
| Immune/Additional | FABP7 HLA | 5.35E−05 | 52 |
| Immune/Additional | FABP7 PECAM1 | 0.000245 | 52 |
| Immune/Additional | FABP7 PTPN22 | 1.22E−05 | 52 |
| Immune/Additional | FABP7 RGS1 | 8.23E−14 | 79 |
| Immune/Additional | FABP7 IRF1 | 2.27E−07 | 52 |
| Immune/Additional | FABP7 CCL5 | 8.87E−10 | 52 |
| Immune/Additional | FABP7 CD38 | 1.05E−09 | 49 |
| Immune/Additional | FABP7 SELL | 2.67E−09 | 52 |
| Immune/Additional | FABP7 HLA | 0.00011 | 52 |
| Immune/Additional | FABP7 S100A9 | 1.11E−05 | 52 |
| Immune/Additional | FABP7 ITGB2 | 3.71E−05 | 52 |
| Immune/Additional | FABP7 PTPRC | 8.11E−05 | 52 |
| Immune/Additional | FABP7 CXCL13 | 2.09E−09 | 48 |
| Immune/Additional | FABP7 PHACTR1 | 7.46E−08 | 78 |
| Immune/Additional | FABP7 SPP1 | 3.72E−10 | 78 |
| Immune/Additional | FABP7 LCP2 | 3.95E−07 | 52 |
| Immune/Additional | FABP7 KRT15 | 2.19E−11 | 79 |
| Immune/Additional | FABP7 CXCL9 | 3.66E−10 | 52 |
| Immune/Additional | FABP7 HCLS1 | 0.000618 | 52 |
| Immune/Additional | FN1 PTN | 2.19E−06 | 79 |
| Immune/Additional | FN1 IGJ | 1.24E−05 | 50 |
| Immune/Additional | FN1 PRAME | 8.56E−11 | 76 |
| Immune/Additional | FN1 BCL2A1 | 6.94E−10 | 80 |
| Immune/Additional | FN1 IFI6 | 1.56E−07 | 75 |
| Immune/Additional | FN1 CFH | 1.53E−07 | 79 |
| Immune/Additional | FN1 HLA | 1.75E−05 | 52 |
| Immune/Additional | FN1 PECAM1 | 2.43E−05 | 52 |
| Immune/Additional | FN1 PTPN22 | 1.91E−06 | 52 |
| Immune/Additional | FN1 RGS1 | 1.86E−14 | 81 |
| Immune/Additional | FN1 IRF1 | 3.87E−08 | 52 |
| Immune/Additional | FN1 CCL5 | 2.24E−10 | 52 |
| Immune/Additional | FN1 CD38 | 1.18E−09 | 49 |
| Immune/Additional | FN1 SELL | 1.60E−09 | 52 |
| Immune/Additional | FN1 HLA | 2.03E−05 | 52 |
| Immune/Additional | FN1 S100A9 | 1.57E−08 | 52 |
| Immune/Additional | FN1 ITGB2 | 7.52E−06 | 52 |
| Immune/Additional | FN1 PTPRC | 2.23E−06 | 52 |
| Immune/Additional | FN1 CXCL13 | 2.70E−08 | 48 |
| Immune/Additional | FN1 PHACTR1 | 1.20E−08 | 78 |
| Immune/Additional | FN1 SPP 1 | 1.19E−10 | 80 |
| Immune/Additional | FN1 LCP2 | 1.06E−07 | 52 |
| Immune/Additional | FN1 KRT15 | 5.41E−11 | 79 |
| Immune/Additional | FN1 CXCL9 | 5.73E−11 | 52 |
| Immune/Additional | FN1 HCLS1 | 3.39E−05 | 52 |
| Immune/Additional | PTN IGJ | 0.000612 | 50 |
| Immune/Additional | PTN PRAME | 3.23E−06 | 76 |
| Immune/Additional | PTN BCL2A1 | 5.21E−06 | 78 |
| Immune/Additional | PTN IFI6 | 3.65E−06 | 73 |
| Immune/Additional | PTN CFH | 0.000585 | 79 |
| Immune/Additional | PTN HLA | 0.000518 | 52 |
| Immune/Additional | PTN PECAM1 | 0.001185 | 52 |
| Immune/Additional | PTN PTPN22 | 0.000136 | 52 |
| Immune/Additional | PTN RGS1 | 6.74E−13 | 79 |
| Immune/Additional | PTN IRF1 | 4.83E−07 | 52 |
| Immune/Additional | PTN CCL5 | 3.78E−09 | 52 |
| Immune/Additional | PTN CD38 | 7.93E−09 | 49 |
| Immune/Additional | PTN SELL | 1.39E−08 | 52 |
| Immune/Additional | PTN HLA | 0.000275 | 52 |
| Immune/Additional | PTN S100A9 | 2.00E−05 | 52 |
| Immune/Additional | PTN ITGB2 | 8.87E−05 | 52 |
| Immune/Additional | PTN PTPRC | 0.00121 | 52 |
| Immune/Additional | PTN CXCL13 | 1.26E−08 | 48 |
| Immune/Additional | PTN PHACTR1 | 9.62E−07 | 78 |
| Immune/Additional | PTN SPP1 | 2.59E−09 | 78 |
| Immune/Additional | PTN LCP2 | 1.54E−06 | 52 |
| Immune/Additional | PTN KRT15 | 4.49E−11 | 79 |
| Immune/Additional | PTN CXCL9 | 1.22E−09 | 52 |
| Immune/Additional | PTN HCLS1 | 0.004588 | 52 |
| Immune/Additional | IGJ PRAME | 7.28E−07 | 50 |
| Immune/Additional | IGJ BCL2A1 | 5.28E−06 | 50 |
| Immune/Additional | IGJ IFI6 | 8.23E−15 | 47 |
| Immune/Additional | IGJ CFH | 0.000244 | 50 |
| Immune/Additional | IGJ HLA | 0.000484 | 50 |
| Immune/Additional | IGJ PECAM1 | 0.000469 | 50 |
| Immune/Additional | IGJ PTPN22 | 1.66E−05 | 50 |
| Immune/Additional | IGJ RGS1 | 7.60E−09 | 50 |
| Immune/Additional | IGJ IRF1 | 8.66E−08 | 50 |
| Immune/Additional | IGJ CCL5 | 2.21E−10 | 50 |
| Immune/Additional | IGJ CD38 | 4.38E−08 | 47 |
| Immune/Additional | IGJ SELL | 2.63E−08 | 50 |

TABLE XX-continued

| type | genes | pval | n |
|---|---|---|---|
| Immune/Additional | IGJ HLA | 0.000321 | 50 |
| Immune/Additional | IGJ S100A9 | 6.51E-05 | 50 |
| Immune/Additional | IGJ ITGB2 | 9.60E-05 | 50 |
| Immune/Additional | IGJ PTPRC | 0.000199 | 50 |
| Immune/Additional | IGJ CXCL13 | 2.02E-09 | 46 |
| Immune/Additional | IGJ PHACTR1 | 5.37E-06 | 50 |
| Immune/Additional | IGJ SPP1 | 2.34E-06 | 49 |
| Immune/Additional | IGJ LCP2 | 2.62E-06 | 50 |
| Immune/Additional | IGJ KRT15 | 1.27E-10 | 50 |
| Immune/Additional | IGJ CXCL9 | 5.41E-11 | 50 |
| Immune/Additional | IGJ HCLS1 | 0.001058 | 50 |
| Immune/Additional | PRAME BCL2A1 | 1.49E-08 | 76 |
| Immune/Additional | PRAME IFI6 | 1.53E-09 | 71 |
| Immune/Additional | PRAME CFH | 2.22E-08 | 76 |
| Immune/Additional | PRAME HLA | 4.16E-07 | 52 |
| Immune/Additional | PRAME PECAM1 | 3.62E-07 | 52 |
| Immune/Additional | PRAME PTPN22 | 6.26E-08 | 52 |
| Immune/Additional | PRAME RGS1 | 1.59E-14 | 76 |
| Immune/Additional | PRAME IRF1 | 1.69E-08 | 52 |
| Immune/Additional | PRAME CCL5 | 4.98E-10 | 52 |
| Immune/Additional | PRAME CD38 | 3.68E-09 | 49 |
| Immune/Additional | PRAME SELL | 2.91E-10 | 52 |
| Immune/Additional | PRAME HLA | 1.01E-07 | 52 |
| Immune/Additional | PRAME S100A9 | 4.66E-07 | 52 |
| Immune/Additional | PRAME ITGB2 | 4.59E-08 | 52 |
| Immune/Additional | PRAME PTPRC | 6.65E-07 | 52 |
| Immune/Additional | PRAME CXCL13 | 6.08E-09 | 48 |
| Immune/Additional | PRAME PHACTR1 | 1.41E-09 | 76 |
| Immune/Additional | PRAME SPP1 | 2.72E-12 | 75 |
| Immune/Additional | PRAME LCP2 | 1.40E-08 | 52 |
| Immune/Additional | PRAME KRT15 | 1.24E-13 | 76 |
| Immune/Additional | PRAME CXCL9 | 1.41E-10 | 52 |
| Immune/Additional | PRAME HCLS1 | 2.34E-07 | 52 |
| Immune/Additional | BCL2A1 IFI6 | 2.60E-07 | 75 |
| Immune/Additional | BCL2A1 CFH | 1.70E-06 | 78 |
| Immune/Additional | BCL2A1 HLA | 4.86E-06 | 52 |
| Immune/Additional | BCL2A1 PECAM1 | 9.68E-06 | 52 |
| Immune/Additional | BCL2A1 PTPN22 | 8.54E-07 | 52 |
| Immune/Additional | BCL2A1 RGS1 | 1.44E-15 | 80 |
| Immune/Additional | BCL2A1 IRF1 | 8.10E-08 | 52 |
| Immune/Additional | BCL2A1 CCL5 | 1.04E-09 | 52 |
| Immune/Additional | BCL2A1 CD38 | 2.63E-09 | 49 |
| Immune/Additional | BCL2A1 SELL | 6.78E-10 | 52 |
| Immune/Additional | BCL2A1 HLA | 7.02E-06 | 52 |
| Immune/Additional | BCL2A1 S100A9 | 1.46E-06 | 52 |
| Immune/Additional | BCL2A1 ITGB2 | 5.56E-06 | 52 |
| Immune/Additional | BCL2A1 PTPRC | 9.48E-06 | 52 |
| Immune/Additional | BCL2A1 CXCL13 | 8.21E-09 | 48 |
| Immune/Additional | BCL2A1 PHACTR1 | 1.47E-07 | 78 |
| Immune/Additional | BCL2A1 SPP1 | 5.11E-11 | 79 |
| Immune/Additional | BCL2A1 LCP2 | 1.96E-07 | 52 |
| Immune/Additional | BCL2A1 KRT15 | 1.03E-10 | 78 |
| Immune/Additional | BCL2A1 CXCL9 | 7.62E-10 | 52 |
| Immune/Additional | BCL2A1 HCLS1 | 2.07E-05 | 52 |
| Immune/Additional | IFI6 CFH | 3.68E-06 | 73 |
| Immune/Additional | IFI6 HLA | 7.56E-05 | 48 |
| Immune/Additional | IFI6 PECAM1 | 5.43E-05 | 48 |
| Immune/Additional | IFI6 PTPN22 | 2.22E-06 | 48 |
| Immune/Additional | IFI6 RGS1 | 2.29E-14 | 75 |
| Immune/Additional | IFI6 IRF1 | 1.67E-07 | 48 |
| Immune/Additional | IFI6 CCL5 | 1.41E-10 | 48 |
| Immune/Additional | IFI6 CD38 | 8.58E-09 | 47 |
| Immune/Additional | IFI6 SELL | 5.75E-09 | 48 |
| Immune/Additional | IFI6 HLA | 0.000195 | 48 |
| Immune/Additional | IFI6 S100A9 | 8.00E-07 | 48 |
| Immune/Additional | IFI6 ITGB2 | 0.00015 | 48 |
| Immune/Additional | IFI6 PTPRC | 2.48E-06 | 48 |
| Immune/Additional | IFI6 CXCL13 | 5.65E-10 | 44 |
| Immune/Additional | IFI6 PHACTR1 | 6.48E-07 | 73 |
| Immune/Additional | IFI6 SPP1 | 4.87E-11 | 74 |
| Immune/Additional | IFI6 LCP2 | 1.34E-06 | 48 |
| Immune/Additional | IFI6 KRT15 | 4.94E-10 | 73 |
| Immune/Additional | IFI6 CXCL9 | 4.76E-11 | 48 |
| Immune/Additional | IFI6 HCLS1 | 0.00025 | 48 |
| Immune/Additional | CFH HLA | 8.66E-06 | 52 |
| Immune/Additional | CFH PECAM1 | 7.69E-05 | 52 |
| Immune/Additional | CFH PTPN22 | 9.54E-06 | 52 |
| Immune/Additional | CFH RG51 | 1.04E-13 | 79 |
| Immune/Additional | CFH IRF1 | 5.53E-08 | 52 |
| Immune/Additional | CFH CCL5 | 2.63E-10 | 52 |
| Immune/Additional | CFH CD38 | 3.05E-09 | 49 |
| Immune/Additional | CFH SELL | 6.80E-11 | 52 |
| Immune/Additional | CFH HLA | 2.71E-05 | 52 |
| Immune/Additional | CFH S100A9 | 4.14E-05 | 52 |
| Immune/Additional | CFH ITGB2 | 8.68E-06 | 52 |
| Immune/Additional | CFH PTPRC | 4.04E-05 | 52 |
| Immune/Additional | CFH CXCL13 | 3.56E-09 | 48 |
| Immune/Additional | CFH PHACTR1 | 6.52E-07 | 78 |
| Immune/Additional | CFH SPP1 | 3.73E-06 | 78 |
| Immune/Additional | CFH LCP2 | 2.72E-07 | 52 |
| Immune/Additional | CFH KRT15 | 2.57E-11 | 79 |
| Immune/Additional | CFH CXCL9 | 1.90E-10 | 52 |
| Immune/Additional | CFH HCLS1 | 0.000201 | 52 |
| Immune/Additional | HLA PECAM1 | 0.00018 | 52 |
| Immune/Additional | HLA PTPN22 | 0.000137 | 52 |
| Immune/Additional | HLA RGS1 | 1.18E-08 | 52 |
| Immune/Additional | HLA IRF1 | 5.15E-07 | 52 |
| Immune/Additional | HLA CCL5 | 1.15E-09 | 52 |
| Immune/Additional | HLA CD38 | 4.54E-08 | 49 |
| Immune/Additional | HLA SELL | 2.06E-08 | 52 |
| Immune/Additional | HLA HLA | 0.000606 | 52 |
| Immune/Additional | HLA S100A9 | 5.76E-06 | 52 |
| Immune/Additional | HLA ITGB2 | 0.000104 | 52 |
| Immune/Additional | HLA PTPRC | 0.000677 | 52 |
| Immune/Additional | HLA CXCL13 | 1.20E-08 | 48 |
| Immune/Additional | HLA PHACTR1 | 4.78E-07 | 52 |
| Immune/Additional | HLA SPP1 | 2.02E-06 | 51 |
| Immune/Additional | HLA LCP2 | 2.60E-06 | 52 |
| Immune/Additional | HLA KRT15 | 1.30E-10 | 52 |
| Immune/Additional | HLA CXCL9 | 6.15E-10 | 52 |
| Immune/Additional | HLA HCLS1 | 0.000831 | 52 |
| Immune/Additional | PECAM1 PTPN22 | 5.46E-05 | 52 |
| Immune/Additional | PECAM1 RGS1 | 2.18E-09 | 52 |
| Immune/Additional | PECAM1 IRF1 | 3.88E-07 | 52 |
| Immune/Additional | PECAM1 CCL5 | 3.68E-09 | 52 |
| Immune/Additional | PECAM1 CD38 | 6.53E-09 | 49 |
| Immune/Additional | PECAM1 SELL | 2.58E-08 | 52 |
| Immune/Additional | PECAM1 HLA | 0.000172 | 52 |
| Immune/Additional | PECAM1 S100A9 | 1.05E-06 | 52 |
| Immune/Additional | PECAM1 ITGB2 | 0.000148 | 52 |
| Immune/Additional | PECAM1 PTPRC | 0.000492 | 52 |
| Immune/Additional | PECAM1 CXCL13 | 3.31E-08 | 48 |
| Immune/Additional | PECAM1 PHACTR1 | 1.99E-05 | 52 |
| Immune/Additional | PECAM1 SPP1 | 4.86E-06 | 51 |
| Immune/Additional | PECAM1 LCP2 | 2.21E-06 | 52 |
| Immune/Additional | PECAM1 KRT15 | 2.02E-10 | 52 |
| Immune/Additional | PECAM1 CXCL9 | 1.00E-09 | 52 |
| Immune/Additional | PECAM1 HCLS1 | 0.00209 | 52 |
| Immune/Additional | PTPN22 RGS1 | 9.07E-09 | 52 |
| Immune/Additional | PTPN22 IRF1 | 4.83E-07 | 52 |
| Immune/Additional | PTPN22 CCL5 | 4.80E-10 | 52 |
| Immune/Additional | PTPN22 CD38 | 3.32E-08 | 49 |
| Immune/Additional | PTPN22 SELL | 3.20E-08 | 52 |
| Immune/Additional | PTPN22 HLA | 7.86E-05 | 52 |
| Immune/Additional | PTPN22 S100A9 | 4.52E-06 | 52 |
| Immune/Additional | PTPN22 ITGB2 | 1.27E-05 | 52 |
| Immune/Additional | PTPN22 PTPRC | 0.000269 | 52 |
| Immune/Additional | PTPN22 CXCL13 | 1.22E-08 | 48 |
| Immune/Additional | PTPN22 PHACTR1 | 9.01E-08 | 52 |
| Immune/Additional | PTPN22 SPP1 | 1.15E-07 | 51 |
| Immune/Additional | PTPN22 LCP2 | 2.41E-06 | 52 |
| Immune/Additional | PTPN22 KRT15 | 1.39E-11 | 52 |
| Immune/Additional | PTPN22 CXCL9 | 1.05E-09 | 52 |
| Immune/Additional | PTPN22 HCLS1 | 0.000267 | 52 |
| Immune/Additional | RGS1 IRF1 | 3.00E-09 | 52 |
| Immune/Additional | RGS1 CCL5 | 5.00E-10 | 52 |
| Immune/Additional | RGS1 CD38 | 8.59E-09 | 49 |
| Immune/Additional | RGS1 SELL | 7.08E-10 | 52 |
| Immune/Additional | RGS1 HLA | 1.24E-08 | 52 |
| Immune/Additional | RGS1 S100A9 | 8.85E-10 | 52 |
| Immune/Additional | RGS1 ITGB2 | 2.49E-09 | 52 |
| Immune/Additional | RGS1 PTPRC | 9.02E-09 | 52 |
| Immune/Additional | RGS1 CXCL13 | 9.90E-10 | 48 |
| Immune/Additional | RGS1 PHACTR1 | 4.53E-15 | 78 |
| Immune/Additional | RGS1 SPP1 | 7.14E-16 | 80 |
| Immune/Additional | RGS1 LCP2 | 1.81E-09 | 52 |

TABLE XX-continued

| type | genes | pval | n |
|---|---|---|---|
| Immune/Additional | RGS1 KRT15 | 9.63E−17 | 79 |
| Immune/Additional | RGS1 CXCL9 | 1.28E−10 | 52 |
| Immune/Additional | RGS1 HCLS1 | 7.83E−09 | 52 |
| Immune/Additional | IRF1 CCL5 | 2.15E−09 | 52 |
| Immune/Additional | IRF1 CD38 | 1.45E−08 | 49 |
| Immune/Additional | IRF1 SELL | 1.31E−08 | 52 |
| Immune/Additional | IRF1 HLA | 5.22E−07 | 52 |
| Immune/Additional | IRF1 S100A9 | 5.05E−08 | 52 |
| Immune/Additional | IRF1 ITGB2 | 5.80E−07 | 52 |
| Immune/Additional | IRF1 PTPRC | 4.43E−07 | 52 |
| Immune/Additional | IRF1 CXCL13 | 5.13E−09 | 48 |
| Immune/Additional | IRF1 PHACTR1 | 1.09E−08 | 52 |
| Immune/Additional | IRF1 SPP1 | 1.90E−08 | 51 |
| Immune/Additional | IRF1 LCP2 | 2.48E−07 | 52 |
| Immune/Additional | IRF1 KRT15 | 1.40E−12 | 52 |
| Immune/Additional | IRF1 CXCL9 | 1.16E−09 | 52 |
| Immune/Additional | IRF1 HCLS1 | 2.76E−07 | 52 |
| Immune/Additional | CCL5 CD38 | 1.06E−09 | 49 |
| Immune/Additional | CCL5 SELL | 1.69E−09 | 52 |
| Immune/Additional | CCL5 HLA | 3.02E−09 | 52 |
| Immune/Additional | CCL5 S100A9 | 1.40E−09 | 52 |
| Immune/Additional | CCL5 ITGB2 | 2.93E−09 | 52 |
| Immune/Additional | CCL5 PTPRC | 3.10E−13 | 52 |
| Immune/Additional | CCL5 CXCL13 | 2.12E−09 | 48 |
| Immune/Additional | CCL5 PHACTR1 | 1.49E−10 | 52 |
| Immune/Additional | CCL5 SPP1 | 3.63E−10 | 51 |
| Immune/Additional | CCL5 LCP2 | 2.51E−09 | 52 |
| Immune/Additional | CCL5 KRT15 | 1.41E−12 | 52 |
| Immune/Additional | CCL5 CXCL9 | 6.43E−10 | 52 |
| Immune/Additional | CCL5 HCLS1 | 1.36E−09 | 52 |
| Immune/Additional | CD38 SELL | 6.31E−09 | 49 |
| Immune/Additional | CD38 HLA | 3.70E−08 | 49 |
| Immune/Additional | CD38 S100A9 | 1.02E−08 | 49 |
| Immune/Additional | CD38 ITGB2 | 1.99E−08 | 49 |
| Immune/Additional | CD38 PTPRC | 5.17E−09 | 49 |
| Immune/Additional | CD38 CXCL13 | 3.25E−09 | 46 |
| Immune/Additional | CD38 PHACTR1 | 4.58E−10 | 49 |
| Immune/Additional | CD38 SPP1 | 1.43E−09 | 48 |
| Immune/Additional | CD38 LCP2 | 3.38E−08 | 49 |
| Immune/Additional | CD38 KRT15 | 1.17E−11 | 49 |
| Immune/Additional | CD38 CXCL9 | 2.23E−10 | 49 |
| Immune/Additional | CD38 HCLS1 | 4.45E−08 | 49 |
| Immune/Additional | SELL HLA | 2.63E−08 | 52 |
| Immune/Additional | SELL S100A9 | 1.25E−08 | 52 |
| Immune/Additional | SELL ITGB2 | 3.37E−08 | 52 |
| Immune/Additional | SELL PTPRC | 1.01E−08 | 52 |
| Immune/Additional | SELL CXCL13 | 2.54E−09 | 48 |
| Immune/Additional | SELL PHACTR1 | 8.28E−12 | 52 |
| Immune/Additional | SELL SPP1 | 1.07E−09 | 51 |
| Immune/Additional | SELL LCP2 | 1.86E−08 | 52 |
| Immune/Additional | SELL KRT15 | 1.15E−12 | 52 |
| Immune/Additional | SELL CXCL9 | 1.03E−09 | 52 |
| Immune/Additional | SELL HCLS1 | 9.23E−09 | 52 |
| Immune/Additional | HLA S100A9 | 6.82E−07 | 52 |
| Immune/Additional | HLA ITGB2 | 0.000111 | 52 |
| Immune/Additional | HLA PTPRC | 0.000408 | 52 |
| Immune/Additional | HLA CXCL13 | 5.87E−09 | 48 |
| Immune/Additional | HLA PHACTR1 | 3.24E−06 | 52 |
| Immune/Additional | HLA SPP1 | 2.32E−06 | 51 |
| Immune/Additional | HLA LCP2 | 2.63E−06 | 52 |
| Immune/Additional | HLA KRT15 | 1.04E−06 | 52 |
| Immune/Additional | HLA CXCL9 | 1.24E−09 | 52 |
| Immune/Additional | HLA HCLS1 | 0.000741 | 52 |
| Immune/Additional | S100A9 ITGB2 | 6.11E−07 | 52 |
| Immune/Additional | S100A9 PTPRC | 2.82E−05 | 52 |
| Immune/Additional | S100A9 CXCL13 | 1.20E−08 | 48 |
| Immune/Additional | S100A9 PHACTR1 | 7.76E−08 | 52 |
| Immune/Additional | S100A9 SPP1 | 1.35E−09 | 51 |
| Immune/Additional | S100A9 LCP2 | 6.68E−08 | 52 |
| Immune/Additional | S100A9 KRT15 | 1.39E−11 | 52 |
| Immune/Additional | S100A9 CXCL9 | 3.73E−10 | 52 |
| Immune/Additional | S100A9 HCLS1 | 2.40E−05 | 52 |
| Immune/Additional | ITGB2 PTPRC | 5.57E−06 | 52 |
| Immune/Additional | ITGB2 CXCL13 | 3.27E−09 | 48 |
| Immune/Additional | ITGB2 PHACTR1 | 1.34E−06 | 52 |
| Immune/Additional | ITGB2 SPP1 | 1.83E−06 | 51 |
| Immune/Additional | ITGB2 LCP2 | 1.74E−06 | 52 |
| Immune/Additional | ITGB2 KRT15 | 1.83E−10 | 52 |
| Immune/Additional | ITGB2 CXCL9 | 1.27E−09 | 52 |
| Immune/Additional | ITGB2 HCLS1 | 0.000143 | 52 |
| Immune/Additional | PTPRC CXCL13 | 1.28E−08 | 48 |
| Immune/Additional | PTPRC PHACTR1 | 9.30E−07 | 52 |
| Immune/Additional | PTPRC SPP1 | 1.52E−06 | 51 |
| Immune/Additional | PTPRC LCP2 | 1.72E−06 | 52 |
| Immune/Additional | PTPRC KRT15 | 1.38E−11 | 52 |
| Immune/Additional | PTPRC CXCL9 | 1.30E−10 | 52 |
| Immune/Additional | PTPRC HCLS1 | 0.001982 | 52 |
| Immune/Additional | CXCL13 PHACTR1 | 1.04E−09 | 48 |
| Immune/Additional | CXCL13 SPP1 | 1.24E−09 | 47 |
| Immune/Additional | CXCL13 LCP2 | 2.17E−09 | 48 |
| Immune/Additional | CXCL13 KRT15 | 4.98E−11 | 48 |
| Immune/Additional | CXCL13 CXCL9 | 1.44E−09 | 48 |
| Immune/Additional | CXCL13 HCLS1 | 8.81E−09 | 48 |
| Immune/Additional | PHACTR1 SPP1 | 1.08E−10 | 77 |
| Immune/Additional | PHACTR1 LCP2 | 5.75E−08 | 52 |
| Immune/Additional | PHACTR1 KRT15 | 1.82E−11 | 78 |
| Immune/Additional | PHACTR1 CXCL9 | 2.74E−11 | 52 |
| Immune/Additional | PHACTR1 HCLS1 | 1.34E−05 | 52 |
| Immune/Additional | SPP1 LCP2 | 8.37E−08 | 51 |
| Immune/Additional | SPP1 KRT15 | 8.66E−13 | 78 |
| Immune/Additional | SPP1 CXCL9 | 1.60E−10 | 51 |
| Immune/Additional | SPP1 HCLS1 | 5.76E−06 | 51 |
| Immune/Additional | LCP2 KRT15 | 1.70E−11 | 52 |
| Immune/Additional | LCP2 CXCL9 | 1.13E−09 | 52 |
| Immune/Additional | LCP2 HCLS1 | 2.91E−06 | 52 |
| Immune/Additional | KRT15 CXCL9 | 6.42E−13 | 52 |
| Immune/Additional | KRT15 HCLS1 | 2.51E−10 | 52 |
| Immune/Additional | CXCL9 HCLS1 | 5.62E−10 | 52 |
| CCP/Immune/Additional | Cl8orf24 HEY1 | 5.85E−05 | 26 |
| CCP/Immune/Additional | Cl8orf24 CCL3 | 3.94E−05 | 26 |
| CCP/Immune/Additional | Cl8orf24 FABP7 | 1.80E−05 | 26 |
| CCP/Immune/Additional | Cl8orf24 FN1 | 5.36E−06 | 28 |
| CCP/Immune/Additional | Cl8orf24 PTN | 5.99E−06 | 26 |
| CCP/Immune/Additional | Cl8orf24 PRAME | 3.08E−05 | 24 |
| CCP/Immune/Additional | Cl8orf24 BCL2A1 | 8.35E−06 | 28 |
| CCP/Immune/Additional | Cl8orf24 IFI6 | 8.84E−06 | 27 |
| CCP/Immune/Additional | Cl8orf24 CFH | 4.86E−05 | 26 |
| CCP/Immune/Additional | Cl8orf24 RGS1 | 3.63E−06 | 28 |
| CCP/Immune/Additional | Cl8orf24 PHACTR1 | 4.73E−05 | 26 |
| CCP/Immune/Additional | Cl8orf24 SPP1 | 4.43E−06 | 28 |
| CCP/Immune/Additional | Cl8orf24 KRT15 | 3.32E−05 | 26 |
| CCP/Immune/Additional | PBK HEY1 | 0.000325 | 26 |
| CCP/Immune/Additional | PBK CCL3 | 0.00014 | 26 |
| CCP/Immune/Additional | PBK FABP7 | 0.000157 | 26 |
| CCP/Immune/Additional | PBK FN1 | 3.72E−05 | 28 |
| CCP/Immune/Additional | PBK PTN | 0.000215 | 26 |
| CCP/Immune/Additional | PBK PRAME | 0.000425 | 24 |
| CCP/Immune/Additional | PBK BCL2A1 | 5.82E−05 | 28 |
| CCP/Immune/Additional | PBK IFI6 | 6.75E−05 | 27 |
| CCP/Immune/Additional | PBK CFH | 0.000292 | 26 |
| CCP/Immune/Additional | PBK RGS1 | 9.29E−06 | 28 |
| CCP/Immune/Additional | PBK PHACTR1 | 0.000384 | 26 |
| CCP/Immune/Additional | PBK SPP1 | 7.27E−06 | 28 |
| CCP/Immune/Additional | PBK KRT15 | 9.68E−05 | 26 |
| CCP/Immune/Additional | PLK1 HEY1 | 5.62E−05 | 27 |
| CCP/Immune/Additional | PLK1 CCL3 | 0.000102 | 26 |
| CCP/Immune/Additional | PLK1 FABP7 | 5.48E−05 | 27 |
| CCP/Immune/Additional | PLK1 FN1 | 2.02E−05 | 29 |
| CCP/Immune/Additional | PLK1 PTN | 4.72E−05 | 27 |
| CCP/Immune/Additional | PLK1 PRAME | 9.46E−05 | 24 |
| CCP/Immune/Additional | PLK1 BCL2A1 | 1.04E−05 | 28 |
| CCP/Immune/Additional | PLK1 IFI6 | 2.14E−05 | 27 |
| CCP/Immune/Additional | PLK1 CFH | 0.000128 | 27 |
| CCP/Immune/Additional | PLK1 RGS1 | 8.92E−06 | 29 |
| CCP/Immune/Additional | PLK1 PHACTR1 | 0.000164 | 26 |
| CCP/Immune/Additional | PLK1 SPP1 | 1.30E−05 | 29 |
| CCP/Immune/Additional | PLK1 KRT15 | 2.78E−05 | 27 |
| CCP/Immune/Additional | DLGAP5 HEY1 | 0.00312 | 27 |
| CCP/Immune/Additional | DLGAP5 CCL3 | 9.72E−05 | 26 |
| CCP/Immune/Additional | DLGAP5 FABP7 | 0.001317 | 27 |
| CCP/Immune/Additional | DLGAP5 FN1 | 0.000619 | 29 |
| CCP/Immune/Additional | DLGAP5 PTN | 0.003429 | 27 |
| CCP/Immune/Additional | DLGAP5 PRAME | 0.000944 | 24 |
| CCP/Immune/Additional | DLGAP5 BCL2A1 | 8.89E−05 | 28 |
| CCP/Immune/Additional | DLGAP5 IFI6 | 0.000124 | 27 |
| CCP/Immune/Additional | DLGAP5 CFH | 0.003343 | 27 |

TABLE XX-continued

| type | genes | pval | n |
|---|---|---|---|
| CCP/Immune/Additional | DLGAP5 RGS1 | 2.08E−05 | 29 |
| CCP/Immune/Additional | DLGAP5 PHACTR1 | 0.001083 | 26 |
| CCP/Immune/Additional | DLGAP5 SPP1 | 1.65E−05 | 29 |
| CCP/Immune/Additional | DLGAP5 KRT15 | 0.000588 | 27 |
| CCP/Immune/Additional | FOXM1 HEY1 | 0.00017 | 26 |
| CCP/Immune/Additional | FOXM1 CCL3 | 5.45E−05 | 26 |
| CCP/Immune/Additional | FOXM1 FABP7 | 9.52E−05 | 26 |
| CCP/Immune/Additional | FOXM1 FN1 | 2.60E−05 | 28 |
| CCP/Immune/Additional | FOXM1 PTN | 0.000135 | 26 |
| CCP/Immune/Additional | FOXM1 PRAME | 0.000248 | 24 |
| CCP/Immune/Additional | FOXM1 BCL2A1 | 2.31E−05 | 28 |
| CCP/Immune/Additional | FOXM1 IFI6 | 2.42E−05 | 27 |
| CCP/Immune/Additional | FOXM1 CFH | 0.000167 | 26 |
| CCP/Immune/Additional | FOXM1 RGS1 | 5.89E−06 | 28 |
| CCP/Immune/Additional | FOXM1 PHACTR1 | 0.00015 | 26 |
| CCP/Immune/Additional | FOXM1 SPP1 | 1.11E−05 | 28 |
| CCP/Immune/Additional | FOXM1 KRT15 | 6.62E−05 | 26 |
| CCP/Immune/Additional | MCM10 HEY1 | 0.000797 | 26 |
| CCP/Immune/Additional | MCM10 CCL3 | 6.76E−05 | 26 |
| CCP/Immune/Additional | MCM10 FABP7 | 0.000278 | 26 |
| CCP/Immune/Additional | MCM10 FN1 | 0.000123 | 28 |
| CCP/Immune/Additional | MCM10 PTN | 0.000778 | 26 |
| CCP/Immune/Additional | MCM10 PRAME | 0.000394 | 24 |
| CCP/Immune/Additional | MCM10 BCL2A1 | 4.19E−05 | 28 |
| CCP/Immune/Additional | MCM10 IFI6 | 2.26E−05 | 27 |
| CCP/Immune/Additional | MCM10 CFH | 0.000605 | 26 |
| CCP/Immune/Additional | MCM10 RGS1 | 1.91E−05 | 28 |
| CCP/Immune/Additional | MCM10 PHACTR1 | 0.000376 | 26 |
| CCP/Immune/Additional | MCM10 SPP1 | 2.95E−05 | 28 |
| CCP/Immune/Additional | MCM10 KRT15 | 0.000253 | 26 |
| CCP/Immune/Additional | CEP55 HEY1 | 0.006628 | 27 |
| CCP/Immune/Additional | CEP55 CCL3 | 7.18E−05 | 26 |
| CCP/Immune/Additional | CEP55 FABP7 | 0.001276 | 27 |
| CCP/Immune/Additional | CEP55 FN1 | 0.001029 | 29 |
| CCP/Immune/Additional | CEP55 PTN | 0.006228 | 27 |
| CCP/Immune/Additional | CEP55 PRAME | 6.91E−05 | 24 |
| CCP/Immune/Additional | CEP55 BCL2A1 | 1.67E−05 | 28 |
| CCP/Immune/Additional | CEP55 IFI6 | 1.61E−05 | 27 |
| CCP/Immune/Additional | CEP55 CFH | 0.004256 | 27 |
| CCP/Immune/Additional | CEP55 RGS1 | 6.16E−05 | 29 |
| CCP/Immune/Additional | CEP55 PHACTR1 | 8.03E−05 | 26 |
| CCP/Immune/Additional | CEP55 SPP1 | 2.23E−05 | 29 |
| CCP/Immune/Additional | CEP55 KRT15 | 0.00161 | 27 |
| CCP/Immune/Additional | RRM2 HEY1 | 0.002325 | 27 |
| CCP/Immune/Additional | RRM2 CCL3 | 0.000657 | 26 |
| CCP/Immune/Additional | RRM2 FABP7 | 0.000572 | 27 |
| CCP/Immune/Additional | RRM2 FN1 | 0.000235 | 29 |
| CCP/Immune/Additional | RRM2 PTN | 0.001985 | 27 |
| CCP/Immune/Additional | RRM2 PRAME | 0.001068 | 24 |
| CCP/Immune/Additional | RRM2 BCL2A1 | 9.16E−05 | 28 |
| CCP/Immune/Additional | RRM2 IFI6 | 5.58E−05 | 27 |
| CCP/Immune/Additional | RRM2 CFH | 0.001764 | 27 |
| CCP/Immune/Additional | RRM2 RGS1 | 2.32E−05 | 29 |
| CCP/Immune/Additional | RRM2 PHACTR1 | 0.001505 | 26 |
| CCP/Immune/Additional | RRM2 SPP1 | 1.44E−05 | 29 |
| CCP/Immune/Additional | RRM2 KRT15 | 7.47E−05 | 27 |
| CCP/Immune/Additional | DTL HEY1 | 3.43E−05 | 27 |
| CCP/Immune/Additional | DTL CCL3 | 4.30E−05 | 26 |
| CCP/Immune/Additional | DTL FABP7 | 4.43E−05 | 27 |
| CCP/Immune/Additional | DTL FN1 | 6.55E−06 | 29 |
| CCP/Immune/Additional | DTL PTN | 3.14E−05 | 27 |
| CCP/Immune/Additional | DTL PRAME | 8.49E−05 | 24 |
| CCP/Immune/Additional | DTL BCL2A1 | 7.58E−06 | 28 |
| CCP/Immune/Additional | DTL IFI6 | 1.61E−05 | 27 |
| CCP/Immune/Additional | DTL CFH | 3.93E−05 | 27 |
| CCP/Immune/Additional | DTL RGS1 | 6.10E−06 | 29 |
| CCP/Immune/Additional | DTL PHACTR1 | 7.43E−05 | 26 |
| CCP/Immune/Additional | DTL SPP1 | 9.41E−06 | 29 |
| CCP/Immune/Additional | DTL KRT15 | 1.93E−05 | 27 |
| CCP/Immune/Additional | CENPF HEY1 | 0.000139 | 27 |
| CCP/Immune/Additional | CENPF CCL3 | 0.000159 | 26 |
| CCP/Immune/Additional | CENPF FABP7 | 5.14E−05 | 27 |
| CCP/Immune/Additional | CENPF FN1 | 3.21E−05 | 29 |
| CCP/Immune/Additional | CENPF PTN | 0.000175 | 27 |
| CCP/Immune/Additional | CENPF PRAME | 6.06E−05 | 24 |
| CCP/Immune/Additional | CENPF BCL2A1 | 1.62E−05 | 28 |
| CCP/Immune/Additional | CENPF IFI6 | 3.12E−05 | 27 |
| CCP/Immune/Additional | CENPF CFH | 0.000172 | 27 |
| CCP/Immune/Additional | CENPF RGS1 | 7.57E−06 | 29 |
| CCP/Immune/Additional | CENPF PHACTR1 | 0.000169 | 26 |
| CCP/Immune/Additional | CENPF SPP1 | 1.05E−05 | 29 |
| CCP/Immune/Additional | CENPF KRT15 | 2.96E−05 | 27 |

TABLE YY

| type | genes | pval | n |
|---|---|---|---|
| Immune/Additional | PRAME RGS1 KRT15 | 6.57E−16 | 76 |
| Immune/Additional | RGS1 SPP1 KRT15 | 9.50E−16 | 78 |
| Immune/Additional | CCL3 RGS1 KRT15 | 1.02E−15 | 78 |
| Immune/Additional | RGS1 PHACTR1 KRT15 | 1.02E−15 | 78 |
| Immune/Additional | HEY1 RGS1 KRT15 | 1.05E−15 | 79 |
| Immune/Additional | PTN RGS1 KRT15 | 1.18E−15 | 79 |
| Immune/Additional | FABP7 RGS1 KRT15 | 1.20E−15 | 79 |
| Immune/Additional | CFH RGS1 KRT15 | 1.23E−15 | 79 |
| Immune/Additional | FN1 RGS1 KRT15 | 1.38E−15 | 79 |
| Immune/Additional | BCL2A1 RGS1 KRT15 | 1.45E−15 | 78 |
| Immune/Additional | FN1 BCL2A1 RGS1 | 2.89E−15 | 80 |
| Immune/Additional | FN1 RGS1 SPP1 | 4.93E−15 | 80 |
| Immune/Additional | BCL2A1 RGS1 SPP1 | 5.11E−15 | 79 |
| Immune/Additional | IFI6 RGS1 KRT15 | 5.70E−15 | 73 |
| Immune/Additional | IFI6 RGS1 SPP1 | 1.11E−14 | 74 |
| Immune/Additional | RGS1 PHACTR1 SPP1 | 1.23E−14 | 77 |
| Immune/Additional | FN1 RGS1 PHACTR1 | 1.88E−14 | 78 |
| Immune/Additional | CCL3 PRAME KRT15 | 1.94E−14 | 76 |
| Immune/Additional | BCL2A1 IFI6 RGS1 | 2.12E−14 | 75 |
| Immune/Additional | HEY1 RGS1 SPP1 | 2.13E−14 | 78 |
| Immune/Additional | PRAME RGS1 PHACTR1 | 2.67E−14 | 76 |
| Immune/Additional | HEY1 RGS1 PHACTR1 | 3.15E−14 | 78 |
| Immune/Additional | BCL2A1 RGS1 PHACTR1 | 3.25E−14 | 78 |
| Immune/Additional | FABP7 RGS1 PHACTR1 | 3.40E−14 | 78 |
| Immune/Additional | HEY1 FABP7 RGS1 | 3.41E−14 | 79 |
| Immune/Additional | PRAME RGS1 SPP1 | 3.64E−14 | 75 |
| Immune/Additional | CFH RGS1 SPP1 | 3.74E−14 | 78 |
| Immune/Additional | HEY1 BCL2A1 RGS1 | 3.86E−14 | 78 |
| Immune/Additional | PTN RGS1 PHACTR1 | 3.95E−14 | 78 |
| Immune/Additional | HEY1 PRAME RGS1 | 4.02E−14 | 76 |
| Immune/Additional | PTN RGS1 SPP1 | 4.11E−14 | 78 |
| Immune/Additional | FN1 PRAME RGS1 | 4.64E−14 | 76 |
| Immune/Additional | CFH RGS1 PHACTR1 | 4.94E−14 | 78 |
| Immune/Additional | FABP7 RGS1 SPP1 | 5.15E−14 | 78 |
| Immune/Additional | PRAME SPP1 KRT15 | 5.41E−14 | 75 |
| Immune/Additional | CCL3 RGS1 PHACTR1 | 5.56E−14 | 78 |
| Immune/Additional | CCL3 RGS1 SPP1 | 6.03E−14 | 77 |
| Immune/Additional | HEY1 CCL3 RGS1 | 6.22E−14 | 78 |
| Immune/Additional | FABP7 BCL2A1 RGS1 | 7.77E−14 | 78 |
| Immune/Additional | PTN BCL2A1 RGS1 | 8.10E−14 | 78 |
| Immune/Additional | PRAME BCL2A1 RGS1 | 9.11E−14 | 76 |
| Immune/Additional | PTN PRAME RGS1 | 9.99E−14 | 76 |
| Immune/Additional | BCL2A1 CFH RGS1 | 1.07E−13 | 78 |
| Immune/Additional | PRAME IFI6 RGS1 | 1.10E−13 | 71 |
| Immune/Additional | CCL3 BCL2A1 RGS1 | 1.12E−13 | 78 |
| Immune/Additional | FN1 IFI6 RGS1 | 1.18E−13 | 75 |
| Immune/Additional | FABP7 PRAME RGS1 | 1.22E−13 | 76 |
| Immune/Additional | HEY1 FN1 RGS1 | 1.31E−13 | 79 |
| Immune/Additional | HEY1 PTN RGS1 | 1.34E−13 | 79 |
| Immune/Additional | IFI6 RGS1 PHACTR1 | 1.49E−13 | 73 |
| Immune/Additional | HEY1 IFI6 RGS1 | 1.65E−13 | 73 |
| Immune/Additional | HEY1 CFH RGS1 | 1.86E−13 | 79 |
| Immune/Additional | CCL3 PRAME RGS1 | 1.91E−13 | 76 |
| Immune/Additional | PRAME CFH RGS1 | 1.97E−13 | 76 |
| Immune/Additional | FABP7 FN1 RGS1 | 2.40E−13 | 79 |
| Immune/Additional | CCL3 FN1 RGS1 | 2.50E−13 | 78 |
| Immune/Additional | FABP7 PRAME KRT15 | 2.70E−13 | 76 |
| Immune/Additional | PRAME PHACTR1 KRT15 | 2.94E−13 | 76 |
| Immune/Additional | FN1 CFH RGS1 | 2.99E−13 | 79 |
| Immune/Additional | FABP7 CFH RGS1 | 3.62E−13 | 79 |
| Immune/Additional | CCL3 SPP1 KRT15 | 3.97E−13 | 77 |
| Immune/Additional | PRAME CFH KRT15 | 4.09E−13 | 76 |
| Immune/Additional | HEY1 PRAME KRT15 | 4.25E−13 | 76 |
| Immune/Additional | FABP7 IFI6 RGS1 | 4.97E−13 | 73 |
| Immune/Additional | FN1 PRAME KRT15 | 5.45E−13 | 76 |
| Immune/Additional | IFI6 CFH RGS1 | 5.48E−13 | 73 |

TABLE YY-continued

| type | genes | pval | n |
|---|---|---|---|
| Immune/Additional | FABP7 PTN RGS1 | 5.52E−13 | 79 |
| Immune/Additional | HEY1 CCL3 KRT15 | 5.81E−13 | 78 |
| Immune/Additional | PTN CFH RGS1 | 5.84E−13 | 79 |
| Immune/Additional | CCL3 FN1 KRT15 | 6.03E−13 | 78 |
| Immune/Additional | CCL3 CFH RGS1 | 6.37E−13 | 78 |
| Immune/Additional | CCL3 FABP7 RGS1 | 6.69E−13 | 78 |
| Immune/Additional | CCL3 PTN KRT15 | 7.34E−13 | 78 |
| Immune/Additional | CCL3 CFH KRT15 | 7.78E−13 | 78 |
| Immune/Additional | PTN PRAME KRT15 | 8.20E−13 | 76 |
| Immune/Additional | CCL3 PHACTR1 KRT15 | 8.53E−13 | 78 |
| Immune/Additional | CCL3 FABP7 KRT15 | 9.58E−13 | 78 |
| Immune/Additional | CCL3 IFI6 RGS1 | 9.78E−13 | 73 |
| Immune/Additional | CCL3 BCL2A1 KRT15 | 9.85E−13 | 78 |
| Immune/Additional | PRAME BCL2A1 KRT15 | 1.25E−12 | 76 |
| Immune/Additional | CFH SPP1 KRT15 | 1.35E−12 | 78 |
| Immune/Additional | FN1 PTN RGS1 | 1.55E−12 | 79 |
| Immune/Additional | PTN IFI6 RGS1 | 1.70E−12 | 73 |
| Immune/Additional | HEY1 SPP1 KRT15 | 1.86E−12 | 78 |
| Immune/Additional | CCL3 PTN RGS1 | 2.20E−12 | 78 |
| Immune/Additional | CCL3 IFI6 KRT15 | 2.24E−12 | 73 |
| Immune/Additional | PRAME IFI6 KRT15 | 2.87E−12 | 71 |
| Immune/Additional | RGS1 CCL5 PTPRC | 3.53E−12 | 52 |
| Immune/Additional | CCL3 PRAME SPP1 | 3.65E−12 | 75 |
| Immune/Additional | BCL2A1 CCL5 PTPRC | 3.67E−12 | 52 |
| Immune/Additional | PTPN22 CCL5 PTPRC | 3.92E−12 | 52 |
| Immune/Additional | PHACTR1 SPP1 KRT15 | 4.11E−12 | 77 |
| Immune/Additional | PRAME CCL5 PTPRC | 4.36E−12 | 52 |
| Immune/Additional | CCL5 PTPRC PHACTR1 | 4.48E−12 | 52 |
| Immune/Additional | FABP7 CCL5 PTPRC | 4.71E−12 | 52 |
| Immune/Additional | CCL5 S100A9 KRT15 | 4.88E−12 | 52 |
| Immune/Additional | HEY1 CCL5 PTPRC | 4.91E−12 | 52 |
| Immune/Additional | CCL5 PTPRC KRT15 | 4.92E−12 | 52 |
| Immune/Additional | PRAME IFI6 SPP1 | 4.93E−12 | 70 |
| Immune/Additional | PRAME SELL KRT15 | 4.93E−12 | 52 |
| Immune/Additional | CCL5 HLA PTPRC | 5.28E−12 | 52 |
| Immune/Additional | CCL3 CCL5 PTPRC | 5.34E−12 | 52 |
| Immune/Additional | CCL5 S100A9 PTPRC | 5.46E−12 | 52 |
| Immune/Additional | PTN SPP1 KRT15 | 5.53E−12 | 78 |
| Immune/Additional | PTN KRT15 CXCL9 | 5.57E−12 | 52 |
| Immune/Additional | FABP7 SPP1 KRT15 | 5.61E−12 | 78 |
| Immune/Additional | CCL5 PTPRC LCP2 | 5.87E−12 | 52 |
| Immune/Additional | CCL5 SELL KRT15 | 5.98E−12 | 52 |
| Immune/Additional | CCL5 SELL PTPRC | 6.10E−12 | 52 |
| Immune/Additional | IRF1 CCL5 PTPRC | 6.13E−12 | 52 |
| Immune/Additional | S100A9 PTPRC KRT15 | 6.37E−12 | 52 |
| Immune/Additional | SELL S100A9 KRT15 | 6.38E−12 | 52 |
| Immune/Additional | S100A9 LCP2 KRT15 | 6.50E−12 | 52 |
| Immune/Additional | PTN CCL5 PTPRC | 6.54E−12 | 52 |
| Immune/Additional | HLA CCL5 PTPRC | 6.65E−12 | 52 |
| Immune/Additional | PRAME PHACTR1 SPP1 | 6.68E−12 | 75 |
| Immune/Additional | FN1 CCL5 PTPRC | 6.74E−12 | 52 |
| Immune/Additional | CFH CCL5 PTPRC | 6.79E−12 | 52 |
| Immune/Additional | FN1 SPP1 KRT15 | 6.83E−12 | 78 |
| Immune/Additional | RGS1 SELL KRT15 | 6.83E−12 | 52 |
| Immune/Additional | PECAM1 CCL5 PTPRC | 6.86E−12 | 52 |
| Immune/Additional | BCL2A1 SPP1 KRT15 | 6.88E−12 | 77 |
| Immune/Additional | S100A9 KRT15 CXCL9 | 6.94E−12 | 52 |
| Immune/Additional | RGS1 KRT15 CXCL9 | 7.07E−12 | 52 |
| Immune/Additional | PRAME KRT15 CXCL9 | 7.25E−12 | 52 |
| Immune/Additional | CCL5 PTPRC HCLS1 | 7.35E−12 | 52 |
| Immune/Additional | SELL ITGB2 KRT15 | 7.68E−12 | 52 |
| Immune/Additional | SELL KRT15 CXCL9 | 7.73E−12 | 52 |
| Immune/Additional | PECAM1 S100A9 KRT15 | 7.83E−12 | 52 |
| Immune/Additional | CCL3 KRT15 CXCL9 | 7.90E−12 | 52 |
| Immune/Additional | CCL5 PTPRC CXCL9 | 7.97E−12 | 52 |
| Immune/Additional | LCP2 KRT15 CXCL9 | 8.01E−12 | 52 |
| Immune/Additional | PECAM1 KRT15 CXCL9 | 8.05E−12 | 52 |
| Immune/Additional | S100A9 KRT15 HCLS1 | 8.43E−12 | 52 |
| Immune/Additional | CCL5 ITGB2 PTPRC | 8.51E−12 | 52 |
| Immune/Additional | PHACTR1 KRT15 CXCL9 | 8.70E−12 | 52 |
| Immune/Additional | FABP7 PRAME SPP1 | 8.72E−12 | 75 |
| Immune/Additional | IRF1 S100A9 KRT15 | 8.92E−12 | 52 |
| Immune/Additional | FN1 PRAME SPP1 | 8.99E−12 | 75 |
| Immune/Additional | SELL PHACTR1 HCLS1 | 9.11E−12 | 52 |
| Immune/Additional | HLA KRT15 CXCL9 | 9.25E−12 | 52 |
| Immune/Additional | HLA KRT15 CXCL9 | 9.70E−12 | 52 |
| Immune/Additional | PRAME IRF1 KRT15 | 1.03E−11 | 52 |
| Immune/Additional | ITGB2 KRT15 CXCL9 | 1.03E−11 | 52 |
| Immune/Additional | FABP7 KRT15 CXCL9 | 1.05E−11 | 52 |
| Immune/Additional | IRF1 KRT15 CXCL9 | 1.05E−11 | 52 |
| Immune/Additional | KRT15 CXCL9 HCLS1 | 1.05E−11 | 52 |
| Immune/Additional | HEY1 KRT15 CXCL9 | 1.06E−11 | 52 |
| Immune/Additional | CCL3 IRF1 KRT15 | 1.09E−11 | 52 |
| Immune/Additional | CCL5 PTPRC SPP1 | 1.10E−11 | 51 |
| Immune/Additional | SELL KRT15 HCLS1 | 1.10E−11 | 52 |
| Immune/Additional | PRAME CCL5 KRT15 | 1.12E−11 | 52 |
| Immune/Additional | CCL5 PHACTR1 KRT15 | 1.12E−11 | 52 |
| Immune/Additional | BCL2A1 KRT15 CXCL9 | 1.14E−11 | 52 |
| Immune/Additional | PTPN22 S100A9 KRT15 | 1.17E−11 | 52 |
| Immune/Additional | CFH SELL KRT15 | 1.20E−11 | 52 |
| Immune/Additional | CCL3 CCL5 KRT15 | 1.24E−11 | 52 |
| Immune/Additional | PTPN22 KRT15 CXCL9 | 1.24E−11 | 52 |
| Immune/Additional | RGS1 CCL5 KRT15 | 1.24E−11 | 52 |
| Immune/Additional | PTPRC KRT15 CXCL9 | 1.26E−11 | 52 |
| Immune/Additional | IRF1 HLA KRT15 | 1.27E−11 | 52 |
| Immune/Additional | SELL PTPRC KRT15 | 1.30E−11 | 52 |
| Immune/Additional | S100A9 ITGB2 KRT15 | 1.31E−11 | 52 |
| Immune/Additional | CCL5 KRT15 CXCL9 | 1.32E−11 | 52 |
| Immune/Additional | PRAME PTPRC KRT15 | 1.33E−11 | 52 |
| Immune/Additional | IRF1 ITGB2 KRT15 | 1.35E−11 | 52 |
| Immune/Additional | IGJ PHACTR1 CXCL9 | 1.36E−11 | 50 |
| Immune/Additional | PECAM1 CCL5 KRT15 | 1.36E−11 | 52 |
| Immune/Additional | SELL PHACTR1 KRT15 | 1.41E−11 | 52 |
| Immune/Additional | CCL5 HLA KRT15 | 1.42E−11 | 52 |
| Immune/Additional | FN1 KRT15 CXCL9 | 1.45E−11 | 52 |
| Immune/Additional | PTPN22 SELL KRT15 | 1.48E−11 | 52 |
| Immune/Additional | IRF1 CCL5 KRT15 | 1.48E−11 | 52 |
| Immune/Additional | IRF1 KRT15 HCLS1 | 1.49E−11 | 52 |
| Immune/Additional | IGJ CCL5 PTPRC | 1.50E−11 | 50 |
| Immune/Additional | BCL2A1 SELL KRT15 | 1.50E−11 | 52 |
| Immune/Additional | HLA S100A9 KRT15 | 1.51E−11 | 52 |
| Immune/Additional | HLA SELL KRT15 | 1.53E−11 | 52 |
| Immune/Additional | BCL2A1 CCL5 KRT15 | 1.57E−11 | 52 |
| Immune/Additional | CCL5 LCP2 KRT15 | 1.57E−11 | 52 |
| Immune/Additional | IGJ KRT15 CXCL9 | 1.59E−11 | 50 |
| Immune/Additional | PRAME PTPN22 KRT15 | 1.62E−11 | 52 |
| Immune/Additional | RGS1 S100A9 KRT15 | 1.62E−11 | 52 |
| Immune/Additional | IRF1 SELL KRT15 | 1.63E−11 | 52 |
| Immune/Additional | CCL3 SELL KRT15 | 1.65E−11 | 52 |
| Immune/Additional | HEY1 CCL5 KRT15 | 1.66E−11 | 52 |
| Immune/Additional | SELL HLA KRT15 | 1.66E−11 | 52 |
| Immune/Additional | SELL LCP2 KRT15 | 1.70E−11 | 52 |
| Immune/Additional | CFH KRT15 CXCL9 | 1.71E−11 | 52 |
| Immune/Additional | IGJ CCL5 KRT15 | 1.75E−11 | 50 |
| Immune/Additional | PRAME KRT15 HCLS1 | 1.77E−11 | 52 |
| Immune/Additional | CFH IRF1 KRT15 | 1.79E−11 | 52 |
| Immune/Additional | CXCL10 RGS1 KRT15 | 1.83E−11 | 50 |
| Immune/Additional | PRAME LCP2 KRT15 | 1.85E−11 | 52 |
| Immune/Additional | FN1 SELL KRT15 | 1.87E−11 | 52 |
| Immune/Additional | HLA IRF1 KRT15 | 1.87E−11 | 52 |
| Immune/Additional | PRAME PECAM1 KRT15 | 1.92E−11 | 52 |
| Immune/Additional | IRF1 LCP2 KRT15 | 1.93E−11 | 52 |
| Immune/Additional | CD38 KRT15 CXCL9 | 1.94E−11 | 49 |
| Immune/Additional | HEY1 PRAME SPP1 | 1.95E−11 | 75 |
| Immune/Additional | SPP1 KRT15 CXCL9 | 1.97E−11 | 51 |
| Immune/Additional | FABP7 SELL KRT15 | 1.98E−11 | 52 |
| Immune/Additional | HLA S100A9 KRT15 | 1.98E−11 | 52 |
| Immune/Additional | SELL ITGB2 PHACTR1 | 1.99E−11 | 52 |
| Immune/Additional | PTN CCL5 KRT15 | 2.00E−11 | 52 |
| Immune/Additional | HEY1 FABP7 KRT15 | 2.02E−11 | 79 |
| Immune/Additional | FABP7 IRF1 KRT15 | 2.02E−11 | 52 |
| Immune/Additional | PTN SELL KRT15 | 2.02E−11 | 52 |
| Immune/Additional | HEY1 RGS1 SELL | 2.04E−11 | 52 |
| Immune/Additional | IGJ PRAME CXCL9 | 2.04E−11 | 50 |
| Immune/Additional | IRF1 PTPRC KRT15 | 2.04E−11 | 52 |
| Immune/Additional | CFH SELL PHACTR1 | 2.05E−11 | 52 |
| Immune/Additional | IRF1 PHACTR1 KRT15 | 2.10E−11 | 52 |
| Immune/Additional | HLA CCL5 KRT15 | 2.12E−11 | 52 |
| Immune/Additional | PTN IRF1 KRT15 | 2.16E−11 | 52 |
| Immune/Additional | PRAME BCL2A1 SPP1 | 2.16E−11 | 75 |
| Immune/Additional | PECAM1 SELL KRT15 | 2.19E−11 | 52 |
| Immune/Additional | CCL5 KRT15 HCLS1 | 2.21E−11 | 52 |
| Immune/Additional | HEY1 SELL KRT15 | 2.22E−11 | 52 |
| Immune/Additional | CXCL10 SELL KRT15 | 2.24E−11 | 50 |
| Immune/Additional | CCL5 ITGB2 KRT15 | 2.27E−11 | 52 |
| Immune/Additional | CXCL10 IRF1 KRT15 | 2.28E−11 | 50 |

TABLE YY-continued

| type | genes | pval | n |
|---|---|---|---|
| Immune/Additional | CXCL10 S100A9 KRT15 | 2.30E−11 | 50 |
| Immune/Additional | FN1 CCL5 KRT15 | 2.33E−11 | 52 |
| Immune/Additional | PTPN22 CCL5 KRT15 | 2.33E−11 | 52 |
| Immune/Additional | RGS1 IRF1 KRT15 | 2.35E−11 | 52 |
| Immune/Additional | CXCL10 CCL5 PTPRC | 2.45E−11 | 50 |
| Immune/Additional | FABP7 CCL5 KRT15 | 2.45E−11 | 52 |
| Immune/Additional | PTN PRAME SPP1 | 2.45E−11 | 75 |
| Immune/Additional | CCL5 CD38 PTPRC | 2.45E−11 | 49 |
| Immune/Additional | CCL5 CD38 KRT15 | 2.51E−11 | 49 |
| Immune/Additional | SELL SPP1 KRT15 | 2.53E−11 | 51 |
| Immune/Additional | BCL2A1 IRF1 KRT15 | 2.56E−11 | 52 |
| Immune/Additional | IRF1 CD38 KRT15 | 2.57E−11 | 49 |
| Immune/Additional | CXCL10 PRAME KRT15 | 2.68E−11 | 50 |
| Immune/Additional | CXCL10 PHACTR1 KRT15 | 2.71E−11 | 50 |
| Immune/Additional | CCL3 IFI6 SPP1 | 2.73E−11 | 72 |
| Immune/Additional | PRAME S100A9 KRT15 | 2.74E−11 | 52 |
| Immune/Additional | FN1 CXCL9 HCLS1 | 2.76E−11 | 52 |
| Immune/Additional | IFI6 KRT15 CXCL9 | 2.78E−11 | 48 |
| Immune/Additional | HEY1 IRF1 KRT15 | 2.79E−11 | 52 |
| Immune/Additional | HEY1 S100A9 KRT15 | 2.79E−11 | 52 |
| Immune/Additional | HEY1 CXCL10 KRT15 | 2.80E−11 | 50 |
| Immune/Additional | CXCL10 FABP7 KRT15 | 2.80E−11 | 50 |
| Immune/Additional | CFH CCL5 KRT15 | 2.82E−11 | 52 |
| Immune/Additional | CXCL10 KRT15 CXCL9 | 2.87E−11 | 50 |
| Immune/Additional | CXCL10 HLA KRT15 | 2.88E−11 | 50 |
| Immune/Additional | CXCL10 RGS1 PTPRC | 2.90E−11 | 50 |
| Immune/Additional | RGS1 LCP2 KRT15 | 2.93E−11 | 52 |
| Immune/Additional | PECAM1 IRF1 KRT15 | 2.95E−11 | 52 |
| Immune/Additional | CXCL10 BCL2A1 KRT15 | 2.96E−11 | 50 |
| Immune/Additional | PTPN22 IRF1 KRT15 | 2.96E−11 | 52 |
| Immune/Additional | CXCL10 HLA KRT15 | 2.97E−11 | 50 |
| Immune/Additional | PRAME CFH SPP1 | 3.01E−11 | 75 |
| Immune/Additional | CXCL10 PTPRC KRT15 | 3.03E−11 | 50 |
| Immune/Additional | FN1 IRF1 KRT15 | 3.06E−11 | 52 |
| Immune/Additional | CCL5 SPP1 KRT15 | 3.07E−11 | 51 |
| Immune/Additional | RGS1 PTPRC KRT15 | 3.15E−11 | 52 |
| Immune/Additional | CXCL10 PTPN22 KRT15 | 3.16E−11 | 50 |
| Immune/Additional | CXCL10 ITGB2 KRT15 | 3.16E−11 | 50 |
| Immune/Additional | CD38 SELL KRT15 | 3.22E−11 | 49 |
| Immune/Additional | HEY1 CFH KRT15 | 3.24E−11 | 79 |
| Immune/Additional | IRF1 SPP1 KRT15 | 3.29E−11 | 51 |
| Immune/Additional | PECAM1 SELL PHACTR1 | 3.33E−11 | 52 |
| Immune/Additional | RGS1 CD38 KRT15 | 3.33E−11 | 49 |
| Immune/Additional | CXCL10 CCL3 KRT15 | 3.36E−11 | 50 |
| Immune/Additional | CXCL10 PTN KRT15 | 3.43E−11 | 50 |
| Immune/Additional | CXCL10 CCL5 KRT15 | 3.43E−11 | 50 |
| Immune/Additional | HEY1 RGS1 LCP2 | 3.44E−11 | 52 |
| Immune/Additional | CXCL10 LCP2 KRT15 | 3.46E−11 | 50 |
| Immune/Additional | CCL3 S100A9 KRT15 | 3.49E−11 | 52 |
| Immune/Additional | IFI6 PHACTR1 CXCL9 | 3.53E−11 | 48 |
| Immune/Additional | CXCL10 KRT15 HCLS1 | 3.55E−11 | 50 |
| Immune/Additional | SELL CXCL13 KRT15 | 3.61E−11 | 48 |
| Immune/Additional | S100A9 SPP1 KRT15 | 3.66E−11 | 51 |
| Immune/Additional | CCL3 FN1 PRAME | 3.67E−11 | 76 |
| Immune/Additional | PRAME ITGB2 KRT15 | 3.72E−11 | 52 |
| Immune/Additional | PRAME IFI6 CXCL9 | 3.77E−11 | 48 |
| Immune/Additional | HEY1 RGS1 S100A9 | 3.82E−11 | 52 |
| Immune/Additional | HEY1 SELL PHACTR1 | 3.85E−11 | 52 |
| Immune/Additional | HEY1 PHACTR1 KRT15 | 3.85E−11 | 78 |
| Immune/Additional | CXCL10 CFH KRT15 | 3.96E−11 | 50 |
| Immune/Additional | CCL5 PTPRC CXCL13 | 4.05E−11 | 48 |
| Immune/Additional | PTPN22 RGS1 KRT15 | 4.09E−11 | 52 |
| Immune/Additional | CXCL13 LCP2 KRT15 | 4.09E−11 | 48 |
| Immune/Additional | CXCL10 FN1 KRT15 | 4.10E−11 | 50 |
| Immune/Additional | CXCL10 SPP1 KRT15 | 4.23E−11 | 49 |
| Immune/Additional | FN1 BCL2A1 SPP1 | 4.23E−11 | 79 |
| Immune/Additional | PECAM1 CD38 KRT15 | 4.24E−11 | 49 |
| Immune/Additional | CCL3 PHACTR1 SPP1 | 4.27E−11 | 77 |
| Immune/Additional | CXCL10 PECAM1 KRT15 | 4.33E−11 | 50 |
| Immune/Additional | RGS1 SELL PHACTR1 | 4.37E−11 | 52 |
| Immune/Additional | IGJ CCL5 PHACTR1 | 4.43E−11 | 50 |
| Immune/Additional | CXCL10 CD38 KRT15 | 4.49E−11 | 48 |
| Immune/Additional | HEY1 RGS1 CD38 | 4.51E−11 | 49 |
| Immune/Additional | PRAME HLA KRT15 | 4.57E−11 | 52 |
| Immune/Additional | CCL3 PRAME IFI6 | 4.61E−11 | 71 |
| Immune/Additional | CCL5 SELL PHACTR1 | 4.81E−11 | 52 |
| Immune/Additional | IGJ SELL KRT15 | 4.84E−11 | 50 |
| Immune/Additional | FN1 HLA CXCL9 | 4.87E−11 | 52 |
| Immune/Additional | CXCL10 RGS1 PHACTR1 | 4.95E−11 | 50 |
| Immune/Additional | SELL PHACTR1 CXCL9 | 4.95E−11 | 52 |
| Immune/Additional | CD38 ITGB2 KRT15 | 4.98E−11 | 49 |
| Immune/Additional | CCL5 CXCL13 KRT15 | 5.03E−11 | 48 |
| Immune/Additional | CXCL13 KRT15 CXCL9 | 5.06E−11 | 48 |
| Immune/Additional | PRAME SELL PHACTR1 | 5.08E−11 | 52 |
| Immune/Additional | RGS1 ITGB2 KRT15 | 5.14E−11 | 52 |
| Immune/Additional | CXCL10 RGS1 IRF1 | 5.15E−11 | 50 |
| Immune/Additional | SELL PHACTR1 LCP2 | 5.22E−11 | 52 |
| Immune/Additional | CCL3 FN1 SPP1 | 5.30E−11 | 77 |
| Immune/Additional | IFI6 SPP1 KRT15 | 5.31E−11 | 72 |
| Immune/Additional | RGS1 KRT15 HCLS1 | 5.32E−11 | 52 |
| Immune/Additional | HEY1 IGJ CCL5 | 5.33E−11 | 50 |
| Immune/Additional | SELL S100A9 PHACTR1 | 5.34E−11 | 52 |
| Immune/Additional | ITGB2 CXCL13 KRT15 | 5.37E−11 | 48 |
| Immune/Additional | CXCL10 HLA RGS1 | 5.43E−11 | 50 |
| Immune/Additional | HEY1 IFI6 SELL | 5.47E−11 | 48 |
| Immune/Additional | CD38 LCP2 KRT15 | 5.53E−11 | 49 |
| Immune/Additional | FN1 CD38 KRT15 | 5.56E−11 | 49 |
| Immune/Additional | IFI6 CCL5 PTPRC | 5.67E−11 | 48 |
| Immune/Additional | IGJ IRF1 KRT15 | 5.68E−11 | 50 |
| Immune/Additional | FABP7 CD38 KRT15 | 5.75E−11 | 49 |
| Immune/Additional | HLA CD38 KRT15 | 6.00E−11 | 49 |
| Immune/Additional | SELL PTPRC PHACTR1 | 6.02E−11 | 52 |
| Immune/Additional | CD38 PTPRC KRT15 | 6.03E−11 | 49 |
| Immune/Additional | HEY1 IFI6 CCL5 | 6.08E−11 | 48 |
| Immune/Additional | CD38 PHACTR1 CXCL9 | 6.09E−11 | 49 |
| Immune/Additional | HEY1 FN1 KRT15 | 6.28E−11 | 79 |
| Immune/Additional | IFI6 CCL5 KRT15 | 6.32E−11 | 48 |
| Immune/Additional | HEY1 RGS1 CCL5 | 6.36E−11 | 52 |
| Immune/Additional | FABP7 S100A9 KRT15 | 6.45E−11 | 52 |
| Immune/Additional | FN1 PHACTR1 KRT15 | 6.46E−11 | 78 |
| Immune/Additional | CCL3 CD38 KRT15 | 6.61E−11 | 49 |
| Immune/Additional | PECAM1 RGS1 KRT15 | 6.70E−11 | 52 |
| Immune/Additional | PTN S100A9 KRT15 | 6.72E−11 | 52 |
| Immune/Additional | HEY1 CXCL10 RGS1 | 6.74E−11 | 50 |
| Immune/Additional | CCL3 CFH SPP1 | 6.74E−11 | 77 |
| Immune/Additional | CCL3 SELL PHACTR1 | 6.86E−11 | 52 |
| Immune/Additional | CD38 HLA KRT15 | 6.89E−11 | 49 |
| Immune/Additional | IRF1 CXCL13 KRT15 | 6.91E−11 | 48 |
| Immune/Additional | CFH PHACTR1 KRT15 | 6.93E−11 | 78 |
| Immune/Additional | CXCL10 PTPRC CXCL9 | 6.96E−11 | 50 |
| Immune/Additional | IRF1 SELL PHACTR1 | 6.99E−11 | 52 |
| Immune/Additional | HLA RGS1 KRT15 | 7.02E−11 | 52 |
| Immune/Additional | PTPRC CXCL13 KRT15 | 7.04E−11 | 48 |
| Immune/Additional | CCL3 IFI6 CXCL9 | 7.06E−11 | 48 |
| Immune/Additional | PTPN22 CD38 KRT15 | 7.08E−11 | 49 |
| Immune/Additional | PTN CD38 KRT15 | 7.13E−11 | 49 |
| Immune/Additional | FABP7 CFH KRT15 | 7.14E−11 | 79 |
| Immune/Additional | HEY1 PTN KRT15 | 7.16E−11 | 79 |
| Immune/Additional | IGJ LCP2 KRT15 | 7.17E−11 | 50 |
| Immune/Additional | FN1 PHACTR1 CXCL9 | 7.19E−11 | 52 |
| Immune/Additional | FN1 IFI6 CXCL9 | 7.20E−11 | 48 |
| Immune/Additional | PTPRC PHACTR1 KRT15 | 7.23E−11 | 52 |
| Immune/Additional | CFH RGS1 SELL | 7.26E−11 | 52 |
| Immune/Additional | CD38 KRT15 HCLS1 | 7.26E−11 | 49 |
| Immune/Additional | CXCL13 KRT15 HCLS1 | 7.32E−11 | 48 |
| Immune/Additional | S100A9 PHACTR1 KRT15 | 7.48E−11 | 52 |
| Immune/Additional | FN1 S100A9 SPP1 | 7.49E−11 | 51 |
| Immune/Additional | FN1 HLA CCL5 | 7.51E−11 | 52 |
| Immune/Additional | FN1 CFH SELL | 7.72E−11 | 52 |
| Immune/Additional | HLA LCP2 KRT15 | 7.75E−11 | 52 |
| Immune/Additional | CXCL10 SELL PHACTR1 | 7.84E−11 | 50 |
| Immune/Additional | FN1 CFH CXCL9 | 7.87E−11 | 52 |
| Immune/Additional | RGS1 S100A9 PHACTR1 | 7.92E−11 | 52 |
| Immune/Additional | PECAM1 CXCL13 KRT15 | 8.25E−11 | 48 |
| Immune/Additional | IFI6 CFH SELL | 8.32E−11 | 48 |
| Immune/Additional | FABP7 IGJ CXCL9 | 8.34E−11 | 50 |
| Immune/Additional | FN1 S100A9 KRT15 | 8.35E−11 | 52 |
| Immune/Additional | CXCL10 PTPN22 RGS1 | 8.42E−11 | 50 |
| Immune/Additional | IGJ PTPRC KRT15 | 8.51E−11 | 50 |
| Immune/Additional | IGJ RGS1 CXCL9 | 8.59E−11 | 50 |
| Immune/Additional | PRAME PTPRC CXCL9 | 8.59E−11 | 52 |
| Immune/Additional | PTN PHACTR1 CXCL9 | 8.62E−11 | 52 |
| Immune/Additional | RGS1 HLA KRT15 | 8.76E−11 | 52 |
| Immune/Additional | IFI6 SELL KRT15 | 8.77E−11 | 48 |
| Immune/Additional | FABP7 FN1 KRT15 | 8.88E−11 | 79 |
| Immune/Additional | FN1 BCL2A1 KRT15 | 8.91E−11 | 78 |

TABLE YY-continued

| type | genes | pval | n |
|---|---|---|---|
| Immune/Additional | FN1 SELL PHACTR1 | 8.91E−11 | 52 |
| Immune/Additional | BCL2A1 SELL PHACTR1 | 8.91E−11 | 52 |
| Immune/Additional | PTPRC PHACTR1 CXCL9 | 8.92E−11 | 52 |
| Immune/Additional | IFI6 IRF1 KRT15 | 9.11E−11 | 48 |
| Immune/Additional | FABP7 PHACTR1 KRT15 | 9.12E−11 | 78 |
| Immune/Additional | FABP7 BCL2A1 KRT15 | 9.23E−11 | 78 |
| Immune/Additional | FN1 CFH KRT15 | 9.28E−11 | 79 |
| Immune/Additional | RGS1 PHACTR1 CXCL9 | 9.60E−11 | 52 |
| Immune/Additional | PHACTR1 LCP2 KRT15 | 9.62E−11 | 52 |
| Immune/Additional | CFH CD38 KRT15 | 9.70E−11 | 49 |
| Immune/Additional | PTPN22 PHACTR1 KRT15 | 9.76E−11 | 52 |
| Immune/Additional | IFI6 CD38 KRT15 | 9.78E−11 | 47 |
| Immune/Additional | CCL3 BCL2A1 SPP1 | 9.79E−11 | 77 |
| Immune/Additional | HLA SELL PHACTR1 | 9.92E−11 | 52 |
| Immune/Additional | HEY1 BCL2A1 KRT15 | 1.01E−10 | 78 |
| Immune/Additional | PTN PHACTR1 KRT15 | 1.01E−10 | 78 |
| Immune/Additional | FN1 PTPN22 CCL5 | 1.02E−10 | 52 |
| Immune/Additional | HEY1 RGS1 CXCL9 | 1.03E−10 | 52 |
| Immune/Additional | FN1 CXCL13 KRT15 | 1.03E−10 | 48 |
| Immune/Additional | CXCL10 RGS1 HLA | 1.04E−10 | 50 |
| Immune/Additional | HLA PTPRC KRT15 | 1.04E−10 | 52 |
| Immune/Additional | CXCL10 FN1 RGS1 | 1.05E−10 | 50 |
| Immune/Additional | BCL2A1 S100A9 KRT15 | 1.05E−10 | 52 |
| Immune/Additional | SELL HLA PHACTR1 | 1.05E−10 | 52 |
| Immune/Additional | CD38 PHACTR1 KRT15 | 1.06E−10 | 49 |
| Immune/Additional | PTPN22 HLA KRT15 | 1.07E−10 | 52 |
| Immune/Additional | PTPN22 CXCL13 KRT15 | 1.07E−10 | 48 |
| Immune/Additional | PTPRC LCP2 KRT15 | 1.07E−10 | 52 |
| Immune/Additional | HEY1 CFH SELL | 1.08E−10 | 52 |
| Immune/Additional | HLA CXCL13 KRT15 | 1.08E−10 | 48 |
| Immune/Additional | HEY1 CCL3 SPP1 | 1.09E−10 | 77 |
| Immune/Additional | CXCL10 IGJ RGS1 | 1.10E−10 | 48 |
| Immune/Additional | PRAME HLA KRT15 | 1.10E−10 | 52 |
| Immune/Additional | CXCL10 IGJ KRT15 | 1.11E−10 | 48 |
| Immune/Additional | IGJ RGS1 KRT15 | 1.11E−10 | 50 |
| Immune/Additional | PTPN22 SELL PHACTR1 | 1.12E−10 | 52 |
| Immune/Additional | HEY1 CCL5 CD38 | 1.13E−10 | 49 |
| Immune/Additional | BCL2A1 IFI6 SPP1 | 1.13E−10 | 74 |
| Immune/Additional | SELL PHACTR1 SPP1 | 1.13E−10 | 51 |
| Immune/Additional | PRAME CD38 KRT15 | 1.14E−10 | 49 |
| Immune/Additional | S100A9 PHACTR1 CXCL9 | 1.14E−10 | 52 |
| Immune/Additional | RGS1 PTPRC CXCL9 | 1.15E−10 | 52 |
| Immune/Additional | PTPN22 LCP2 KRT15 | 1.16E−10 | 52 |
| Immune/Additional | FN1 IGJ CXCL9 | 1.17E−10 | 50 |
| Immune/Additional | FN1 PTPRC CXCL9 | 1.19E−10 | 52 |
| Immune/Additional | PTN SELL PHACTR1 | 1.19E−10 | 52 |
| Immune/Additional | IFI6 CCL5 HLA | 1.19E−10 | 48 |
| Immune/Additional | CD38 SPP1 KRT15 | 1.21E−10 | 48 |
| Immune/Additional | IFI6 CCL5 PHACTR1 | 1.22E−10 | 48 |
| Immune/Additional | FN1 S100A9 CXCL9 | 1.24E−10 | 52 |
| Immune/Additional | HEY1 RGS1 IRF1 | 1.25E−10 | 52 |
| Immune/Additional | CCL3 FN1 CFH | 1.26E−10 | 78 |
| Immune/Additional | CXCL10 RGS1 CCL5 | 1.28E−10 | 50 |
| Immune/Additional | S100A9 PTPRC CXCL9 | 1.28E−10 | 52 |
| Immune/Additional | HEY1 RGS1 PTPRC | 1.30E−10 | 52 |
| Immune/Additional | CXCL10 CXCL13 KRT15 | 1.30E−10 | 46 |
| Immune/Additional | FN1 PRAME CXCL9 | 1.30E−10 | 52 |
| Immune/Additional | CD38 PTPRC CXCL9 | 1.31E−10 | 49 |
| Immune/Additional | FABP7 CXCL13 KRT15 | 1.32E−10 | 48 |
| Immune/Additional | IGJ CFH CXCL9 | 1.33E−10 | 50 |
| Immune/Additional | CCL3 FABP7 SPP1 | 1.34E−10 | 77 |
| Immune/Additional | RGS1 CXCL13 KRT15 | 1.36E−10 | 48 |
| Immune/Additional | CD38 S100A9 KRT15 | 1.37E−10 | 49 |
| Immune/Additional | HEY1 RGS1 ITGB2 | 1.40E−10 | 52 |
| Immune/Additional | HEY1 CD38 CXCL9 | 1.40E−10 | 49 |
| Immune/Additional | FABP7 SELL PHACTR1 | 1.40E−10 | 52 |
| Immune/Additional | CXCL10 IFI6 KRT15 | 1.41E−10 | 47 |
| Immune/Additional | HEY1 CD38 SELL | 1.43E−10 | 49 |
| Immune/Additional | BCL2A1 PHACTR1 KRT15 | 1.43E−10 | 78 |
| Immune/Additional | IFI6 CCL5 CXCL9 | 1.44E−10 | 48 |
| Immune/Additional | IFI6 S100A9 CXCL9 | 1.45E−10 | 48 |
| Immune/Additional | FABP7 FN1 PRAME | 1.48E−10 | 76 |
| Immune/Additional | BCL2A1 CFH KRT15 | 1.48E−10 | 78 |
| Immune/Additional | CXCL10 RGS1 HCLS1 | 1.54E−10 | 50 |
| Immune/Additional | FABP7 PTN KRT15 | 1.54E−10 | 79 |
| Immune/Additional | HLA CXCL13 KRT15 | 1.54E−10 | 48 |
| Immune/Additional | ITGB2 PTPRC KRT15 | 1.54E−10 | 52 |
| Immune/Additional | CXCL10 CFH RGS1 | 1.55E−10 | 50 |
| Immune/Additional | IFI6 SELL PHACTR1 | 1.55E−10 | 48 |
| Immune/Additional | PTN CFH KRT15 | 1.57E−10 | 79 |
| Immune/Additional | BCL2A1 PTPRC KRT15 | 1.57E−10 | 52 |
| Immune/Additional | CFH RGS1 CXCL9 | 1.58E−10 | 52 |
| Immune/Additional | PTPN22 SPP1 KRT15 | 1.58E−10 | 51 |
| Immune/Additional | HEY1 RGS1 HLA | 1.60E−10 | 52 |
| Immune/Additional | CFH LCP2 KRT15 | 1.60E−10 | 52 |
| Immune/Additional | PTPN22 ITGB2 KRT15 | 1.60E−10 | 52 |
| Immune/Additional | CFH CCL5 SELL | 1.61E−10 | 52 |
| Immune/Additional | S100A9 SPP1 CXCL9 | 1.61E−10 | 51 |
| Immune/Additional | HEY1 PECAM1 RGS1 | 1.62E−10 | 52 |
| Immune/Additional | CCL3 PTPRC KRT15 | 1.62E−10 | 52 |
| Immune/Additional | IGJ CCL5 CXCL9 | 1.63E−10 | 50 |
| Immune/Additional | BCL2A1 CD38 KRT15 | 1.63E−10 | 49 |
| Immune/Additional | PTN PTPRC KRT15 | 1.64E−10 | 52 |
| Immune/Additional | IFI6 PECAM1 CXCL9 | 1.64E−10 | 48 |
| Immune/Additional | PTPN22 PTPRC KRT15 | 1.64E−10 | 52 |
| Immune/Additional | HEY1 PTPN22 RGS1 | 1.66E−10 | 52 |
| Immune/Additional | CXCL10 SELL HLA | 1.68E−10 | 50 |
| Immune/Additional | CFH RGS1 CCL5 | 1.68E−10 | 52 |
| Immune/Additional | CCL3 FN1 BCL2A1 | 1.69E−10 | 78 |
| Immune/Additional | PHACTR1 SPP1 CXCL9 | 1.69E−10 | 51 |
| Immune/Additional | CXCL10 SELL PTPRC | 1.70E−10 | 50 |
| Immune/Additional | CCL3 PTN SPP1 | 1.70E−10 | 77 |
| Immune/Additional | CCL3 PTPN22 KRT15 | 1.70E−10 | 52 |
| Immune/Additional | CXCL10 HLA SELL | 1.71E−10 | 50 |
| Immune/Additional | BCL2A1 PHACTR1 KRT15 | 1.73E−10 | 52 |
| Immune/Additional | PRAME RGS1 SELL | 1.74E−10 | 52 |
| Immune/Additional | PTPN22 KRT15 HCLS1 | 1.76E−10 | 52 |
| Immune/Additional | HEY1 RGS1 HCLS1 | 1.77E−10 | 52 |
| Immune/Additional | HEY1 CD38 KRT15 | 1.77E−10 | 49 |
| Immune/Additional | IGJ PRAME CCL5 | 1.77E−10 | 50 |
| Immune/Additional | HEY1 CCL3 CD38 | 1.78E−10 | 49 |
| Immune/Additional | IGJ SELL PHACTR1 | 1.79E−10 | 50 |
| Immune/Additional | HEY1 IFI6 CXCL9 | 1.80E−10 | 48 |
| Immune/Additional | PTN PTPN22 KRT15 | 1.80E−10 | 52 |
| Immune/Additional | PTN LCP2 KRT15 | 1.81E−10 | 52 |
| Immune/Additional | FN1 PTN KRT15 | 1.82E−10 | 79 |
| Immune/Additional | CXCL10 FABP7 RGS1 | 1.83E−10 | 50 |
| Immune/Additional | PTPRC KRT15 HCLS1 | 1.83E−10 | 52 |
| Immune/Additional | HEY1 FN1 CCL5 | 1.84E−10 | 52 |
| Immune/Additional | HEY1 IGJ RGS1 | 1.84E−10 | 50 |
| Immune/Additional | CXCL10 PHACTR1 CXCL9 | 1.86E−10 | 50 |
| Immune/Additional | FN1 CFH CCL5 | 1.88E−10 | 52 |

TABLE ZZ

| type | genes | pval | n |
|---|---|---|---|
| Immune/Additional | PTN PRAME RGS1 KRT15 | 3.64E−15 | 76 |
| Immune/Additional | FABP7 PTN RGS1 KRT15 | 5.29E−15 | 79 |
| Immune/Additional | HEY1 PRAME RGS1 KRT15 | 5.52E−15 | 76 |
| Immune/Additional | PTN CFH RGS1 KRT15 | 5.99E−15 | 79 |
| Immune/Additional | PRAME RGS1 PHACTR1 KRT15 | 6.10E−15 | 76 |
| Immune/Additional | CCL3 PRAME RGS1 KRT15 | 6.66E−15 | 76 |
| Immune/Additional | HEY1 RGS1 PHACTR1 KRT15 | 7.41E−15 | 78 |
| Immune/Additional | PTN RGS1 SPP1 KRT15 | 7.42E−15 | 78 |
| Immune/Additional | HEY1 CCL3 RGS1 KRT15 | 7.48E−15 | 78 |
| Immune/Additional | CCL3 PTN RGS1 KRT15 | 7.64E−15 | 78 |
| Immune/Additional | PRAME CFH RGS1 KRT15 | 8.15E−15 | 76 |
| Immune/Additional | PRAME BCL2A1 RGS1 KRT15 | 8.23E−15 | 76 |
| Immune/Additional | FN1 PRAME RGS1 KRT15 | 8.34E−15 | 76 |
| Immune/Additional | FABP7 PRAME RGS1 KRT15 | 8.36E−15 | 76 |
| Immune/Additional | PTN RGS1 PHACTR1 KRT15 | 8.79E−15 | 78 |
| Immune/Additional | HEY1 BCL2A1 RGS1 KRT15 | 8.98E−15 | 78 |
| Immune/Additional | HEY1 PTN RGS1 KRT15 | 9.18E−15 | 79 |
| Immune/Additional | CFH RGS1 PHACTR1 KRT15 | 1.01E−14 | 78 |
| Immune/Additional | HEY1 FN1 RGS1 KRT15 | 1.02E−14 | 79 |
| Immune/Additional | HEY1 RGS1 SPP1 KRT15 | 1.02E−14 | 78 |
| Immune/Additional | CFH RGS1 SPP1 KRT15 | 1.03E−14 | 78 |
| Immune/Additional | FN1 RGS1 SPP1 KRT15 | 1.05E−14 | 78 |
| Immune/Additional | CCL3 RGS1 PHACTR1 KRT15 | 1.07E−14 | 78 |
| Immune/Additional | PRAME RGS1 SPP1 KRT15 | 1.08E−14 | 75 |
| Immune/Additional | RGS1 PHACTR1 SPP1 KRT15 | 1.08E−14 | 77 |
| Immune/Additional | CCL3 RGS1 SPP1 KRT15 | 1.09E−14 | 77 |
| Immune/Additional | HEY1 FABP7 RGS1 KRT15 | 1.11E−14 | 79 |

TABLE ZZ-continued

| | | | |
|---|---|---|---|
| Immune/Additional | CCL3 FN1 RGS1 KRT15 | 1.11E-14 | 78 |
| Immune/Additional | FABP7 RGS1 PHACTR1 KRT15 | 1.12E-14 | 78 |
| Immune/Additional | CCL3 CFH RGS1 KRT15 | 1.14E-14 | 78 |
| Immune/Additional | PTN BCL2A1 RGS1 KRT15 | 1.15E-14 | 78 |
| Immune/Additional | FN1 RGS1 PHACTR1 KRT15 | 1.18E-14 | 78 |
| Immune/Additional | HEY1 CFH RGS1 KRT15 | 1.20E-14 | 79 |
| Immune/Additional | CCL3 FABP7 RGS1 KRT15 | 1.22E-14 | 78 |
| Immune/Additional | FABP7 RGS1 SPP1 KRT15 | 1.26E-14 | 78 |
| Immune/Additional | FABP7 FN1 RGS1 KRT15 | 1.27E-14 | 79 |
| Immune/Additional | FN1 PTN RGS1 KRT15 | 1.27E-14 | 79 |
| Immune/Additional | BCL2A1 RGS1 PHACTR1 KRT15 | 1.29E-14 | 78 |
| Immune/Additional | BCL2A1 RGS1 SPP1 KRT15 | 1.33E-14 | 77 |
| Immune/Additional | CCL3 BCL2A1 RGS1 KRT15 | 1.36E-14 | 78 |
| Immune/Additional | FABP7 CFH RGS1 KRT15 | 1.37E-14 | 79 |
| Immune/Additional | FN1 CFH RGS1 KRT15 | 1.39E-14 | 79 |
| Immune/Additional | BCL2A1 CFH RGS1 KRT15 | 1.45E-14 | 78 |
| Immune/Additional | FN1 BCL2A1 RGS1 KRT15 | 1.50E-14 | 78 |
| Immune/Additional | FABP7 BCL2A1 RGS1 KRT15 | 1.55E-14 | 78 |
| Immune/Additional | FN1 BCL2A1 RGS1 SPP1 | 1.81E-14 | 79 |
| Immune/Additional | PRAME IFI6 RGS1 KRT15 | 2.42E-14 | 71 |
| Immune/Additional | HEY1 FABP7 PTN RGS1 | 3.09E-14 | 79 |
| Immune/Additional | CCL3 IFI6 RGS1 KRT15 | 5.86E-14 | 73 |
| Immune/Additional | IFI6 RGS1 SPP1 KRT15 | 5.95E-14 | 72 |
| Immune/Additional | FABP7 IFI6 RGS1 KRT15 | 6.01E-14 | 73 |
| Immune/Additional | HEY1 IFI6 RGS1 KRT15 | 6.44E-14 | 73 |
| Immune/Additional | PTN IFI6 RGS1 KRT15 | 6.54E-14 | 73 |
| Immune/Additional | PTN RGS1 PHACTR1 SPP1 | 6.54E-14 | 77 |
| Immune/Additional | FN1 IFI6 RGS1 KRT15 | 6.58E-14 | 73 |
| Immune/Additional | IFI6 RGS1 PHACTR1 KRT15 | 6.61E-14 | 73 |
| Immune/Additional | IFI6 CFH RGS1 KRT15 | 6.90E-14 | 73 |
| Immune/Additional | FN1 RGS1 PHACTR1 SPP1 | 7.42E-14 | 77 |
| Immune/Additional | BCL2A1 IFI6 RGS1 SPP1 | 7.76E-14 | 74 |
| Immune/Additional | BCL2A1 IFI6 RGS1 KRT15 | 8.11E-14 | 73 |
| Immune/Additional | FN1 BCL2A1 IFI6 RGS1 | 8.15E-14 | 75 |
| Immune/Additional | FABP7 PTN RGS1 PHACTR1 | 8.77E-14 | 78 |
| Immune/Additional | PTN CFH RGS1 SPP1 | 8.97E-14 | 78 |
| Immune/Additional | PTN PRAME RGS1 PHACTR1 | 9.33E-14 | 76 |
| Immune/Additional | CCL3 PTN PRAME KRT15 | 9.68E-14 | 76 |
| Immune/Additional | FN1 IFI6 RGS1 SPP1 | 9.75E-14 | 74 |
| Immune/Additional | FN1 PTN BCL2A1 RGS1 | 9.82E-14 | 78 |
| Immune/Additional | FN1 BCL2A1 RGS1 PHACTR1 | 1.01E-13 | 78 |
| Immune/Additional | HEY1 PTN RGS1 SPP1 | 1.10E-13 | 78 |
| Immune/Additional | FABP7 FN1 RGS1 PHACTR1 | 1.14E-13 | 78 |
| Immune/Additional | CCL3 PRAME BCL2A1 KRT15 | 1.15E-13 | 76 |
| Immune/Additional | FABP7 RGS1 PHACTR1 SPP1 | 1.15E-13 | 77 |
| Immune/Additional | HEY1 RGS1 PHACTR1 SPP1 | 1.17E-13 | 77 |
| Immune/Additional | CCL3 RGS1 PHACTR1 SPP1 | 1.17E-13 | 77 |
| Immune/Additional | FN1 PRAME RGS1 PHACTR1 | 1.26E-13 | 76 |
| Immune/Additional | FN1 PTN RGS1 PHACTR1 | 1.29E-13 | 78 |
| Immune/Additional | CCL3 PRAME SPP1 KRT15 | 1.30E-13 | 75 |
| Immune/Additional | BCL2A1 RGS1 PHACTR1 SPP1 | 1.32E-13 | 77 |
| Immune/Additional | CFH RGS1 PHACTR1 SPP1 | 1.35E-13 | 77 |
| Immune/Additional | FABP7 FN1 BCL2A1 RGS1 | 1.38E-13 | 78 |
| Immune/Additional | HEY1 PTN PRAME RGS1 | 1.43E-13 | 76 |
| Immune/Additional | HEY1 FN1 BCL2A1 RGS1 | 1.47E-13 | 78 |
| Immune/Additional | HEY1 FABP7 RGS1 PHACTR1 | 1.49E-13 | 78 |
| Immune/Additional | PTN PRAME RGS1 SPP1 | 1.50E-13 | 75 |
| Immune/Additional | HEY1 FABP7 RGS1 SPP1 | 1.53E-13 | 78 |
| Immune/Additional | HEY1 BCL2A1 RGS1 SPP1 | 1.55E-13 | 77 |
| Immune/Additional | HEY1 CCL3 PRAME KRT15 | 1.56E-13 | 76 |
| Immune/Additional | PRAME RGS1 PHACTR1 SPP1 | 1.56E-13 | 75 |
| Immune/Additional | HEY1 FN1 RGS1 PHACTR1 | 1.62E-13 | 78 |
| Immune/Additional | FN1 CFH RGS1 PHACTR1 | 1.67E-13 | 78 |
| Immune/Additional | HEY1 CCL3 RGS1 SPP1 | 1.69E-13 | 77 |
| Immune/Additional | FABP7 PTN RGS1 SPP1 | 1.71E-13 | 78 |
| Immune/Additional | FN1 PRAME RGS1 SPP1 | 1.71E-13 | 75 |
| Immune/Additional | CCL3 PRAME PHACTR1 KRT15 | 1.72E-13 | 76 |
| Immune/Additional | PTN BCL2A1 RGS1 SPP1 | 1.75E-13 | 77 |
| Immune/Additional | PTN CFH RGS1 PHACTR1 | 1.76E-13 | 78 |
| Immune/Additional | HEY1 FN1 RGS1 SPP1 | 1.77E-13 | 78 |
| Immune/Additional | FABP7 PTN PRAME RGS1 | 1.77E-13 | 78 |
| Immune/Additional | CCL3 FN1 BCL2A1 RGS1 | 1.78E-13 | 78 |
| Immune/Additional | PTN BCL2A1 RGS1 PHACTR1 | 1.78E-13 | 78 |
| Immune/Additional | HEY1 PTN RGS1 PHACTR1 | 1.81E-13 | 78 |
| Immune/Additional | HEY1 PTN BCL2A1 RGS1 | 1.82E-13 | 78 |
| Immune/Additional | CCL3 FN1 RGS1 PHACTR1 | 1.82E-13 | 78 |
| Immune/Additional | FN1 BCL2A1 CFH RGS1 | 1.87E-13 | 78 |
| Immune/Additional | CCL3 FABP7 PRAME KRT15 | 1.90E-13 | 76 |
| Immune/Additional | CCL3 FN1 PRAME KRT15 | 1.95E-13 | 76 |
| Immune/Additional | FN1 CFH RGS1 SPP1 | 1.97E-13 | 78 |
| Immune/Additional | HEY1 PRAME RGS1 SPP1 | 2.00E-13 | 75 |
| Immune/Additional | HEY1 CCL3 FABP7 RGS1 | 2.02E-13 | 78 |
| Immune/Additional | HEY1 FABP7 BCL2A1 RGS1 | 2.05E-13 | 78 |
| Immune/Additional | CCL3 FN1 RGS1 SPP1 | 2.11E-13 | 77 |
| Immune/Additional | HEY1 FN1 PRAME RGS1 | 2.17E-13 | 76 |
| Immune/Additional | CCL3 PRAME RGS1 PHACTR1 | 2.17E-13 | 76 |
| Immune/Additional | HEY1 PRAME RGS1 PHACTR1 | 2.18E-13 | 76 |
| Immune/Additional | HEY1 CFH RGS1 SPP1 | 2.26E-13 | 78 |
| Immune/Additional | FABP7 PTN BCL2A1 RGS1 | 2.26E-13 | 78 |
| Immune/Additional | FABP7 PRAME RGS1 PHACTR1 | 2.27E-13 | 76 |
| Immune/Additional | FN1 PTN RGS1 SPP1 | 2.28E-13 | 78 |
| Immune/Additional | HEY1 BCL2A1 RGS1 PHACTR1 | 2.31E-13 | 78 |
| Immune/Additional | FN1 PTN PRAME RGS1 | 2.31E-13 | 76 |
| Immune/Additional | CCL3 PRAME CFH KRT15 | 2.38E-13 | 76 |
| Immune/Additional | FN1 PRAME BCL2A1 RGS1 | 2.40E-13 | 76 |
| Immune/Additional | HEY1 FABP7 PRAME RGS1 | 2.46E-13 | 76 |
| Immune/Additional | FABP7 BCL2A1 RGS1 PHACTR1 | 2.54E-13 | 78 |
| Immune/Additional | HEY1 FABP7 FN1 RGS1 | 2.55E-13 | 79 |
| Immune/Additional | FABP7 FN1 RGS1 SPP1 | 2.63E-13 | 78 |
| Immune/Additional | PRAME BCL2A1 RGS1 PHACTR1 | 2.68E-13 | 76 |
| Immune/Additional | PRAME PHACTR1 SPP1 KRT15 | 2.74E-13 | 75 |
| Immune/Additional | BCL2A1 CFH RGS1 SPP1 | 2.86E-13 | 77 |
| Immune/Additional | HEY1 CCL3 PTN RGS1 | 2.89E-13 | 78 |
| Immune/Additional | CCL3 FABP7 RGS1 PHACTR1 | 2.90E-13 | 78 |
| Immune/Additional | HEY1 CCL3 FN1 RGS1 | 2.95E-13 | 78 |
| Immune/Additional | CCL3 BCL2A1 RGS1 PHACTR1 | 2.99E-13 | 78 |
| Immune/Additional | FABP7 BCL2A1 RGS1 SPP1 | 3.04E-13 | 77 |
| Immune/Additional | CCL3 BCL2A1 RGS1 SPP1 | 3.07E-13 | 77 |
| Immune/Additional | FABP7 CFH RGS1 PHACTR1 | 3.09E-13 | 78 |
| Immune/Additional | FABP7 CFH RGS1 SPP1 | 3.11E-13 | 78 |
| Immune/Additional | FABP7 FN1 PRAME RGS1 | 3.12E-13 | 76 |
| Immune/Additional | PRAME CFH RGS1 PHACTR1 | 3.13E-13 | 76 |
| Immune/Additional | HEY1 CCL3 RGS1 PHACTR1 | 3.17E-13 | 78 |
| Immune/Additional | BCL2A1 CFH RGS1 PHACTR1 | 3.21E-13 | 78 |
| Immune/Additional | CCL3 PTN RGS1 SPP1 | 3.23E-13 | 77 |
| Immune/Additional | FABP7 PTN CFH RGS1 | 3.26E-13 | 79 |
| Immune/Additional | FABP7 PRAME RGS1 SPP1 | 3.27E-13 | 75 |
| Immune/Additional | CCL3 PRAME RGS1 SPP1 | 3.37E-13 | 75 |
| Immune/Additional | FABP7 PRAME SPP1 KRT15 | 3.45E-13 | 75 |
| Immune/Additional | PTN BCL2A1 CFH RGS1 | 3.48E-13 | 78 |
| Immune/Additional | PRAME BCL2A1 RGS1 SPP1 | 3.48E-13 | 75 |
| Immune/Additional | HEY1 CFH RGS1 PHACTR1 | 3.49E-13 | 78 |
| Immune/Additional | PRAME CFH SPP1 KRT15 | 3.56E-13 | 75 |
| Immune/Additional | HEY1 CCL3 BCL2A1 RGS1 | 3.57E-13 | 78 |
| Immune/Additional | CCL3 PTN RGS1 PHACTR1 | 3.58E-13 | 78 |
| Immune/Additional | PRAME BCL2A1 SPP1 KRT15 | 3.62E-13 | 75 |
| Immune/Additional | HEY1 PRAME BCL2A1 RGS1 | 3.64E-13 | 76 |
| Immune/Additional | HEY1 FABP7 CFH RGS1 | 3.75E-13 | 79 |
| Immune/Additional | CCL3 CFH RGS1 SPP1 | 3.77E-13 | 77 |
| Immune/Additional | PTN PRAME BCL2A1 RGS1 | 3.78E-13 | 76 |
| Immune/Additional | PRAME IFI6 RGS1 SPP1 | 3.81E-13 | 70 |
| Immune/Additional | IFI6 RGS1 PHACTR1 SPP1 | 3.89E-13 | 72 |
| Immune/Additional | HEY1 CCL3 PRAME RGS1 | 4.17E-13 | 76 |
| Immune/Additional | PRAME CFH RGS1 SPP1 | 4.32E-13 | 75 |
| Immune/Additional | CCL3 FN1 PRAME RGS1 | 4.39E-13 | 76 |
| Immune/Additional | PTN PRAME CFH RGS1 | 4.39E-13 | 76 |
| Immune/Additional | HEY1 PRAME SPP1 KRT15 | 4.41E-13 | 75 |
| Immune/Additional | FN1 PRAME CFH RGS1 | 4.42E-13 | 76 |
| Immune/Additional | HEY1 IFI6 RGS1 SPP1 | 4.44E-13 | 72 |
| Immune/Additional | HEY1 BCL2A1 CFH RGS1 | 4.53E-13 | 78 |
| Immune/Additional | HEY1 PRAME CFH RGS1 | 4.67E-13 | 76 |
| Immune/Additional | CCL3 CFH RGS1 PHACTR1 | 4.76E-13 | 78 |
| Immune/Additional | PTN PRAME SPP1 KRT15 | 4.92E-13 | 75 |
| Immune/Additional | CCL3 FABP7 RGS1 SPP1 | 5.06E-13 | 77 |
| Immune/Additional | IFI6 CFH RGS1 SPP1 | 5.56E-13 | 72 |
| Immune/Additional | PRAME IFI6 RGS1 PHACTR1 | 5.61E-13 | 71 |
| Immune/Additional | FN1 PRAME SPP1 KRT15 | 5.68E-13 | 75 |
| Immune/Additional | CCL3 PRAME IFI6 KRT15 | 5.91E-13 | 71 |
| Immune/Additional | HEY1 FABP7 IFI6 RGS1 | 5.92E-13 | 73 |
| Immune/Additional | PTN IFI6 RGS1 SPP1 | 6.17E-13 | 72 |
| Immune/Additional | CCL3 IFI6 RGS1 SPP1 | 6.22E-13 | 72 |
| Immune/Additional | CCL3 PTN BCL2A1 RGS1 | 6.42E-13 | 78 |
| Immune/Additional | FABP7 IFI6 RGS1 SPP1 | 6.57E-13 | 72 |
| Immune/Additional | FABP7 PRAME BCL2A1 RGS1 | 6.62E-13 | 76 |
| Immune/Additional | CCL3 FABP7 BCL2A1 RGS1 | 6.78E-13 | 78 |
| Immune/Additional | CCL3 FN1 CFH RGS1 | 6.93E-13 | 78 |
| Immune/Additional | HEY1 CCL3 CFH RGS1 | 6.98E-13 | 78 |
| Immune/Additional | HEY1 PRAME IFI6 RGS1 | 7.06E-13 | 71 |
| Immune/Additional | FABP7 BCL2A1 CFH RGS1 | 7.06E-13 | 78 |
| Immune/Additional | PRAME BCL2A1 IFI6 RGS1 | 7.69E-13 | 71 |

TABLE ZZ-continued

| | | | |
|---|---|---|---|
| Immune/Additional | FN1 PRAME IFI6 RGS1 | 7.95E-13 | 71 |
| Immune/Additional | CCL3 PRAME BCL2A1 RGS1 | 8.06E-13 | 76 |
| Immune/Additional | BCL2A1 IFI6 RGS1 PHACTR1 | 8.07E-13 | 73 |
| Immune/Additional | FABP7 IFI6 RGS1 PHACTR1 | 8.22E-13 | 73 |
| Immune/Additional | CCL3 FABP7 FN1 RGS1 | 8.25E-13 | 78 |
| Immune/Additional | FABP7 FN1 CFH RGS1 | 8.35E-13 | 79 |
| Immune/Additional | FN1 IFI6 RGS1 PHACTR1 | 8.44E-13 | 73 |
| Immune/Additional | HEY1 BCL2A1 IFI6 RGS1 | 8.46E-13 | 73 |
| Immune/Additional | FABP7 BCL2A1 IFI6 RGS1 | 8.64E-13 | 73 |
| Immune/Additional | CCL3 PTN PRAME RGS1 | 8.71E-13 | 76 |
| Immune/Additional | PTN PRAME IFI6 RGS1 | 8.71E-13 | 71 |
| Immune/Additional | FABP7 PRAME IFI6 RGS1 | 8.83E-13 | 71 |
| Immune/Additional | HEY1 PTN CFH RGS1 | 9.30E-13 | 79 |
| Immune/Additional | CCL3 BCL2A1 CFH RGS1 | 9.50E-13 | 78 |
| Immune/Additional | CCL3 FABP7 PRAME RGS1 | 9.60E-13 | 76 |
| Immune/Additional | HEY1 FN1 PTN RGS1 | 9.82E-13 | 79 |
| Immune/Additional | PRAME BCL2A1 CFH RGS1 | 9.87E-13 | 76 |
| Immune/Additional | CCL3 PRAME IFI6 RGS1 | 1.00E-12 | 71 |
| Immune/Additional | HEY1 IFI6 RGS1 PHACTR1 | 1.02E-12 | 73 |
| Immune/Additional | HEY1 CCL3 IFI6 RGS1 | 1.03E-12 | 73 |
| Immune/Additional | CCL3 BCL2A1 IFI6 RGS1 | 1.09E-12 | 73 |
| Immune/Additional | HEY1 FN1 IFI6 RGS1 | 1.15E-12 | 73 |
| Immune/Additional | HEY1 FABP7 PRAME KRT15 | 1.16E-12 | 76 |
| Immune/Additional | FABP7 FN1 PTN RGS1 | 1.20E-12 | 79 |
| Immune/Additional | PRAME IFI6 CFH RGS1 | 1.22E-12 | 71 |
| Immune/Additional | HEY1 FN1 CFH RGS1 | 1.25E-12 | 79 |
| Immune/Additional | FABP7 PRAME CFH RGS1 | 1.27E-12 | 76 |
| Immune/Additional | PTN BCL2A1 IFI6 RGS1 | 1.30E-12 | 73 |
| Immune/Additional | CCL3 IFI6 RGS1 PHACTR1 | 1.31E-12 | 73 |
| Immune/Additional | PRAME IFI6 SPP1 KRT15 | 1.32E-12 | 70 |
| Immune/Additional | FN1 PTN CFH RGS1 | 1.39E-12 | 79 |
| Immune/Additional | BCL2A1 IFI6 CFH RGS1 | 1.42E-12 | 73 |
| Immune/Additional | IFI6 CFH RGS1 PHACTR1 | 1.42E-12 | 73 |
| Immune/Additional | HEY1 PRAME CFH KRT15 | 1.52E-12 | 76 |
| Immune/Additional | FABP7 PRAME PHACTR1 KRT15 | 1.55E-12 | 76 |
| Immune/Additional | PRAME BCL2A1 PHACTR1 KRT15 | 1.55E-12 | 76 |
| Immune/Additional | HEY1 PRAME BCL2A1 KRT15 | 1.57E-12 | 76 |
| Immune/Additional | PTN IFI6 RGS1 PHACTR1 | 1.57E-12 | 73 |
| Immune/Additional | PRAME CFH PHACTR1 KRT15 | 1.57E-12 | 76 |
| Immune/Additional | FN1 PRAME PHACTR1 KRT15 | 1.61E-12 | 76 |
| Immune/Additional | HEY1 PTN IFI6 RGS1 | 1.69E-12 | 73 |
| Immune/Additional | CCL3 PRAME CFH RGS1 | 1.76E-12 | 76 |
| Immune/Additional | CCL3 PTN CFH RGS1 | 1.87E-12 | 78 |
| Immune/Additional | HEY1 PRAME PHACTR1 KRT15 | 1.90E-12 | 76 |
| Immune/Additional | FABP7 FN1 PRAME KRT15 | 1.94E-12 | 76 |
| Immune/Additional | CCL3 FN1 PTN RGS1 | 2.00E-12 | 78 |
| Immune/Additional | FABP7 PRAME BCL2A1 KRT15 | 2.01E-12 | 76 |
| Immune/Additional | FABP7 FN1 IFI6 RGS1 | 2.07E-12 | 73 |
| Immune/Additional | HEY1 IFI6 CFH RGS1 | 2.08E-12 | 73 |
| Immune/Additional | CCL3 CFH SPP1 KRT15 | 2.20E-12 | 77 |
| Immune/Additional | PTN PRAME PHACTR1 KRT15 | 2.29E-12 | 76 |
| Immune/Additional | FABP7 PRAME CFH KRT15 | 2.32E-12 | 76 |
| Immune/Additional | CCL3 PTN CFH KRT15 | 2.36E-12 | 78 |
| Immune/Additional | CCL3 PTN SPP1 KRT15 | 2.37E-12 | 77 |
| Immune/Additional | FN1 IFI6 CFH RGS1 | 2.53E-12 | 73 |
| Immune/Additional | FN1 PRAME CFH KRT15 | 2.58E-12 | 76 |
| Immune/Additional | PRAME BCL2A1 CFH KRT15 | 2.62E-12 | 76 |
| Immune/Additional | FABP7 PTN PRAME KRT15 | 2.65E-12 | 76 |
| Immune/Additional | CCL3 FABP7 CFH RGS1 | 2.67E-12 | 78 |
| Immune/Additional | FABP7 IFI6 CFH RGS1 | 2.74E-12 | 73 |
| Immune/Additional | CCL3 PHACTR1 SPP1 KRT15 | 2.88E-12 | 77 |
| Immune/Additional | HEY1 CCL3 PTN KRT15 | 2.90E-12 | 78 |
| Immune/Additional | HEY1 FN1 PRAME KRT15 | 2.99E-12 | 76 |
| Immune/Additional | HEY1 CCL3 SPP1 KRT15 | 3.02E-12 | 77 |
| Immune/Additional | CCL3 FN1 SPP1 KRT15 | 3.09E-12 | 77 |
| Immune/Additional | CCL3 FABP7 PTN RGS1 | 3.11E-12 | 78 |
| Immune/Additional | CCL3 FN1 PTN KRT15 | 3.15E-12 | 78 |
| Immune/Additional | HEY1 PTN PRAME KRT15 | 3.27E-12 | 76 |
| Immune/Additional | CCL3 FABP7 SPP1 KRT15 | 3.35E-12 | 77 |
| Immune/Additional | CCL3 BCL2A1 SPP1 KRT15 | 3.35E-12 | 77 |
| Immune/Additional | PTN PRAME CFH KRT15 | 3.39E-12 | 76 |
| Immune/Additional | CCL3 IFI6 CFH RGS1 | 3.71E-12 | 73 |
| Immune/Additional | CCL3 FABP7 IFI6 RGS1 | 3.77E-12 | 73 |
| Immune/Additional | HEY1 CCL3 PHACTR1 KRT15 | 3.86E-12 | 78 |
| Immune/Additional | CCL3 FN1 IFI6 RGS1 | 3.87E-12 | 73 |
| Immune/Additional | PTN IFI6 CFH RGS1 | 4.18E-12 | 73 |
| Immune/Additional | HEY1 CCL3 CFH KRT15 | 4.23E-12 | 78 |
| Immune/Additional | CCL3 FN1 CFH KRT15 | 4.32E-12 | 78 |
| Immune/Additional | FABP7 PTN IFI6 RGS1 | 4.32E-12 | 73 |
| Immune/Additional | FN1 PTN PRAME KRT15 | 4.34E-12 | 76 |
| Immune/Additional | HEY1 CCL3 BCL2A1 KRT15 | 4.37E-12 | 78 |
| Immune/Additional | HEY1 CCL3 FN1 KRT15 | 4.41E-12 | 78 |
| Immune/Additional | CCL3 FN1 PHACTR1 KRT15 | 4.43E-12 | 78 |
| Immune/Additional | FN1 PRAME BCL2A1 KRT15 | 4.45E-12 | 76 |
| Immune/Additional | HEY1 CCL3 FABP7 KRT15 | 4.85E-12 | 78 |
| Immune/Additional | CCL3 FABP7 FN1 KRT15 | 4.90E-12 | 78 |
| Immune/Additional | CCL3 FN1 BCL2A1 KRT15 | 5.05E-12 | 78 |
| Immune/Additional | CCL3 PTN PHACTR1 KRT15 | 5.16E-12 | 78 |
| Immune/Additional | CCL3 CFH PHACTR1 KRT15 | 5.46E-12 | 78 |
| Immune/Additional | PTN PRAME BCL2A1 KRT15 | 5.86E-12 | 76 |
| Immune/Additional | CCL3 FABP7 CFH KRT15 | 5.95E-12 | 78 |
| Immune/Additional | CCL3 PTN BCL2A1 KRT15 | 6.02E-12 | 78 |
| Immune/Additional | CCL3 FABP7 PTN KRT15 | 6.09E-12 | 78 |
| Immune/Additional | CCL3 BCL2A1 CFH KRT15 | 6.33E-12 | 78 |
| Immune/Additional | CCL3 PRAME IFI6 SPP1 | 6.43E-12 | 70 |
| Immune/Additional | CCL3 FABP7 PHACTR1 KRT15 | 7.08E-12 | 78 |
| Immune/Additional | HEY1 CFH SPP1 KRT15 | 7.22E-12 | 78 |
| Immune/Additional | FN1 PTN IFI6 RGS1 | 7.22E-12 | 73 |
| Immune/Additional | CCL3 BCL2A1 PHACTR1 KRT15 | 7.24E-12 | 78 |
| Immune/Additional | CCL3 FABP7 BCL2A1 KRT15 | 8.01E-12 | 78 |
| Immune/Additional | PTN CFH SPP1 KRT15 | 8.62E-12 | 78 |
| Immune/Additional | CCL3 PTN IFI6 RGS1 | 9.08E-12 | 73 |
| Immune/Additional | CCL3 IFI6 SPP1 KRT15 | 9.33E-12 | 72 |
| Immune/Additional | HEY1 CCL3 IFI6 KRT15 | 1.02E-11 | 73 |
| Immune/Additional | CFH PHACTR1 SPP1 KRT15 | 1.02E-11 | 77 |
| Immune/Additional | FABP7 CFH SPP1 KRT15 | 1.06E-11 | 78 |
| Immune/Additional | HEY1 FABP7 SPP1 KRT15 | 1.23E-11 | 78 |
| Immune/Additional | FN1 CFH SPP1 KRT15 | 1.24E-11 | 78 |
| Immune/Additional | CCL3 FN1 PRAME SPP1 | 1.29E-11 | 75 |
| Immune/Additional | CCL3 FN1 IFI6 KRT15 | 1.30E-11 | 73 |
| Immune/Additional | HEY1 PRAME IFI6 KRT15 | 1.35E-11 | 71 |
| Immune/Additional | CCL3 PTN PRAME SPP1 | 1.37E-11 | 75 |
| Immune/Additional | PRAME IFI6 PHACTR1 KRT15 | 1.41E-11 | 71 |
| Immune/Additional | HEY1 PHACTR1 SPP1 KRT15 | 1.42E-11 | 77 |
| Immune/Additional | FABP7 PRAME IFI6 KRT15 | 1.43E-11 | 71 |
| Immune/Additional | BCL2A1 CFH SPP1 KRT15 | 1.44E-11 | 77 |
| Immune/Additional | CCL3 IFI6 PHACTR1 KRT15 | 1.51E-11 | 73 |
| Immune/Additional | CCL3 PRAME PHACTR1 SPP1 | 1.54E-11 | 75 |
| Immune/Additional | HEY1 PTN SPP1 KRT15 | 1.59E-11 | 78 |
| Immune/Additional | HEY1 FN1 SPP1 KRT15 | 1.61E-11 | 78 |
| Immune/Additional | PRAME BCL2A1 IFI6 KRT15 | 1.62E-11 | 71 |
| Immune/Additional | PRAME IFI6 CFH KRT15 | 1.63E-11 | 71 |
| Immune/Additional | CCL3 PTN IFI6 KRT15 | 1.67E-11 | 73 |
| Immune/Additional | CCL3 FABP7 IFI6 KRT15 | 1.73E-11 | 73 |
| Immune/Additional | CCL3 BCL2A1 IFI6 KRT15 | 1.82E-11 | 73 |
| Immune/Additional | PTN PRAME IFI6 KRT15 | 1.84E-11 | 71 |
| Immune/Additional | HEY1 BCL2A1 SPP1 KRT15 | 1.91E-11 | 77 |
| Immune/Additional | FN1 PRAME IFI6 KRT15 | 1.91E-11 | 71 |
| Immune/Additional | CCL3 IFI6 CFH KRT15 | 2.09E-11 | 73 |
| Immune/Additional | CCL3 FABP7 PRAME SPP1 | 2.24E-11 | 75 |
| Immune/Additional | HEY1 CCL3 PRAME SPP1 | 2.63E-11 | 75 |
| Immune/Additional | FABP7 PRAME PHACTR1 SPP1 | 2.75E-11 | 75 |
| Immune/Additional | FABP7 PTN PRAME SPP1 | 2.77E-11 | 75 |
| Immune/Additional | FN1 PRAME PHACTR1 SPP1 | 2.80E-11 | 75 |
| Immune/Additional | BCL2A1 PHACTR1 SPP1 KRT15 | 2.80E-11 | 77 |
| Immune/Additional | FABP7 FN1 PRAME SPP1 | 2.83E-11 | 75 |
| Immune/Additional | FN1 PHACTR1 SPP1 KRT15 | 2.84E-11 | 77 |
| Immune/Additional | PTN PHACTR1 SPP1 KRT15 | 2.85E-11 | 77 |
| Immune/Additional | CCL3 PRAME BCL2A1 SPP1 | 2.86E-11 | 75 |
| Immune/Additional | FABP7 PHACTR1 SPP1 KRT15 | 3.01E-11 | 77 |
| Immune/Additional | FABP7 PRAME IFI6 SPP1 | 3.29E-11 | 70 |
| Immune/Additional | SELL HLA ITGB2 KRT15 | 3.45E-11 | 52 |
| Immune/Additional | FABP7 BCL2A1 SPP1 KRT15 | 3.50E-11 | 77 |
| Immune/Additional | RGS1 SELL ITGB2 KRT15 | 3.57E-11 | 52 |
| Immune/Additional | BCL2A1 CCL5 S100A9 KRT15 | 3.63E-11 | 52 |
| Immune/Additional | IRF1 SELL ITGB2 KRT15 | 3.66E-11 | 52 |
| Immune/Additional | CCL3 PRAME CFH SPP1 | 3.69E-11 | 75 |
| Immune/Additional | PRAME BCL2A1 IFI6 SPP1 | 3.69E-11 | 70 |
| Immune/Additional | RGS1 SELL KRT15 HCLS1 | 3.69E-11 | 52 |
| Immune/Additional | BCL2A1 RGS1 CCL5 PTPRC | 3.73E-11 | 52 |
| Immune/Additional | RGS1 CCL5 PTPRC PHACTR1 | 3.73E-11 | 52 |
| Immune/Additional | FN1 PRAME IFI6 SPP1 | 3.74E-11 | 70 |
| Immune/Additional | PRAME RGS1 CCL5 PTPRC | 3.75E-11 | 52 |
| Immune/Additional | BCL2A1 CCL5 PTPRC PHACTR1 | 3.81E-11 | 52 |
| Immune/Additional | BCL2A1 CCL5 PTPRC KRT15 | 3.81E-11 | 52 |
| Immune/Additional | FABP7 FN1 SPP1 KRT15 | 3.88E-11 | 78 |
| Immune/Additional | CCL5 SELL PTPRC PHACTR1 | 3.88E-11 | 52 |
| Immune/Additional | FN1 BCL2A1 SPP1 KRT15 | 3.91E-11 | 77 |
| Immune/Additional | CCL3 RGS1 CCL5 PTPRC | 3.94E-11 | 52 |
| Immune/Additional | HLA CCL5 SELL KRT15 | 3.98E-11 | 52 |

TABLE ZZ-continued

| | | | |
|---|---|---|---|
| Immune/Additional | PRAME IFI6 PHACTR1 SPP1 | 4.02E-11 | 70 |
| Immune/Additional | FN1 PTN SPP1 KRT15 | 4.06E-11 | 78 |
| Immune/Additional | FABP7 CCL5 S100A9 PTPRC | 4.07E-11 | 52 |
| Immune/Additional | FABP7 PTN SPP1 KRT15 | 4.13E-11 | 78 |
| Immune/Additional | PTPN22 CCL5 PTPRC PHACTR1 | 4.16E-11 | 52 |
| Immune/Additional | CCL5 SELL PTPRC KRT15 | 4.18E-11 | 52 |
| Immune/Additional | PTN PRAME IFI6 SPP1 | 4.25E-11 | 70 |
| Immune/Additional | PTN PRAME PHACTR1 SPP1 | 4.31E-11 | 75 |
| Immune/Additional | RGS1 CCL5 PTPRC KRT15 | 4.31E-11 | 52 |
| Immune/Additional | FABP7 BCL2A1 CCL5 PTPRC | 4.34E-11 | 52 |
| Immune/Additional | PTN BCL2A1 SPP1 KRT15 | 4.35E-11 | 77 |
| Immune/Additional | RGS1 CCL5 PTPRC LCP2 | 4.36E-11 | 52 |
| Immune/Additional | HEY1 RGS1 CCL5 PTPRC | 4.37E-11 | 52 |
| Immune/Additional | HLA RGS1 CCL5 PTPRC | 4.37E-11 | 52 |
| Immune/Additional | IRF1 CCL5 SELL PTPRC | 4.39E-11 | 52 |
| Immune/Additional | FABP7 CCL5 PTPRC PHACTR1 | 4.45E-11 | 52 |
| Immune/Additional | CCL5 PTPRC LCP2 HCLS1 | 4.50E-11 | 52 |
| Immune/Additional | HEY1 CCL5 S100A9 KRT15 | 4.52E-11 | 52 |
| Immune/Additional | CCL5 S100A9 LCP2 KRT15 | 4.52E-11 | 52 |
| Immune/Additional | FABP7 CCL5 S100A9 KRT15 | 4.55E-11 | 52 |
| Immune/Additional | RGS1 CCL5 HLA PTPRC | 4.56E-11 | 52 |
| Immune/Additional | SELL S100A9 PHACTR1 KRT15 | 4.56E-11 | 52 |
| Immune/Additional | FABP7 RGS1 CCL5 PTPRC | 4.57E-11 | 52 |
| Immune/Additional | HEY1 FABP7 PRAME SPP1 | 4.61E-11 | 75 |
| Immune/Additional | PRAME RGS1 SELL KRT15 | 4.61E-11 | 52 |
| Immune/Additional | CCL3 BCL2A1 CCL5 PTPRC | 4.63E-11 | 52 |
| Immune/Additional | CCL5 SELL S100A9 KRT15 | 4.65E-11 | 52 |
| Immune/Additional | PRAME PTPN22 CCL5 PTPRC | 4.67E-11 | 52 |
| Immune/Additional | BCL2A1 CCL5 S100A9 PTPRC | 4.67E-11 | 52 |
| Immune/Additional | PTPN22 CCL5 PTPRC LCP2 | 4.68E-11 | 52 |
| Immune/Additional | PRAME CCL5 PTPRC PHACTR1 | 4.70E-11 | 52 |
| Immune/Additional | CCL5 SELL ITGB2 KRT15 | 4.71E-11 | 52 |
| Immune/Additional | HEY1 PRAME IFI6 SPP1 | 4.72E-11 | 70 |
| Immune/Additional | BCL2A1 CCL5 HLA PTPRC | 4.73E-11 | 52 |
| Immune/Additional | IRF1 CCL5 S100A9 KRT15 | 4.74E-11 | 52 |
| Immune/Additional | HEY1 PTPN22 CCL5 PTPRC | 4.75E-11 | 52 |
| Immune/Additional | PRAME CCL5 S100A9 KRT15 | 4.75E-11 | 52 |
| Immune/Additional | PTPN22 CCL5 PTPRC KRT15 | 4.75E-11 | 52 |
| Immune/Additional | RGS1 SELL S100A9 KRT15 | 4.77E-11 | 52 |
| Immune/Additional | PTN RGS1 CCL5 PTPRC | 4.81E-11 | 52 |
| Immune/Additional | CCL5 SELL PTPRC LCP2 | 4.82E-11 | 52 |
| Immune/Additional | HEY1 BCL2A1 CCL5 PTPRC | 4.84E-11 | 52 |
| Immune/Additional | RGS1 CCL5 S100A9 PTPRC | 4.84E-11 | 52 |
| Immune/Additional | CCL3 CCL5 S100A9 KRT15 | 4.85E-11 | 52 |
| Immune/Additional | CCL5 HLA S100A9 KRT15 | 4.87E-11 | 52 |
| Immune/Additional | BCL2A1 PTPN22 CCL5 PTPRC | 4.89E-11 | 52 |
| Immune/Additional | PTPN22 RGS1 CCL5 PTPRC | 4.89E-11 | 52 |
| Immune/Additional | CCL5 PTPRC LCP2 CXCL9 | 4.91E-11 | 52 |
| Immune/Additional | HEY1 CCL5 PTPRC KRT15 | 4.93E-11 | 52 |
| Immune/Additional | PRAME CCL5 PTPRC KRT15 | 4.93E-11 | 52 |
| Immune/Additional | RGS1 CCL5 SELL PTPRC | 4.94E-11 | 52 |
| Immune/Additional | PTPN22 CCL5 HLA PTPRC | 4.95E-11 | 52 |
| Immune/Additional | PRAME BCL2A1 SELL KRT15 | 4.96E-11 | 52 |
| Immune/Additional | BCL2A1 HLA CCL5 PTPRC | 4.98E-11 | 52 |
| Immune/Additional | FABP7 CCL5 PTPRC LCP2 | 5.02E-11 | 52 |
| Immune/Additional | CCL5 SELL KRT15 HCLS1 | 5.06E-11 | 52 |
| Immune/Additional | CCL3 CCL5 SELL KRT15 | 5.07E-11 | 52 |
| Immune/Additional | PRAME BCL2A1 PHACTR1 SPP1 | 5.07E-11 | 75 |
| Immune/Additional | RGS1 IRF1 CCL5 PTPRC | 5.07E-11 | 52 |
| Immune/Additional | CCL3 PTPN22 CCL5 PTPRC | 5.09E-11 | 52 |
| Immune/Additional | PRAME IFI6 CFH SPP1 | 5.11E-11 | 70 |
| Immune/Additional | RGS1 SELL LCP2 KRT15 | 5.11E-11 | 52 |
| Immune/Additional | CCL5 S100A9 PTPRC LCP2 | 5.12E-11 | 52 |
| Immune/Additional | BCL2A1 CCL5 PTPRC LCP2 | 5.13E-11 | 52 |
| Immune/Additional | CCL5 SELL LCP2 KRT15 | 5.14E-11 | 52 |
| Immune/Additional | CCL3 CCL5 PTPRC PHACTR1 | 5.18E-11 | 52 |
| Immune/Additional | CCL3 FABP7 CCL5 PTPRC | 5.20E-11 | 52 |
| Immune/Additional | CCL5 PTPRC PHACTR1 LCP2 | 5.20E-11 | 52 |
| Immune/Additional | CCL5 PTPRC PHACTR1 KRT15 | 5.21E-11 | 52 |
| Immune/Additional | PRAME BCL2A1 CCL5 PTPRC | 5.24E-11 | 52 |
| Immune/Additional | CCL5 S100A9 PHACTR1 KRT15 | 5.25E-11 | 52 |
| Immune/Additional | HLA CCL5 S100A9 KRT15 | 5.26E-11 | 52 |
| Immune/Additional | FN1 PRAME BCL2A1 SPP1 | 5.29E-11 | 75 |
| Immune/Additional | PRAME CCL5 HLA PTPRC | 5.29E-11 | 52 |
| Immune/Additional | FABP7 PRAME CCL5 PTPRC | 5.31E-11 | 52 |
| Immune/Additional | PRAME IRF1 SELL KRT15 | 5.31E-11 | 52 |
| Immune/Additional | CCL5 S100A9 KRT15 CXCL9 | 5.31E-11 | 52 |
| Immune/Additional | CCL5 S100A9 PTPRC PHACTR1 | 5.34E-11 | 52 |
| Immune/Additional | PTN PRAME KRT15 CXCL9 | 5.37E-11 | 52 |
| Immune/Additional | FABP7 PTN CCL5 PTPRC | 5.38E-11 | 52 |
| Immune/Additional | IRF1 SELL S100A9 KRT15 | 5.38E-11 | 52 |
| Immune/Additional | FABP7 PTPN22 CCL5 PTPRC | 5.40E-11 | 52 |
| Immune/Additional | CCL5 HLA PTPRC PHACTR1 | 5.40E-11 | 52 |
| Immune/Additional | CFH CCL5 S100A9 KRT15 | 5.42E-11 | 52 |
| Immune/Additional | FABP7 CCL5 SELL PTPRC | 5.44E-11 | 52 |
| Immune/Additional | PECAM1 RGS1 CCL5 PTPRC | 5.44E-11 | 52 |
| Immune/Additional | CCL5 S100A9 PTPRC KRT15 | 5.45E-11 | 52 |
| Immune/Additional | FABP7 PRAME SELL KRT15 | 5.47E-11 | 52 |
| Immune/Additional | HLA SELL KRT15 CXCL9 | 5.48E-11 | 52 |
| Immune/Additional | PTPN22 IRF1 CCL5 PTPRC | 5.50E-11 | 52 |
| Immune/Additional | CCL5 HLA S100A9 PTPRC | 5.50E-11 | 52 |
| Immune/Additional | PTPN22 CCL5 S100A9 PTPRC | 5.51E-11 | 52 |
| Immune/Additional | IRF1 CCL5 PTPRC LCP2 | 5.53E-11 | 52 |
| Immune/Additional | PRAME CCL5 S100A9 PTPRC | 5.55E-11 | 52 |
| Immune/Additional | PRAME SELL HLA KRT15 | 5.56E-11 | 52 |
| Immune/Additional | CCL5 PTPRC LCP2 KRT15 | 5.56E-11 | 52 |
| Immune/Additional | CCL3 PRAME CCL5 PTPRC | 5.61E-11 | 52 |
| Immune/Additional | RGS1 SELL KRT15 CXCL9 | 5.61E-11 | 52 |
| Immune/Additional | PRAME SELL PTPRC KRT15 | 5.62E-11 | 52 |
| Immune/Additional | BCL2A1 IRF1 CCL5 PTPRC | 5.62E-11 | 52 |
| Immune/Additional | RGS1 CCL5 PTPRC CXCL9 | 5.63E-11 | 52 |
| Immune/Additional | S100A9 PTPRC LCP2 KRT15 | 5.63E-11 | 52 |
| Immune/Additional | PTN RGS1 KRT15 CXCL9 | 5.65E-11 | 52 |
| Immune/Additional | SELL HLA S100A9 KRT15 | 5.65E-11 | 52 |
| Immune/Additional | SELL ITGB2 PHACTR1 KRT15 | 5.65E-11 | 52 |
| Immune/Additional | CCL5 S100A9 KRT15 HCLS1 | 5.66E-11 | 52 |
| Immune/Additional | PTN PRAME SELL KRT15 | 5.68E-11 | 52 |
| Immune/Additional | FABP7 S100A9 PTPRC KRT15 | 5.70E-11 | 52 |
| Immune/Additional | HEY1 CCL5 PTPRC PHACTR1 | 5.71E-11 | 52 |
| Immune/Additional | CCL3 RGS1 SELL KRT15 | 5.71E-11 | 52 |
| Immune/Additional | FN1 RGS1 CCL5 PTPRC | 5.71E-11 | 52 |
| Immune/Additional | CFH RGS1 CCL5 PTPRC | 5.74E-11 | 52 |
| Immune/Additional | CCL3 CCL5 S100A9 PTPRC | 5.75E-11 | 52 |
| Immune/Additional | HEY1 FABP7 CCL5 PTPRC | 5.76E-11 | 52 |
| Immune/Additional | HEY1 PRAME PHACTR1 SPP1 | 5.77E-11 | 75 |
| Immune/Additional | HLA PHACTR1 KRT15 CXCL9 | 5.77E-11 | 52 |
| Immune/Additional | HLA PTPN22 CCL5 PTPRC | 5.79E-11 | 52 |
| Immune/Additional | SELL S100A9 PTPRC KRT15 | 5.80E-11 | 52 |
| Immune/Additional | CFH PTPN22 CCL5 PTPRC | 5.82E-11 | 52 |
| Immune/Additional | CCL5 HLA PTPRC KRT15 | 5.82E-11 | 52 |
| Immune/Additional | FABP7 SELL S100A9 KRT15 | 5.84E-11 | 52 |
| Immune/Additional | PRAME CCL5 SELL PTPRC | 5.84E-11 | 52 |
| Immune/Additional | IRF1 CCL5 SELL KRT15 | 5.84E-11 | 52 |
| Immune/Additional | PRAME SELL PHACTR1 KRT15 | 5.85E-11 | 52 |
| Immune/Additional | PRAME CCL5 PTPRC LCP2 | 5.86E-11 | 52 |
| Immune/Additional | RGS1 CCL5 PTPRC HCLS1 | 5.87E-11 | 52 |
| Immune/Additional | CCL3 PRAME SELL KRT15 | 5.88E-11 | 52 |
| Immune/Additional | PTN BCL2A1 CCL5 PTPRC | 5.88E-11 | 52 |
| Immune/Additional | FABP7 CCL5 HLA PTPRC | 5.90E-11 | 52 |
| Immune/Additional | PTN PTPN22 CCL5 PTPRC | 5.90E-11 | 52 |
| Immune/Additional | PRAME SELL KRT15 CXCL9 | 5.90E-11 | 52 |
| Immune/Additional | PECAM1 SELL S100A9 KRT15 | 5.90E-11 | 52 |
| Immune/Additional | HEY1 CCL5 PTPRC LCP2 | 5.92E-11 | 52 |
| Immune/Additional | CCL3 S100A9 PTPRC KRT15 | 5.94E-11 | 52 |
| Immune/Additional | HEY1 PRAME CCL5 PTPRC | 5.96E-11 | 52 |
| Immune/Additional | RGS1 CCL5 S100A9 KRT15 | 5.96E-11 | 52 |
| Immune/Additional | BCL2A1 PECAM1 CCL5 PTPRC | 6.00E-11 | 52 |
| Immune/Additional | HEY1 PRAME SELL KRT15 | 6.02E-11 | 52 |
| Immune/Additional | PTN CCL5 S100A9 KRT15 | 6.02E-11 | 52 |
| Immune/Additional | PTPN22 CCL5 SELL PTPRC | 6.02E-11 | 52 |
| Immune/Additional | S100A9 PTPRC PHACTR1 KRT15 | 6.05E-11 | 52 |
| Immune/Additional | BCL2A1 CCL5 SELL KRT15 | 6.06E-11 | 52 |
| Immune/Additional | CCL5 S100A9 ITGB2 KRT15 | 6.06E-11 | 52 |
| Immune/Additional | CCL5 HLA PTPRC LCP2 | 6.07E-11 | 52 |
| Immune/Additional | HLA RGS1 SELL KRT15 | 6.08E-11 | 52 |
| Immune/Additional | PRAME HLA SELL KRT15 | 6.09E-11 | 52 |
| Immune/Additional | PRAME LCP2 KRT15 CXCL9 | 6.11E-11 | 52 |
| Immune/Additional | HEY1 CCL3 CCL5 PTPRC | 6.14E-11 | 52 |
| Immune/Additional | IRF1 CCL5 PTPRC PHACTR1 | 6.15E-11 | 52 |
| Immune/Additional | HEY1 CCL5 S100A9 PTPRC | 6.16E-11 | 52 |
| Immune/Additional | S100A9 PTPRC KRT15 CXCL9 | 6.16E-11 | 52 |
| Immune/Additional | PRAME CCL5 SELL KRT15 | 6.18E-11 | 52 |
| Immune/Additional | RGS1 CCL5 SELL KRT15 | 6.19E-11 | 52 |

Example 5

In this example we determined a model for differentiating melanoma samples from nevus samples based on a computed score.

Methods

Approximately 600 skin lesions were acquired from two separate sites (coded "Munich" and "Provitro"), with relatively equal numbers from both locations. Each site provided both malignant and benign samples, with all major histological subtypes represented. The diagnosis for each case was confirmed, using a second dermatopathologist who was blinded to the diagnosis of the first dermatopathologist. If there was discordance, a third dermatopathologist adjudicated the diagnosis.

An H&E stained slide from each case was then reviewed by a pathologist, and the lesion of interest identified for each case. The corresponding tissue was macrodissected from 5 unstained slides (4 mm thickness) and pooled into a single tube. The RNA was then extracted from the tissue, the RNA was DNAsed using DNAse I and cDNA synthesized. We then pre-amplified all genes of interest including 7 housekeeper normalization genes) in one multiplex reaction. Finally, quantitative PCR was used to measure the expression of each gene. The expression values were calculated by determining the CT (Crossing Threshold) of each gene. Each sample was run in triplicate by splitting each sample into 3 aliquots after the cDNA synthesis.

The three measurements of each gene were then averaged and normalized by the averaged expression of all seven housekeeper genes. Each gene was studied to determine if its expression could differentiate between malignant melanoma and benign nevi samples; if genes were effective at this, they were further analyzed to see which genes had correlating data (an indication that these genes measure the same biological pathway). Genes with correlating data were grouped together in sets, with the average expression of the set used to differentiate melanoma and nevi.

Results

We acquired ~600 samples from two German sites (labeled Munich and Provitro [Berlin]). Each site contributed roughly even numbers of malignant and benign samples, with all major histologic subtypes represented in the samples from each site. We first identified the lesion of interest in each sample and then extracted the RNA from each sample and measured the RNA expression level of the potential signature genes and 7 housekeeper normalization genes (Table 11).

TABLE 11

List of potential signature genes tested and housekeeper genes used for normalization.

| Gene | Function | Gene | Function |
| --- | --- | --- | --- |
| PTN | Potential Signature | CD38 | Potential Signature |
| CFH | Potential Signature | RGS1 | Potential Signature |
| IGJ | Potential Signature | DLGAP5 | Potential Signature |
| HEY1 | Potential Signature | MCM10 | Potential Signature |
| PECAM1 | Potential Signature | RRM2 | Potential Signature |
| HCLS1 | Potential Signature | CCL5 | Potential Signature |
| HLA-DRA | Potential Signature | CXCL13 | Potential Signature |
| HLA-DMA | Potential Signature | CXCL9 | Potential Signature |
| BCL2A1 | Potential Signature | CENPF | Potential Signature |
| FABP7 | Potential Signature | PBK | Potential Signature |
| PTPRC | Potential Signature | CXCL10 | Potential Signature |
| IFI6 | Potential Signature | FOXM1 | Potential Signature |
| S100A9 | Potential Signature | PLK1 | Potential Signature |
| FN1 | Potential Signature | CEP55 | Potential Signature |
| ITGB2 | Potential Signature | DTL | Potential Signature |
| PTPN22 | Potential Signature | SKA1 | Potential Signature |
| PHACTR1 | Potential Signature | CCL5 | Potential Signature |
| CCL3 | Potential Signature | CLTC | Housekeeper |
| PRAME | Potential Signature | MRFAP1 | Housekeeper |

TABLE 11-continued

List of potential signature genes tested and housekeeper genes used for normalization.

| Gene | Function | Gene | Function |
| --- | --- | --- | --- |
| KRT15 | Potential Signature | PPP2CA | Housekeeper |
| SPP1 | Potential Signature | PSMA1 | Housekeeper |
| LCP2 | Potential Signature | RPL13A | Housekeeper |
| IRF1 | Potential Signature | RPL8 | Housekeeper |
| SELL | Potential Signature | TXNL1 | Housekeeper |

Figure 5:
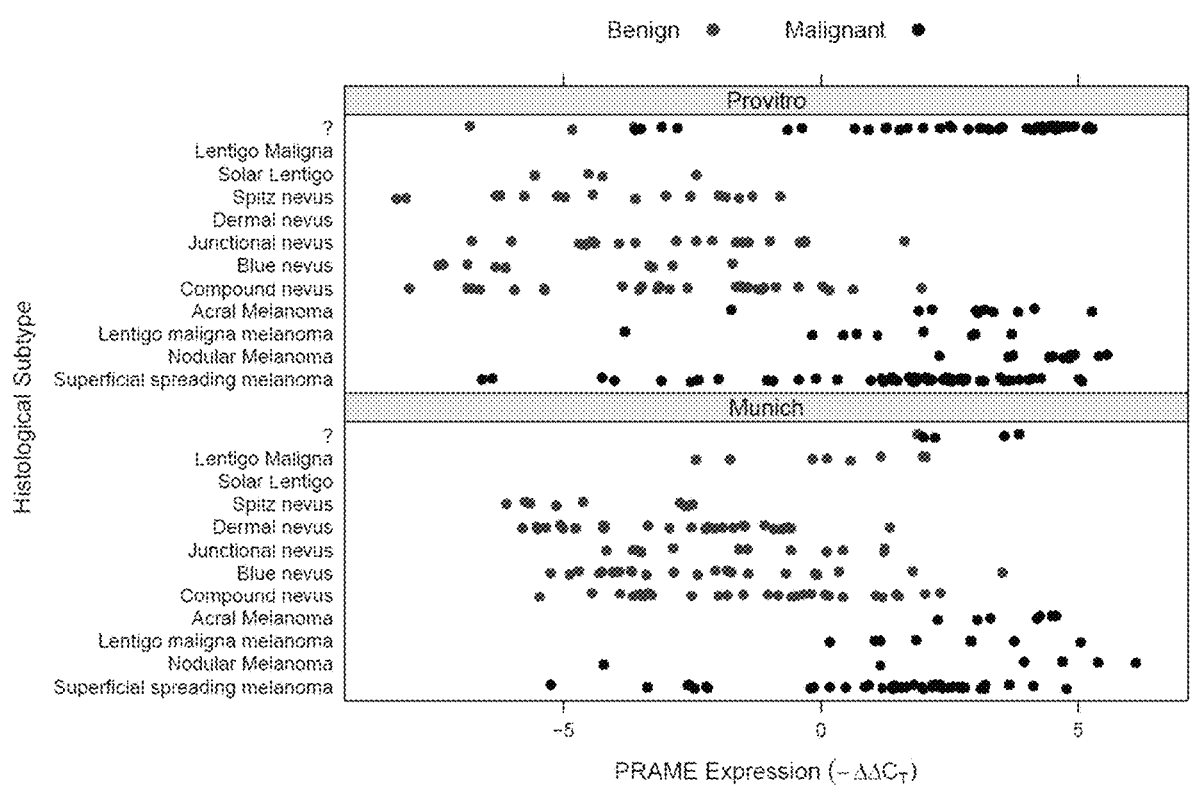
FIG. 5 shows the normalized expression of PRAME in each sample, as differentiated by both site and histological subtype. Malignant samples are black, while benign samples are colored grey.
Figure 6:
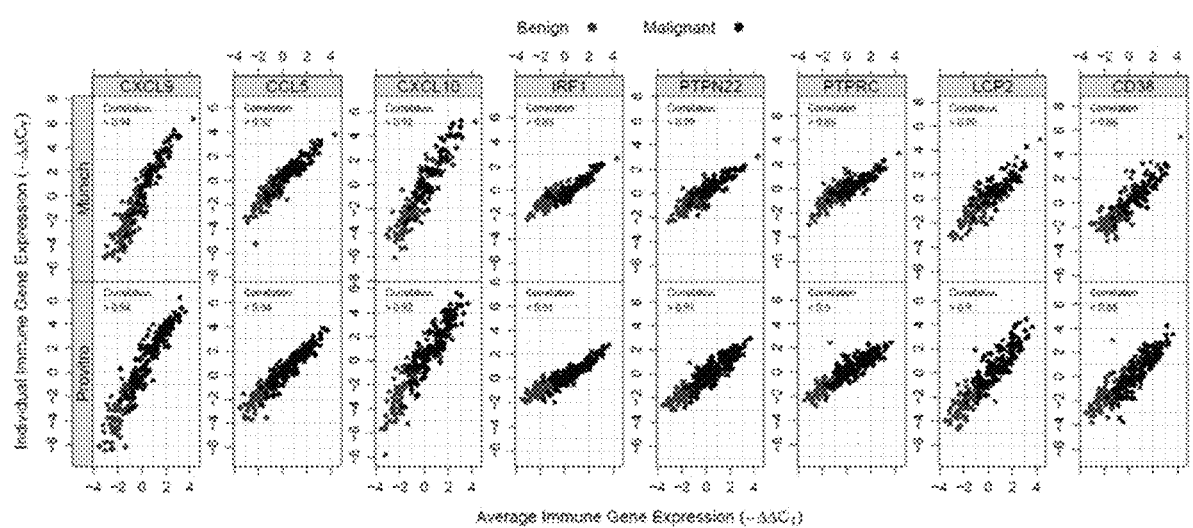
FIG. 6 shows the expression of each of the best 8 immune genes. Each of the genes had a linear relationship with the average expression of all 8 of the immune genes (indicating that they all measure the same biological process). Furthermore, all immune genes can differentiate melanoma and nevi samples (black and grey colored, respectively).

The ability of each gene was then analyzed to determine if its expression was effective in differentiating the malignant melanoma and benign nevi samples. We determined that PRAME was a very effective biomarker (FIG. 5). Furthermore, we also found that a large number of immune genes were also able to strongly differentiate melanoma and nevi. We further investigated 8 of these immune genes and found that their data was highly correlated, as the expression of each individual immune gene had a linear relationship with the average of all 8 immune genes (FIG. 6). This may indicate that they are measuring the same biological process, and they were thus grouped together into an "immune" set. The averaged expression of all 8 immune genes was calculated and then used when analyzing the dataset. Finally, we also noted that the cell cycle gene S100A9 also was able to differentiate many melanoma and nevi samples.

Figure 7:
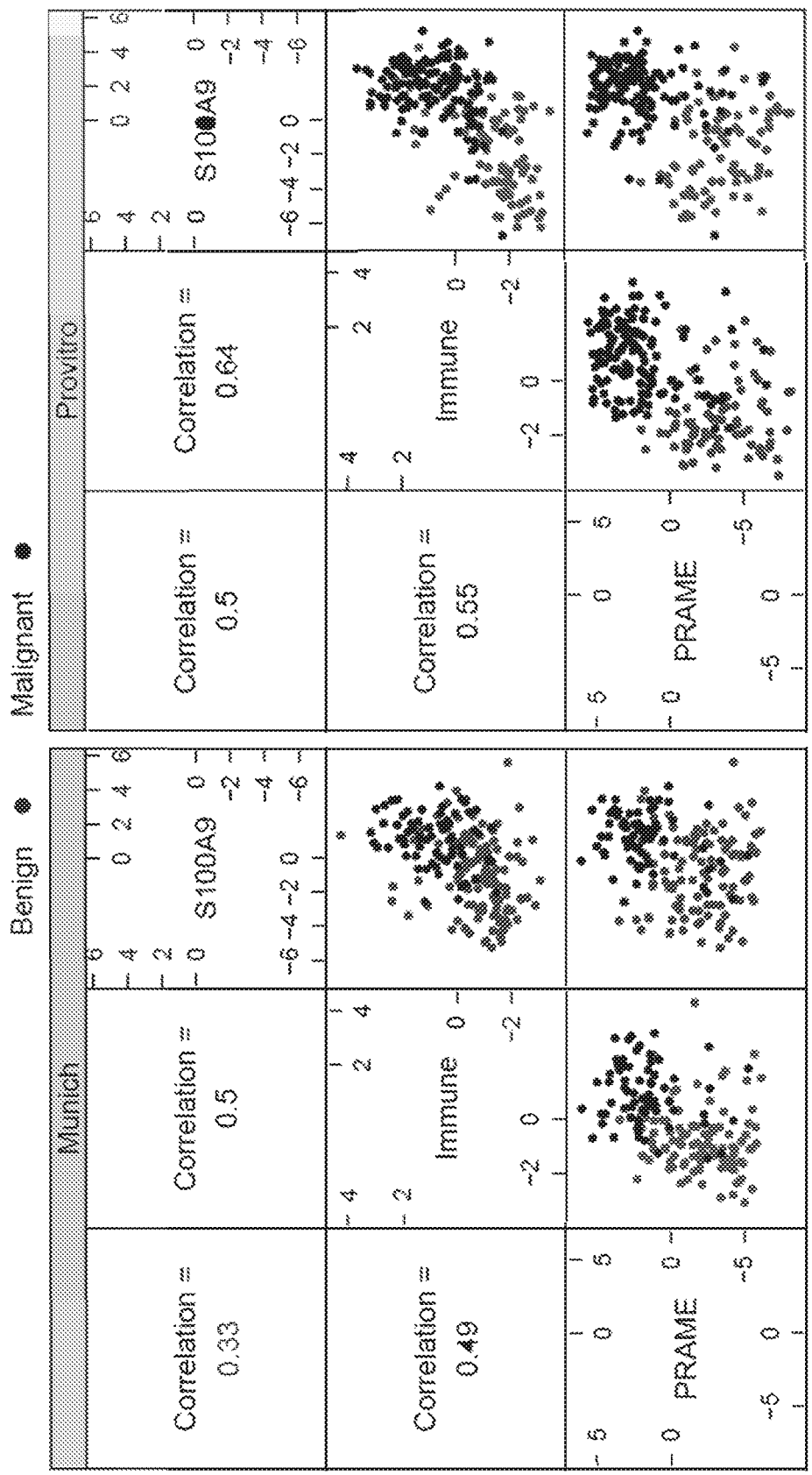
FIG. 7 shows graphs of the expression of each marker (of PRAME, the average of the 8 immune genes, and S100A9) graphed against the other markers. Data from each site graphed separately. The lack of high correlation between each biomarker indicates that they each are likely measuring different biological processes and each has independent value.
Figure 8:
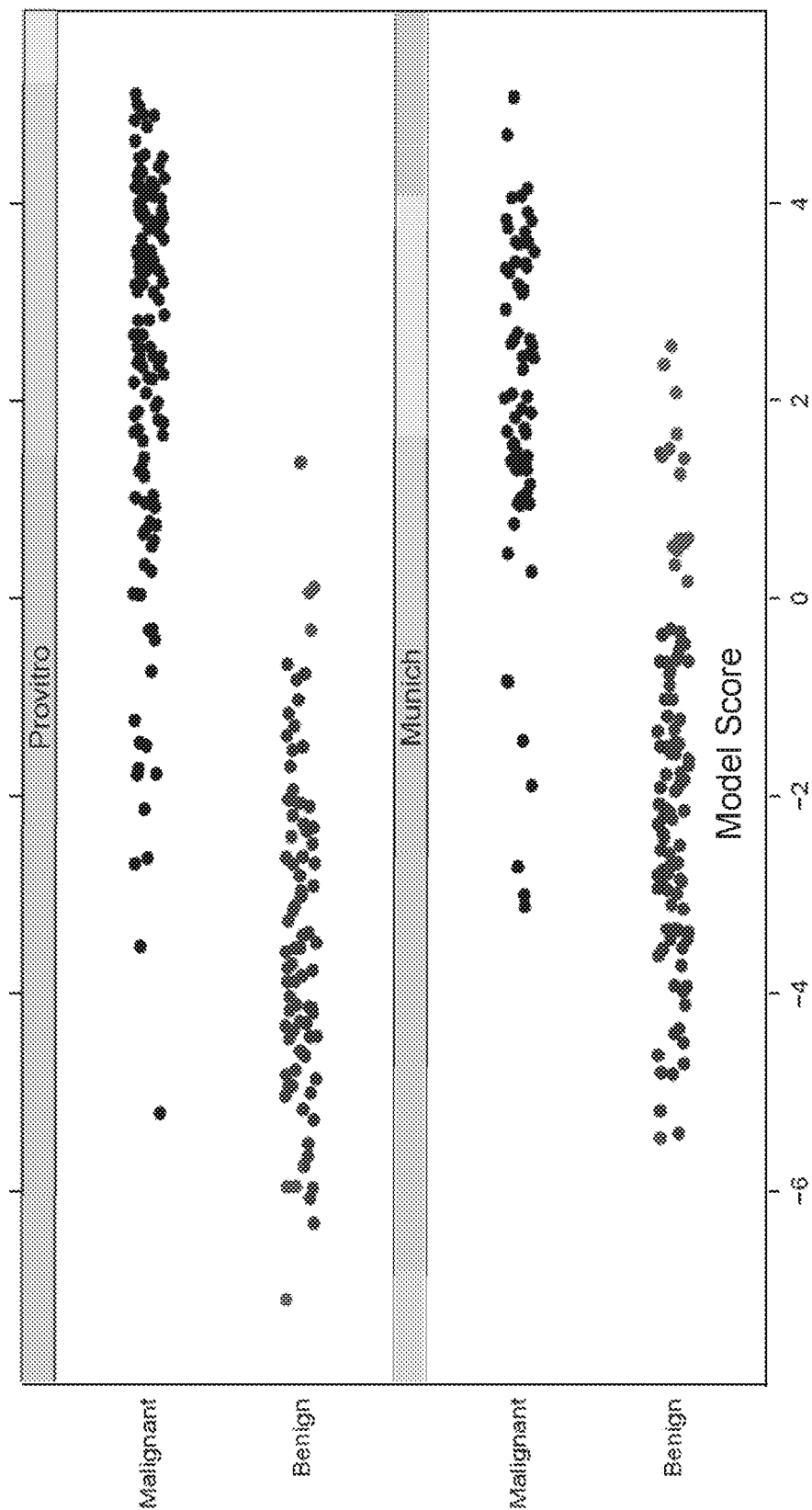
FIG. 8 shows the score generated by the diagnostic model, using the expression of PRAME, the immune genes, and S100A9. This score was used to differentiate malignant melanoma and benign nevi.
Figure 9:
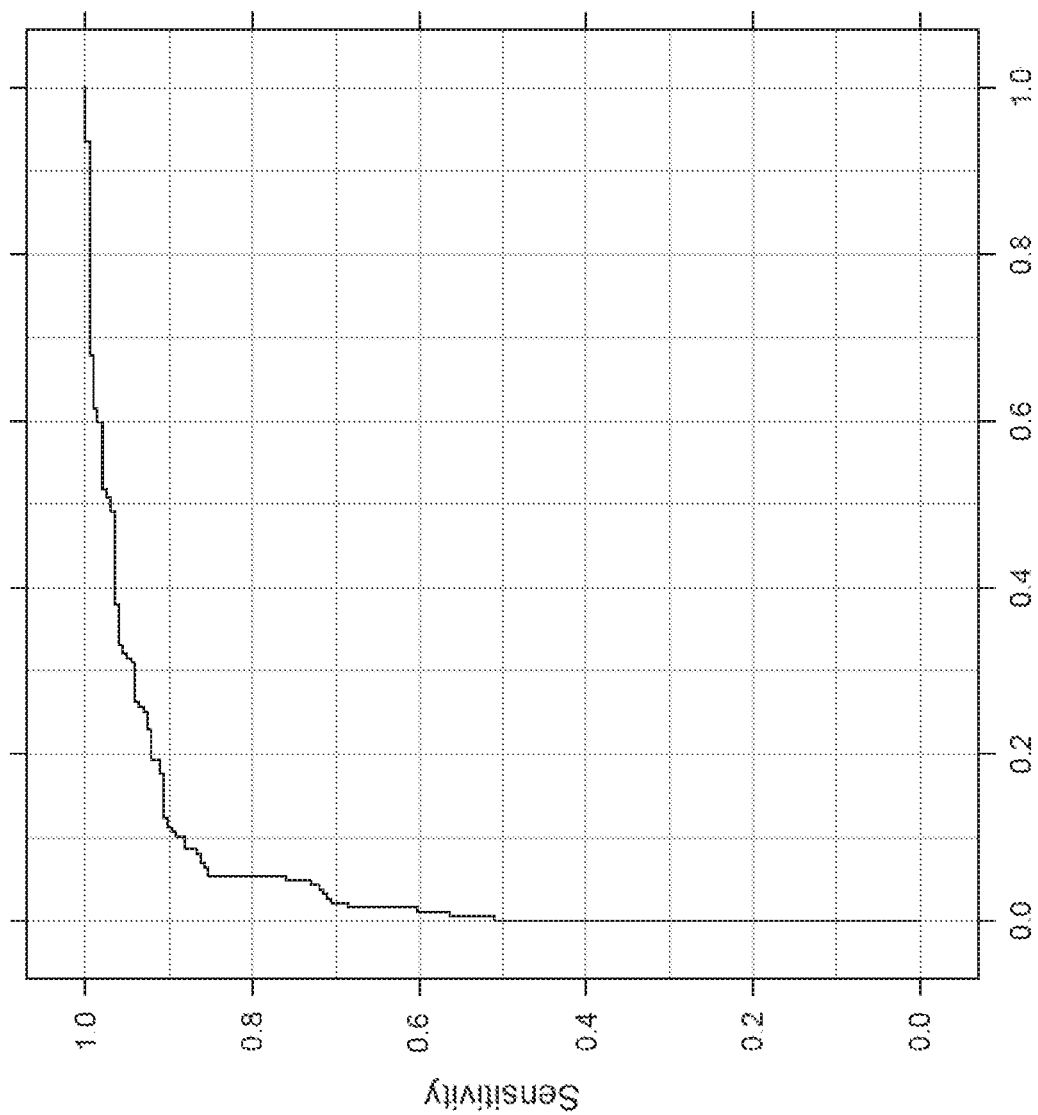
FIG. 9 shows an AUROC curve generated from the dataset, using the score produced from the model. The AUC of the ROC curve is ~0.96.

We next created a combined diagnostic model, using these three sets of biomarkers (PRAME, the immune genes, and S100A9). When the expression of each biomarker was graphed against the other, we did not see a high correlation, indicating that each biomarker is likely measuring a different biological process and has independent value (see FIG. 7). We ran the data through a logistic regression model, to best determine how each biomarker could be weighted in the model, to maximize the model's ability to differentiate melanoma and nevi. The most effective model was found with the following weightings for the expression of each biomarker set: (0.525×PRAME)+(0.677×Immune)+(0.357×S100A9). The model then takes the data from each patient and generates a score, which can be used to differentiate melanoma and nevi (see FIG. 8). This current dataset was then used to generate a ROC curve (see FIG. 9), which had an AUC of ~0.96.

Example 6

In this example we determined a diagnostic model for differentiating between malignant melanoma and non-malignant nevi and then further refined the diagnostic model.

Methods

Patient samples were acquired and prepared as described above in Example 5. Likewise, RNA extraction, preparation, and quantification of gene expression were also carried out in the same fashion as described above in Example 5. The same list of potential signature genes and the same housekeeper genes were assayed as in Example 5 (Table 11). Like Example 5, the measured expression of each gene was averaged and normalized by the averaged expression of all seven housekeeper genes. Each gene was analyzed to determine if its expression could differentiate between malignant melanoma samples and benign nevi samples. Genes that were effective at differentiating between malignant melanoma samples and benign nevi samples were further analyzed to determine which genes had correlating data. Correlating data indicated that the genes measured the same biological pathway. Genes with correlating data were grouped together in sets, with the average expression of the set used to differentiate melanoma and nevi.

Results

Building the Diagnostic Model

As described in Example 5, each gene was analyzed to determine if its expression was effective in differentiating the malignant melanoma samples from the benign nevi samples. In this analysis, we used forward selection to choose predictors for inclusion in a diagnostic model that would differentiate melanoma and nevi samples. As in Example 5, we selected PRAME, S100A9, and an immune component score as the predictors to differentiate the malignant melanoma samples from the benign nevi samples. The immune component score was made up of eight immune genes (CXCL9, CCL5, CXCL10, IRF1, PTPN22, PTPRC, LCP2, AND CD38) that all had highly correlated data (FIG. 6). These eight immune genes were grouped and their values averaged to create an immune component score. As in Example 5, we also determined that these three predictors (PRAME, S100A9, or the immune component) had expression patterns only moderately correlated with each other (FIG. 7), indicating that each predictor largely provides independent information when distinguishing melanoma and nevi samples.

We next created a combined diagnostic model using PRAME, S100A9, and the immune component score. The combined diagnostic model that we created was a linear model based on the gene expression data from the three predictors (PRAME, S100A9 and the immune component). In generating the linear model, we used generalized logistic regression to calculate the best weightings for each of the three predictors that would most effectively differentiate the melanoma and nevi samples in this dataset. The calculated best weightings were as follows: 1.149 for PRAME, 0.922 for S100A9, and 0.698 for the immune component score. Using these best weightings, the gene expression data for the three predictors was then used to generate a score that could be used to help differentiate between benign nevi samples and melanoma samples. The gene expression data for each predictor was multiplied by the respective best weighting and then the three weighted values were combined. This combined value, as shown here, represented a score that could be used to help differentiate between benign nevi samples and melanoma samples:

Score=(1.149×PRAME)+(0.922×S100A9)+(0.698× Immune component)

Figure 10:
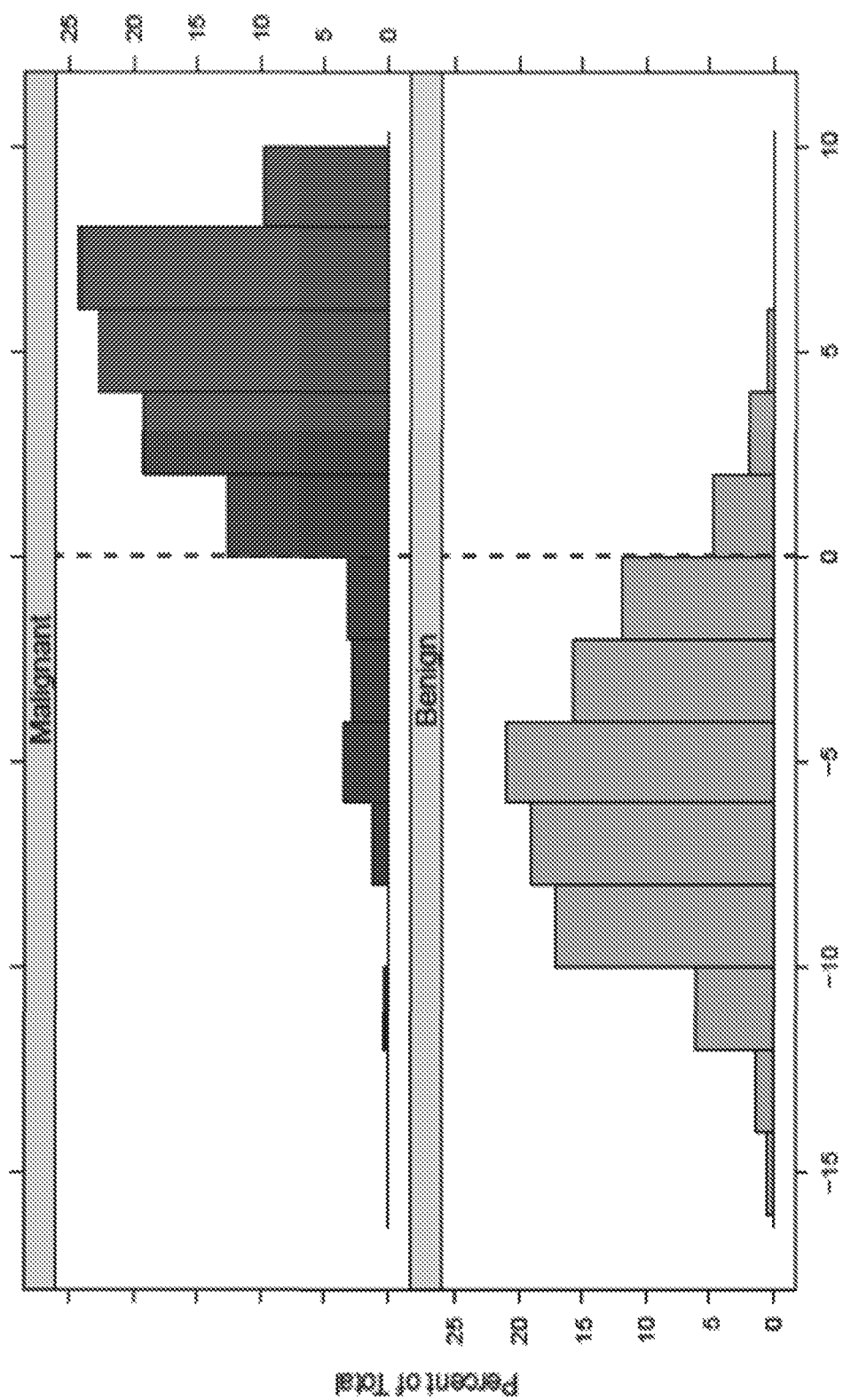
FIG. 10 shows the distribution of scores (x-axis) from all tested samples. The data are differentiated by primary diagnosis. The top panel shows scores for malignant samples. The bottom panel shows scores of benign samples.
Figure 11:
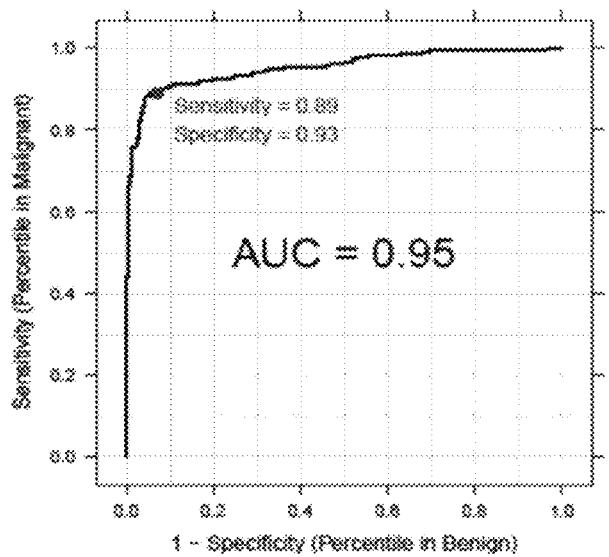
FIG. 11 shows an AUROC curve generated from the dataset based on the ability of the model to differentiate melanoma and nevi samples. The AUC of the ROC is ~0.95. Sensitivity and specificity are shown.

We then generated and plotted scores for all 544 samples (FIG. 10). In the plotted scores we observed a bi-modal distribution. Nearly all samples with a score greater than zero were melanoma (dark gray bars), while nearly all nevi samples (light gray bars) had a score less than zero. Using this data, a ROC curve was generated that had an AUC of ~0.95 and an associated p-value of 2.0×10-63 (FIG. 11). From this ROC curve we selected a cutoff point to differentiate between melanoma samples and nevi samples. In selecting the cutoff point we sought to maximize the sensitivity of the model, while maintaining the highest possible specificity. We selected a cutoff point with a sensitivity of 0.89 and a specificity of 0.93. We then adjusted the calculation of the score so that the selected cutoff point would be at a value of zero. Thus the adjusted score calculation was:

$$\text{Adjusted score} = \frac{(1.149 \times}{PRAME)} + \frac{(0.922 \times}{S100A9)} + \frac{(0.698 \times \text{Immune}}{\text{component})} - 0.334$$

Refining the Diagnostic Model

To improve the robustness and precision of the assay, we wanted to determine additional measurements for the PRAME and S100A9 predictors. We tested additional amplicons corresponding to PRAME and S100A9. We sought to determine if any other amplicons produced a reliable and correlated signal for these genes. We tested four additional PRAME amplicons.

We also tested amplicons that corresponded to six other genes that we determined would have expression that was highly correlated to S100A9: S100A7, S100A8, S100A10, S100A12, S100A14 and PI3.

We determined that one PRAME amplicon had low failure rates and had values highly correlated with the PRAME amplicon previously used in the model. We averaged its measurement with the other PRAME measurement to provide a PRAME component.

We chose four other potential genes which produced data with low failure rates and were highly correlated with the S100A9 amplicon selected in the training set. These four genes, S100A7, S100A8, S100A12, and PI3 were averaged with S100A9 to yield a single S100-related component, or S100 score.

Thus, we were able to create a refined signature for the three predictors, PRAME, S100-related component, and the immune component. The refined signature included additional measurements for the PRAME and S100-related predictors determined above. The refined signature included a total of 15 amplicons that measured 14 signature genes comprising two measurements of the PRAME gene, one measurement each of S100 related genes S100A9, S100A7, S100A8, S100A12, and PI3, and measurements of eight highly correlated immune genes (CXCL9, CCL5, CXCL10, IRF1, PTPN22, PTPRC, LCP2, AND CD38)(Table 12). Along with these 15 signature amplicons, we also included amplicons corresponding to nine different housekeeper genes for normalization, for a total of 24 amplicons in our refined signature (Table 12).

TABLE 12

Signature and housekeeper genes comprising the refined signature.

| Gene | Amplicons | Component |
|------|-----------|-----------|
| PRAME | 2 | PRAME |
| S100A7 | 1 | S100-related |
| S100A8 | 1 | |
| S100A9 | 1 | |
| S100A12 | 1 | |
| PI3 | 1 | |
| CCL5 | 1 | Immune |
| CD38 | 1 | |
| CXCL10 | 1 | |
| CXCL9 | 1 | |
| IRF1 | 1 | |
| LCP2 | 1 | |
| PTPRC | 1 | |
| SELL | 1 | |
| CLTC | 1 | Housekeeper |
| MRFAP1 | 1 | |
| PPP2CA | 1 | |
| PSMA1 | 1 | |
| RPL13A | 1 | |
| RPL8 | 1 | |
| RPS29 | 1 | |
| SLC25A3 | 1 | |
| TXNL1 | 1 | |

Lastly, we performed a concordance study to verify that the changes to the multiplex PCR reaction would not alter the data generated from the 10 signature amplicons retained from the initial signature. The qPCR assay relies on the fact that all the measured genes are pre-amplified in a single multiplex PCR reaction. Since the refined signature differed from the initial signature, it was important to ascertain that the different amplicon set of the refined signature did not alter the multiplex PCR reaction and consequently alter the data generated from the 10 amplicons retained from the initial signature set. Therefore, we retested RNA expression in 74 RNA samples from the initial training set using the refined signature. The scores of the retested RNA samples demonstrated an extremely high correlation (correlation coefficient of 0.99) when compared to the scores generated from the training set. Thus, the refined signature did not alter the data generated from any of the amplicons of the refined signature. Accordingly, the refined signature produced a refined, adjusted score calculation of:

$$\text{Refined, adjusted score} = (1.223 \times PRAME\ \text{component}) + (1.023 \times S100\ \text{component}) + (0.704 \times \text{Immune component}) + 0.267$$

Example 7

In this example we clinically validated a diagnostic model for differentiating between malignant melanoma and non-malignant nevi.

Methods

A validation cohort was generated by acquiring more than 400 skin lesions from four separate sites: Cleveland Clinic, Moffit Cancer Center, Northwestern University and the University of Utah (Table 13).

Each site provided both malignant and benign samples, with all major histological subtypes represented. The diagnosis for each case was confirmed, using a second dermatopathologist who was blinded to the diagnosis of the first dermatopathologist. If there was discordance in the diagnoses, a third dermatopathologist adjudicated the diagnosis. The melanoma subtypes included superficial spreading melanoma, nodular melanoma, lentigo maligna melanoma, desmoplastic melanoma, and subtypes classified as a not otherwise specified (Table 14).

TABLE 14

Clinical information for melanoma samples used in the clinical validation.

|  | SSM | Nod | Acral | LMM | Desm | NOS | Overall |
|---|---|---|---|---|---|---|---|
| Total Number | 105 | 38 | 9 | 31 | 5 | 23 | 211 |

SSM = Superficial Spreading Melanoma,
Nod = Nodular melanoma,
LMM = Lentigo Maligna Melanoma,
Desm = Desmoplastic,
NOS = Not Otherwise Specified subtype
Only samples that produced analyzable results were included.

The nevi subtypes included blue nevi, compound nevi, junctional nevi, dermal nevi, deep penetrating nevi, dysplastic nevi, and subtypes classified as a not otherwise specified (Table 15).

TABLE 15

Clinical information for nevi samples used in the clinical validation.

|  | Blue | Comp | Junc | Spitz | Derm | Deep Pen | NOS | Overall | Dyspl* |
|---|---|---|---|---|---|---|---|---|---|
| Total Number | 22 | 101 | 20 | 7 | 41 | 7 | 28 | 226 | 70 |

Comp = Compound, Junc = Junctional, Derm = Dermal, Deep Pen = Deep Penetrating, NOS = Not Otherwise Specified subtype, Dyspl = Dysplastic.
*Dysplastic nevi were scored as an attribute of a subtype, not as a specific subtype.

TABLE 13

Sources of samples for the clinical validation cohort.

|  | Diagnosis | | |
|---|---|---|---|
| Institution | Benign | Malignant | Total |
| Cleveland Clinic | 62 | 65 | 127 |
| Moffit Cancer Center | 80 | 57 | 137 |
| Northwestern University | 26 | 46 | 72 |
| University of Utah | 58 | 43 | 101 |
| Total | 226 | 211 | 437 |

Only samples that produced analyzable results were included.

The patient samples were prepared as described above in Example 5. RNA extraction, RNA preparation, and quantification of gene expression were also carried out as described above in Example 5. The same list of potential signature genes and the same housekeeper genes were assayed as in Example 5 (Table 11). Likewise, as in Example 5, the measured expression of each gene was averaged and normalized by the averaged expression of all seven housekeeper genes. Then, a refined, adjusted score was generated for each patient sample using the refined, adjusted score calculation of:

$$\text{Refined, adjusted score} = (1.223 \times PRAME\ \text{component}) + (1.023 \times S100\ \text{component}) + (0.704 \times \text{Immune component}) + 0.267$$

Results

Figure 12:
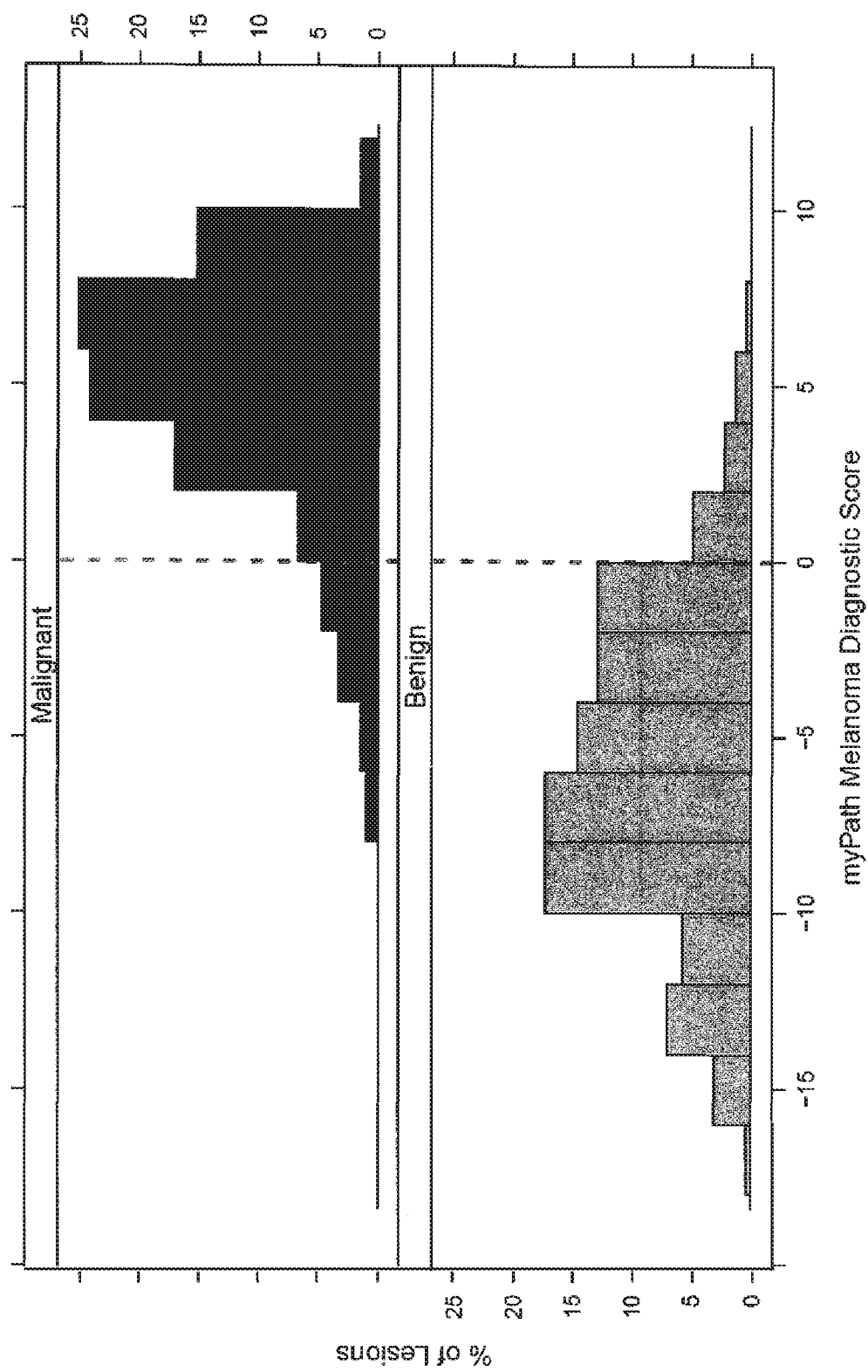
FIG. 12 shows the distribution of scores (x-axis) from all tested samples for the validation cohort. The data are differentiated by primary diagnosis. The top panel shows scores for malignant samples. The bottom panel shows scores of benign samples.
Figure 13:
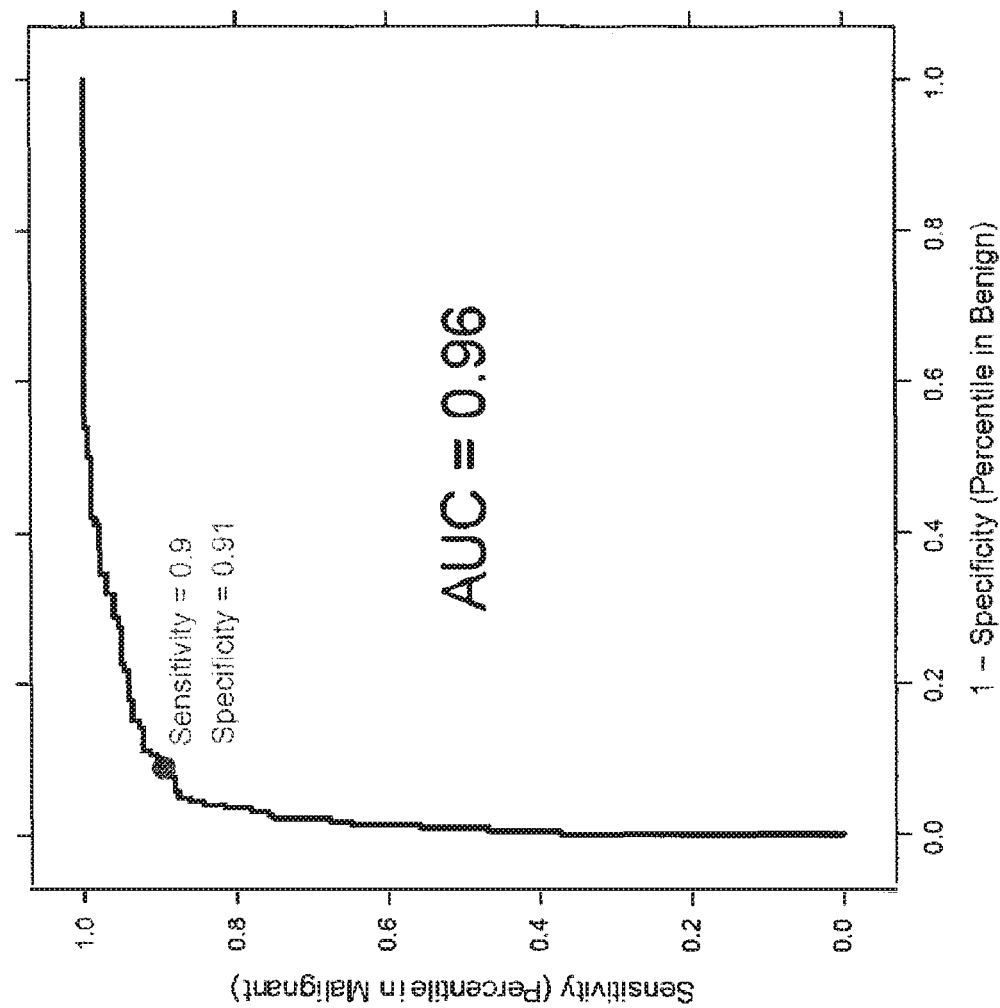
FIG. 13 shows an AUROC curve generated based on the validation cohort. The AUC of the ROC is ~0.96. Sensitivity and specificity are shown.

The refined, adjusted scores were plotted for each patient sample (FIG. 12). The plotted refined, adjusted scores resulted in a bimodal distribution similar to that seen in FIG. 10 of Example 6. Nearly all melanoma samples had scores greater than zero (FIG. 12, upper panel) and nearly all nevi samples had scores less than zero (FIG. 12, lower panel). This data was then used to generate a validation ROC curve that had an AUC of ~0.96 with a sensitivity of 0.9 and a specificity of 0.91 (FIG. 13). The p-value associated with the validation ROC curve was $3.7 \times 10^{-63}$. The validation ROC curve was then compared to the ROC curve generated in Example 6 (FIG. 11) to determine if the diagnostic model had been validated. The validation ROC curve had an AUC of ~0.96, a sensitivity of 0.9, and a specificity of 0.91 compared to the ROC curve of Example 6 which had an AUC of ~0.95, a sensitivity of 0.89, and a specificity of 0.93. The close agreement of the validation ROC curve and the ROC curve of Example 6 indicated that the validation cohort validated the diagnostic model of Example 6.

Next, the performance of the diagnostic model was analyzed within individual histological subtypes for those subtypes with 30 or more samples (Table 16).

TABLE 16

Assay performance within individual subtypes in the clinical validation.

| Subtype | Correct call | Incorrect call | Sensitivity | Specificity |
|---|---|---|---|---|
| Compound Nevus | 95 | 6 | | 94% |
| Dermal Nevus | 40 | 1 | | 98% |
| All Nevi | 206 | 20 | | 91% |
| Superficial Spread Melanoma | 90 | 15 | 86% | |
| Nodular Melanoma | 37 | 1 | 97% | |
| Lentigo Maligna Melanoma | 28 | 3 | 90% | |
| All Melanomas | 189 | 22 | 90% | |

Only subtypes groups with ≥ 30 samples were reported.

There were two benign subtypes, compound and dermal, with more than 30 samples. The scoring of compound and dermal subtypes resulted in specificities of 94% and 98%, respectively, with an overall specificity of 91% for all nevi. There were three malignant subtypes, superficial spreading melanoma, nodular melanoma, and lentigo maligna melanoma with more than 30 samples. The scoring of superficial spreading melanoma, nodular melanoma, and lentigo maligna melanoma resulted in sensitivities of 86%, 97%, and 90%, respectively, with an overall sensitivity of 90% for all melanomas.

Example 8

In this example we developed a different approach to interpreting the diagnostic score by designating an indeterminate zone. Samples with scores falling between −2.0 and −0.1 were classified as indeterminate and are neither consistent with benign nevus nor consistent with malignant melanoma. Samples with scores between −16.7 and −2.1 were classified as consistent with benign nevus. Samples with scores between 0 and 11.1 were classified as consistent with malignant melanoma.

Figure 14:
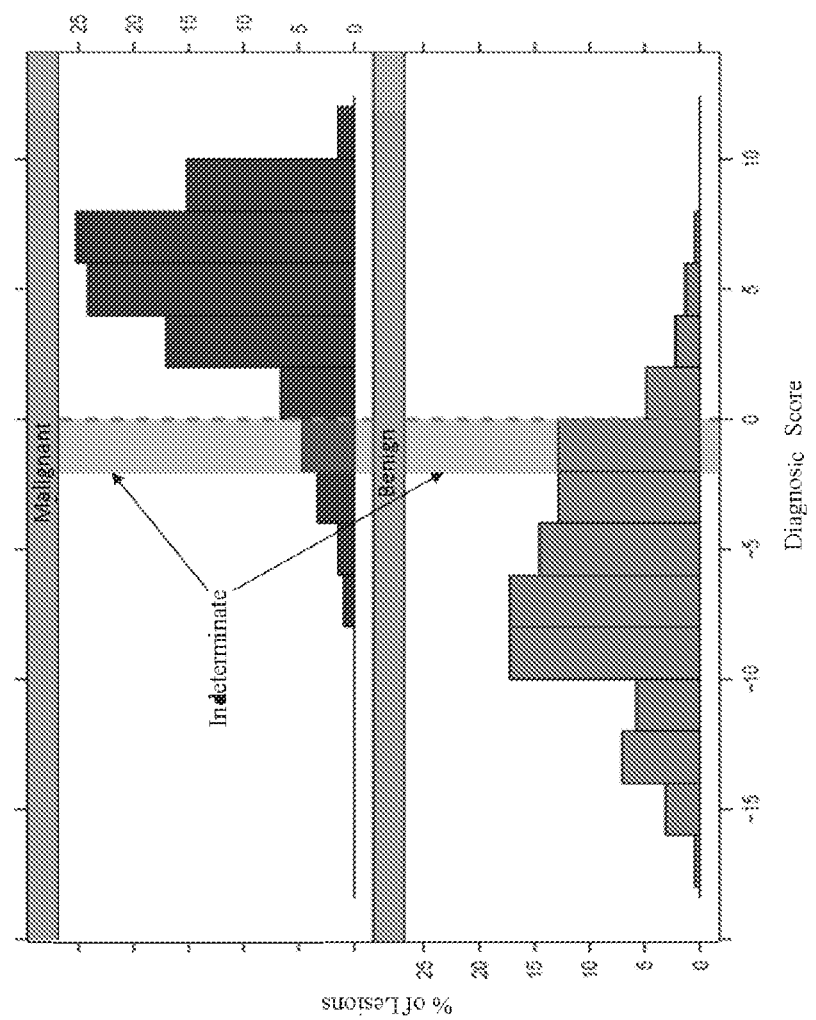
FIG. 14 shows the distribution of scores (x-axis) from all tested samples for the validation cohort when implementing the Indeterminate Zone. The data are differentiated by primary diagnosis. The top panel shows scores for malignant samples. The bottom panel shows scores of benign samples.

The refined, adjusted scores were plotted for each patient sample (FIG. 14). The scoring of samples as either consistent with benign nevus, indeterminate, or consistent with malignant melanoma resulted in a sensitivity of 94% and a specificity of 90% after indeterminate samples were removed from analysis. 9% of samples scored as indeterminate (5% of the total melanomas and 13% of the total nevi samples tested) (FIG. 14).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A method for treating melanoma in a patient in need thereof, the method comprising:
   measuring in a sample taken from a site on the patient mRNA expression of a panel of genes normalized to one or more housekeeping genes, the panel of genes comprising:
   PRAME, S100A7, S100A8, S100A9, S100A12, PI3, CCL5, CD38, CXCL10, CXCL9, IRF1, LCP2, PTPRC, and SELL;
   calculating a combined score of the measured mRNA expression of each of the panel of genes;
   classifying the sample as being a malignancy based on the combined score exceeding a reference value; and
   administering to the patient having the malignancy a treatment comprising one or more of:
   excising the malignancy;
   reexcising the site of the sample to remove additional tissue;
   lymph node dissection;
   radiation therapy;
   chemotherapy;
   biological therapy;
   immunotherapy;
   targeted therapy; and
   a melanoma drug.

2. The method of claim 1, wherein
   excising the malignancy comprises excising a border of normal skin and/or a layer of tissue beneath the malignancy;
   biological therapy comprises administering one or more of interferon, interleukin-2, and ipilimumab;
   immunotherapy comprises administering one or more of interferon-alpha, anti-CTLA-4, a vaccine, a Bacille Calmette-Guerin vaccine, interleukin 2, and T-cell therapy;
   targeted therapy comprises administering one or more of vemurafenib, a BRAF inhibitor, and a KIT inhibitor; and
   a melanoma drug comprises one or more drugs selected from aldesleukin, dabrafenib, dacarbazine, interferon alfa-2b, peginterferon alfa-2b, ipilimumab, trametinib, vemurafenib, a Bacille Calmette-Guerin (BCG) vaccine, interleukin-2, imiquimod, temozolomide, and a beta-adrenergic-blocker.

3. The method of claim 1, wherein the reference value is selected using an ROC curve of expression levels of the panel of genes in malignant melanoma and benign samples from a reference population of patients, wherein the ROC curve has a sensitivity of at least 0.8.

4. The method of claim 1, wherein the panel of genes further comprises S100A10, and S100A14.

5. The method of claim 1, wherein the one or more housekeeping genes is selected from the group consisting of CLTC, PPP2CA, MRFAP1, PSMA1, RPL13A, TXNL1, SLC25A3, RPS29, RPL8, PSMC1, and RPL.

6. The method of claim 1, wherein the panel of genes further comprises PTPN22.

7. The method of claim 1, wherein the combined score is calculated by logistic regression which determines coefficients for a weighted summing of the expression of the panel of genes.

8. The method of claim 1, wherein the expression of the panel of genes is measured by qPCR.

9. The method of claim 1, wherein the sample is a skin lesion.

10. A method for treating melanoma in a patient, the method comprising:
    measuring in a first sample from the patient mRNA expression of a panel of genes normalized to one or more housekeeping genes, the panel of genes comprising:
        PRAME, S100A7, S100A8, S100A9, S100A12, PI3, CCL5, CD38, CXCL10, CXCL9, IRF1, LCP2, PTPRC, and SELL;
    calculating a first combined score of the measured mRNA expression of each of the panel of genes;
    classifying the sample as having a low risk of being a malignancy based on the combined score not exceeding a reference value; and
    administering to the patient having a low risk of malignancy a treatment comprising a regimen of watchful waiting;
    measuring in a second sample from the patient expression of the panel of genes;
    calculating a second combined score from the expression of the panel of genes;
    classifying the second sample as having a high risk of being a malignancy based on the second combined score exceeding a reference value; and
    administering to the patient having a high risk of malignancy a treatment comprising one or more of:
        excising the malignancy;
        reexcising the site of the sample to remove additional tissue;
        lymph node dissection;
        radiation therapy;
        chemotherapy;
        biological therapy;
        immunotherapy;
        targeted therapy; and
        a melanoma drug.

11. The method of claim 10, wherein
    excising the malignancy comprises excising a border of normal skin and/or a layer of tissue beneath the malignancy;
    biological therapy comprises administering one or more of interferon, interleukin-2, and ipilimumab;
    immunotherapy comprises administering one or more of interferon-alpha, anti-CTLA-4, a vaccine, a Bacille Calmette-Guerin vaccine, interleukin 2, and T-cell therapy;
    targeted therapy comprises administering one or more of vemurafenib, a BRAF inhibitor, and a KIT inhibitor; and
    a melanoma drug comprises one or more drugs selected from aldesleukin, dabrafenib, dacarbazine, interferon alfa-2b, peginterferon alfa-2b, ipilimumab, trametinib, vemurafenib, a Bacille Calmette-Guerin (BCG) vaccine, interleukin-2, imiquimod, temozolomide, and a beta-adrenergic-blocker.

12. The method of claim 10, wherein the reference value is selected using an ROC curve of expression levels of the panel of genes in malignant melanoma and benign samples from a reference population of patients, wherein the ROC curve has a sensitivity of at least 0.8.

13. The method of claim 10, wherein the panel of genes further comprises S100A10, and S100A14.

14. The method of claim 10, wherein the one or more housekeeping genes is selected from the group consisting of CLTC, PPP2CA, MRFAP1, PSMA1, RPL13A, TXNL1, SLC25A3, RPS29, RPL8, PSMC1, and RPL.

15. The method of claim 10, wherein the panel of genes further comprises PTPN22.

16. The method of claim 10, wherein the combined score is calculated by logistic regression which determines coefficients for a weighted summing of the expression of the panel of genes.

17. The method of claim 10, wherein the expression of the panel of genes is measured by qPCR.

18. The method of claim 10, wherein the sample is a skin lesion.

* * * * *